United States Patent
Patel et al.

(10) Patent No.: US 7,930,923 B2
(45) Date of Patent: Apr. 26, 2011

(54) QUARTZ CRYSTAL MICROBALANCE WITH NANOCRYSTALLINE OXIDE SEMICONDUCTOR THIN FILMS AND METHOD OF DETECTING VAPORS AND ODORS INCLUDING ALCOHOLIC BEVERAGES, EXPLOSIVE MATERIALS AND VOLATILIZED CHEMICAL COMPOUNDS

(75) Inventors: Nirmalkumar G. Patel, Jacksonville, FL (US); Jay S. Huebner, Jacksonville, FL (US); Brian E. Stadelmaier, Jacksonville, FL (US); Jason J. Saredy, Jacksonville, FL (US)

(73) Assignee: The University of North Florida Board of Trustees, Jacksonville, FL (US)

( * ) Notice: Subject to any disclaimer, the term of this patent is extended or adjusted under 35 U.S.C. 154(b) by 2 days.

(21) Appl. No.: 12/416,922

(22) Filed: Apr. 1, 2009

(65) Prior Publication Data
US 2010/0251802 A1    Oct. 7, 2010

(51) Int. Cl.
*G01N 29/02* (2006.01)
*G01N 33/497* (2006.01)

(52) U.S. Cl. ............... 73/23.34; 73/23.3; 73/24.01

(58) Field of Classification Search ............ 73/24.01, 73/24.02, 24.03, 24.04, 24.05, 24.06, 23.3, 73/23.34, 23.4
See application file for complete search history.

(56) References Cited

U.S. PATENT DOCUMENTS

| | | | |
|---|---|---|---|
| 6,360,585 B1 | 3/2002 | Potyrailo et al. | |
| 6,500,547 B1 | 12/2002 | Potyrailo | |
| 6,537,498 B1 * | 3/2003 | Lewis et al. | 422/82.01 |
| 6,837,095 B2 * | 1/2005 | Sunshine et al. | 73/23.2 |
| 6,890,486 B2 | 5/2005 | Penelle | |
| 7,293,450 B2 | 11/2007 | Liu et al. | |
| 7,329,536 B2 | 2/2008 | Zeng et al. | |
| 7,390,397 B2 | 6/2008 | Lamprecht et al. | |
| 7,461,539 B2 | 12/2008 | Galun et al. | |

(Continued)

OTHER PUBLICATIONS

J. Zhang, J.Q. Hu, F.R. Zhu, H. Gong, S.J. O'Shea. "ITO thin films coated quartz crystal microbalance as gas sensor for NO detection." Sens. Actuators B 87 (2002) pp. 159-167.*

(Continued)

*Primary Examiner* — Lisa M Caputo
*Assistant Examiner* — Punam Roy
(74) *Attorney, Agent, or Firm* — Mark Young, P.A.

(57) ABSTRACT

A nanocrystalline ITO thin film formed on a quartz crystal microbalance (QCM) facilitates detection of gaseous compounds emitted from an analyte. Adsorption of gas molecules onto the nanocrystalline ITO thin film changes the resonant frequency of the quartz crystal. Parameters such as the frequency of oscillation, surface resistance, integrated frequency response, integrated surface resistance response, initial response slope, average return to baseline slope, and/or return to baseline time/initial response time ratio of the quartz crystal with the nanocrystalline ITO thin film formed thereon are determined. Using the determined parameters and principal component analysis, principal components for the gaseous compounds are also determined. These determined principal components may be compared with known principal components corresponding to known analytes. The analyte may include any distinguishable substance, in any state that emits at least one gaseous compound that can be adsorbed on the nanocrystalline ITO thin film. Nonlimiting examples of analytes include alcoholic beverages, fruits, explosive compounds, VOCs, petroleum-based fuels, alkanes, aldehydes and ketones.

14 Claims, 139 Drawing Sheets

PCA score plot of volatile organic compounds

U.S. PATENT DOCUMENTS

| | | |
|---|---|---|
| 7,464,580 B2 | 12/2008 | Zeng et al. |
| 2003/0186461 A1* | 10/2003 | Boehr et al. ............... 436/181 |
| 2004/0045096 A1 | 3/2004 | Mani et al. |
| 2006/0006871 A1 | 1/2006 | Uchida et al. |
| 2006/0057635 A1 | 3/2006 | Mansson et al. |
| 2007/0210349 A1 | 9/2007 | Lu et al. |
| 2008/0202926 A1 | 8/2008 | Hontsu et al. |
| 2008/0204043 A1 | 8/2008 | Wang et al. |
| 2009/0049890 A1* | 2/2009 | Zhong et al. ............... 73/23.3 |

OTHER PUBLICATIONS

Stanford Research Systems' QCM200 Quartz Crystal Microbalance Data Sheet. Online Publication on Feb. 10, 2005.*

Nirmal Patel, Jay Huebner, Jason Saredy and Brian Stadelmaier, "Odor Sensing With Indium Tin Oxide Thin Films on Quartz Crystal Microbalance," Sensors & Transducers Journal, vol. 91, Issue 4, published Apr. 30, 2008, pp. 116-126, published by International Frequency Sensor Association (IFSA), Toronto, Ontario, Canada.

* cited by examiner

Scanning electron micrographs of (a) ITO-Pt, At cut; (b) ITO-Au, IT cut; and (c) ITO-Au, At cut.

Characterization parameters of ITO-QCM odor sensors

| Parameters | Au AT-cut | Pt At-cut | Au IT-Cut |
|---|---|---|---|
| Change in frequency (Hz) | -2.4 | -1.9 | -0.6 |
| Change in surface resistance (Ohms) | -0.045 | 0 | -0.017 |
| Response time (Sec) | 8.58 | 7.52 | 4.29 |
| Initial response slope (Hz/sec) | -0.279 | -0.252 | -0.139 |
| Return to baseline slope (Hz/sec) | 0.137 | 0.236 | 0.0125 |
| Full width at half maximum (sec) | 9.8 | 10.8 | 12.3 |

Grain size statistics for ITO-quartz crystals

| Parameters | Pt, AT-cut | Au, IT-cut | Au, AT-cut |
|---|---|---|---|
| Sample size | 127 | 232 | 27 |
| Average Grain size diameter (nm) | 98.2 | 52.0 | 43.4 |
| ±1-sigma standard deviation (nm) | ±33.0 | ±11.7 | ±11.7 |

FIGURE 7

Illustration of measured parameters on frequency and surface resistance versus time plots. Where:
A is integrated frequency response (Hz · sec)
B is integrated surface resistance response (Ω · sec)
C is initial response slope (Hz/sec)
D is average return to baseline slope (Hz/sec)
E is return to baseline time / initial response time ratio.

Change in frequency and surface resistance responses as ITO-QCM film was exposed to odors from beers: 1-Michelob Ultra Pomegranate Raspberry, 2-Michelob Ultra Tuscan Orange Grapefruit Red, 3-Michelob Ultra Lime Cactus, 4-Beck's Bier, 5-Beck's Premier Light, 6-Beck's Dark, 7-Sam Adam's Light, 8-Samuel Adams White Ale, 9-Samuel Adams Cherry Wheat

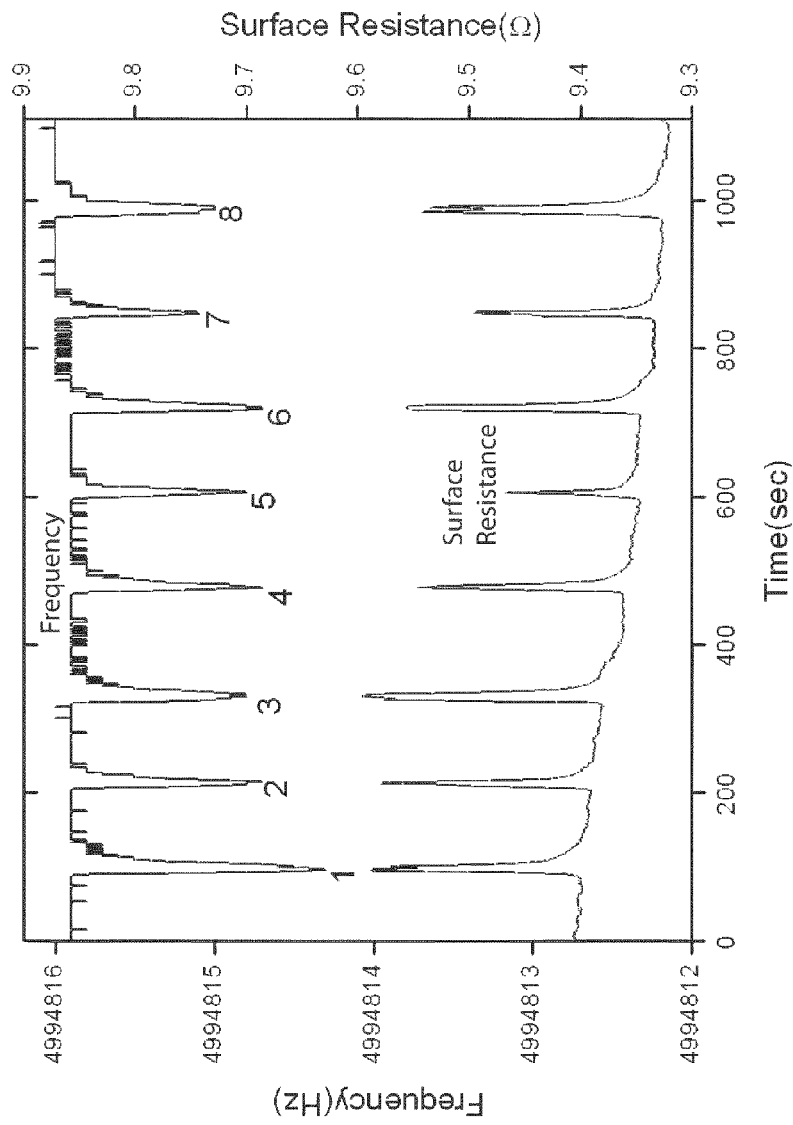

FIGURE 10

Change in frequency and surface resistance responses as ITO-QCM film was exposed to odors from wines: 1-Sutter Home Sauvignon Blanc California, 2-Glen Ellen Chardonnay California, 3-Lindemans Bin 65 Chardonnay Australia, 4-Sutter Home Merlot California, 5-Lindemans Bin 50 Shiraz Australia, 6-Lindemans Bin 45 Cabernet Sauvignon Australia, 7-Cruz Garcia Real Sangria Spain, 8-Sutter Home White Zinfandel California Change in frequency and surface resistance responses as the ITO-QCM film was exposed to odors from brandy: 1-Paul Masson Grande Amber, 2-Vendome Platinum VSOP, 3-Hennessy Very Special Cognac, 4-Kelt Tour du Monde VSOP Cognac Change in frequency and surface resistance responses as the ITO-QCM film was exposed to odors from gins: 1-Gordon's London Dry, 2-Beefeater London Dry, 3-Fleischmann's Extra Dry, 4-Seagram's Extra Dry Change in frequency and surface resistance responses as the ITO-QCM film was exposed to odors from rums: 1-Tropical Isle Palms Coconut Barbados 2-Tropical Isle Palms Barbados, 3-Captain Morgan Original Spiced Change in frequency and surface resistance responses as the ITO-QCM film was exposed to odors from tequilas: 1-Cuesta Rey Silver, 2-Cuesta Rey Gold, 3-Jose Cuervo Especial Oro, 4-Jose Cuervo Black Medallion Anejo Change in frequency and surface resistance responses as the ITO-QCM film was exposed to odors from vodkas: 1- Absolut Country of Sweden, 2- Northern Arctic Charcoal Filtered, 3- Smirnoff Watermelon, 4- Denaka, 5- Denaka Rasberry Platinum Change in frequency and surface resistance responses as the ITO-QCM film was exposed to odors from whiskeys: 1- Jim Beam Kentucky Straight Bourbon, 2- Jack Daniels Old No. 7, 3- Early Times Kentucky, 4- Old Grand-Dad, 5- Lord Calvert Canadian, 6- Canadian Mist, 7- Maker's Mark Kentucky Straight Bourbon, 8- Gentleman Jack The average change in ITO-QCM frequency response to odors from each category of alcoholic beverages The average change in ITO-QCM surface resistance response to odors from each category of alcoholic beverages.

| Sample (Alcohol %) | Integrated Frequency Response (Hz-sec) | Integrated Surface Resistance Response (Ω-Sec) | Initial Response Slope (Hz/Sec) | Average Return to Baseline Slope (Hz/sec) | Return to baseline time/Initial response time ratio |
|---|---|---|---|---|---|
| Beers | | | | | |
| 1 Michelob Ultra Pomegrante Rasberry (4.2%) | -15.5 | 2.32 | -0.1329 | 0.0424 | 3.14 |
| 2 Michelob Ultra Tuscan Orange Grapefruit (4.2%) | -8.2 | 1.8 | -0.186 | 0.0243 | 7.66 |
| 3 Michelob Ultra Lime Cactus (4.2%) | -15 | 2.72 | -0.1281 | 0.0301 | 4.25 |
| 4 Beck's Bier (4.8%) | -19.8 | 2.76 | -0.1024 | 0.0239 | 4.3 |
| 5 Beck's Premier Light (2.3%) | -8.2 | 2.48 | -0.0666 | 0.0245 | 3.81 |
| 6 Beck's Dark (4.8%) | -10.5 | 3.05 | -0.0931 | 0.0146 | 5.32 |
| 7 Sam Adam's Light (4.05%) | -14.1 | 2.61 | -0.1165 | 0.0245 | 4.75 |
| 8 Samuel Adams White Ale (5.4%) | -12.6 | 2.94 | -0.1049 | 0.0262 | 4.01 |
| 9 Samuel Adams Cherry Wheat (5.35%) | -7.6 | 3.5 | -0.0508 | 0.0328 | 1.54 |

Data parameters chart for all beer odors measured with ITO-QCM

FIGURE 19

| Sample (Alcohol %) | Integrated Frequency Response (Hz-sec) | Integrated Surface Resistance Response (Ω-Sec) | Initial Response Slope (Hz/Sec) | Average Return to Baseline Slope (Hz/sec) | Return to baseline time/Initial response time ratio |
|---|---|---|---|---|---|
| Wines | | | | | |
| 1 Sutter Home Sauvignon Blanc California (13%) | -26.3 | 2.3 | -0.2127 | 0.0392 | 3.8 |
| 2 Glen Ellen Chardonnay California (12.5%) | -15.3 | 1.75 | -0.1242 | 0.0622 | 2 |
| 3 Lindemans Bin 65 Chardonnay Australia (13.5%) | -19 | 2.83 | -0.1138 | 0.0365 | 3.11 |
| 4 Sutter Home Merlot California (13.0%) | -16.4 | 1.73 | -0.1397 | 0.0386 | 3.63 |
| 5 Lindemans Bin 50 Shiraz Australia (13.5%) | -12.7 | 1.14 | -0.128 | 0.0489 | 2.62 |
| 6 Lindemans Bin 45 Cabernet Sauvignon Australia (13.5%) | -17.4 | 2.61 | -0.2131 | 0.0486 | 4.61 |
| 7 Cruz Garcia Real Sangria Spain (7 to 10%) | -10.7 | 1.34 | -0.1199 | 0.04 | 3 |
| 8 Sutter Home White Zinfandel California (9.5%) | -19 | 3.3 | -0.0932 | 0.0282 | 3.16 |

Data parameters chart for all wine odors measured with ITO-QCM

FIGURE 20

| Sample (Alcohol %) | Integrated Frequency Response (Hz-sec) | Integrated Surface Resistance Response (Ω-Sec) | Initial Response Slope (Hz/Sec) | Average Return to Baseline Slope (Hz/sec) | Return to baseline time/Initial response time ratio |
|---|---|---|---|---|---|
| Rums | | | | | |
| 1 Tropical Isle Palms Coconut Barbados (21%) | -13.5 | 0.65 | -0.1304 | 0.0933 | 1.4 |
| 2 Tropical Isle Palms Barbados (40%) | -30.8 | 0.03 | -0.3728 | 0.1538 | 2.43 |
| 3 Captain Morgan Original Spiced (35%) | -19.4 | -0.09 | -0.1355 | 0.0648 | 2.09 |
| Whiskeys | | | | | |
| 1 Jim Beam Kentucky Straight Bourbon (40%) | -29.1 | 5.88 | -0.2585 | 0.1786 | 1.44 |
| 2 Jack Daniels Old No. 7 (40%) | -37.8 | 1.76 | -0.3518 | 0.1667 | 2.11 |
| 3 Early Times Kentucky (40%) | -37.2 | 3.36 | -0.3106 | 0.1471 | 2.11 |
| 4 Old Grand-Dad (43%) | -46.1 | 3.13 | -0.2713 | 0.2174 | 1.25 |
| 5 Lord Calvert Canadian (40%) | -22.9 | 2.29 | -0.256 | 0.1023 | 2.5 |
| 6 Canadian Mist (40%) | -29.7 | 4.02 | -0.2381 | 0.1257 | 1.89 |
| 7 Maker's Mark Kentucky Straight Bourbon (45%) | -35.5 | 3.98 | -0.3 | 0.1503 | 2 |
| 8 Gentleman Jack (40%) | -28.1 | 3.61 | -0.2235 | 0.1404 | 1.6 |

Data parameters chart for all rum and whiskey odors measured with ITO-QCM

FIGURE 21

| Sample (Alcohol %) | Integrated Frequency Response (Hz-sec) | Integrated Surface Resistance Response (Ω-Sec) | Initial Response Slope (Hz/Sec) | Average Return to Baseline Slope (Hz/sec) | Return to baseline time/Initial response time ratio |
|---|---|---|---|---|---|
| Brandy | | | | | |
| 1 Paul Masson Grande Amber (40%) | -25.4 | 1.01 | -0.2047 | 0.1366 | 1.5 |
| 2 Vendome Platinum VSOP (40%) | -31.1 | 0.74 | -0.3728 | 0.1302 | 2.86 |
| 3 Hennessy Very Special Cognac (40%) | -25.7 | 0.47 | -0.1524 | 0.0882 | 1.73 |
| 4 Kelt Tour du Monde VSOP Cognac (40%) | -35.8 | 0.88 | -0.2703 | 0.1503 | 1.8 |
| Gins | | | | | |
| 1 Gordon's London Dry (40%) | -25.3 | 0.77 | -0.2328 | 0.0758 | 3.12 |
| 2 Beefeater London Dry (47%) | -33.4 | 0.28 | -0.2795 | 0.0787 | 3.55 |
| 3 Fleischmann's Extra Dry (40%) | -17.3 | 0.54 | -0.1862 | 0.0769 | 2.43 |
| 4 Seagram's Extra Dry (40%) | -28.3 | 0.88 | -0.3054 | 0.107 | 2.85 |

Data parameters chart for all brandy and gin odors measured with ITO-QCM

FIGURE 22

| Sample (Alcohol %) | Integrated Frequency Response (Hz-sec) | Integrated Surface Resistance Response (Ω-Sec) | Initial Response Slope (Hz/Sec) | Average Return to Baseline Slope (Hz/sec) | Return to baseline time/Initial response time ratio |
|---|---|---|---|---|---|
| Vodkas | | | | | |
| 1 Absolut Country of Sweden (40%) | -34.7 | 1.19 | -0.3063 | 0.0691 | 4.43 |
| 2 Northern Arctic Charcoal Filtered (40%) | -29 | 0.98 | -0.3727 | 0.0797 | 4.67 |
| 3 Smirnoff Watermelon (35%) | -15.8 | 0.55 | -0.1995 | 0.0932 | 2.14 |
| 4 Denaka (40%) | -32.7 | 1.14 | -0.3324 | 0.1059 | 3.14 |
| 5 Denaka Rasberry Platinum (35%) | -26.8 | 0.74 | -0.1862 | 0.0972 | 1.91 |
| Tequila | | | | | |
| 1 Cuesta Rey Silver (40%) | -20.1 | 1.43 | -0.3963 | 0.0756 | 5.25 |
| 2 Cuesta Rey Gold (40%) | -36.2 | 2.82 | -0.3324 | 0.0804 | 4.14 |
| 3 Jose Cuervo Especial Oro (40%) | -27.3 | 2.02 | -0.2381 | 0.0931 | 2.56 |
| 4 Jose Cuervo Black Medallion Anejo (40%) | -28.6 | 2.58 | -0.2678 | 0.0714 | 3.75 |
| Average of all | -23.376 | 1.974 | -0.214 | 0.083 | 3.052 |
| Standard deviation of all | 9.466 | 1.267 | 0.095 | 0.049 | 1.323 |

FIGURE 23

Data parameters chart for all vodka and tequila odors measured with ITO-QCM

PCA plot of beers and wines data.

Average change in ITO-QCM frequency response to different brands of vodka

PCA plot of ITO-QCM measurements of different brands of vodka odors

PCA plot of ITO-QCM odor measurements of Northern Artic Charcoal Filtered and Denaka vodkas 2D PCA plot of ITO-QCM odor measurements of Absolut Country of Sweden and Denaka vodkas PCA plot of ITO-QCM odor measurements of Denaka (40%) and Denaka Raspberry Platinum vodkas (35%)

PCA plot of ITO-QCM odor measurements of Northern Artic Charcoal Filtered (40%) and Denaka Raspberry Platinum vodkas (35%)

Average change in ITO-QCM frequency response to Absolut brands of vodka having 40% alcohol and different flavors PCA plot of ITO-QCM measurements of Absolut brands of vodka having different flavors Average change in ITO-QCM frequency response to different brands of whiskey Average change in ITO-QCM frequency response to different brands of brandy Average change in ITO-QCM frequency response to different brands of tequila PCA plot of ITO-QCM odor measurements for different brands of tequila PCA plot of ITO-QCM odor measurements for different brands of gin Comparison of ITO-QCM explosive samples measurements with 1018 Å ITO and 2300 Å ITO thickness over quartz crystals ITO-QCM measurement of TNT sample Equilibrium headspace vapor concentrations

| Sample | 1,3-Dinitrobenzene | 2,4-Dintrotoluene | 2,4,6-Trinitrotoluene |
|---|---|---|---|
| U.S. Military TNT (Year 1966) | 550 ng/L | 350 ng/ L | 70 ng/L |

FIGURE 47

| Sample | Integrated Freq Response (Hz-sec) | Initial Response Slope (Hz/sec) | Ave Return to Baseline Slope (Hz\sec) | Ave. all Change Freq Data Points (Hz) | Integrated Surface Resistance Response (Ω-sec) |
|---|---|---|---|---|---|
| Compound A5,1 | 29.53 | 0.254 | -0.309 | 1.47 | 0.281 |
| Compound A5,2 | 16.8 | 0.251 | -0.329 | 1.2 | 0.226 |
| Compound A5,3 | 26 | 0.175 | -0.149 | 1 | 0.504 |
| Compound A5,4 | 33.05 | 0.308 | -0.409 | 1.73 | 0.166 |
| Compound A5,5 | 34.91 | 0.29 | -0.17 | 1.29 | 0.123 |
| | | | | | |
| Compound B, 1 | 77.08 | 0.256 | -0.179 | 1.79 | 0.118 |
| Compound B, 2 | 58.79 | 0.262 | -0.144 | 1.78 | 0.286 |
| Compound B, 3 | 68.52 | 0.436 | -0.232 | 2.36 | 0.348 |
| Compound B, 4 | 36 | 0.236 | -0.252 | 1.34 | 0.028 |
| Compound B, 5 | 37.13 | 0.37 | -0.273 | 1.69 | 0.021 |
| | | | | | |
| PETN, 1 | 47.84 | 0.558 | -0.242 | 2.27 | 0.05 |
| PETN, 2 | 46.92 | 0.327 | -0.284 | 1.96 | 0.116 |
| PETN, 3 | 41.91 | 0.275 | -0.265 | 1.75 | -0.023 |
| PETN, 4 | 42.21 | 0.327 | -0.316 | 1.9 | -0.054 |
| PETN, 5 | 71.12 | 0.266 | -0.22 | 2.1 | 0.132 |
| | | | | | |
| RDX, 1 | 52.46 | 0.358 | -0.386 | 2.51 | 0.018 |
| RDX, 2 | 45.9 | 0.292 | -0.352 | 2.18 | 0.014 |
| RDX, 3 | 51.04 | 0.299 | -0.238 | 1.88 | 0.003 |
| RDX, 4 | 43.21 | 0.4 | -0.22 | 1.49 | -0.067 |
| RDX, 5 | 51.35 | 0.308 | -0.161 | 1.59 | 0.052 |

ITO-QCM calculated parameters used for PCA for explosive sample measurements

FIGURE 50

| Sample | Integrated Freq Response (Hz-sec) | Initial Response Slope (Hz/sec) | Ave Return to Baseline Slope (Hz\sec) | Ave. all Change Freq Data Points (Hz) | Integrated Surface Resistance Response (Ω-sec) |
|---|---|---|---|---|---|
| TNT, 1 | 37.76 | 0.382 | -0.581 | 2.09 | 0.179 |
| TNT, 2 | 28.92 | 0.209 | -0.248 | 1.31 | 0.221 |
| TNT, 3 | 41.55 | 0.353 | -0.323 | 1.8 | 0.119 |
| TNT, 4 | 38.53 | 0.3 | -0.228 | 1.54 | 0.119 |
| TNT, 5 | 29.69 | 0.208 | -0.288 | 1.41 | 0.089 |
|  |  |  |  |  |  |
| Tetryl+TNT, 1 | 19.79 | 0.2 | -0.273 | 1.04 | 0.203 |
| Tetryl+TNT, 2 | 37.51 | 0.292 | -0.174 | 1.17 | 0.907 |
| Tetryl+TNT, 3 | 26.54 | 0.2 | -0.078 | 0.68 | 0.761 |
| Tetryl+TNT, 4 | 62.19 | 0.266 | -0.057 | 0.94 | 0.458 |
| Tetryl+TNT, 5 | 34.4 | 0.177 | -0.117 | 1.14 | 0.466 |
|  |  |  |  |  |  |
| Hexolite, 1 | 38.95 | 0.267 | -0.288 | 1.76 | 0.237 |
| Hexolite, 2 | 49.94 | 0.291 | -0.109 | 1.13 | 0.189 |
| Hexolite, 3 | 53.66 | 0.299 | -0.128 | 1.34 | -0.167 |
| Hexolite, 4 | 58.12 | 0.271 | -0.188 | 1.75 | -0.121 |
| Hexolite, 5 | 49.17 | 0.286 | -0.162 | 1.29 | 0.163 |
|  |  |  |  |  |  |
| Average of all | 43.39 | 0.293 | -0.239 | 1.59 | 0.176 |
| Standard Deviation of all | 14.01 | 0.076 | 0.103 | 0.43 | 0.227 |

ITO-QCM calculated parameters used for PCA for explosive sample measurements

FIGURE 51

| Sample, Measurement # | Integrated Freq Response (Hz-sec) | Initial Response Slope (Hz/sec) | Ave Return to Baseline Slope (Hz/sec) | Ave. all Change Freq Data Points(Hz) | Integrated Surface Resistance Response (Ω-sec) |
|---|---|---|---|---|---|
| Acetone, 1 | -136.5384 | -1.312741 | 0.6545008 | -5.308009 | -0.7492875 |
| Acetone, 2 | -139.9039 | -1.389348 | 0.5196209 | -4.223634 | -0.650558 |
| Acetone, 3 | -156.2574 | -1.378286 | 0.6273867 | -4.954097 | -1.071085 |
| Acetone, 4 | -133.3892 | -1.132301 | 0.51401 | -4.475439 | -0.8140323 |
| Acetone, 5 | -146.6814 | -1.271356 | 0.605339 | -5.230464 | -0.9661441 |
| | | | | | |
| Acetonitrile1 | -107.633 | -1.875124 | 0.320281 | -3.155002 | -0.405885 |
| Acetonitrile2 | -92.75937 | -1.001269 | 0.2590483 | -2.7305 | -0.399451 |
| Acetonitrile3 | -105.8972 | -1.147158 | 0.400383 | -3.593004 | -0.5575761 |
| Acetonitrile4 | -103.5854 | -0.9591608 | 0.3430901 | -2.822325 | -0.3540415 |
| Acetonitrile5 | -121.051 | -1.08672 | 0.4664667 | -4.220409 | -0.5464039 |
| | | | | | |
| Benzene1 | -91.97445 | -1.020281 | 0.4252862 | -3.386562 | -1.295806 |
| Benzene2 | -112.5165 | -0.9162154 | 0.3724057 | -3.527278 | -1.176416 |
| Benzene3 | -119.725 | -0.9332799 | 0.2681424 | -2.350815 | -1.561532 |
| Benzene4 | -147.061 | -1.183255 | 0.5348568 | -4.379329 | -1.865088 |
| Benzene5 | -132.9208 | -1.154458 | 0.459651 | -3.592943 | -1.594254 |

Measured parameters using ITO-QCM vapor sensors for VOCs

FIGURE 57

| Sample, Measurement # | Integrated Freq Response (Hz-sec) | Initial Response Slope (Hz/sec) | Ave Return to Baseline Slope (Hz/sec) | Ave. all Change Freq Data Points(Hz) | Integrated Surface Resistance Response (Ω-sec) |
|---|---|---|---|---|---|
| Chloroform1 | -206.0523 | -2.011351 | 0.5788815 | -5.796297 | -0.7536072 |
| Chloroform2 | -186.9691 | -1.615623 | 0.7359288 | -6.045488 | -0.9997265 |
| Chloroform3 | -177.9495 | -1.313432 | 0.5029756 | -4.920595 | -0.6174892 |
| Chloroform4 | -232.1377 | -2.230211 | 0.6353373 | -6.529573 | -0.8791648 |
| Chloroform5 | -190.9287 | -3.115729 | 0.5223588 | -5.297267 | -0.7440693 |
|  |  |  |  |  |  |
| Ethanol1 | -59.19463 | -0.9467456 | 0.2346832 | -2.358031 | -0.3882672 |
| Ethanol2 | -75.22003 | -0.6330366 | 0.3709592 | -2.675973 | -0.4407754 |
| Ethanol3 | -73.80068 | -0.6837234 | 0.2901309 | -2.25883 | -0.4662064 |
| Ethanol4 | -67.07961 | -0.8105787 | 0.3292953 | -2.693676 | -0.2865804 |
| Ethanol5 | -59.1982 | -0.5740154 | 0.2823291 | -2.186017 | -0.4876485 |
|  |  |  |  |  |  |
| Isopropyl Alcohol1 | -57.64761 | -0.550176 | 0.2226464 | -1.946861 | -0.5195069 |
| Isopropyl Alcohol2 | -48.30668 | -0.4082446 | 0.1998501 | -1.909446 | -0.3441285 |
| Isopropyl Alcohol3 | -66.04442 | -0.5974112 | 0.2520449 | -2.601505 | -0.5502239 |
| Isopropyl Alcohol4 | -59.04915 | -0.5321497 | 0.2605611 | -2.682846 | -0.3187075 |
| Isopropyl Alcohol5 | -56.45557 | -0.5069989 | 0.1665187 | -1.967719 | -0.4885669 |
|  |  |  |  |  |  |

Measured parameters using ITO-QCM vapor sensors for VOCs

FIGURE 58

| Sample, Measurement # | Integrated Freq Response (Hz-sec) | Initial Response Slope (Hz/sec) | Ave Return to Baseline Slope (Hz/sec) | Ave. all Change Freq Data Points(Hz) | Integrated Surface Resistance Response ($\Omega$-sec) |
|---|---|---|---|---|---|
| Chloroform1 | -206.0523 | -2.011351 | 0.5788815 | -5.796297 | -0.7536072 |
| Chloroform2 | -186.9691 | -1.615623 | 0.7359288 | -6.045488 | -0.9997265 |
| Chloroform3 | -177.9495 | -1.313432 | 0.5029756 | -4.920595 | -0.6174892 |
| Chloroform4 | -232.1377 | -2.230211 | 0.6353373 | -6.529573 | -0.8791648 |
| Chloroform5 | -190.9287 | -3.115729 | 0.5223588 | -5.297267 | -0.7440693 |
| | | | | | |
| Ethanol1 | -59.19463 | -0.9467456 | 0.2346832 | -2.358031 | -0.3882672 |
| Ethanol2 | -75.22003 | -0.6330366 | 0.3709592 | -2.675973 | -0.4407754 |
| Ethanol3 | -73.80068 | -0.6837234 | 0.2901309 | -2.25883 | -0.4662064 |
| Ethanol4 | -67.07961 | -0.8105787 | 0.3292953 | -2.693676 | -0.2865804 |
| Ethanol5 | -59.1982 | -0.5740154 | 0.2823291 | -2.186017 | -0.4876485 |
| | | | | | |
| Isopropyl Alcohol1 | -57.64761 | -0.550176 | 0.2226464 | -1.946861 | -0.5195069 |
| Isopropyl Alcohol2 | -48.30668 | -0.4082446 | 0.1998501 | -1.909446 | -0.3441285 |
| Isopropyl Alcohol3 | -66.04442 | -0.5974112 | 0.2520449 | -2.601505 | -0.5502239 |
| Isopropyl Alcohol4 | -59.04915 | -0.5321497 | 0.2605611 | -2.682846 | -0.3187075 |
| Isopropyl Alcohol5 | -56.45557 | -0.5069989 | 0.1665187 | -1.967719 | -0.4885669 |
| | | | | | |

Measured parameters using ITO-QCM vapor sensors for VOCs

FIGURE 59

| Sample, Measurement # | Integrated Freq Response (Hz-sec) | Initial Response Slope (Hz/sec) | Ave Return to Baseline Slope (Hz/sec) | Ave. all Change Freq Data Points(Hz) | Integrated Surface Resistance Response ($\Omega$-sec) |
|---|---|---|---|---|---|
| Methanol1 | -125.9092 | -1.440272 | 0.4209911 | -4.043156 | -0.3149775 |
| Methanol2 | -110.7373 | -1.047177 | 0.4269428 | -3.469115 | -0.21675 |
| Methanol3 | -123.9303 | -1.190213 | 0.4646921 | -3.657729 | -0.2261768 |
| Methanol4 | -96.26659 | -0.8344107 | 0.4145022 | -3.110018 | -0.1626348 |
| Methanol5 | -126.521 | -1.065419 | 0.481162 | -3.939784 | -0.1055534 |
| | | | | | |
| Methylene Chloride1 | -175.1031 | -1.316382 | 0.6585221 | -5.56768 | -0.5875301 |
| Methylene Chloride2 | -173.4084 | -1.376694 | 0.4556035 | -4.537598 | -0.3896066 |
| Methylene Chloride3 | -224.4409 | -1.902875 | 0.7342198 | -6.608124 | -0.5689849 |
| Methylene Chloride4 | -215.5206 | -1.832042 | 0.7118944 | -6.489997 | -0.7376814 |
| Methylene Chloride5 | -161.2764 | -1.288152 | 0.5159168 | -5.101155 | -0.4197804 |
| | | | | | |

Measured parameters using ITO-QCM vapor sensors for VOCs

FIGURE 60

| Sample, Measurement # | Integrated Freq Response (Hz-sec) | Initial Response Slope (Hz/sec) | Ave Return to Baseline Slope (Hz/sec) | Ave. all Change Freq Data Points(Hz) | Integrated Surface Resistance Response (Ω-sec) |
|---|---|---|---|---|---|
| Tetrahydrofuran 1 | -150.8125 | -1.637955 | 0.4258312 | -4.414231 | -1.243947 |
| Tetrahydrofuran 2 | -160.6374 | -1.279636 | 0.5119388 | -4.564365 | -1.362539 |
| Tetrahydrofuran 3 | -156.1099 | -1.574902 | 0.5035771 | -4.829123 | -1.346682 |
| Tetrahydrofuran 4 | -195.0851 | -1.8384 | 0.6634696 | -5.919385 | -1.305855 |
| Tetrahydrofuran 5 | -152.0238 | -1.342486 | 0.6384608 | -5.367301 | -1.146239 |
|  |  |  |  |  |  |
| Toluene1 | -56.64878 | -0.5364267 | 0.1906233 | -2.489265 | -1.699538 |
| Toluene2 | -78.20448 | -0.7202305 | 0.1355271 | -2.259645 | -1.964898 |
| Toluene3 | -74.24747 | -0.5961847 | 0.235915 | -3.122643 | -2.550879 |
| Toluene4 | -75.06567 | -0.8090795 | 0.143395 | -2.730943 | -2.036551 |
| Toluene5 | -77.06085 | -0.6415902 | 0.1780194 | -3.080318 | -2.31956 |

Measured parameters using ITO-QCM vapor sensors for VOCs

FIGURE 61

| Sample, Measurement # | Integrated Freq Response (Hz-sec) | Initial Response Slope (Hz/sec) | Ave Return to Baseline Slope (Hz/sec) | Ave. all Change Freq Data Points(Hz) | Integrated Surface Resistance Response (Ω-sec) |
|---|---|---|---|---|---|
| M-Xylene1 | -44.21706 | -0.4284774 | 0.410883 | -2.843521 | -2.393616 |
| M-Xylene2 | -55.36348 | -0.5402421 | 0.3122512 | -2.79447 | -2.268862 |
| M-Xylene, 3 | -64.703 | -0.62794 | 0.2152 | -2.08 | -2.453 |
| M-Xylene, 4 | -65.186 | -0.68128 | 0.2595 | -2.261 | -2.261 |
| M-Xylene, 5 | -59.54102 | -0.912254 | 0.2729661 | -3.470479 | -2.18707 |
|  |  |  |  |  |  |
| Benzyl Alcohol1 | -11.701 | -0.086384 | 0.0434972 | -0.507 | 1.002 |
| Benzyl Alcohol2 | -9.613 | -0.06225358 | 0.022913 | -0.354 | 1.209 |
| Benzyl Alcohol3 | -1.905 | -0.070838 | 0.051186 | -0.188 | 1.358 |
| Benzyl Alcohol4 | -7.812 | -0.047183 | 0.02229 | -0.324 | 0.605 |
| Benzyl Alcohol5 | -8.104 | -0.06309 | 0.030184 | -0.309 | 1.566 |
|  |  |  |  |  |  |

Measured parameters using ITO-QCM vapor sensors for VOCs

FIGURE 62

| Sample, Measurement # | Integrated Freq Response (Hz-sec) | Initial Response Slope (Hz/sec) | Ave Return to Baseline Slope (Hz/sec) | Ave. all Change Freq Data Points(Hz) | Integrated Surface Resistance Response (Ω-sec) |
|---|---|---|---|---|---|
| Dimethylformamide1 | -6.485 | -0.016081 | 0.0573806 | -0.224 | 1.97565 |
| Dimethylformamide2 | -2.388 | -0.079067 | 0.08029 | -0.236 | 1.42624 |
| Dimethylformamide3 | -0.9947 | -0.03948 | 0.104602 | -0.14 | 2.23569 |
| Dimethylformamide4 | -0.33 | -0.06147 | 0.01823985 | -0.33 | 2.11652 |
| Dimethylformamide5 | -1.998 | -0.058881 | 0.043048 | -0.165 | 1.67218 |
| Average of all | -100.204 | -0.959 | 0.3571 | -3.252 | -0.6061 |
| Standard Deviation of all | 62.471 | 0.617 | 0.2028 | 1.779 | 1.1357 |

Measured parameters using ITO-QCM vapor sensors for VOCs

FIGURE 63

Average Change in surface resistance of ITO-QCM vapor sensor to volatile organic compounds Initial response slope of ITO-QCM gas sensor as a function of vapor pressure of VOCs Average return to baseline slope of ITO-QCM gas sensor as a function of vapor pressure of VOCs

| Alkanes | Formula | Manufacturer | Molecular Weight (g/mol) | Vapor Pressure (mm of Hg) (25°C) |
|---|---|---|---|---|
| Pentane | $C_5H_{12}$ | Matheson | 72.15 | 514 |
| Hexane | $C_6H_{14}$ | Fisher | 86.18 | 151 |
| Heptane | $C_7H_{16}$ | Fisher | 100.2 | 46 |
| Octane | $C_8H_{18}$ | Fisher | 114.21 | 14.1 |
| Nonane | $C_9H_{20}$ | Sigma | 128.26 | 4.45 |
| Decane | $C_{10}H_{22}$ | Mallinckrodt | 142.28 | 1.43 |
| Dodecane | $C_{12}H_{26}$ | Matheson | 170.38 | 0.135 |
| Squalane | $C_{30}H_{62}$ | Eastman | 422.82 | 0.000275 |

FIGURE 84

Raw Data Parameters Chart for Aldehyde Vapors Measured with ITO-QCM Sensor

| Sample | Integrated Freq Response (Hz-sec) | Initial Response Slope (Hz/sec) | Ave Return to Baseline Slope (Hz/sec) | Ave. all Change Freq Data Points (Hz) | Integrated Surface Resistance Response (Ω-sec) |
|---|---|---|---|---|---|
| Anisaldehyde1 | -9.421 | -0.035 | 0.027 | -0.24 | 0.581 |
| Anisaldehyde2 | -15.114 | -0.025 | 0.029 | -0.368 | 0.678 |
| Anisaldehyde3 | -11.317 | -0.033 | 0.022 | -0.251 | 0.92 |
| Anisaldehyde4 | -18.413 | -0.035 | 0.031 | -0.375 | 1.398 |
| Anisaldehyde5 | -17.906 | -0.035 | 0.022 | -0.343 | 1.351 |
| Benzaldehyde1 | -36.743 | -0.086 | 0.082 | -0.851 | 5.09 |
| Benzaldehyde2 | -57.345 | -0.129 | 0.035 | -0.746 | 4.042 |
| Benzaldehyde3 | -35.037 | -0.089 | 0.061 | -0.742 | 4.329 |
| Benzaldehyde4 | -39.431 | -0.1 | 0.051 | -0.668 | 3.057 |
| Benzaldehyde5 | -40.138 | -0.076 | 0.031 | -0.556 | 6.067 |

FIGURE 98

Raw Data Parameters Chart for Aldehyde Vapors Measured with ITO-QCM Sensor

| Sample | Integrated Freq Response (Hz-sec) | Initial Response Slope (Hz/sec) | Ave Return to Baseline Slope (Hz/sec) | Ave. all Change Freq Data Points (Hz) | Integrated Surface Resistance Response (Ω-sec) |
|---|---|---|---|---|---|
| Butyraldehyde1 | -202.127 | -0.472 | 0.27 | -3.524 | 0.652 |
| Butyraldehyde2 | -204.724 | -0.423 | 0.293 | -4.006 | 0.27 |
| Butyraldehyde3 | -212.836 | -0.504 | 0.313 | -4.331 | 0.709 |
| Butyraldehyde4 | -240.3 | -0.533 | 0.343 | -4.507 | 0.516 |
| Butyraldehyde5 | -216.588 | -0.58 | 0.236 | -3.931 | 0.682 |
|  |  |  |  |  |  |
| Cinnamaldehyde1 | -8.911 | -0.03 | 0.046 | -0.269 | 2.226 |
| Cinnamaldehyde2 | -9.216 | -0.024 | 0.025 | -0.225 | 1.28 |
| Cinnamaldehyde3 | -10.017 | -0.026 | 0.02 | -0.227 | 0.576 |
| Cinnamaldehyde4 | -11.308 | -0.022 | 0.013 | -0.185 | 1.128 |
| Cinnamaldehyde5 | -8.027 | -0.013 | 0.033 | -0.186 | 0.544 |

FIGURE 99

Raw Data Parameters Chart for Aldehyde Vapors Measured with ITO-QCM Sensor

| Sample | Integrated Freq Response (Hz-sec) | Initial Response Slope (Hz/sec) | Ave Return to Baseline Slope (Hz/sec) | Ave. all Change Freq Data Points (Hz) | Integrated Surface Resistance Response (Ω-sec) |
|---|---|---|---|---|---|
| Citral1 | -28.328 | -0.079 | 0.061 | -0.671 | 1.173 |
| Citral2 | -32.64 | -0.072 | 0.034 | -0.651 | 1.016 |
| Citral3 | -25.334 | -0.067 | 0.039 | -0.549 | 1.468 |
| Citral4 | -26.424 | -0.093 | 0.026 | -0.419 | 1.475 |
| Citral5 | -23.017 | -0.06 | 0.041 | -0.468 | 0.869 |
| Crotonaldehyde1 | -87.317 | -0.214 | 0.183 | -1.922 | 1.057 |
| Crotonaldehyde2 | -106.4 | -0.235 | 0.154 | -2.16 | 0.939 |
| Crotonaldehyde3 | -78.419 | -0.255 | 0.159 | -1.5 | 1 |
| Crotonaldehyde4 | -111.405 | -0.331 | 0.156 | -2.215 | 3.181 |
| Crotonaldehyde5 | -123.963 | -0.305 | 0.135 | -1.977 | 1.995 |

FIGURE 100

Raw Data Parameters Chart for Aldehyde Vapors Measured with ITO-QCM Sensor

| Sample | Integrated Freq Response (Hz-sec) | Initial Response Slope (Hz/sec) | Ave Return to Baseline Slope (Hz/sec) | Ave. all Change Freq Data Points (Hz) | Integrated Surface Resistance Response (Ω-sec) |
|---|---|---|---|---|---|
| Furaldehyde1 | -30.752 | -0.057 | 0.02 | -0.41 | 2.018 |
| Furaldehyde2 | -21.724 | -0.052 | 0.044 | -0.47 | 3.751 |
| Furaldehyde3 | -22.518 | -0.065 | 0.065 | -0.562 | 3.967 |
| Furaldehyde4 | -27.145 | -0.07 | 0.059 | -0.642 | 5.505 |
| Furaldehyde5 | -26.335 | -0.042 | 0.029 | -0.41 | 4.156 |
|  |  |  |  |  |  |
| Glutaraldehyde1 | -27.116 | -0.059 | 0.044 | -0.553 | 2.946 |
| Glutaraldehyde2 | -25.731 | -0.067 | 0.093 | -0.713 | 6.001 |
| Glutaraldehyde3 | -12.02 | -0.04 | 0.088 | -0.413 | 5.523 |
| Glutaraldehyde4 | -16.924 | -0.078 | 0.069 | -0.561 | 4.18 |
| Glutaraldehyde5 | -14.432 | -0.052 | 0.11 | -0.464 | 4.61 |

FIGURE 101

Raw Data Parameters Chart for Aldehyde Vapors Measured with ITO-QCM Sensor

| Sample | Integrated Freq Response (Hz-sec) | Initial Response Slope (Hz/sec) | Ave Return to Baseline Slope (Hz/sec) | Ave. all Change Freq Data Points (Hz) | Integrated Surface Resistance Response (Ω-sec) |
|---|---|---|---|---|---|
| Heptaldehyde1 | -30.347 | -0.048 | 0.024 | -0.409 | 0.574 |
| Heptaldehyde2 | -44.165 | -0.059 | 0.014 | -0.384 | 0.393 |
| Heptaldehyde3 | -20.119 | -0.053 | 0.034 | -0.418 | 0.312 |
| Heptaldehyde4 | -29.36 | -0.073 | 0.022 | -0.458 | 0.588 |
| Heptaldehyde5 | -25.334 | -0.077 | 0.022 | -0.429 | 0.417 |
| Valeraldehyde1 | -227.397 | -0.539 | 0.153 | -2.85 | 1.104 |
| Valeraldehyde2 | -168.312 | -0.357 | 0.166 | -2.543 | 0.603 |
| Valeraldehyde3 | -165.8 | -0.324 | 0.154 | -2.552 | 0.617 |
| Valeraldehyde4 | -177.817 | -0.616 | 0.141 | -2.827 | 1.056 |
| Valeraldehyde5 | -144.528 | -0.51 | 0.15 | -2.778 | 1.002 |

FIGURE 102

Raw Data Parameters Chart for Aldehyde Vapors Measured with ITO-QCM Sensor

| Sample | Integrated Freq Response (Hz-sec) | Initial Response Slope (Hz/sec) | Ave Return to Baseline Slope (Hz/sec) | Ave. all Change Freq Data Points (Hz) | Integrated Surface Resistance Response (Ω-sec) |
|---|---|---|---|---|---|
| Propionaldehyde1 | -240.31 | -0.645 | 0.676 | -6.14 | -0.133 |
| Propionaldehyde2 | -302.566 | -0.651 | 0.525 | -6.425 | -0.239 |
| Propionaldehyde3 | -269.504 | -0.893 | 0.46 | -5.731 | -0.278 |
| Propionaldehyde4 | -315.406 | -1.06 | 0.388 | -6.065 | -0.296 |
| Propionaldehyde5 | -278.146 | -1.075 | 0.306 | -5.142 | -0.397 |
| | | | | | |
| Salicylaldehyde1 | -29.146 | -0.074 | 0.041 | -0.607 | 3.061 |
| Salicylaldehyde2 | -50.464 | -0.115 | 0.037 | -0.661 | 3.184 |
| Salicylaldehyde3 | -38.138 | -0.068 | 0.036 | -0.626 | 3.241 |
| Salicylaldehyde4 | -32.614 | -0.071 | 0.034 | -0.525 | 2.201 |
| Salicylaldehyde5 | -33.862 | -0.061 | 0.016 | -0.384 | 1.835 |
| | | | | | |
| Average of all | -81.603 | -0.215 | 0.116 | -1.537 | 1.863 |
| Standard Deviation of all | 89.861 | 0.264 | 0.139 | 1.76 | 1.739 |

FIGURE 103

Raw Data Parameters Chart for Ketone Vapors Measured with ITO-QCM Sensor

| Sample | Integrated Freq Response (Hz-sec) | Initial Response Slope (Hz/sec) | Ave Return to Baseline Slope (Hz/sec) | Ave. all Change Freq Data Points (Hz) | Integrated Surface Resistance Response (Ω-sec) |
|---|---|---|---|---|---|
| Acetone1 | -176.912 | -1.181 | 0.615 | -5.032 | -0.33 |
| Acetone2 | -182.588 | -1.482 | 0.491 | -5.052 | -0.181 |
| Acetone3 | -217.258 | -2.828 | 0.585 | -6.451 | -0.149 |
| Acetone4 | -196.752 | -1.372 | 0.557 | -5.156 | -0.297 |
| Acetone5 | -155.797 | -1.388 | 0.41 | -4.449 | -0.201 |
|  |  |  |  |  |  |
| Acetyl Acetone1 | -51.64 | -0.517 | 0.125 | -1.513 | 3.96 |
| Acetyl Acetone2 | -36.398 | -0.389 | 0.268 | -1.649 | 4.445 |
| Acetyl Acetone3 | -35.372 | -0.282 | 0.172 | -1.219 | 4.375 |
| Acetyl Acetone4 | -39.724 | -0.311 | 0.13 | -1.2 | 1.97 |
| Acetyl Acetone5 | -41.46 | -0.337 | 0.189 | -1.382 | 3.374 |

FIGURE 109

Raw Data Parameters Chart for Ketone Vapors Measured with ITO-QCM Sensor

| Sample | Integrated Freq Response (Hz-sec) | Initial Response Slope (Hz/sec) | Ave Return to Baseline Slope (Hz/sec) | Ave. all Change Freq Data Points (Hz) | Integrated Surface Resistance Response (Ω-sec) |
|---|---|---|---|---|---|
| Butanedione1 | -6.611 | -0.033 | 0.018 | -0.194 | 0.151 |
| Butanedione2 | -5.006 | -0.04 | 0.031 | -0.217 | 0.088 |
| Butanedione3 | -7.411 | -0.033 | 0.015 | -0.19 | 0.041 |
| Butanedione4 | -5.408 | -0.036 | 0.033 | -0.235 | 0.127 |
| Butanedione5 | -4.604 | -0.03 | 0.023 | -0.199 | 0.121 |
|  |  |  |  |  |  |
| Butyric Acid1 | -59.551 | -0.267 | 0.046 | -0.726 | 2.524 |
| Butyric Acid2 | -47.536 | -0.208 | 0.046 | -0.723 | 1.993 |
| Butyric Acid3 | -78.551 | -0.257 | 0.043 | -0.809 | 3.798 |
| Butyric Acid4 | -47.544 | -0.245 | 0.057 | -0.821 | 2.369 |
| Butyric Acid5 | -61.654 | -0.246 | 0.049 | -0.802 | 2.546 |

FIGURE 110

Raw Data Parameters Chart for Ketone Vapors Measured with ITO-QCM Sensor

| Sample | Integrated Freq Response (Hz-sec) | Initial Response Slope (Hz/sec) | Ave Return to Baseline Slope (Hz/sec) | Ave. all Change Freq Data Points (Hz) | Integrated Surface Resistance Response (Ω-sec) |
|---|---|---|---|---|---|
| Chloroacetone1 | -31.525 | -0.208 | 0.104 | -0.978 | 2.493 |
| Chloroacetone2 | -22.825 | -0.256 | 0.125 | -0.786 | 2.728 |
| Chloroacetone3 | -25.013 | -0.25 | 0.177 | -1.04 | 3.49 |
| Chloroacetone4 | -27.657 | -0.191 | 0.163 | -1.061 | 3.351 |
| Chloroacetone5 | -24.835 | -0.19 | 0.209 | -1.177 | 3.388 |
| | | | | | |
| Heptanone1 | -67.383 | -0.341 | 0.097 | -1.374 | 0.912 |
| Heptanone2 | -54.245 | -0.351 | 0.082 | -1.108 | 1.815 |
| Heptanone3 | -46.752 | -0.255 | 0.076 | -1.035 | 1.286 |
| Heptanone4 | -43.465 | -0.349 | 0.103 | -0.987 | 2.266 |
| Heptanone5 | -48.954 | -0.262 | 0.072 | -0.977 | 1.221 |

FIGURE 111

Raw Data Parameters Chart for Ketone Vapors Measured with ITO-QCM Sensor

| Sample | Integrated Freq Response (Hz-sec) | Initial Response Slope (Hz/sec) | Ave Return to Baseline Slope (Hz/sec) | Ave. all Change Freq Data Points (Hz) | Integrated Surface Resistance Response ($\Omega$-sec) |
|---|---|---|---|---|---|
| MIBK1 | -70.402 | -0.341 | 0.069 | -1.002 | 1.77 |
| MIBK2 | -83.34 | -0.5 | 0.09 | -1.157 | 2.673 |
| MIBK3 | -70.788 | -0.455 | 0.106 | -1.241 | 1.914 |
| MIBK4 | -51.761 | -0.36 | 0.133 | -1.4 | 1.913 |
| MIBK5 | -50.443 | -0.291 | 0.109 | -1.144 | 1.794 |
| Pentanone1 | -89.484 | -0.58 | 0.182 | -1.931 | 2.868 |
| Pentanone2 | -93.66 | -0.699 | 0.244 | -2.527 | 2.27 |
| Pentanone3 | -67.397 | -0.492 | 0.366 | -2.402 | 2.911 |
| Pentanone4 | -75.285 | -0.588 | 0.184 | -1.786 | 2.339 |
| Pentanone5 | -61.956 | -0.427 | 0.213 | -1.875 | 2.092 |

FIGURE 112

Raw Data Parameters Chart for Ketone Vapors Measured with ITO-QCM Sensor

| Sample | Integrated Freq Response (Hz-sec) | Initial Response Slope (Hz/sec) | Ave Return to Baseline Slope (Hz/sec) | Ave. all Change Freq Data Points (Hz) | Integrated Surface Resistance Response ($\Omega$-sec) |
|---|---|---|---|---|---|
| MEK1 | -171.894 | -1.219 | 0.405 | -3.988 | 0.219 |
| MEK2 | -149.85 | -1.215 | 0.411 | -3.359 | 0.409 |
| MEK3 | -147.084 | -0.982 | 0.406 | -3.548 | 0.446 |
| MEK4 | -151.635 | -1.344 | 0.411 | -3.988 | 0.396 |
| MEK5 | -149.351 | -1.191 | 0.587 | -4.254 | 0.542 |
| Average of all | -74.106 | -0.552 | 0.201 | -1.87 | 1.738 |
| Standard Deviation of all | 57.173 | 0.544 | 0.175 | 1.577 | 1.393 |

FIGURE 113

Raw Data Parameters for Food Odors Measured with ITO-QCM

| Analyte | Change in frequency response (Hz) | Change in resistance response (Ω) | Initial response time (sec) | Initial response slope (Hz/sec) | Return to baseline slope (Hz/sec) | Full width half maximum (sec) |
|---|---|---|---|---|---|---|
| Kiwi | 1.2 | 0.016 | 16.1 | -0.075 | 0.149 | 17.7 |
| Mango | 2.3 | 0.018 | 22.5 | -0.102 | 0.186 | 20.1 |
| Papaya | 1.7 | 0.031 | 17.2 | -0.099 | 0.11 | 17.9 |
| Pineapple | 1.6 | 0.018 | 20.4 | -0.078 | 0.135 | 22.7 |
| Strawberry | 2.2 | 0.029 | 15 | -0.146 | 0.147 | 26.3 |
| Honeydew | 3.2 | 0.074 | 29 | -0.11 | 0.186 | 25.6 |
| Cantaloupe | 2.9 | 0.036 | 17.2 | -0.169 | 0.203 | 19.2 |
| Watermelon | 4.8 | 0.044 | 31.1 | -0.154 | 0.241 | 34.2 |
| Red grape | 4.1 | 0.055 | 10.7 | -0.382 | 0.272 | 13 |
| Ambrosia Apple | 1.4 | 0.108 | 11.8 | -0.119 | 0.112 | 15.6 |
| Red Delicious Apple | 1.3 | 0.087 | 11.8 | -0.11 | 0.104 | 14.2 |
| Granny Smith Apple | 1.3 | 0.101 | 9.7 | -0.135 | 0.093 | 16.4 |
| Rome Apple | 1 | 0.125 | 9.7 | -0.103 | 0.08 | 16.7 |
| Jazzenza Apple | 1.8 | 0.222 | 8.6 | -0.209 | 0.127 | 10 |
| Gala Apple | 1.8 | 0.139 | 11.8 | -0.152 | 0.124 | 18.8 |

FIGURE 117

Raw Data Parameters for Food Odors Measured with ITO-QCM

| Analyte | Change in frequency response (Hz) | Change in resistance response (Ω) | Initial response time (sec) | Initial response slope (Hz/sec) | Return to baseline slope (Hz/sec) | Full width half maximum (sec) |
|---|---|---|---|---|---|---|
| Navel Orange1 | 1.5 | 0.06 | 16.1 | -0.093 | 0.093 | 18.6 |
| Tangerine1 | 1.5 | 0.067 | 19.3 | -0.078 | 0.114 | 17.2 |
| Tangerine2 | 1.5 | 0.042 | 13.9 | -0.108 | 0.101 | 17.6 |
| Navel Orange2 | 1.2 | 0.052 | 10.7 | -0.112 | 0.076 | 14.7 |
| Red Onion | 2.9 | 0.205 | 10.7 | -0.27 | 0.179 | 15.8 |
| Yellow Onion | 1.2 | 0.095 | 14 | -0.086 | 0.12 | 18.7 |
| White Onion | 1.3 | 0.081 | 14 | -0.093 | 0.085 | 17.5 |
| Garlic outer shell | 1.7 | 0.104 | 11.8 | -0.144 | 0.082 | 19.2 |
| Garlic inner shell | 1.5 | 0.116 | 7.5 | -0.199 | 0.133 | 20.5 |
| Garlic core | 1.7 | 0.063 | 18.2 | -0.093 | 0.161 | 15 |

FIGURE 118

Raw Data Parameters for Food Odors Measured with ITO-QCM

| Analyte | Change in frequency response (Hz) | Change in resistance response (Ω) | Initial response time (sec) | Initial response slope (Hz/sec) | Return to baseline slope (Hz/sec) | Full width half maximum (sec) |
|---|---|---|---|---|---|---|
| Sharp Cheddar Cheese | 1.4 | 0.04 | 11.8 | -0.118 | 0.101 | 14.8 |
| Swiss Cheese | 1.5 | 0.04 | 16.1 | -0.093 | 0.101 | 15.3 |
| American Cheese | 2 | 0.043 | 25.8 | -0.078 | 0.158 | 15.5 |
| White Merlot Wine | 2.1 | 0.025 | 8.6 | -0.244 | 0.129 | 16.8 |
| White Zinfandel Wine | 1.9 | 0.015 | 12.9 | -0.147 | 0.132 | 12.6 |
| Pinot Grigio Wine | 2.5 | 0.03 | 7.5 | -0.333 | 0.108 | 15.2 |
| Average(mean) of all | 1.9 | 0.07 | 14.9 | -0.143 | 0.134 | 17.9 |
| Standard deviation of all | 0.9 | 0.051 | 6 | 0.075 | 0.047 | 4.6 |

FIGURE 119

SRS QCM200 Data File
Data Taken on [DATE] at 3:17:30 PM

| Frequency | Surface Resistance | Time |
|---|---|---|
| 4.99E+06 | 9.40E+00 | 3.79E+01 |
| 4.99E+06 | 9.40E+00 | 3.80E+01 |
| 4.99E+06 | 9.40E+00 | 3.81E+01 |
| 4.99E+06 | 9.40E+00 | 3.81E+01 |
| 4.99E+06 | 9.40E+00 | 3.82E+01 |
| 4.99E+06 | 9.40E+00 | 3.82E+01 |

FIGURE 133

```
'ITOQCMCalculations
'****************************************
Cls
DIM templine AS STRING
DIM header AS STRING
DIM headerloop AS INTEGER
DIM temp(6000, 6) AS STRING
DIM AbsFreq(6000) AS DOUBLE 'Absolute frequency value, column 1
DIM AbsSurfRes(6000) AS DOUBLE 'Absolute surface resistance value,
column 2
DIM AbsChangeMass(6000) AS DOUBLE 'Change in mass value, not
used for PCA, column 5
DIM FreqVal (6000) AS DOUBLE   'Relative change in frequency value,
column 3
DIM SurfResVal (6000) AS DOUBLE'Relative change in surface
resistance value, column 4
DIM TimeVal (6000) AS DOUBLE   'Time value, column 6

DIM X, XX AS INTEGER
DIM DataPoints AS INTEGER

OPEN "C:\Documents and Settings\cap1522\Desktop\ITOQCMData.txt"
FOR INPUT AS #1
'FOR headerloop = 1 TO 13 STEP 1 'Skip the first 13 lines of file, header
'LINE INPUT #1, header
'NEXT headerloop WHILE NOT EOF(1)
X=X+1
DataPoints = DataPoints +1
LINE INPUT #1, templine
temp(X,1) = MID$(templine, 1, 17) 'Absolute frequency value, column 1
temp(X,2) = MID$(templine, 19, 13)'Absolute surface resistance value,
column 2
```

FIGURE 134

```
temp(X,3) = MID$(templine, 32, 13)'Relative change in frequency value,
column 3
temp(X,4) = MID$(templine, 46, 13)'Relative change in surface resistance
value, column 4
temp(X,5) = MID$(templine, 61, 13)'Change in mass value, not used for
PCA, column 5
temp(X,6) = MID$(templine, 75, 13)'Time value, column 6
WEND
CLOSE #1

FOR XX = 1 TO DataPoints STEP 1
AbsFreq(XX) = VAL(temp(XX,1))    'Absolute frequency value, column 1
AbsSurfRes(XX) = VAL(temp(XX,2))    'Absolute surface resistance value,
column 2
FreqVal(XX) = VAL(temp(XX,3))    'Relative change in frequency value,
column 3
SurfResVal(XX) = VAL(temp(XX,4))'Relative change in surface resistance
value, column 4
AbsChangeMass(XX) = VAL(temp(XX,5))    'Change in mass value, not
used for PCA, column 5
TimeVal(XX) = VAL(temp(XX,6))    'Time value, column 6
NEXT XX ' Start Calculate Change in Frequency Response Parameters ----------------
-----
DIM FreqDerivative (6000) AS DOUBLE
DIM FreqDerivativeMovingAve (6000) AS DOUBLE
DIM StartFreqTime  AS DOUBLE
DIM MinFreqTime  AS DOUBLE
DIM EndFreqTime  AS DOUBLE DIM SampleFreqVals (6000)  AS DOUBLE
DIM StartFreqVal  AS DOUBLE
DIM MinFreqVal  AS DOUBLE
DIM EndFreqVal  AS DOUBLE
```

FIGURE 135

```
DIM FreqResponseStart AS INTEGER
DIM FreqResponseEnd AS INTEGER

DIM InitialResponseSlope AS DOUBLE
DIM ReturnBaselineSlope AS DOUBLE
DIM AverageAll AS DOUBLE
DIM TotalFreqSum AS DOUBLE
DIM IntegratedFreq AS DOUBLE
DIM Y, Y2 AS INTEGER
DIM ResponseDataPoints AS INTEGER FOR Y = 2 to DataPoints STEP 1
FreqDerivative (Y) = (FreqVal (Y-1) - FreqVal (Y))/(TimeVal (Y-1) -
TimeVal (Y))

IF Y > 41 THEN
FreqDerivativeMovingAve(Y) = (FreqDerivative (Y) + FreqDerivative (Y-1)
+ FreqDerivative (Y-2) + FreqDerivative (Y-3) + _
FreqDerivative (Y-4) + FreqDerivative (Y-5) + FreqDerivative (Y-6) +
FreqDerivative (Y-7) + _
FreqDerivative (Y-8) + FreqDerivative (Y-9) + FreqDerivative (Y-10) +
FreqDerivative (Y-11) + _
FreqDerivative (Y-12) + FreqDerivative (Y-13) + FreqDerivative (Y-14) +
FreqDerivative (Y-15) + _
FreqDerivative (Y-16) + FreqDerivative (Y-17) + FreqDerivative (Y-18) +
FreqDerivative (Y-19) + _
FreqDerivative (Y-20) + + FreqDerivative (Y-21) + FreqDerivative (Y-22) +
FreqDerivative (Y-23) + _
FreqDerivative (Y-24) + FreqDerivative (Y-25) + FreqDerivative (Y-26) +
FreqDerivative (Y-27) + _
FreqDerivative (Y-28) + FreqDerivative (Y-29) + FreqDerivative (Y-30) + _
FreqDerivative (Y-31) + FreqDerivative (Y-32) + FreqDerivative (Y-33) + _
FreqDerivative (Y-34) + FreqDerivative (Y-35) + FreqDerivative (Y-36) +
FreqDerivative (Y-37) + _
FreqDerivative (Y-38) + FreqDerivative (Y-39))/40
ENDIF
```

FIGURE 136

```
IF (MinFreqVal >= FreqVal (Y)) THEN
MinFreqVal = FreqVal(Y)
MinFreqTime = TimeVal (Y)
ENDIF IF (FreqResponseStart = 0) AND (FreqResponseEnd = 0) THEN
  IF (FreqDerivative (Y) < -4.0) THEN    'start of change in frequency
response
  StartFreqVal = FreqVal (Y-1)
  StartFreqTime = TimeVal (Y-1)
  FreqResponseStart = 1
  ENDIF
ENDIF IF (FreqResponseStart = 1) AND (FreqResponseEnd = 0) THEN
SampleFreqVals (Y) = FreqVal (Y)
TotalFreqSum = TotalFreqSum + FreqVal (Y)
ResponseDataPoints = ResponseDataPoints + 1

IntegratedFreq     = IntegratedFreq + ((TimeVal(Y+1) -
TimeVal(Y))*((FreqVal (Y+1) - StartFreqVal) + (FreqVal (Y) -
StartFreqVal)))/2

IF (FreqResponseEnd = 0) AND (TimeVal (Y) > MinFreqTime + 4) AND
(FreqVal (Y) = StartFreqVal - 0.2) AND _
(FreqDerivativeMovingAve (Y) < 0) THEN
FreqResponseEnd = 1
EndFreqVal = FreqVal (Y-39)
EndFreqTime = TimeVal (Y-39)
ENDIF 'Return to baseline
IF (FreqResponseEnd >= 0) AND (FreqVal (Y) >= StartFreqVal - 0.1) AND
(TimeVal (Y) > MinFreqTime + 4) AND _
(FreqDerivativeMovingAve (Y) > 0) THEN
```

FIGURE 137

```
FreqResponseEnd = 1
EndFreqVal = FreqVal (Y)
EndFreqTime = TimeVal (Y)
ENDIF

ENDIF

NEXT Y
' End Calculate Change in Frequency Response Parameters -----------------
------

' Start Calculate Change in Surface Resistance Response Parameters -----
---------
DIM Z AS INTEGER
DIM StartSurfResTime  AS DOUBLE
DIM StartSurfResVal  AS DOUBLE
DIM EndSurfaceResTime AS DOUBLE DIM SurfResResponseStart AS INTEGER
DIM SurfResResponseEnd AS INTEGER
DIM IntegratedSurfRes AS DOUBLE OPEN "C:\Documents and
Settings\cap1522\Desktop\ITOQCMCalculationsOutput.txt" FOR OUTPUT
AS #2

FOR Z = 2 to DataPoints STEP 1

'Start Surface Resistance Measurement 1 second before start of
frequency response
IF (SurfResResponseStart = 0) AND (TimeVal(Z) >= StartFreqTime - 1.0)
THEN
StartSurfResTime = TimeVal(Z)
StartSurfResVal = SurfResVal (Z)
SurfResResponseStart = 1
ENDIF
```

FIGURE 138

```
IF (SurfResResponseStart = 1) AND (SurfResResponseEnd = 0) THEN
IntegratedSurfRes   = IntegratedSurfRes + ((TimeVal(Z+1) -
TimeVal(Z))*((SurfResVal (Z+1) - StartSurfResVal) + (SurfResVal (Z) -
StartSurfResVal)))/2
ENDIF IF TimeVal(Z) = EndFreqTime THEN
EndSurfaceResTime = TimeVal(Z)
SurfResResponseEnd = 1
ENDIF NEXT Z
' End Calculate Change in Surface Resistance Response Parameters ------
----

InitialResponseSlope = (MinFreqVal - StartFreqVal)/(MinFreqTime -
StartFreqTime)
ReturnBaselineSlope = (EndFreqVal - MinFreqVal)/(EndFreqTime -
MinFreqTime)
AverageAll = TotalFreqSum/ResponseDataPoints OPEN "C:\Documents and
Settings\cap1522\Desktop\ITOQCMCalculationsOutput.txt" FOR OUTPUT
AS #2
PRINT #2, "Initial Response Slope = ", InitialResponseSlope
PRINT #2, "Return to Baseline Slope = ", ReturnBaselineSlope
PRINT #2, "Average of All Freq Data Points = ", AverageAll
PRINT #2, "Integrated Freq Response = ", IntegratedFreq
PRINT #2, "Integrated Surface Resistance Response = ",
IntegratedSurfRes
CLOSE #2

END
```

FIGURE 139

QUARTZ CRYSTAL MICROBALANCE WITH NANOCRYSTALLINE OXIDE SEMICONDUCTOR THIN FILMS AND METHOD OF DETECTING VAPORS AND ODORS INCLUDING ALCOHOLIC BEVERAGES, EXPLOSIVE MATERIALS AND VOLATILIZED CHEMICAL COMPOUNDS

GOVERNMENT LICENSE RIGHTS

The U.S. Government has a paid-up license in this invention and the right in limited circumstances to require the patent owner to license others on reasonable terms as provided for by the terms of DOD: W911SR-07-C-0099, awarded by the United States Army.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

This invention generally relates to detection of gaseous chemical compounds, and, more particularly, to rapid detection using a quartz crystal microbalance equipped with a nanocrystalline oxide semiconductor thin film.

BACKGROUND

Detection of gaseous chemical compounds is useful for a wide array of applications, including (without limitation) quality control in food processing; detection and management of fuel supplies and exhausts; and detection of drugs, explosives and dangerous or illegal substances. By way of example, detecting compounds in fuel vapors enables determination and verification of fuel ratings (e.g., octane ratings and ocetane numbers). As another example, volatile organic compound detection facilitates pollution control and monitoring environmental safety. Additionally, detecting odors from foods and beverages, such as alcoholic beverages, enables product identification and quality control in production. Furthermore, rapid detection of trace signatures from explosives improves security at airports and for border control and enhances quality control in production.

Transportation facilities have a variety of vehicles, run by a variety of petroleum fuels and emitting varying amounts of pollutants. Gasoline consists of a complex mixture of hydrocarbons, most of which are alkanes with 4-10 carbon atoms per molecule. The octane number of gasoline is a measure of its resistance to knock (i.e., detonation of unburned fuel/air mixture beyond the boundary of a flame front when the mixture is subjected to a combination of heat and pressure). The octane rating is measured by the value of research octane number (RON) and motor octane number (MON). The octane value shown on gas pumps in Europe and Australia is RON, while the octane value shown on the gas stations in the Canada and United States and some other counties is the average of the RON and MON and known as (R+M)/2. The difference between RON and MON is 8 to 10 points. Therefore, the "regular" 87 octane fuel in the United States and Canada would be about 91 to 92 octane in Europe and Australia.

The quality control of fuels plays a major role in reducing pollution from vehicles. Different types of gasoline are manufactured, distributed to gas pumps and sold to users under controlled government regulations and guidelines. To increase the octane rating, gasoline are mixed with several types of additives such as (i) oxygenates such as alcohol (ethanol, methanol, isopropyl alcohol and t-butanol) and ethers (Methyl Tertiary Butyl Ether (MTBE), tertiary amyl methyl ether (TAME), ethyl tertiary butyl ether (ETBE), etc. (ii) antioxidants and stabilizers (ethylene diamine and phenylene diamine), (iii) antiknock agents (tetra-ethyl lead, Methylcyclopentadienyl Manganese Tricarbonly (MMT), ferrocenetoluene and isooctane), (iv) lead scavengers (v) fuel dyes (such as solvent Red 24, Red 26, Yellow 124 and Blue 35) and (vi) hybrid compounds (such as detergent agent, combustion catalyst and corrosion inhibitor) in different countries. Such additives are controlled under the regulation of each country's environment protection agency.

In the United States, for example, fuel station pumps are inspected periodically (e.g., twice per year). Inspectors check supply meters, collect fuel samples and the samples to accredited laboratories for testing of octane and adulteration. Various types of lower priced chemicals such as kerosene, industrial solvents, ether, naphtha and other chemicals may be widely used for adulteration of gasoline. In addition, unbalanced and prohibited additives may be added to increase the octane grade. Such adulterated gasoline may compromise performance, increase emission of pollutants and deposits of carbon in the vehicle engine. Gasoline quality is checked in accredited laboratories by standard reference methods, which are time consuming and expensive. In addition, analytical instruments, calibration mixtures, consumable spares and trained personnel are required to conduct the test. A portable, low cost and easy to operate sensors system can be very useful to government authorities for rapidly and efficiently test the quality of gasoline and diesel. It potentially could be installed in the automobile vehicles so that drivers can have quick information about the quality of purchased gasoline.

Governmental agencies also regulate many volatile organic compounds (VOCs), particularly those that are hazardous, such as benzene, toluene, and xylene. Such compounds are extremely harmful if inhaled over their threshold limit value (TLV). TLV, a recommended guideline for industrial workplace exposure developed by the American Conference of Governmental Industrial Hygienists (ACGIH), is based upon time weighted average (TWA) exposure during an 8 hour/day and 40 hour/week work schedule. TLV-TWA for benzene is 0.5 ppm, toluene is 50 ppm, and xylene is 100 ppm.

Analytical instruments such as infrared spectroscopy and gas chromatography offer high sensitivity, but they cannot practicably be used for real-time measurement of VOCs in the field. They require large sample collection time and analysis time. In addition, they require reagents and skilled operators.

Human sensory panels are used for testing quality, color, taste and odor of foods and beverages. Human smell also has poor sensing reproducibility because of possible infection, fatigue, time of day and prior odors analyzed. Electronic noses consist of arrays of odor sensors which can be applied to monitoring the ripening of wine and cheese; quality assurance of raw foods and food products; cooking processes, fermentation processes; industrial processes such as flavoring and blending; benchmarking; packaging interaction effects; freshness and aging control. While known sensing devices have refined the olfactometry process, they have shortcomings. For example, they cannot continuously work for long time periods or operate remotely.

Alcohol, water and aroma are three major components of alcoholic beverages. The discrimination of alcoholic beverages using electronic noses has been reported based on alcohol content and not true differences in the aroma profiles. Several isolation approaches such as distillation, adsorption method, liquid-liquid extraction, desalcoholization and dehydration using gas chromatography procedures were applied to remove alcohol and water content from the beverages and to isolate aroma for detection using the electronic nose. All isolation approaches required setting of equipment, relatively lengthy analysis time and skilled operation.

What is needed is a cost-effective, easy to use, portable sensor system that operates without need of an external or integrated heater and also reliably detects a wide variety of odors and vapors with exceptional sensitivity, selectivity and response time. The invention is directed to overcoming one or more of the problems and solving one or more of the needs as set forth above.

SUMMARY OF THE INVENTION

To solve one or more of the problems set forth above, in an exemplary implementation of the invention, a sensor for sensing gaseous chemicals is provided. The sensor comprises a nanocrystalline semiconductor (e.g., ITO) oxide thin film formed on a quartz crystal microbalance (QCM). Adsorption (i.e., surface assimilation) of gas molecules onto the nanocrystalline semiconductor thin film changes the resonant frequency. The physical structure and chemical character of the nanocrystalline oxide semiconductor thin film plays an important role in response properties of the sensor.

In one exemplary embodiment, the oxide semiconductor comprises indium tin oxide (ITO). An indium tin oxide (ITO) quartz crystal microbalance (QCM) sensor system according to principles of the invention includes a quartz crystal with a pair of electrodes. The quartz crystal has a sensing surface and is configured for installation in and oscillation in a crystal holder. The electrodes are configured for electrically coupling the quartz crystal to a crystal oscillator. A nanocrystalline ITO thin film is formed (e.g., by process of thermal evaporation) on the sensing surface of the quartz crystal. The nanocrystalline ITO thin film acts as an adsorbent that attracts at least one gaseous compound emitted from an analyte.

By way of example and not limitation, the nanocrystalline ITO thin film may have a thickness of about 50 to 300 nm and an average grain size of about 10 to 100 nm. Illustratively, and/or without limitation, the quartz crystal may be a 5 MHz quartz crystal AT cut or a 5 MHz quartz crystal IT cut. The electrodes may comprise gold or platinum.

An oscillator operably coupled to a crystal holder serves as a means for oscillating the quartz crystal with the nanocrystalline ITO thin film formed thereon. A controller with or without a compatible computing device provides a means for determining parameters such as the frequency of oscillation, surface resistance, integrated frequency response, integrated surface resistance response, initial response slope, average return to baseline slope, and/or return to baseline time/initial response time ratio of the quartz crystal with the nanocrystalline ITO thin film formed thereon. If a computing device is included, the system may be configured to perform principal component analysis for purposes of determining principal components for the at least one gaseous compound. Determined principal components may be compared with known principal components corresponding to known analytes. The analyte may include any distinguishable substance, in any state that emits at least one gaseous compound that can be adsorbed on the nanocrystalline ITO thin film. Nonlimiting examples of analytes include alcoholic beverages, fruits, explosive compounds, VOCs, a petroleum-based fuels, alkanes, aldehydes and ketones.

A sampling vessel (e.g., ajar) with an opening provides one volume to contain the analyte and additional volume to at least temporarily contain the emitted gaseous compounds. The quartz crystal with the nanocrystalline ITO thin film formed thereon may be positioned within the additional volume, abutting the additional volume or in close proximity to the additional volume.

An exemplary method of detecting an analyte using an indium tin oxide (ITO) quartz crystal microbalance is also provided. The exemplary method entails providing an indium tin oxide (ITO) quartz crystal microbalance (QCM) sensor system, such as that described above. The quartz crystal with the nanocrystalline ITO thin film formed on the sensing surface is exposed for a determined time period to at least one gaseous compound emitted from an analyte. The quartz crystal with the nanocrystalline ITO thin film formed on the sensing surface is oscillated in the presence of the gaseous compounds emitted from the analyte. At least one detection parameter of the quartz crystal with the nanocrystalline ITO thin film formed on the sensing surface oscillating in the presence of the at least one gaseous compound emitted from the analyte is determined. The analyte may be determined based upon the detection parameter(s). By way of example and not limitation, the detection parameter may include a measurable parameter such as frequency of oscillation of the quartz crystal with the nanocrystalline ITO thin film formed thereon, and/or surface resistance of the quartz crystal with the nanocrystalline ITO thin film formed thereon, and/or integrated frequency response, and/or integrated surface resistance response, and/or initial response slope, and/or average return to baseline slope, and/or return to baseline time/initial response time ratio for the quartz crystal with the nanocrystalline ITO thin film formed thereon. Principal component analysis may be applied to determine principal components for the gaseous compounds, which may then be compared with known (e.g., predetermined) principal components corresponding to known analytes (i.e., for gaseous emissions from known analytes).

BRIEF DESCRIPTION OF THE DRAWINGS

The foregoing and other aspects, objects, features and advantages of the invention will become better understood with reference to the following description, appended claims, and accompanying drawings, where:

FIG. 7 is tables showing characterization parameters of ITO-QCM odor sensors and grain size statistics for ITO-quartz crystals in accordance with principles of the invention; FIG. 10 is a graph that illustrates change in frequency and surface resistance responses as an ITO-QCM film was exposed to odors from wines: 1—Sutter Home Sauvignon Blanc California, 2—Glen Ellen Chardonnay California, 3—Lindemans Bin 65 Chardonnay Australia, 4—Sutter Home Merlot California, 5—Lindemans Bin 50 Shiraz Australia, 6—Lindemans Bin 45 Cabernet Sauvignon Australia, 7—Cruz Garcia Real Sangria Spain, 8—Sutter Home White Zinfandel California; FIGS. 19 through 23 are tables that provide raw data parameters for beer, wine, and liquor odors measured with ITO-QCM; FIG. 47 is a table of equilibrium headspace vapor concentrations above military grade TNT (ng/L) at 22° C.; FIGS. 50 through 51 are tables of ITO-QCM calculated parameters used for PCA for explosive sample measurements; FIGS. 57 through 63 are ITO-QCM calculated parameters used for PCA for VOC sample measurements; FIG. 84 is a table of different alkanes used in the ITO-QCM measurements; FIGS. 98 to 103 comprise tables showing raw data parameters for aldehyde vapors measured with an ITO-QCM sensor; FIGS. 109 to 113 comprise tables showing raw data parameters for ketone vapors measured with an ITO-QCM sensor; FIGS. 117 to 119 comprise tables showing raw data parameters for food and beverage odors measured with an ITO-QCM sensor; FIG. 133 provides an excerpt of ITO-QCM data from a data acquisition log for an exemplary 10-second ITO-QCM measurement for a volatile organic compound vapor; and FIGS. 134 through 139 provide an exemplary Basic language computer program that calculates PCA coordinates of ITO-QCM vapor/odor measurements after completing measurements in accordance with principles of the invention.

Figure 1:
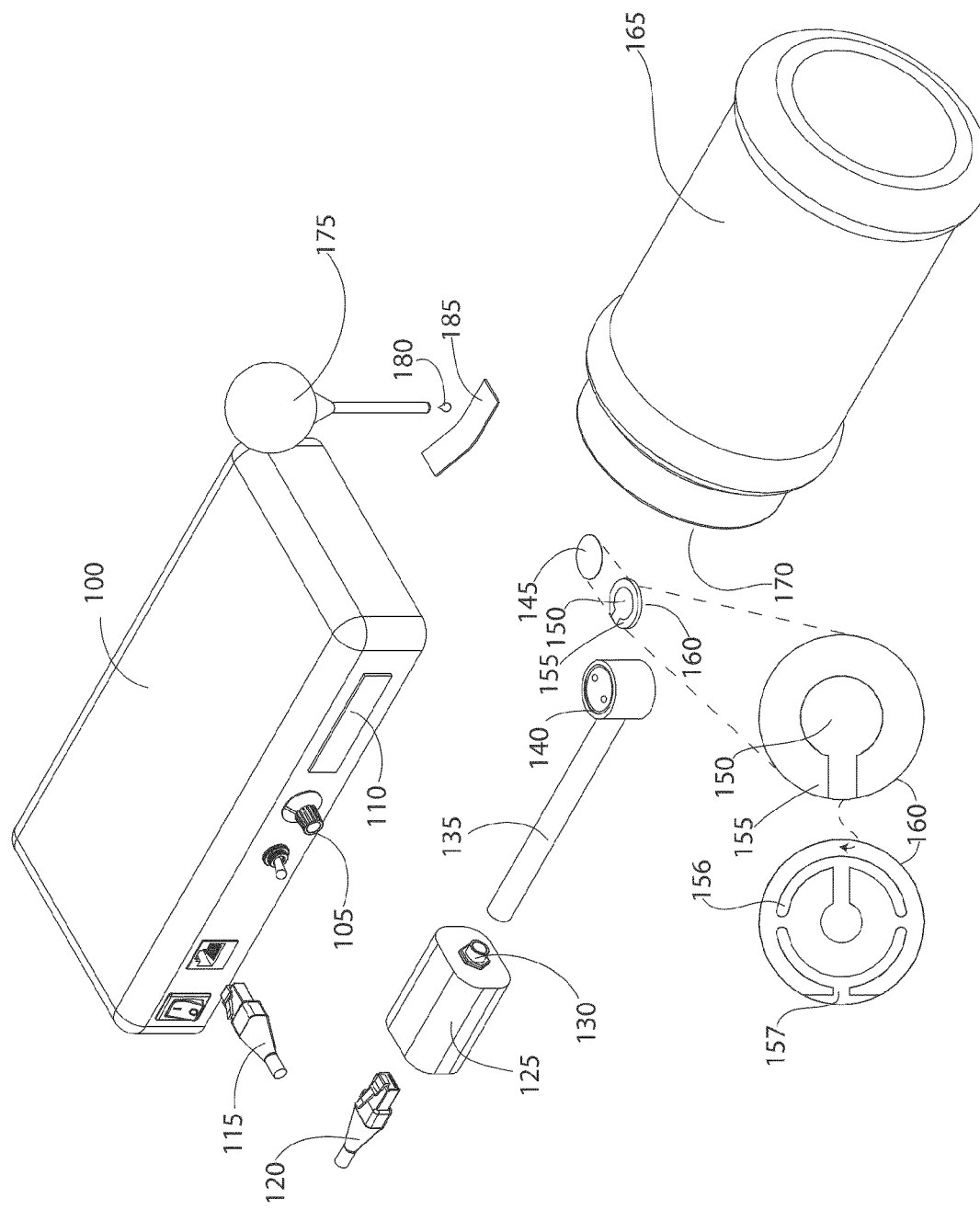
FIG. 1 shows a perspective view of an exemplary sensor system according to principles of the invention.
Figure 2:
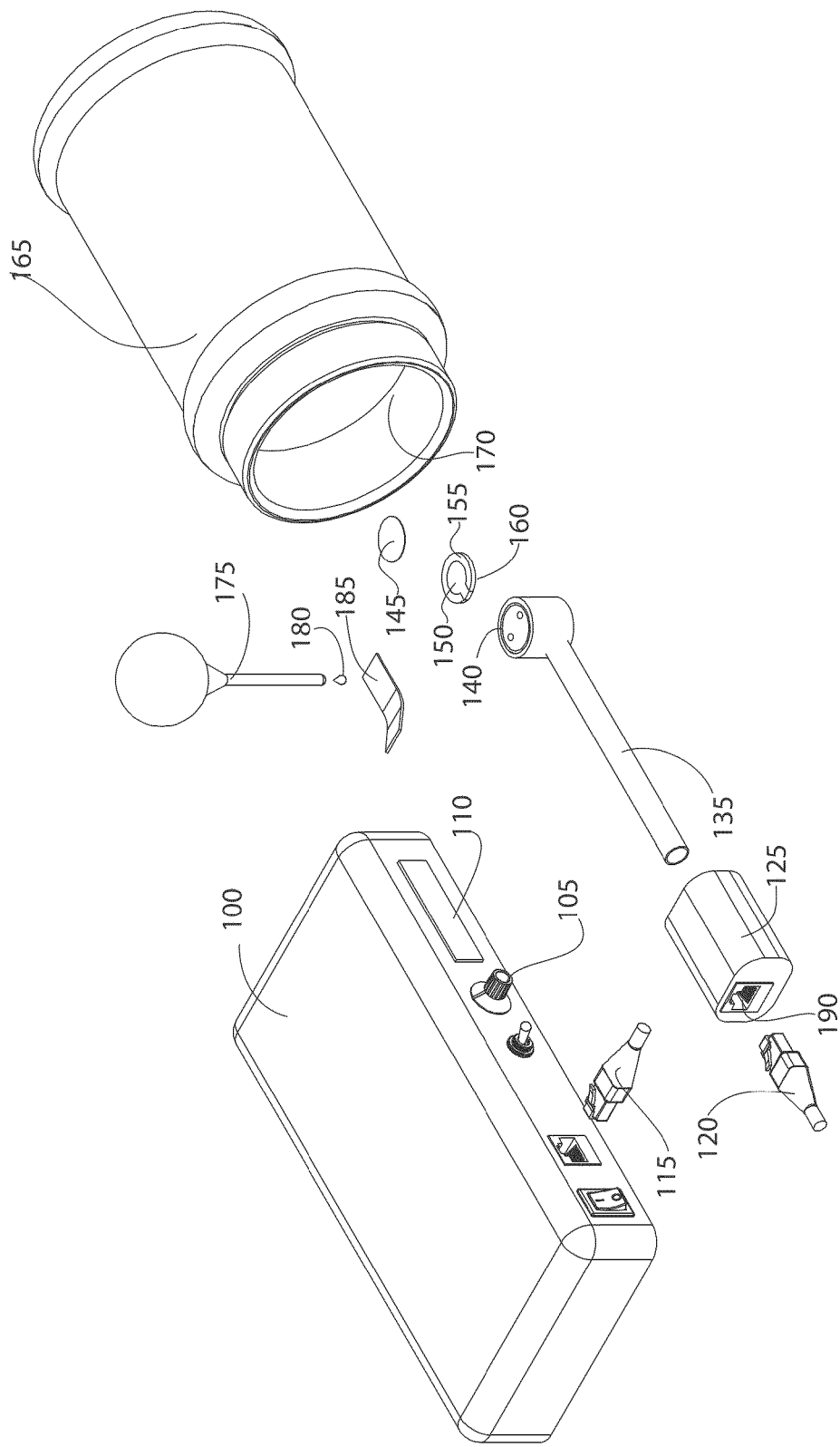
FIG. 2 shows another perspective view of another exemplary sensor system according to principles of the invention.

Those skilled in the art will appreciate that the figures are not intended to be drawn to any particular scale; nor are the figures intended to illustrate every embodiment of the invention. The invention is not limited to the exemplary embodiments depicted in the figures or the arrangements, or the shapes, configurations, relative sizes, ornamental aspects, proportions, thicknesses, chemical compounds, brands, concentrations, equations or steps shown in the figures.

In some graphs, the curves or lines representing determined values for different analytes may be hard to differentiate because they may be close together, intersecting and/or overlapping, and the Figures are provided in black and white. Those skilled in the art will appreciate that even where the separate lines and curves cannot easily be differentiated, the graphs are useful for visually depicting various relationships, including similarities, dissimilarities and relative values. Additionally, data used to generate graphs included in the Figures are presented in tables, which are also included in the Figures.

DETAILED DESCRIPTION

Referring to FIGS. 1 through 4, in which like parts are indicated with the same reference numerals, various views of an exemplary sensor and a sensor array according to principles of the invention are shown. An exemplary ITO-QCM system according to principles of the invention includes a controller 100, a crystal oscillator 125, a crystal holder 135, and a quartz crystal assembly 160 with a quartz crystal wafer 155 sandwiched between electrodes 150, 156 (as shown in the magnified view), and a nanocrystalline indium tin oxide (ITO) thin film 145 formed on the surface of the crystal 160 which will be exposed to vapors and/or odors. The holder 135 includes a mounting cavity 140 which contains electrical contacts that connect electrode (e.g., gold) contact surface circuits 156, 157 to the oscillator 125. One electrode 157 is connected to the top electrode 150. The oscillator 125 contains an oscillator circuit configured to drive the quartz crystal at its resonant frequency. The controller 100 is connected to the crystal oscillator 125 through a compatible port 190, such as with a CAT-5 cable 115-120 or any other means of wired or wireless communicative coupling. The controller 100 may further be connected by any compatible means to a computer (not shown) equipped with compatible data collection and analysis software, such as LabVIEW® (National Instruments). The crystal holder 135 is connected to a connector 130 (e.g., a BNC connector) of the crystal oscillator 125. A vessel 165 (e.g., glass jar) is provided as a chamber for testing gaseous components 200.

Exemplary sensors according to principles of the invention may be fabricated using any method of forming a uniform nanocrystalline oxide semiconductor (e.g., ITO) thin film on the quartz crystal. By way of example and not limitation, an ITO thin film may be deposited on a quartz crystal substrate at 250° C. substrate temperature via thermal evaporation in a vacuum chamber evacuated to approximately the order of $10^{-6}$ torr. The thicknesses of film may be about 50 to 300 nm, e.g., 200 nm. Any other method of forming a uniform nanocrystalline semiconductor (e.g., ITO) thin film on the quartz crystal, without compromising the integrity of the crystal or its electrodes, may be utilized within the scope of the invention.

Except for the nanocrystalline indium tin oxide (ITO) thin film 145 formed on the surface of the crystal 160, the aforementioned components are common features of a QCM system such as Stanford Research Systems, Model: QCM200. Indeed the system is intended to represent a broad category of QCM systems capable of measuring a mass by measuring a change in frequency and surface resistance of a quartz crystal resonator. Separate components as described above may be used to control operation and measure frequency and resistance. Alternatively, one or more dedicated control and processing circuits and related firmware or software may be utilized to perform these same functions in a more compact unit. The invention is not limited to any particular QCM system, so long as the system is capable of measuring a mass by measuring a change in frequency and surface resistance of a quartz crystal resonator with a nanocrystalline indium tin oxide (ITO) thin film formed thereon.

Figure 6:
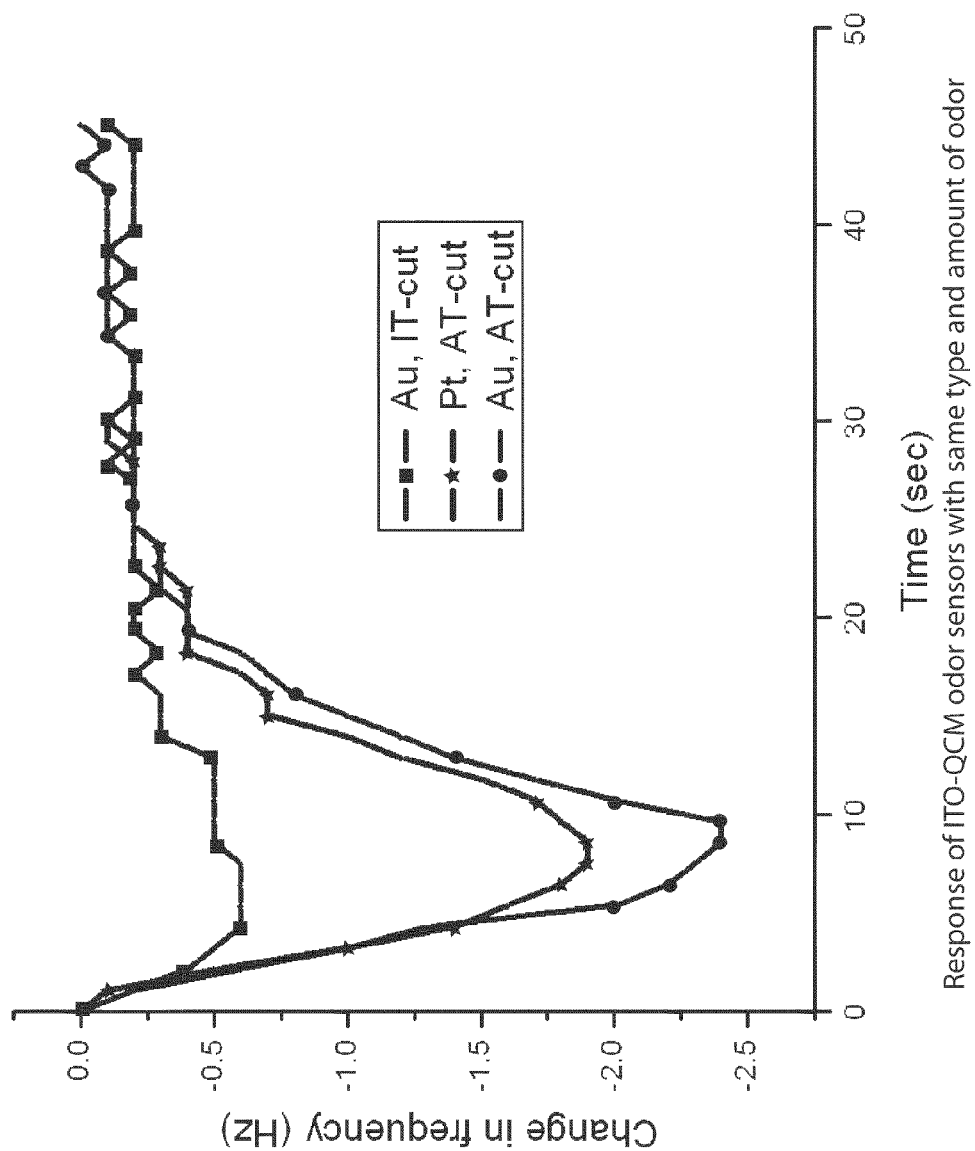
FIG. 6 is a graph that shows a response of ITO-QCM sensors with the same type and amount of odor.

In order to identify preferred ITO-QCM crystals, ITO thin films were deposited on three different types of 5 MHz quartz crystals: (i) Pt, AT cut, (ii) Au, IT cut and (iii) Au, AT cut at 250° C. substrate temperature in a single run of deposition. Then, all three ITO-QCM sensors were tested with the same type and amount of test gas in an open jar, as described below. FIGS. 6 and 7 show the response of change in frequency with time. As the response of the ITO-Au, AT cut QCM odor sensor was higher than that of ITO-Au, IT cut and ITO-Pt, AT cut QCM sensors, the ITO-Au, AT cut QCM odor sensor was preferred. Several characterization parameters were determined as set forth in the tables of FIG. 7. Of course, this test may be performed for other test gasses, in other testing vessels, under other conditions, to ascertain a preferred ITO-QCM crystal. Those skilled in the art will appreciate that the invention is not limited to the preferred crystal configuration, namely a 5 MHz, ITO-Au, AT cut QCM. Rather other piezoelectric crystals suitable for use in a microbalance with a nanocrystalline oxide semiconductor thin film formed thereon may be utilized and are intended to come within the scope of the invention.

Figure 5:
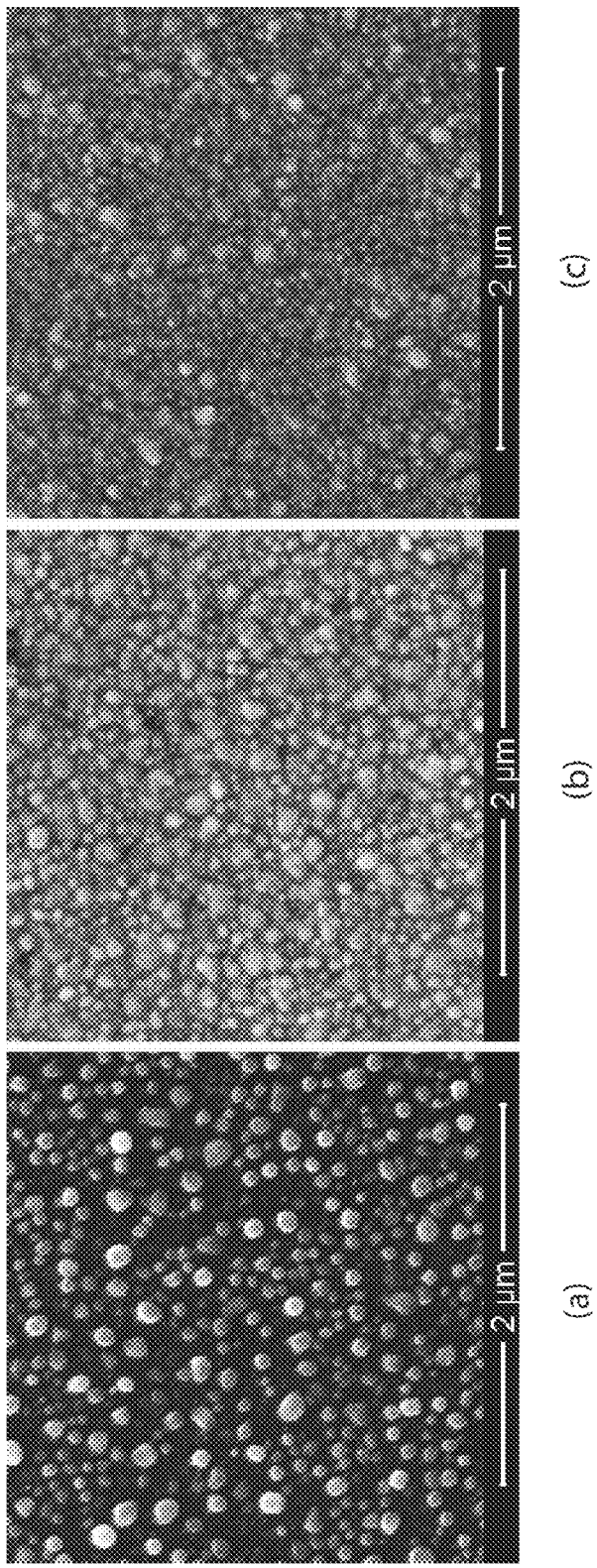
FIG. 5 is a series of scanning electron micrographs of (a) ITO-Pt, AT cut, (b) ITO-Au, IT cut and (c) ITO-Au, At cut for a thin film on a QCM according to principles of the invention.

The surface morphology of ITO-QCMs was examined under the environmental scanning electron microscope (FEI, Quanta 200), as shown in FIG. 5. The chemical composition was verified using the EDAX (Energy Dispersive Analysis of X-Rays) unit attached to the SEM. FIG. 5 shows the scanning electron micrographs of ITO-Pt, AT cut (left), Au, IT cut (center) and Au, AT cut (right). As can be seen in FIG. 7, the grain size of ITO thin films deposited on Au, AT cut is smaller and denser than Au, IT cut and Pt, AT cut quartz crystals. An image processing software program called "ImageJ" from the U.S. National Institute of Health was used to segment the grains and estimate the grain size. Results are given in Grain Size Table of FIG. 7. A nanocrystalline (i.e., having at least one dimension$\leq$100 nm and being single crystalline) ITO thin film according to principles of the invention serves as an adsorbent and facilitates adsorption of gaseous compounds emitted from tested substances (i.e., analytes). Grain sizes in the range of 10 to 100 nm may be used. For example, for various tests, the grain sizes of ITO-Au, AT cut were in the range of 43.4±11.7 nm, which was smaller than that of the other two ITO films on Pt, AT cut and Au, IT cut quartz crystals, as shown in FIGS. 5 and 7. It is believed that a smaller grain of ITO-QCM facilitates adsorption which yields a better response of change in frequency.

Piezoelectric crystals such as quartz, BaTiO3 and PZT (Pb, La, Zr, TiOx), have found widespread applications in electronic equipment, computers, communication equipment and microbalances. The vibrational frequency of an oscillating piezoelectric crystal is decreased on adsorption of a foreign particle or analyte onto its surface.

In operation, a quartz crystal microbalance (QCM) measures a mass per unit area by measuring the change in frequency of a quartz crystal resonator. This frequency is dependent on the mass of the crystal, as well as the mass of any layers confined to the electrode areas of the crystal. Thus, the frequency is altered by changes in mass on the surface of the electrodes or in any layers on those electrodes. In general, the change in resonant frequency of these devices can be correlated to the amount of mass change. The resonance is disturbed by the addition or removal of a small mass due to adsorption on a nanocrystalline indium tin oxide (ITO) thin film formed on the surface of the quartz crystal. As mass is deposited on the nanocrystalline indium tin oxide (ITO) thin film covering the crystal, the mass increases and the frequency of oscillation decreases from the initial value. With some simplifying assumptions, the change in vibrational frequency ($\Delta f$) can be quantified and correlated precisely to the mass (m) of material deposited on the crystal surface area (A) using Sauerbrey's equation:

$$\Delta f = \frac{2 f_0^2 \cdot \Delta m}{A \cdot \sqrt{\rho_q \mu_q}} \quad \text{Eq. 1}$$

where:
$\Delta f$=the observed frequency change in Hz,
$\Delta m$=the change in mass per unit area in g/cm$^2$, and
$f_0$=the resonant frequency of the fundamental mode of the crystal in Hz,
A=the piezoelectrically active area
$\rho_q$=density of quartz=2.648 g/cm$^3$, and
$\mu_q$=shear modulus of AT-cut quartz=2.947×10$^{11}$ g/cm·s$^2$.

The theoretical detection limit of a quartz crystal having 10 MHz frequency can be calculated to be as small as 10$^{-12}$ gram for deposited substance. Such crystals with suitable coating adsorbents for a particular molecule can be used as highly sensitive and selective sensors for gases, biological species, DNA, protein, bioamines, enzymes and antibodies.

The quartz crystal microbalance interfaced with a computer may be used to simultaneous measure change in the frequency as well as the changes in the surface resistance of the sensitive ITO thin film deposited over the quartz crystal of QCM in the presence of the test gasses.

Figure 3:
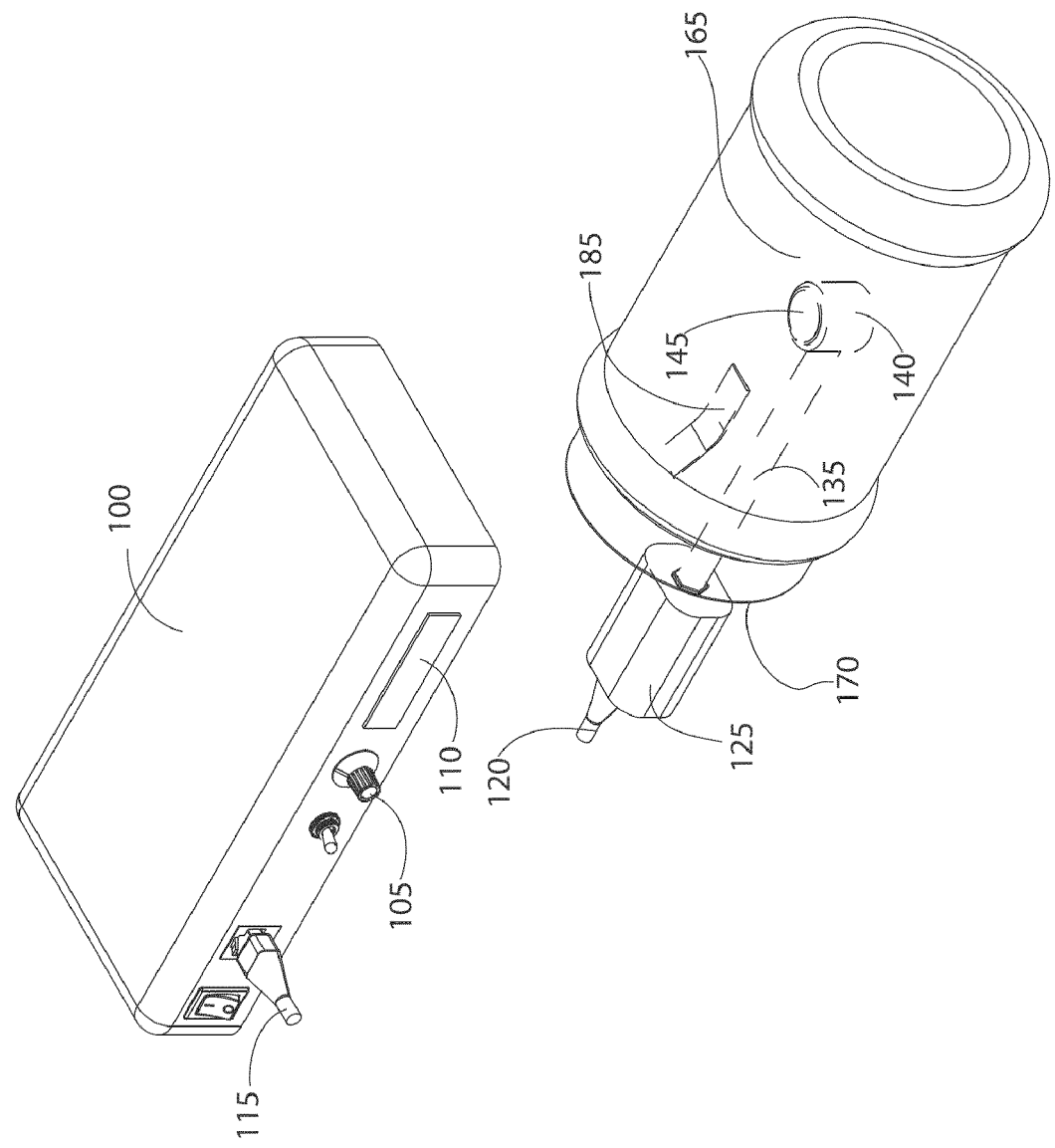
FIG. 3 shows another perspective view of an exemplary sensor system configured for sensing a gaseous analyte according to principles of the invention.
Figure 4:
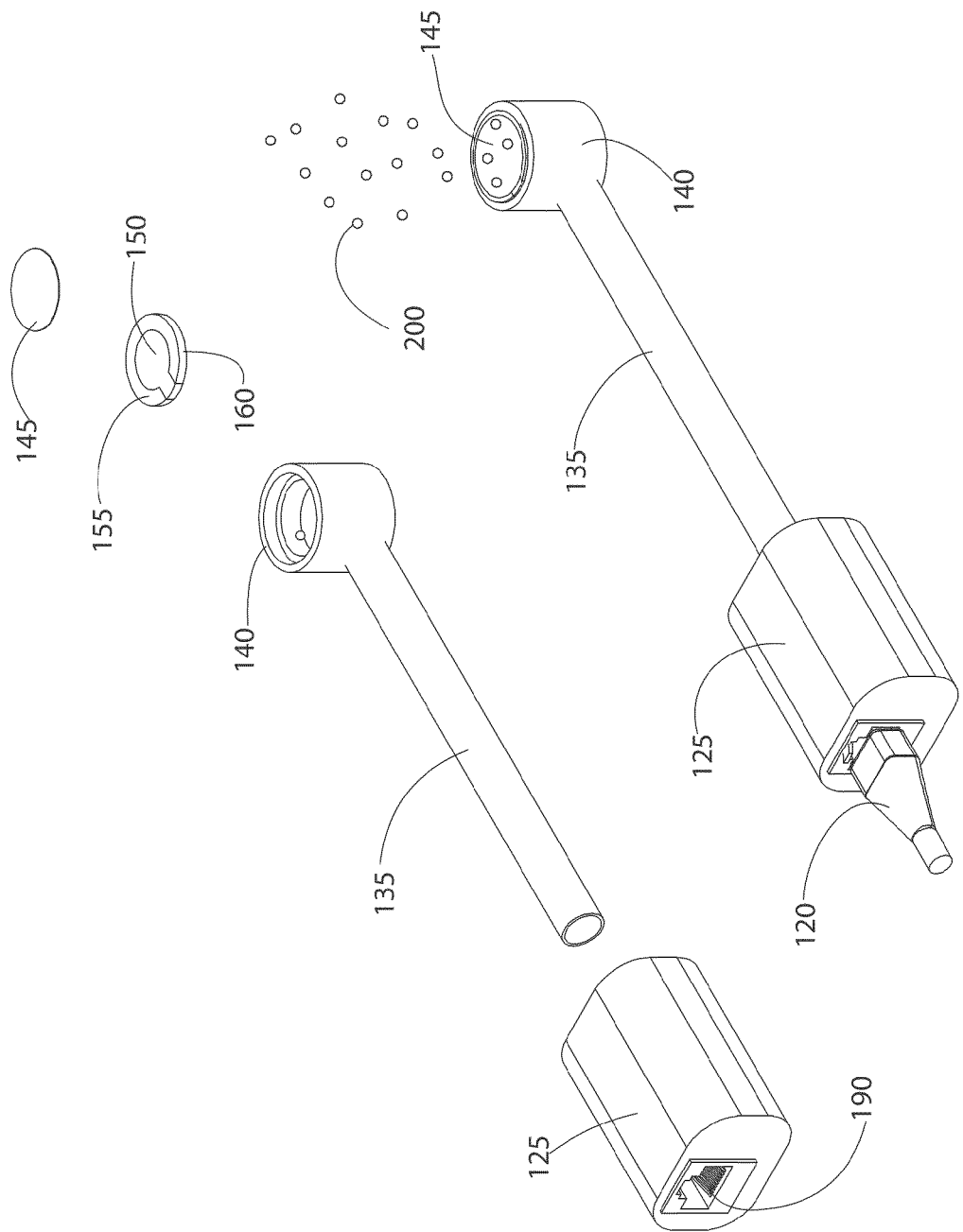
FIG. 4 shows exploded and assembled perspective views of an exemplary quartz crystal microbalance (QCM) with a nanocrystalline ITO thin film according to principles of the invention.

An exemplary testing setup includes a vessel 165 (e.g., a 500 ml glass jar). The crystal holder containing the ITO-QCM sensor is placed in the vessel 165 for the testing of gaseous compounds 200 (conceptually illustrated in FIG. 4) introduced in the vessel. By way of example and not limitation, using a pipette, dropper or similar device 175 (FIGS. 1 and 2), a determined amount (15 µl) of a liquid sample (e.g., a fuel, VOC or alcoholic beverage) may be applied over one end of a sample medium 185 (e.g., a paper strip having 20 cm length, 2 cm width and 0.3 mm thickness) or other suitable carrier. The medium 185 may be inserted in the vessel (e.g., open glass jar) and kept a determined distance (e.g., 2 cm) above the surface of the ITO film for a determined period of time (e.g., 10 seconds) as shown in FIG. 3, and then removed from the vessel 165. A digital timer may be used to measure the 10 second time period.

As an alternative method of exposing the ITO-QCM sensor to gaseous compounds, a headspace analysis may be used. A volatile solid or liquid sample may be put into a tightly sealed vessel 165. Vapors from the sample are released into the headspace air within the vessel until reaching the saturation equilibrium concentration. Dynamic headspace analysis refers to sampling the headspace of the sample with an open container. Static headspace analysis refers to sampling the headspace of the sample in a closed container.

Tests performed using the process described above for various alcoholic beverages, fuels, volatile organic compounds and explosives show that measured parameters may be used to identify particular gaseous compounds. A nanocrystalline ITO-QCM odor sensor according to principles of the invention enables detection of various gases at ambient temperature. The sensor does not require a heater or temperature controlling circuits. The absence of a heater not only saves power consumption and space, but also reduces any possibility of fire during testing of the flammable vapors. There is also no need of any reagents, pre-sample conditioning, special sample preparation, or isolation techniques to isolate a test gas. Such ITO-QCM sensors can be ready to use at any time. The response time of ITO-QCM odor sensor with tested gasses is very fast, nearly in real time.

Figure 8:
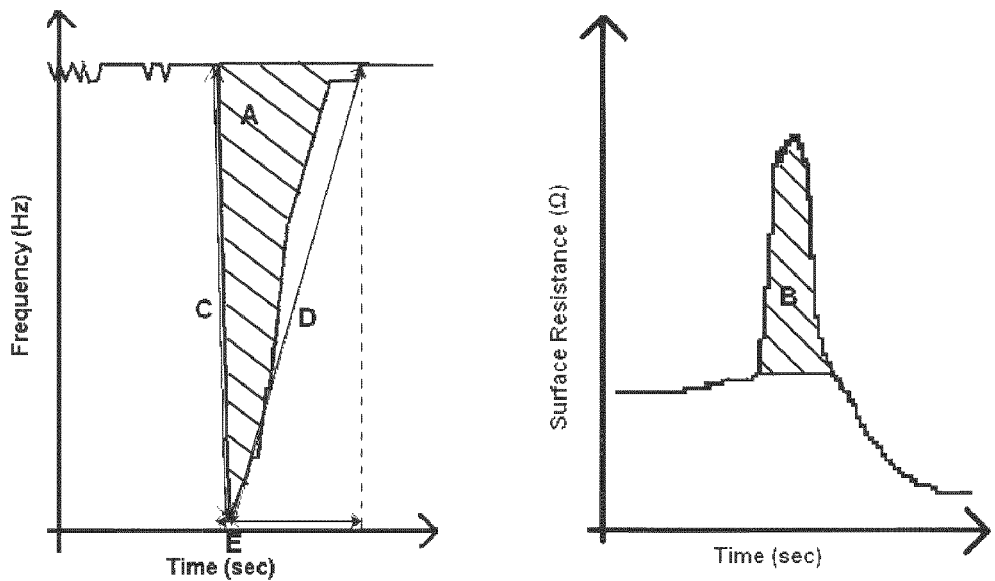
FIG. 8 comprises graphs that illustrate measured parameters on the frequency and surface resistance vs. time plots, where A is Integrated Frequency Response (Hz-sec), B is Integrated Surface Resistance Response (Ω-Sec), C is Initial Response Slope (Hz/Sec), D is Average Return to Baseline Slope (Hz/sec), E is return to baseline time/Initial response time ratio in accordance with principles of the invention.

In each test, changes in QCM frequency and surface resistance as a function of time were recorded as gas molecules were adsorbed on the nanocrystalline ITO film, and then desorbed after the samples were removed from the jar. Referring to FIGS. 8 and 57, measured parameters on frequency and surface resistance vs. time plots are conceptually illustrated. Such measured parameters include A—Integrated Frequency Response (Hz-sec), B—Integrated Surface Resistance Response (Ω-Sec), C—Initial Response Slope (Hz/Sec), D—Average Return to Baseline Slope (Hz/sec), E—Return to baseline time/Initial response time ratio, and/or the average of all change in frequency data points (Hz). FIGS. 9 through 43 provide graphs, plots and data pertaining to measured parameters for alcoholic beverages; FIGS. 44 to 56 provide graphs, plots and data pertaining to measured parameters for explosives; FIGS. 58 to 69 provide graphs, plots and data pertaining to measured parameters for VOCs; and FIGS. 70 to 98 provide graphs, plots and data pertaining to measured parameters for fuel compounds.

Changes in frequency and surface resistance as a function of time were recorded as odor (i.e., gas) molecules from alcoholic beverages on a sample medium 185 were adsorbed on the ITO film of the ITO-QCM, and then desorbed after the samples were removed from the jar. Measurements were taken for 9 beers, 4 brandy, 4 gins, 3 rums, 4 tequilas, 5 vodkas, 8 whiskeys, and 8 wines, as shown in FIGS. 9 through 43. The ITO-QCM sensor responded with changes in frequency, as well as changes in surface resistance for all odors tested. The test data is tabulated in FIGS. 19 through 23.

Figure 9:
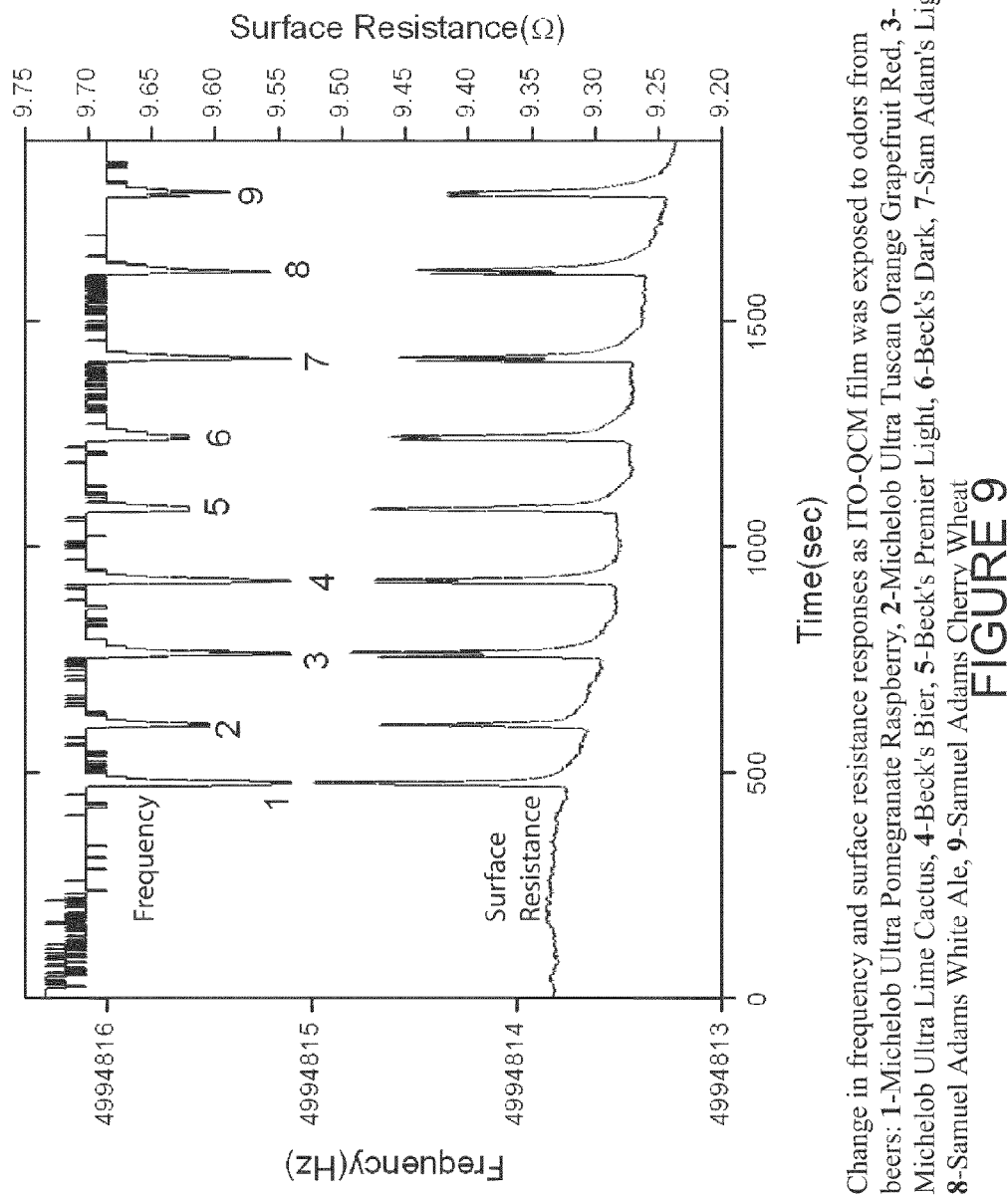
FIG. 9 is a graph that illustrates change in frequency and surface resistance responses as an ITO-QCM film was exposed to odors from beers: 1—Michelob Ultra Pomegranate Raspberry, 2—Michelob Ultra Tuscan Orange Grapefruit Red, 3—Michelob Ultra Lime Cactus, 4—Beck's Bier, 5—Beck's Premier Light, 6—Beck's Dark, 7—Sam Adams Light, 8—Samuel Adams White Ale, and 9—Samuel Adams Cherry Wheat.
Figure 11:
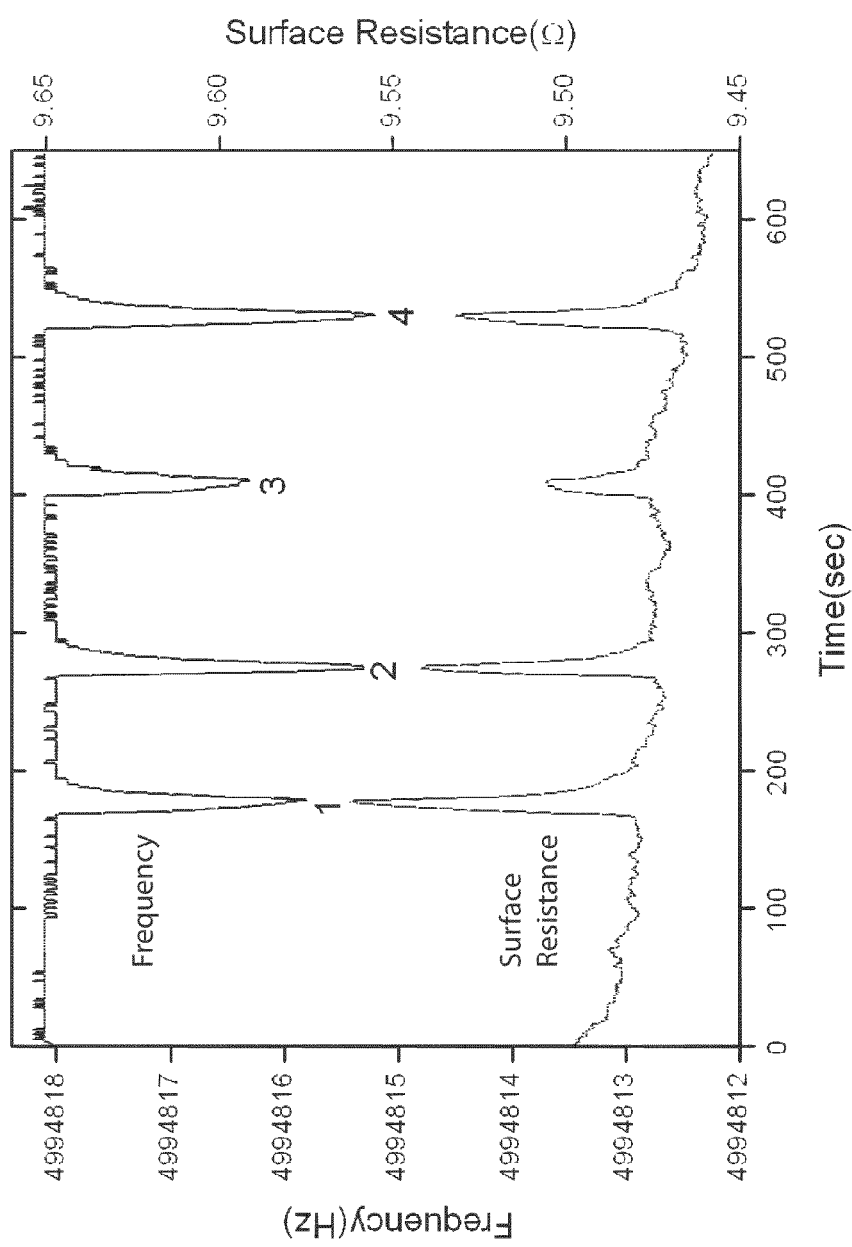
FIG. 11 is a graph that illustrates change in frequency and surface resistance responses as an ITO-QCM film was exposed to odors from brandy: 1—Paul Masson Grande Amber, 2—Vendome Platinum VSOP, 3—Hennessy Very Special Cognac, 4—Kelt Tour du Monde VSOP Cognac.
Figure 12:
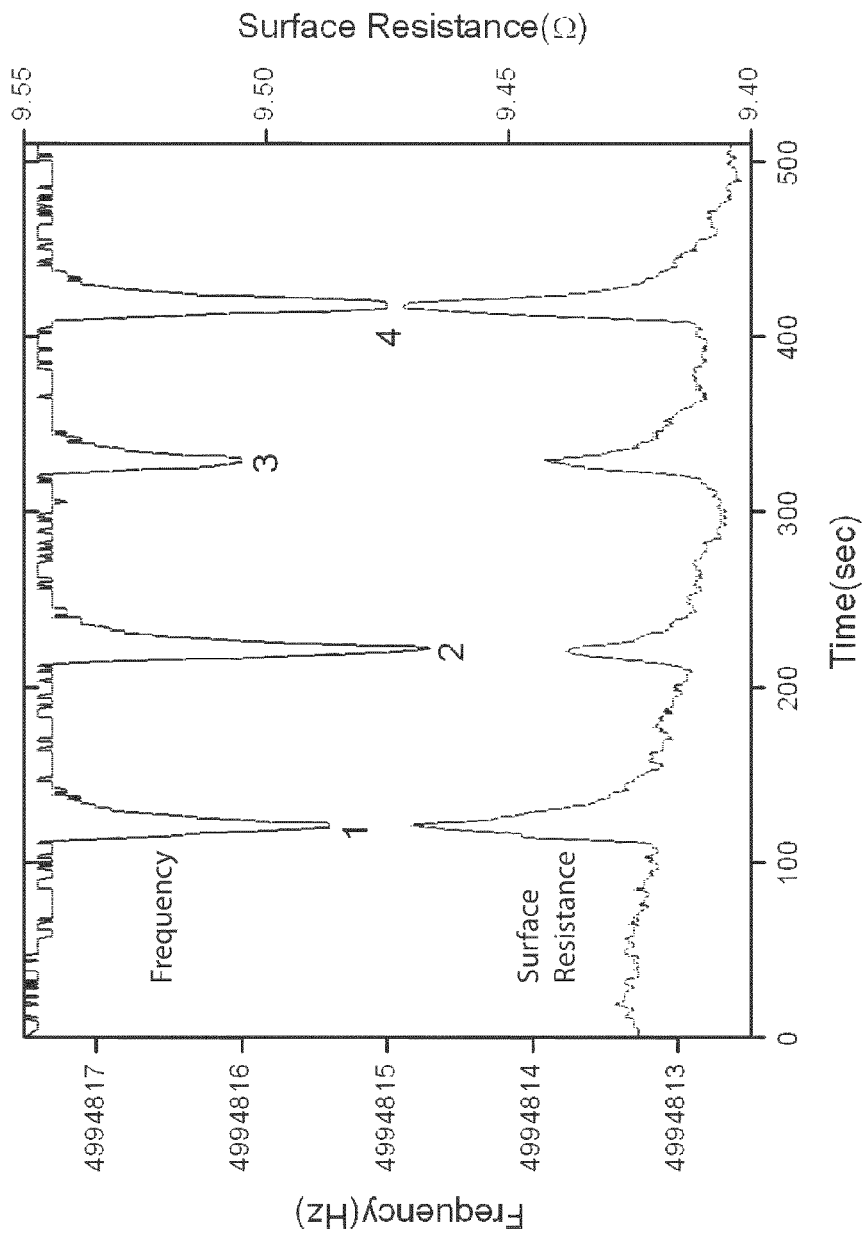
FIG. 12 is a graph that illustrates change in frequency and surface resistance responses as an ITO-QCM film was exposed to odors from gins: 1—Gordon's London Dry, 2—Beefeater London Dry, 3—Fleischmann's Extra Dry, 4—Seagram's Extra Dry.
Figure 13:
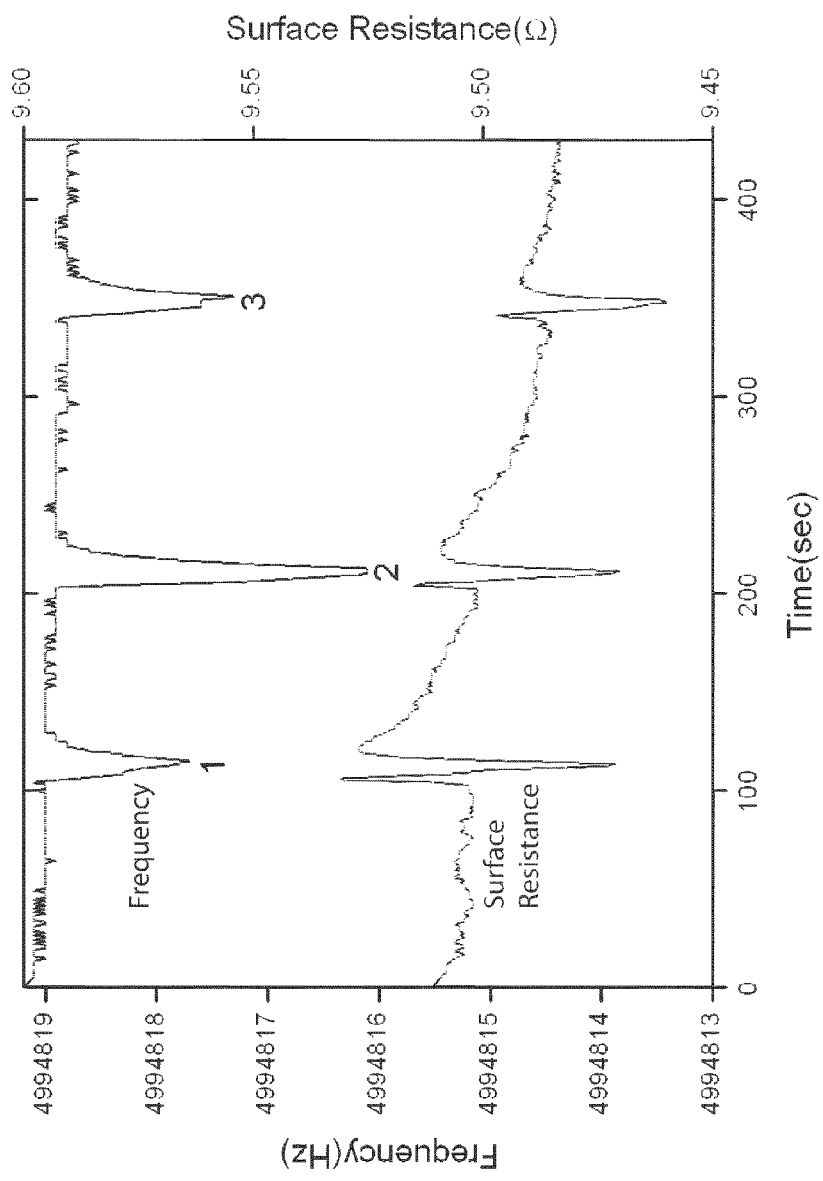
FIG. 13 is a graph that illustrates change in frequency and surface resistance responses as an ITO-QCM film was exposed to odors from rums: 1—Tropical Isle Palms Coconut Barbados 2—Tropical Isle Palms Barbados, 3—Captain Morgan Original Spiced.
Figure 14:
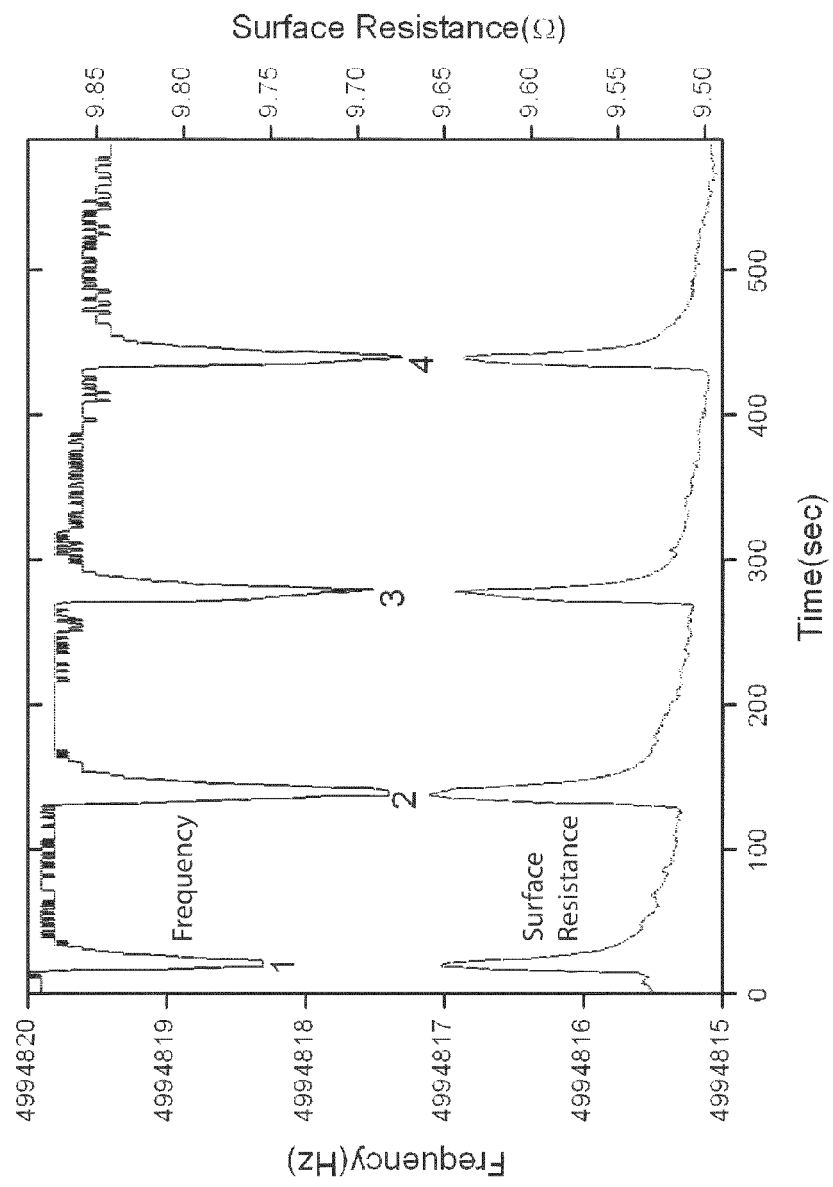
FIG. 14 is a graph that illustrates change in frequency and surface resistance responses as an ITO-QCM film was exposed to odors from tequilas: 1—Cuesta Rey Silver, 2—Cuesta Rey Gold, 3—Jose Cuervo Especial Oro, 4—Jose Cuervo Black Medallion Anejo.
Figure 15:
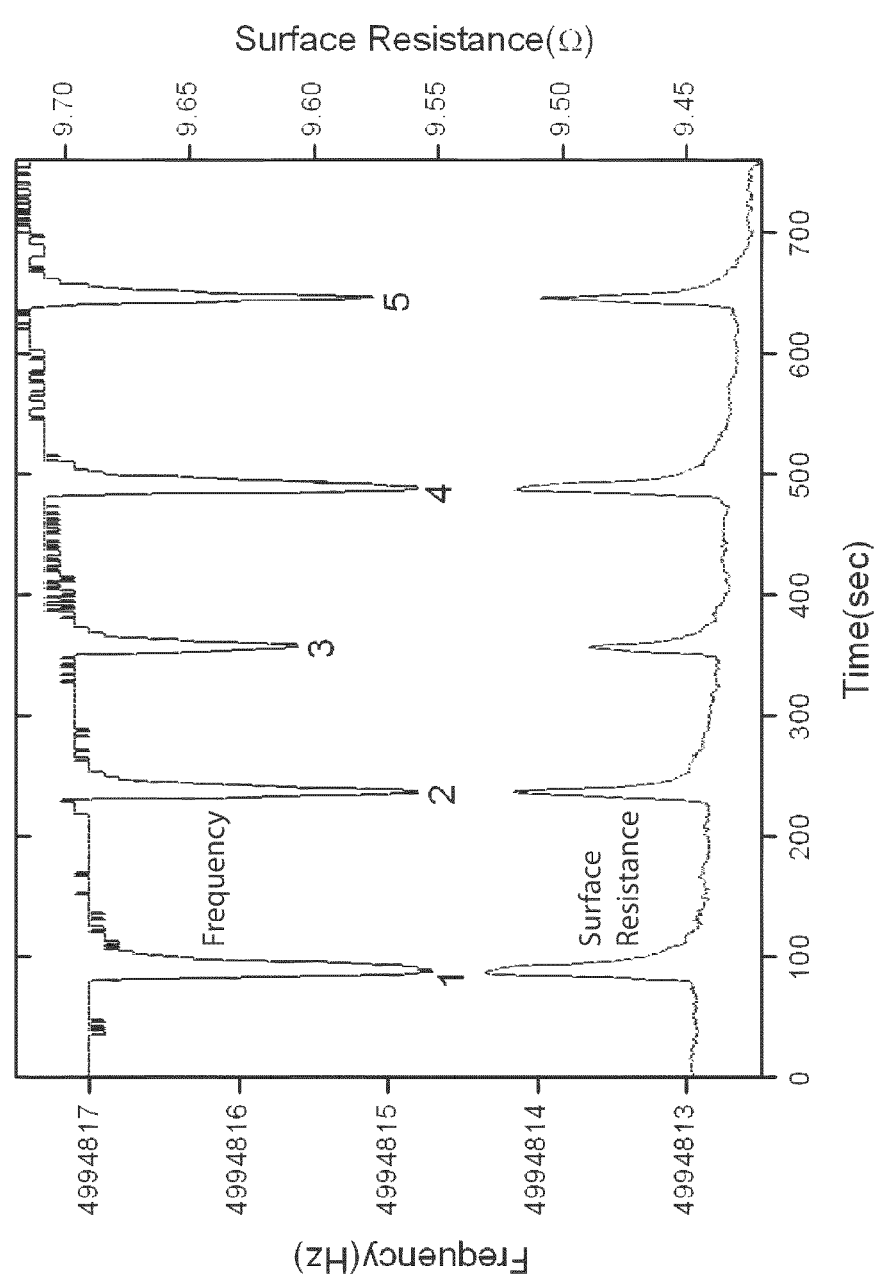
FIG. 15 is a graph that illustrates change in frequency and surface resistance responses as an ITO-QCM film was exposed to odors from vodkas: 1—Absolut Country of Sweden, 2—Northern Arctic Charcoal Filtered, 3—Smirnoff Watermelon, 4—Denaka, 5—Denaka Raspberry Platinum.
Figure 16:
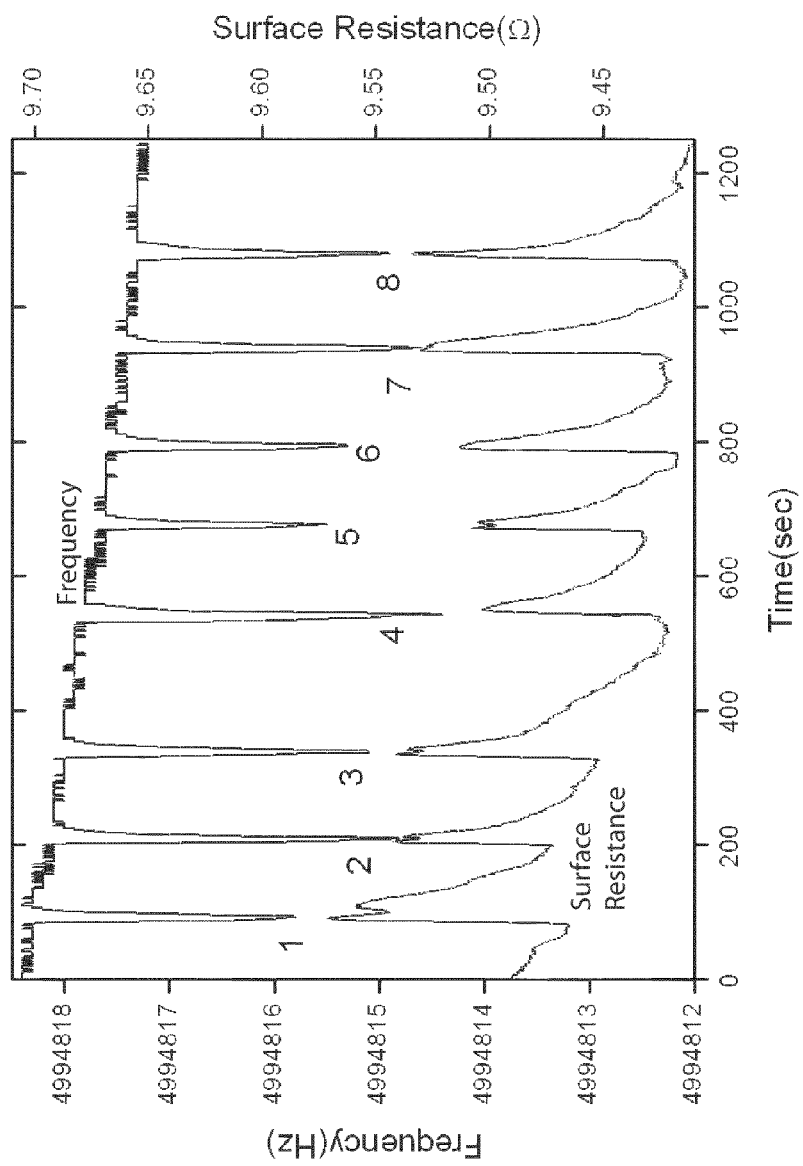
FIG. 16 is a graph that illustrates change in frequency and surface resistance responses as an ITO-QCM film was exposed to odors from whiskeys: 1—Jim Beam Kentucky Straight Bourbon, 2—Jack Daniels Old No. 7, 3—Early Times Kentucky, 4—Old Grand-Dad, 5—Lord Calvert Canadian, 6—Canadian Mist, 7—Maker's Mark Kentucky Straight Bourbon, 8—Gentleman Jack.
Figure 18:
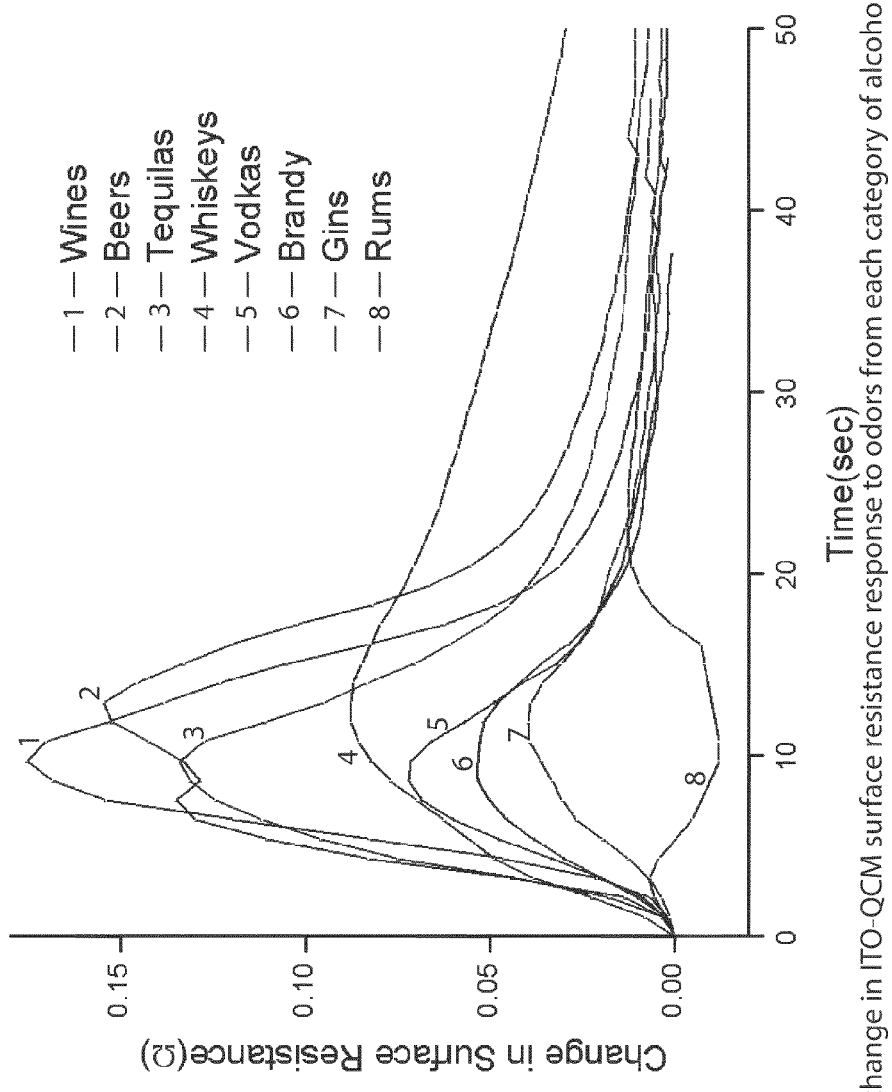
FIG. 18 is a graph that illustrates the average change in ITO-QCM surface resistance response to odors from each category of alcoholic beverages.

A system using an ITO-QCM sensor according to principles of the invention detected, classified and produced a unique signature for each category of alcohol beverages such as beer, wine, vodka, whiskeys, brandy, rums, tequila and gins by giving different measured parameters such as change in frequency, integrated frequency response, initial response slope, average return to baseline slope and transient response time. The ITO-QCM system also measured and provided a unique parameter of integrated surface resistance responses. The change in surface resistance for all the alcoholic beverages samples, except rums was positive. Rums show initially little positive peak and then large negative peak value, which show totally different signatures. Graphs showing changes in frequency and surface resistance are provided in FIGS. 9 through 18. Specifically, FIG. 9 illustrates change in frequency and surface resistance responses as an ITO-QCM film was exposed to odors from beers: Michelob Ultra Pomegranate Raspberry, Michelob Ultra Tuscan Orange Grapefruit Red, Michelob Ultra Lime Cactus, Beck's Bier, Beck's Premier Light, Beck's Dark, Sam Adams Light, Samuel Adams White Ale, and Samuel Adams Cherry Wheat. FIG. 10 illustrates change in frequency and surface resistance responses as an ITO-QCM film was exposed to odors from wines: Sutter Home Sauvignon Blanc California, Glen Ellen Chardonnay California, Lindemans Bin 65 Chardonnay Australia, Sutter Home Merlot California, Lindemans Bin 50 Shiraz Australia, Lindemans Bin 45 Cabernet Sauvignon Australia, Cruz Garcia Real Sangria Spain, and Sutter Home White Zinfandel California. FIG. 11 illustrates change in frequency and surface resistance responses as an ITO-QCM film was exposed to odors from brandy: Paul Masson Grande Amber, Vendome Platinum VSOP, Hennessy Very Special Cognac, Kelt Tour du Monde VSOP Cognac. FIG. 12 illustrates change in frequency and surface resistance responses as an ITO-QCM film was exposed to odors from gins: Gordon's London Dry, Beefeater London Dry, Fleischmann's Extra Dry, Seagram's Extra Dry. FIG. 13 illustrates change in frequency and surface resistance responses as an ITO-QCM film was exposed to odors from rums: Tropical Isle Palms Coconut Barbados Tropical Isle Palms Barbados, Captain Morgan Original Spiced. FIG. 14 illustrates change in frequency and surface resistance responses as an ITO-QCM film was exposed to odors from tequilas: Cuesta Rey Silver, Cuesta Rey Gold, Jose Cuervo Especial Oro, Jose Cuervo Black Medallion Anejo. FIG. 15 illustrates change in frequency and surface resistance responses as an ITO-QCM film was exposed to odors from vodkas: Absolut Country of Sweden, Northern Arctic Charcoal Filtered, Smirnoff Watermelon, Denaka, Denaka Raspberry Platinum. FIG. 16 illustrates change in frequency and surface resistance responses as an ITO-QCM film was exposed to odors from whiskeys: Jim Beam Kentucky Straight Bourbon, Jack Daniels Old No. 7, Early Times Kentucky, Old Grand-Dad, Lord Calvert Canadian, Canadian Mist, Maker's Mark Kentucky Straight Bourbon, Gentleman Jack. FIG. 18 illustrates the change in surface resistance of ITO-QCM response to odors from each category of alcoholic beverages.

Figure 17:
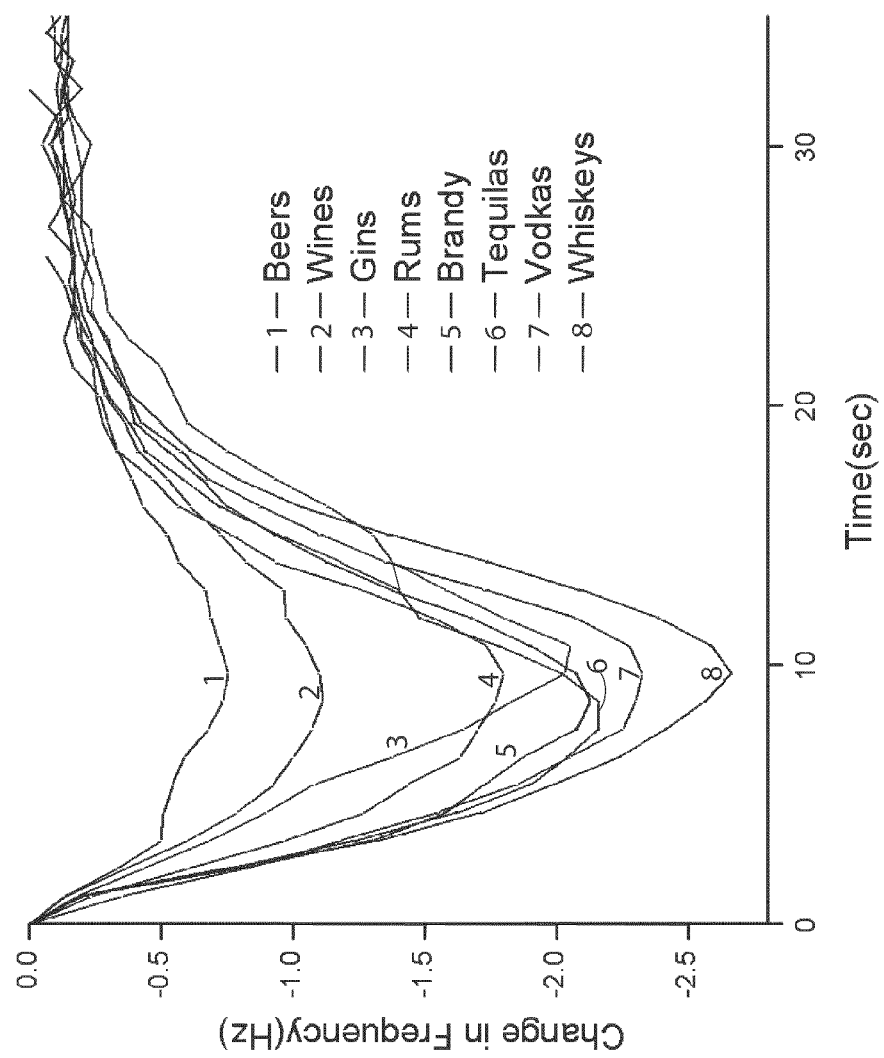
FIG. 17 is a graph that illustrates the average change in ITO-QCM frequency response to odors from each category of tested alcoholic beverages.
Figure 26:
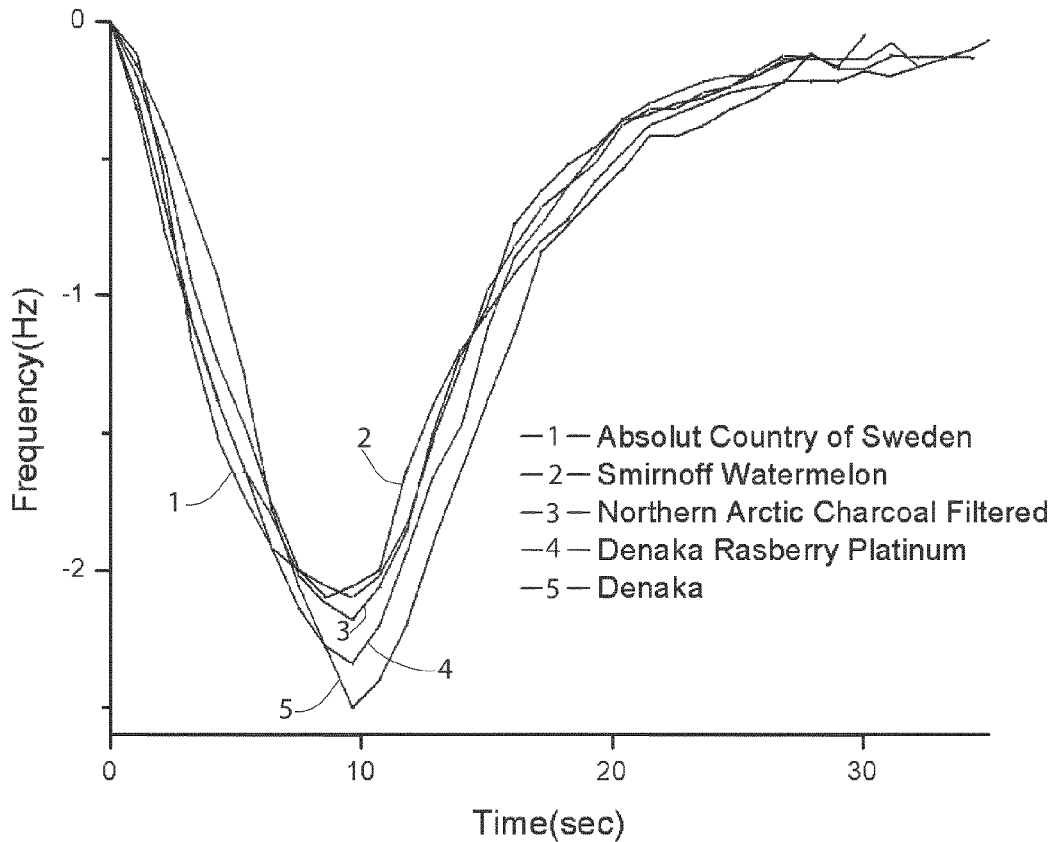
FIG. 26 is a graph that illustrates a composite average of ITO-QCM odor measurements with 5 different brands of vodka having two different percentages of alcohol.
Figure 32:
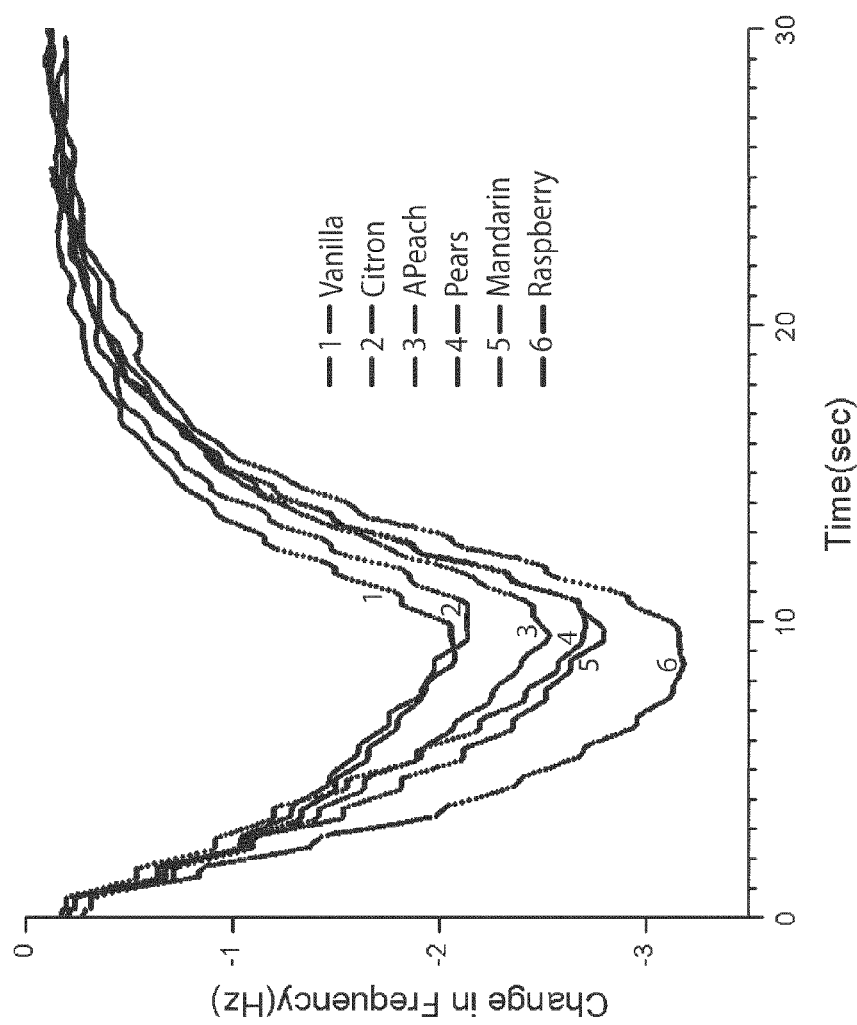
FIG. 32 is a graph of average change in ITO-QCM frequency response to Absolut brand vodkas having 40% alcohol and different flavors.
Figure 34:
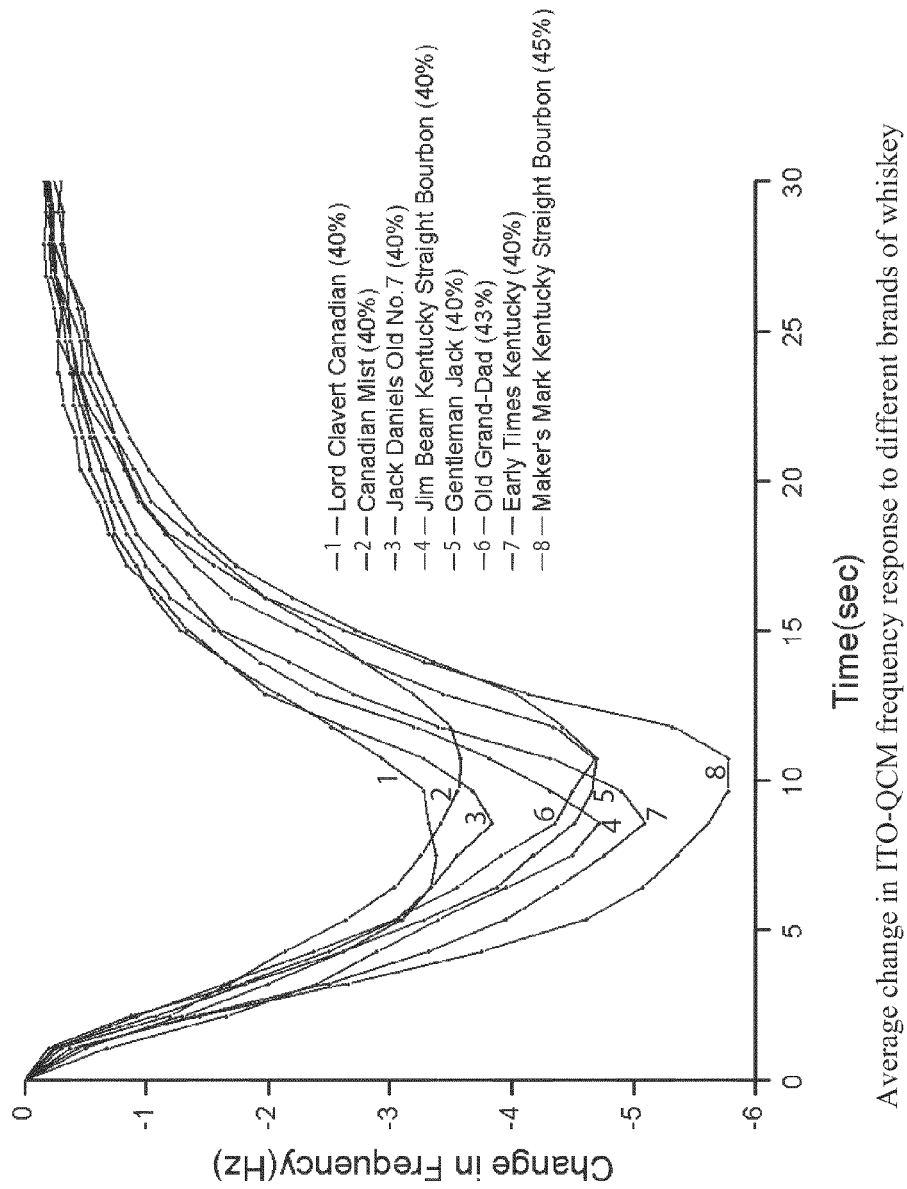
FIG. 34 is a graph of average change in ITO-QCM frequency response for different brands of whiskey.
Figure 36:
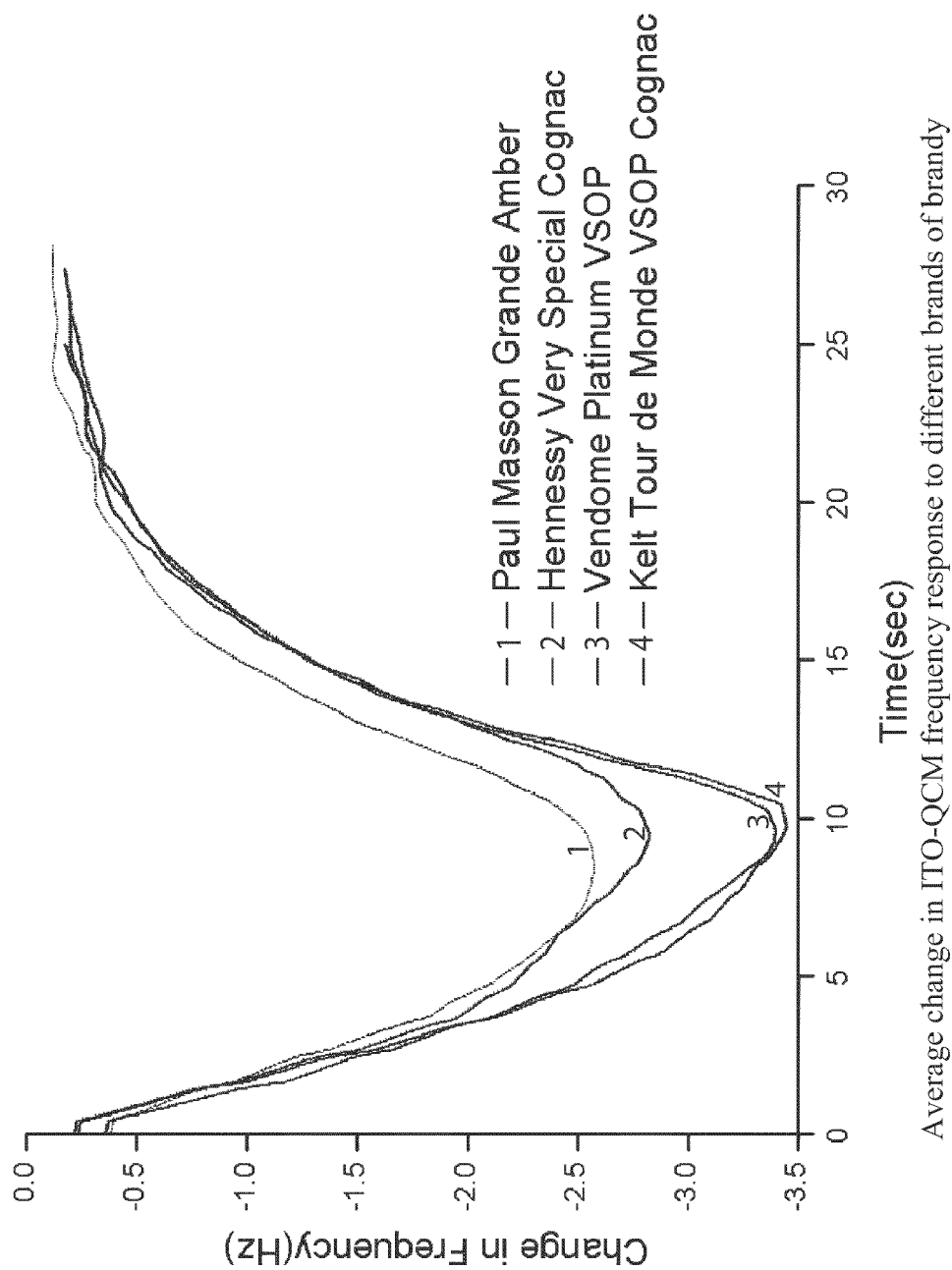
FIG. 36 is a graph of average changes in ITO-QCM frequency response for different brands of brandy.
Figure 38:
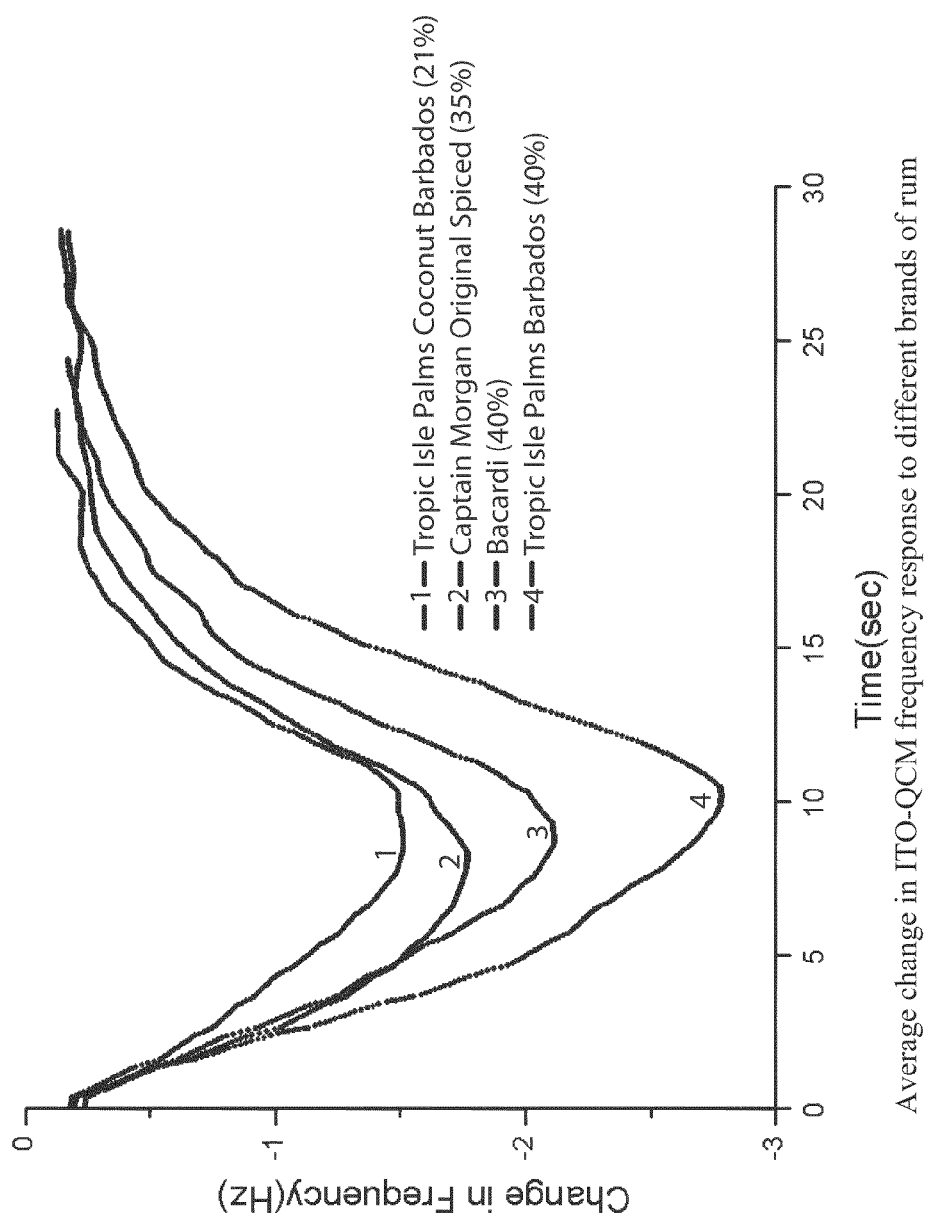
FIG. 38 is a graph of average change in ITO-QCM frequency response for different brands of rum.
Figure 40:
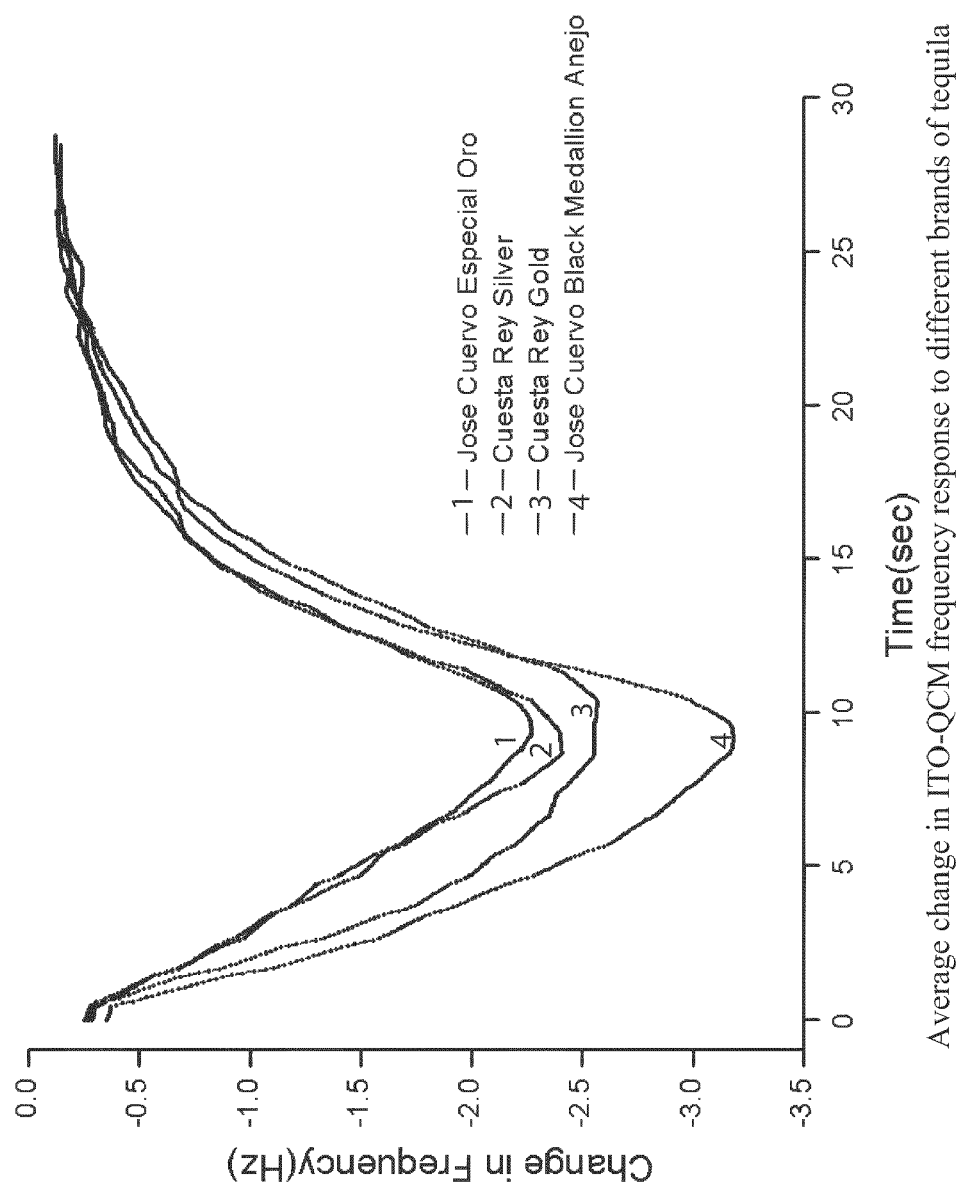
FIG. 40 is a graph of average change in ITO-QCM frequency response for different brands of tequila.
Figure 42:
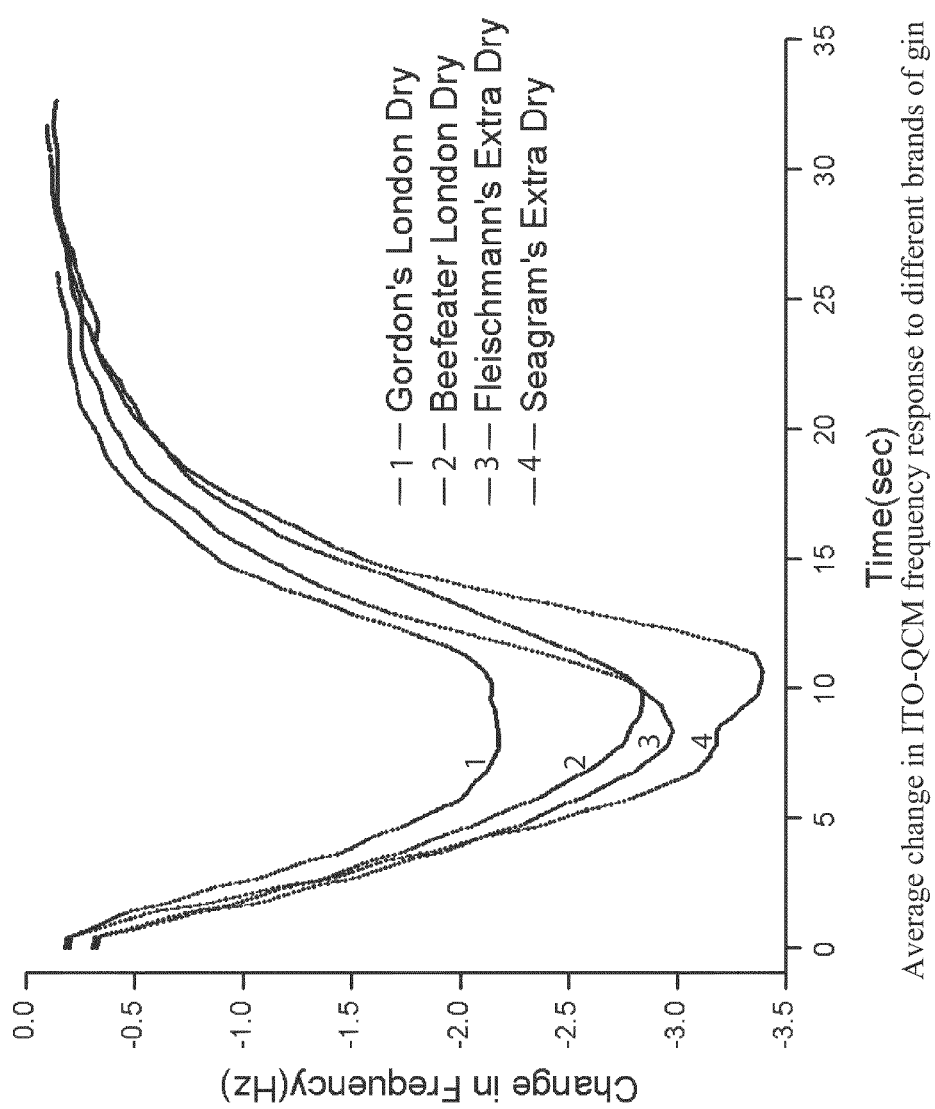
FIG. 42 is a graph of average change in ITO-QCM frequency response for different brands of gin.

Additionally, graphs showing average changes in ITO-QCM frequency response for various beverages are provided in FIGS. 26, 32, 34, 36, 38 and 40. In particular, FIG. 17 illustrates the average change in ITO-QCM frequency response to odors from each category of tested alcoholic beverages. FIG. 26 illustrates a composite average of ITO-QCM odor measurements with 5 different brands of vodka having two different percentages of alcohol. FIG. 32 illustrates average change in ITO-QCM frequency response for Absolut® brand vodkas having 40% alcohol and different flavors. FIG. 34 illustrates average change in ITO-QCM frequency response for different brands of whiskey. FIG. 36 illustrates average changes in ITO-QCM frequency response for different brands of brandy. FIG. 38 illustrates average change in ITO-QCM frequency response for different brands of rum. FIG. 40 illustrates average change in ITO-QCM frequency response for different brands of tequila. FIG. 42 illustrates average change in ITO-QCM frequency response for different brands of gin.

PCA, a well-known statistical analysis, takes multi-variable input data represented by a chart and re-maps the original data onto a new coordinate system that is more efficient at representing the variation contained within the data set. The steps for performing PCA analysis on data such as that given in the tables of FIGS. 19 through 23 are well known in the art and covered in many textbooks on the subject. While the ITO-QCM output measurement graphs, and/or the raw data in FIGS. 9 through 23, reveal no intuitive way to classify the various odors, PCA allows similarities and differences among the analytes measured to be seen as shown in FIGS. 24, 25, 27, 28-31, 33, 35, 37, 39, 41, 43.

Figure 24:
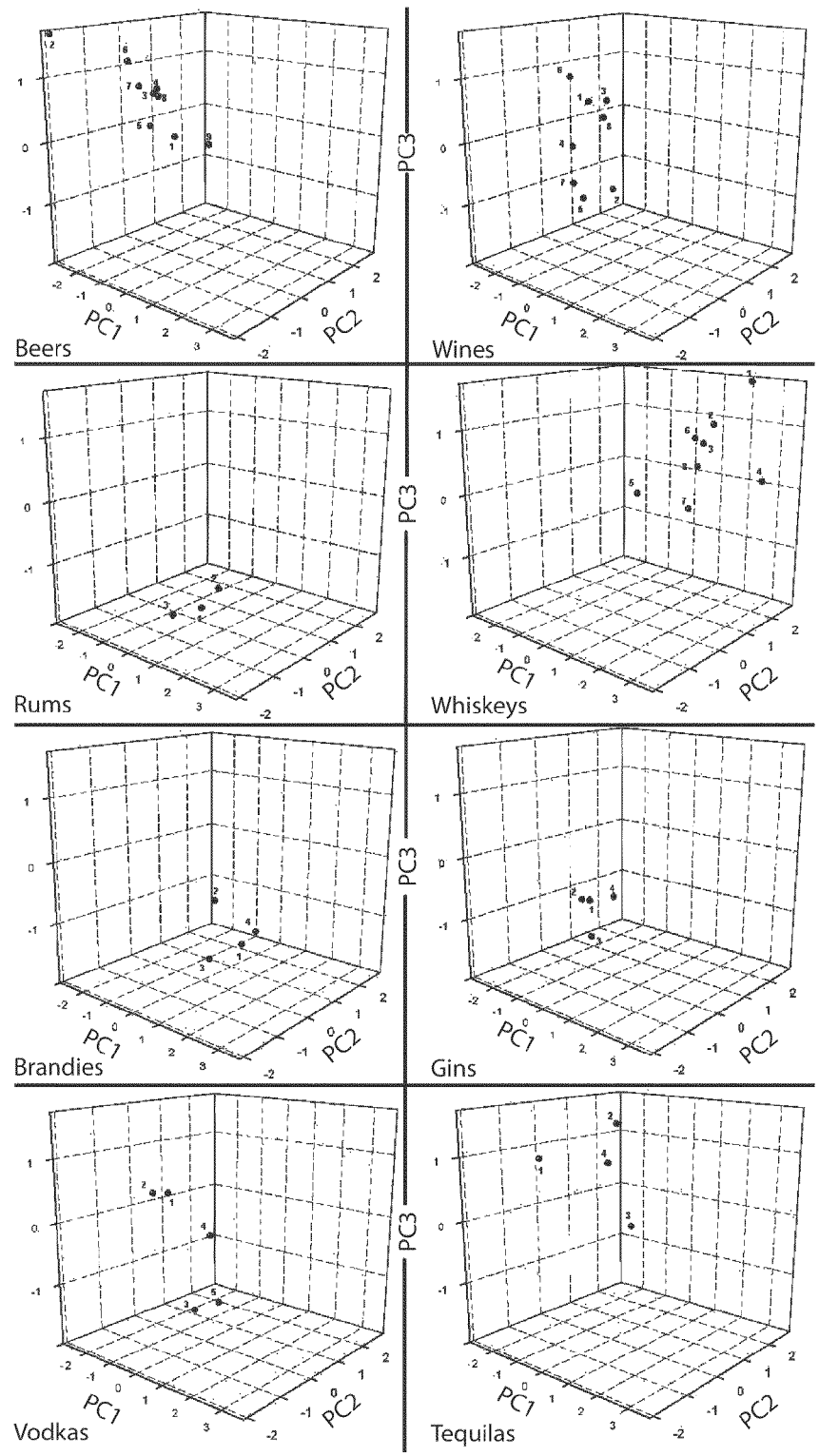
FIG. 24 is principal component analysis (PCA) plots of ITO-QCM odor measurements for beers, wines, and liquors.
Figure 25:
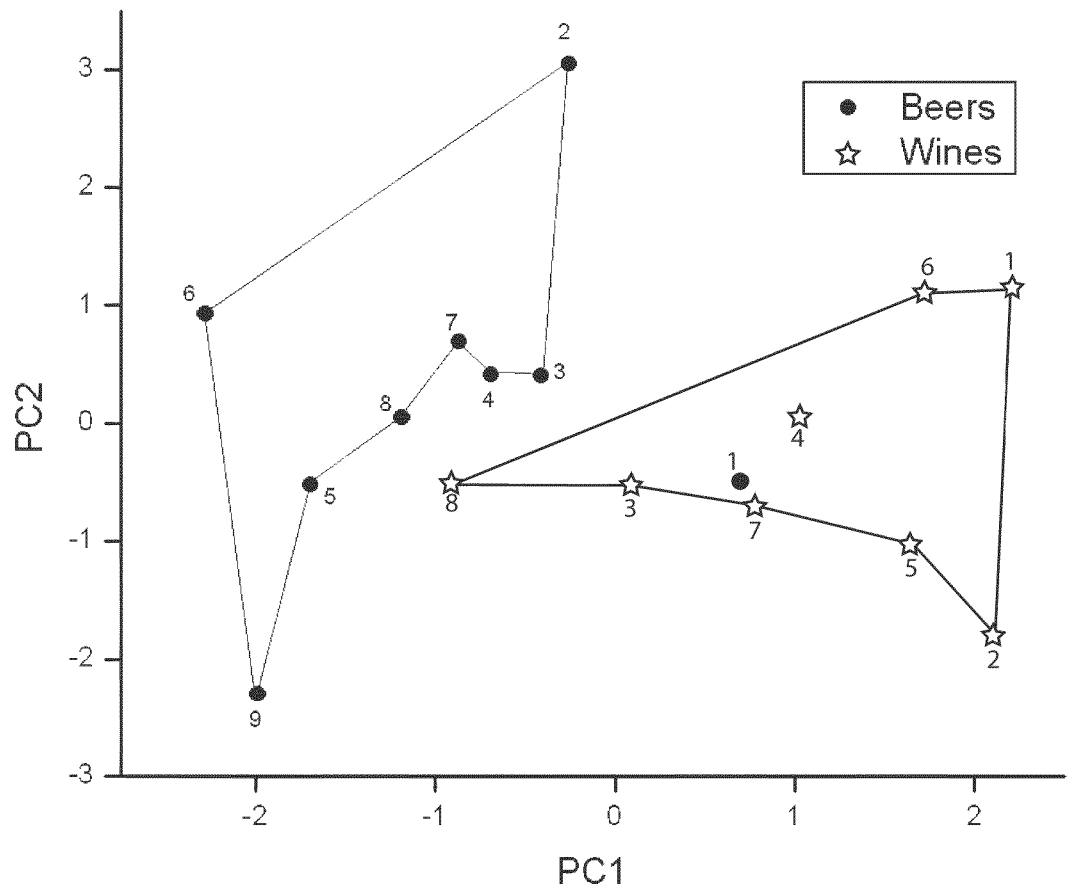
FIG. 25 is PCA plots of ITO-QCM odor measurements for beers and wines.
Figure 27:
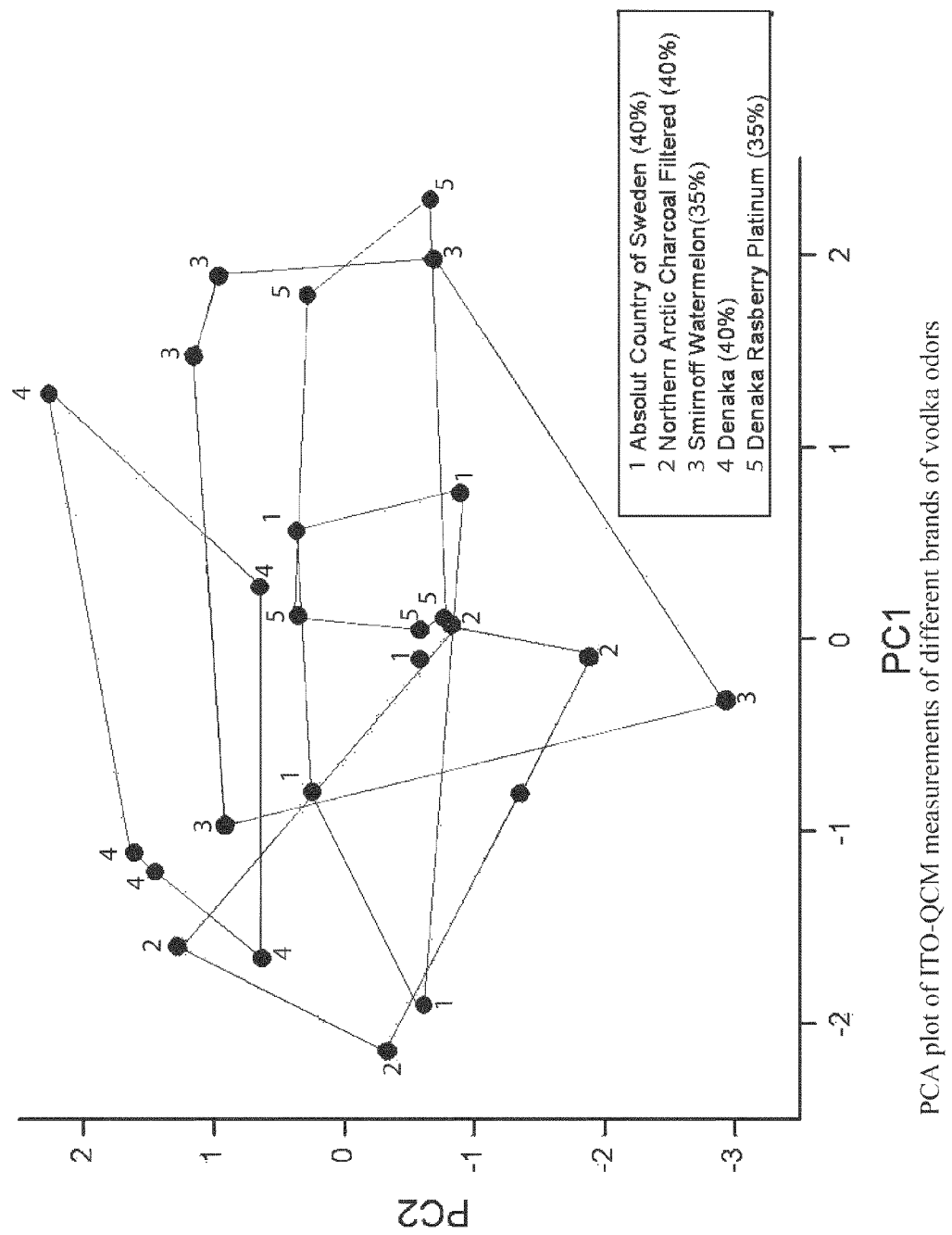
FIG. 27 is PCA plots of ITO-QCM odor measurements for different brands of vodka.
Figure 28:
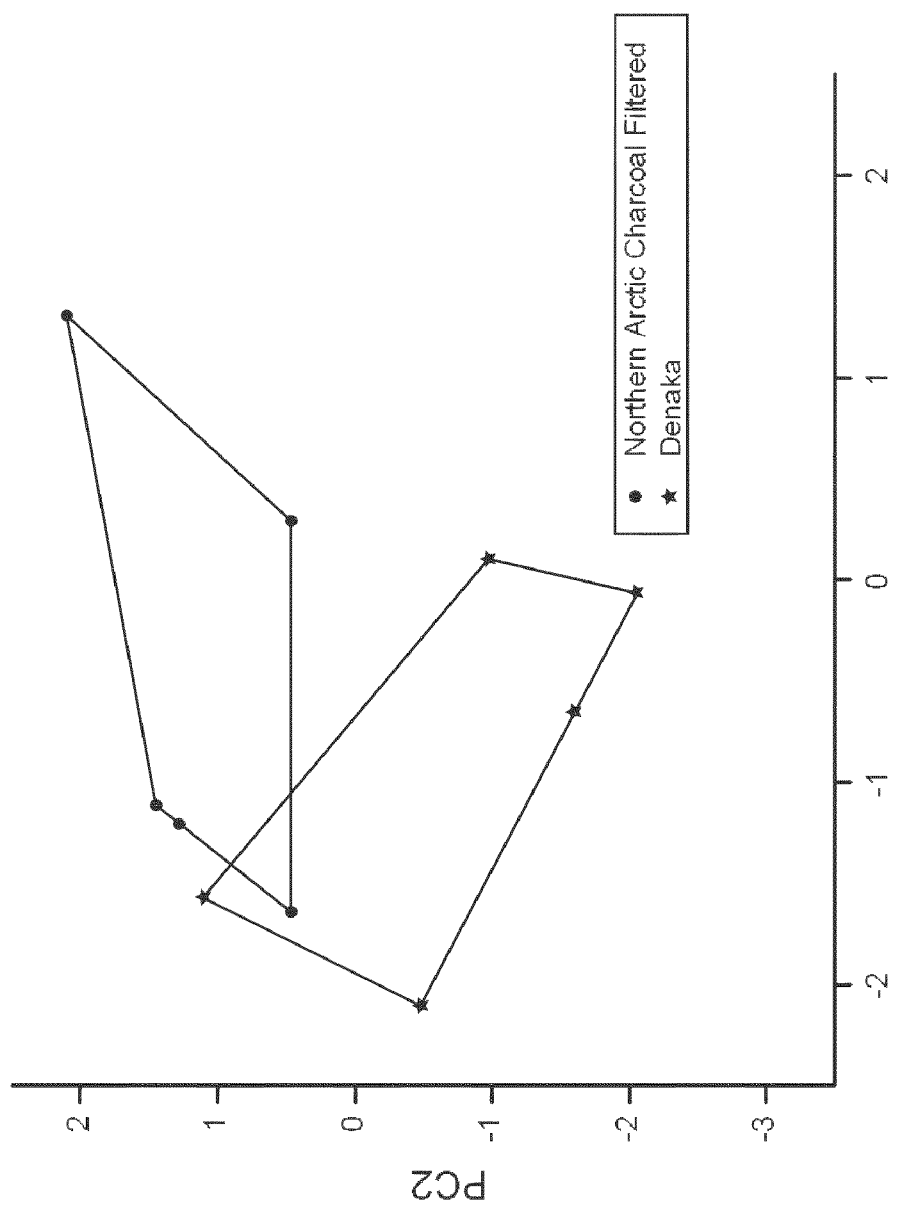
FIG. 28 is PCA plots of ITO-QCM odor measurements for Northern Arctic Charcoal Filtered and Denaka vodkas.
Figure 29:
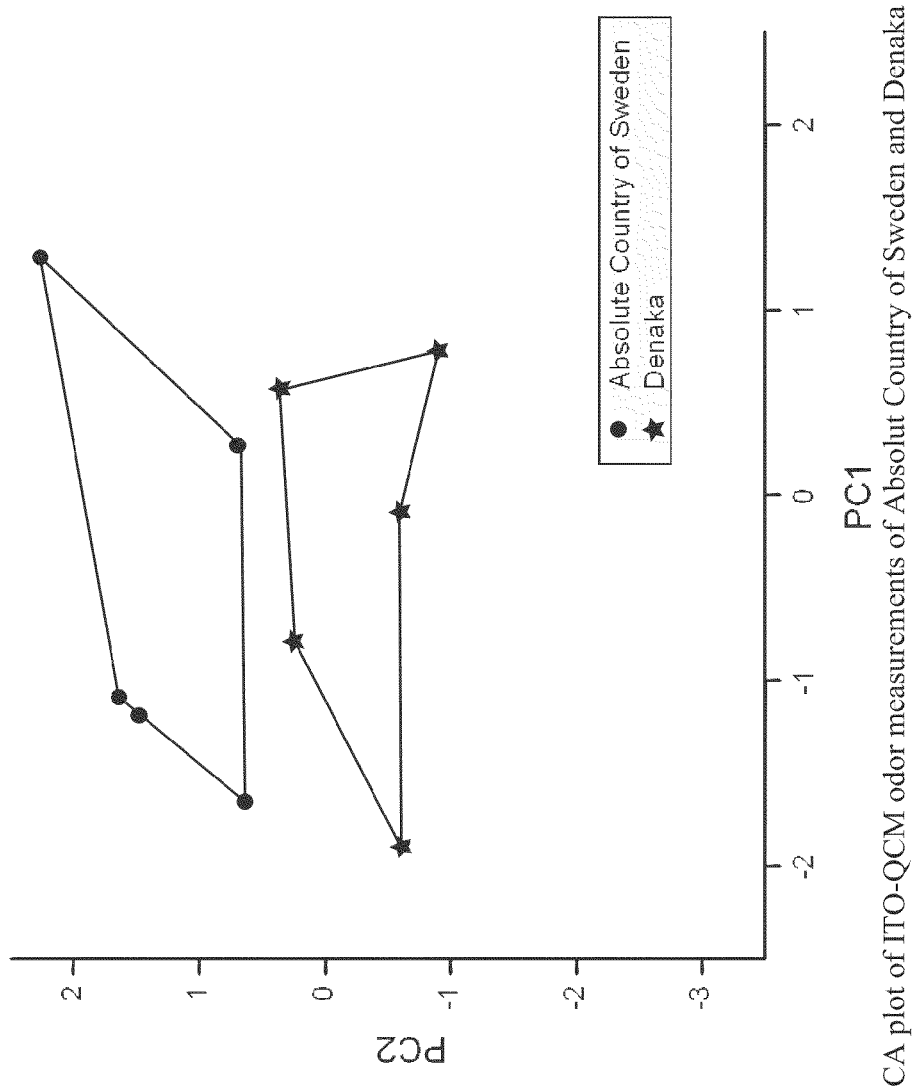
FIG. 29 is PCA plots of ITO-QCM odor measurements of Absolut Country of Sweden and Denaka vodkas.
Figure 30:
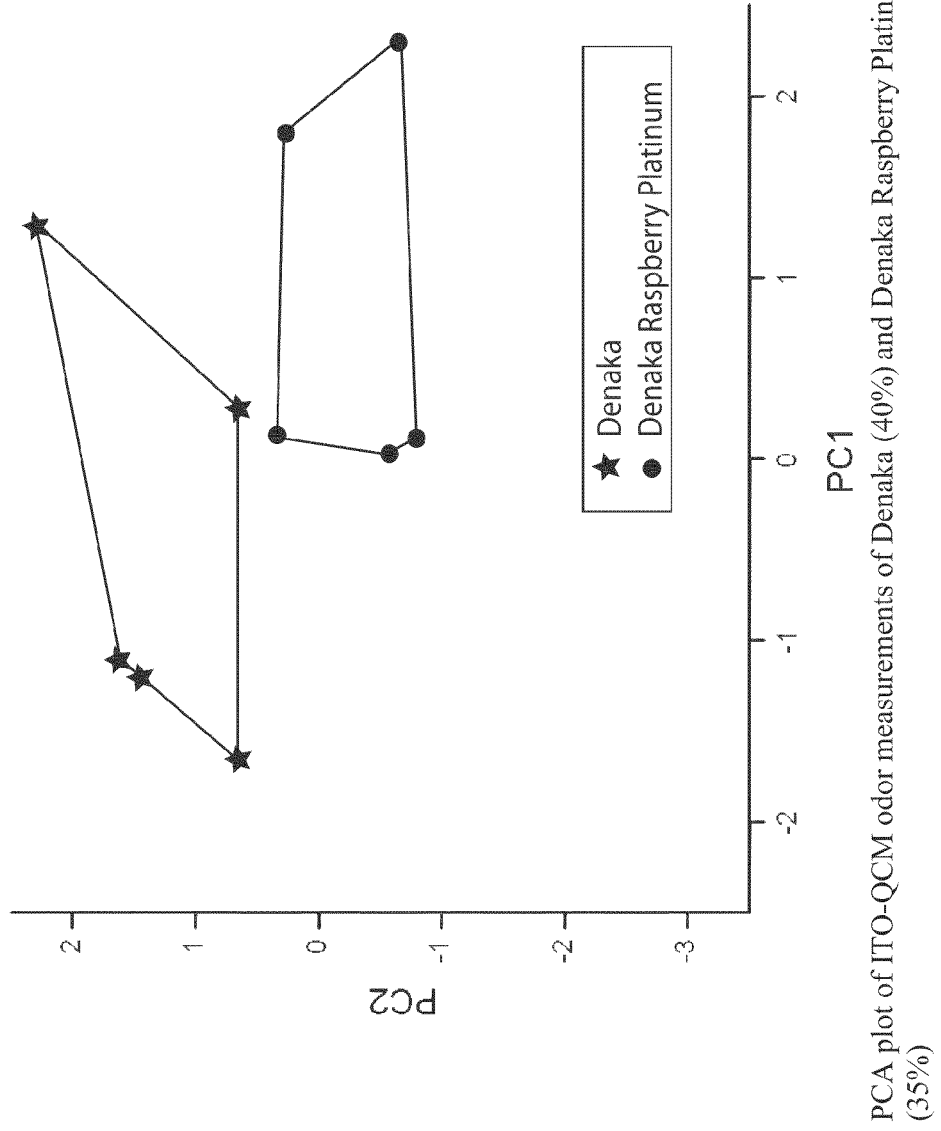
FIG. 30 is PCA plots of ITO-QCM odor measurements of Denaka (40%) and Denaka Raspberry Platinum vodkas (35%)
Figure 31:
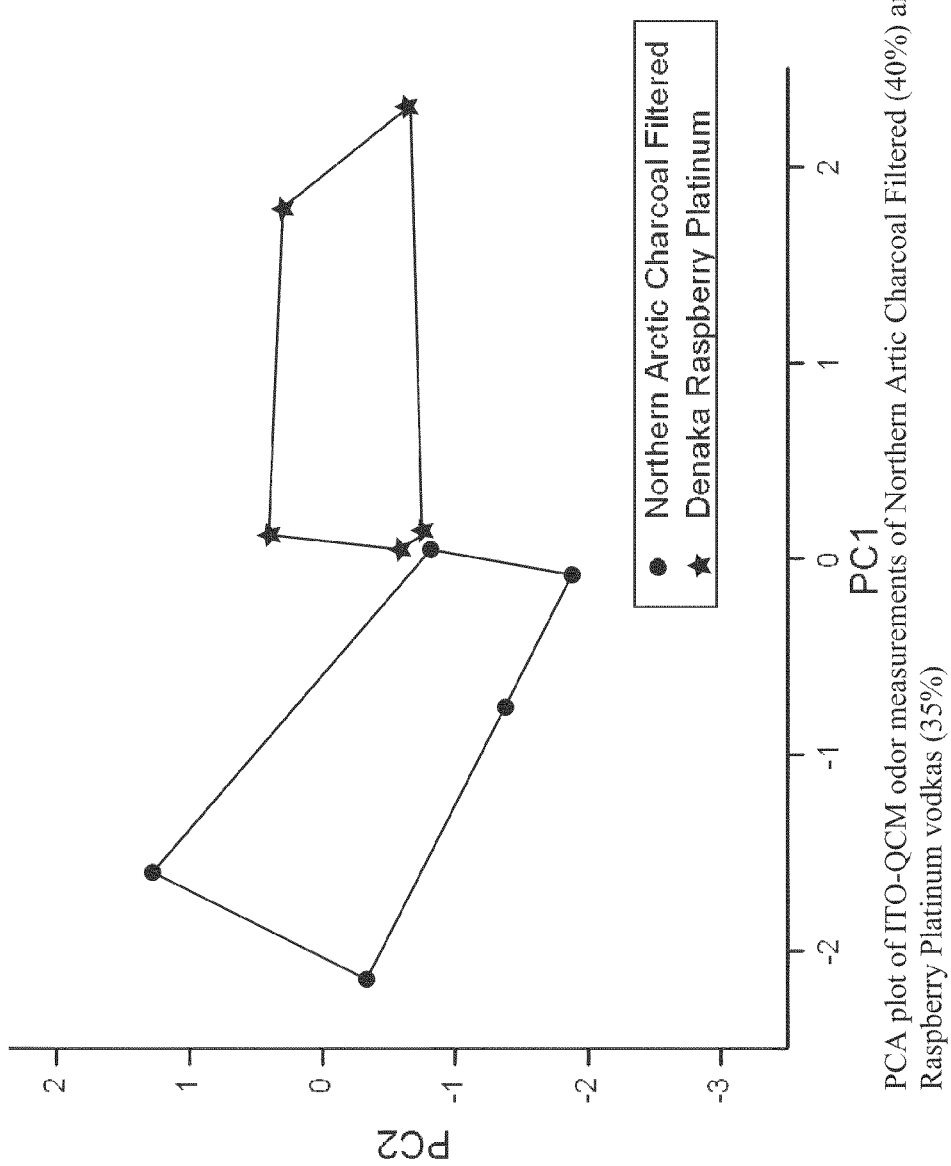
FIG. 31 is PCA plots of ITO-QCM odor measurements of Northern Arctic Charcoal Filtered (40%) and Denaka Raspberry Platinum vodkas (35%)
Figure 33:
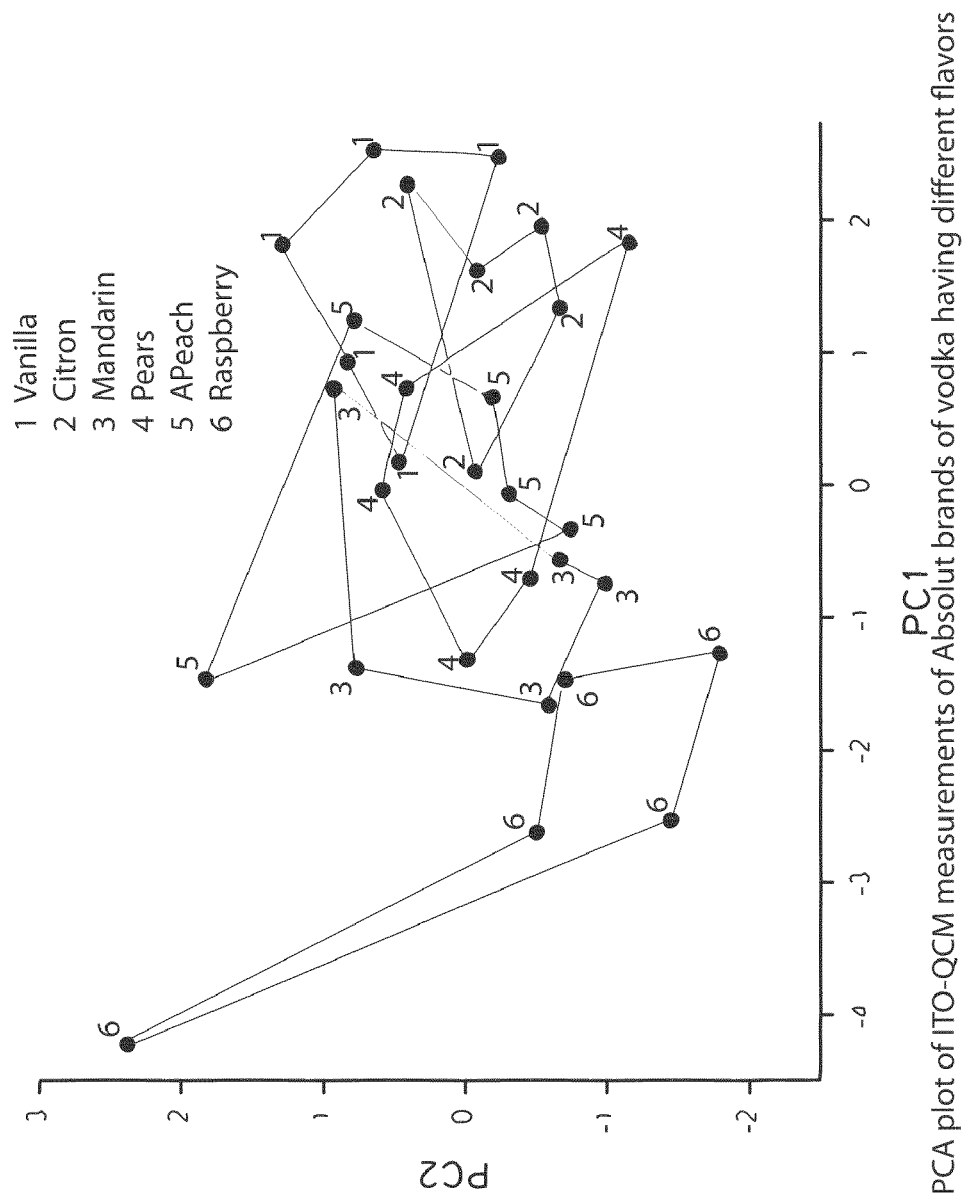
FIG. 33 is PCA plots of ITO-QCM measurements of Absolut brand vodkas having different flavors.
Figure 35:
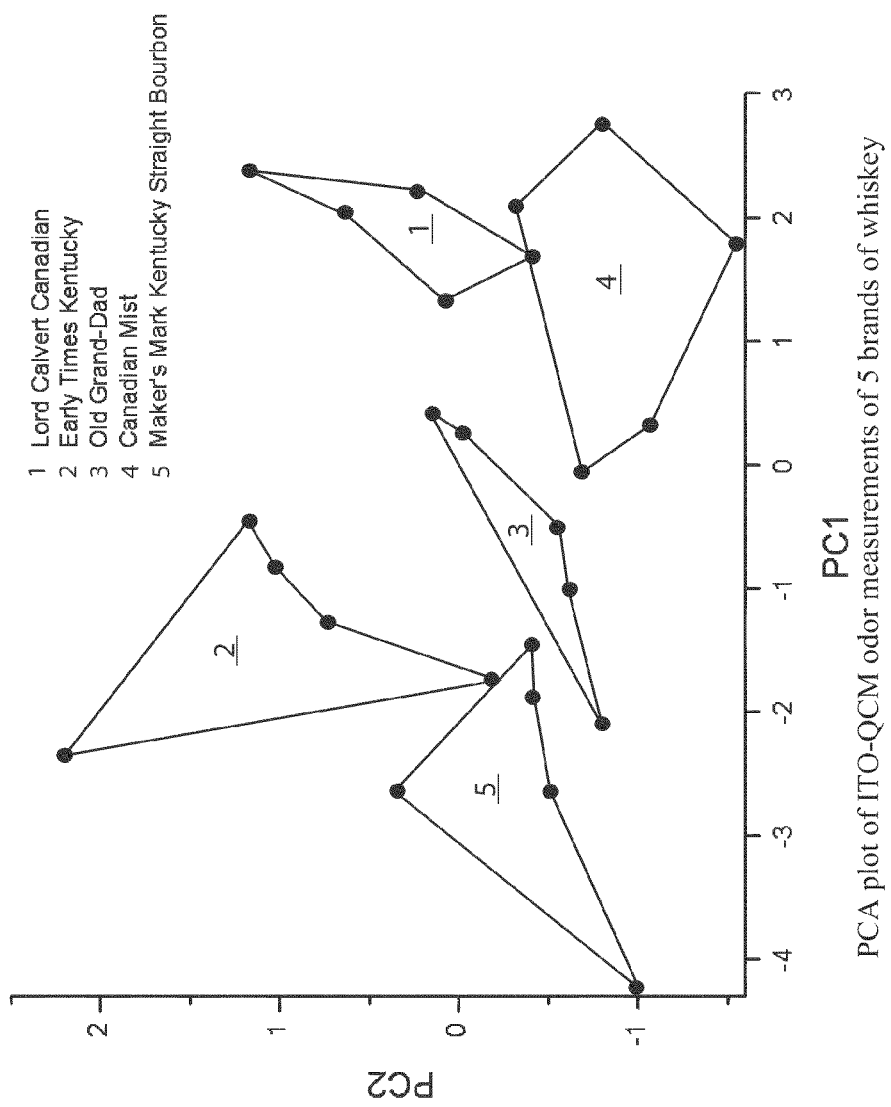
FIG. 35 is PCA plots of ITO-QCM odor measurements of 5 brands of whiskey.
Figure 37:
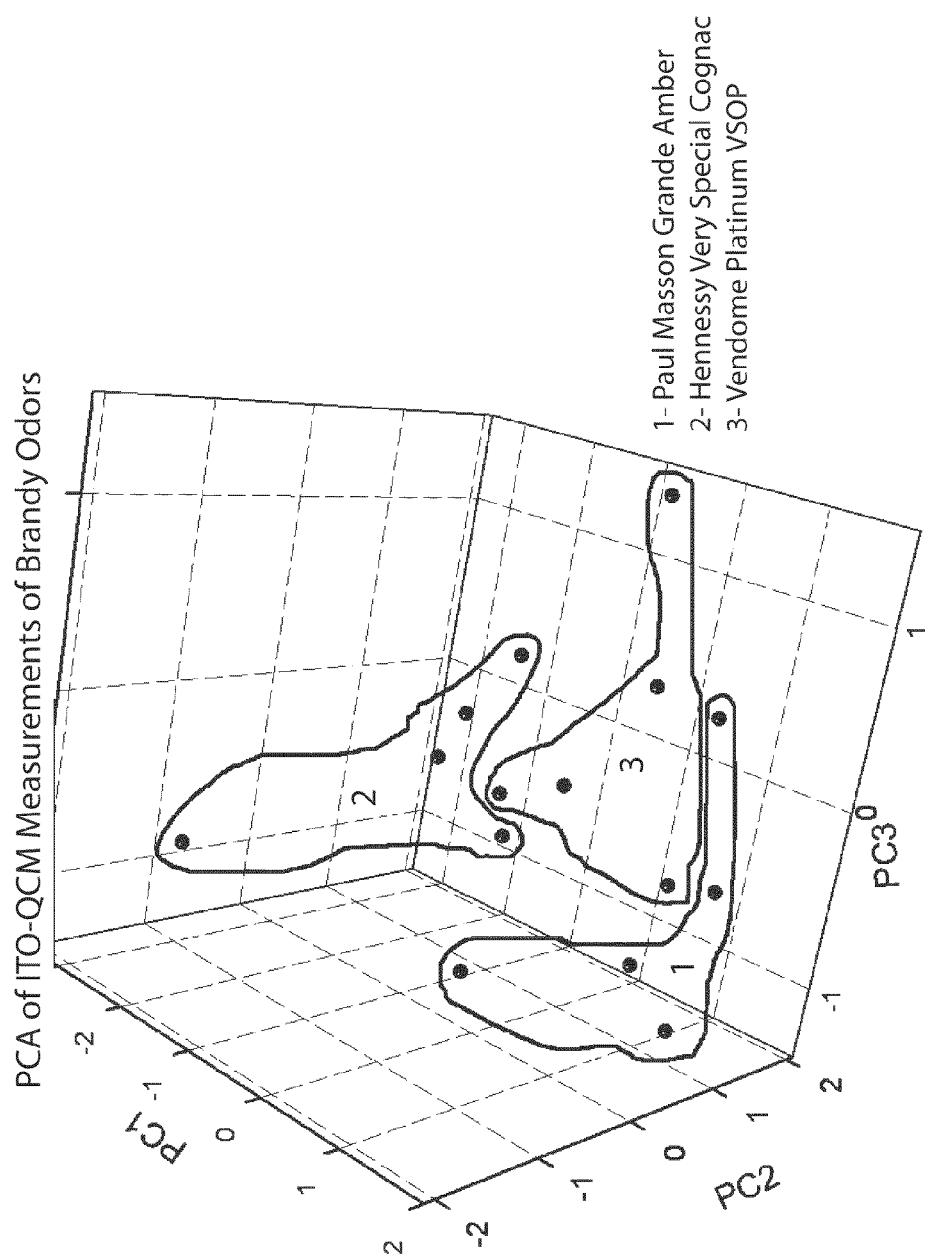
FIG. 37 is 3-D PCA plots of ITO-QCM odor measurements for three different brands of brandy.
Figure 39:
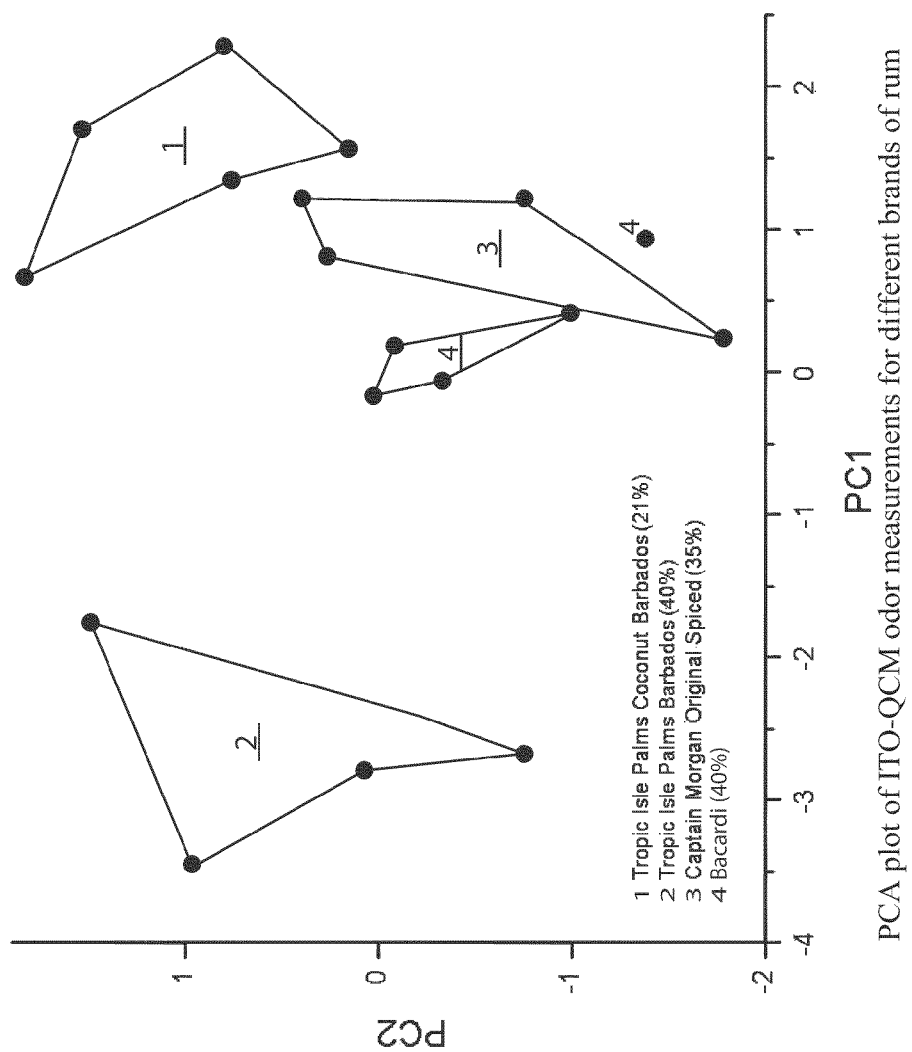
FIG. 39 is PCA plots of ITO-QCM odor measurements for different brands of rum.
Figure 41:
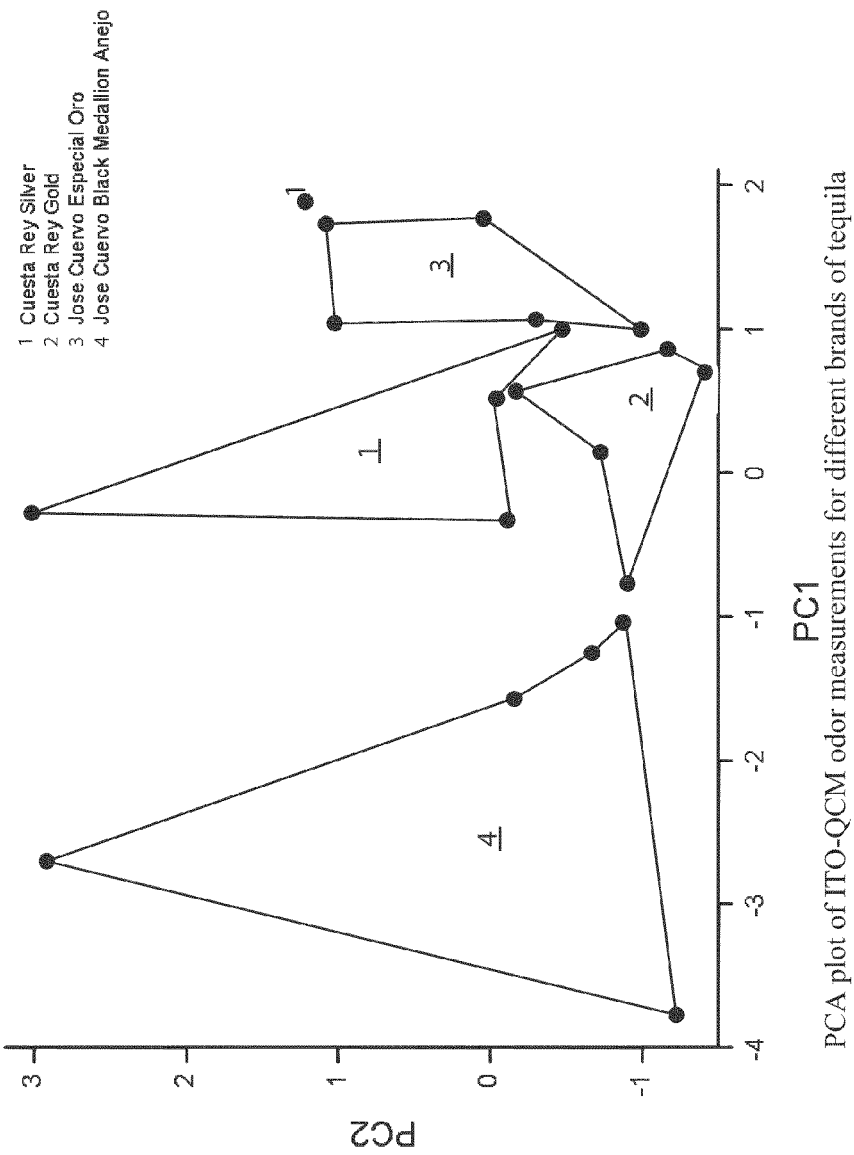
FIG. 41 is PCA plots of ITO-QCM odor measurements for different brands of tequila.
Figure 43:
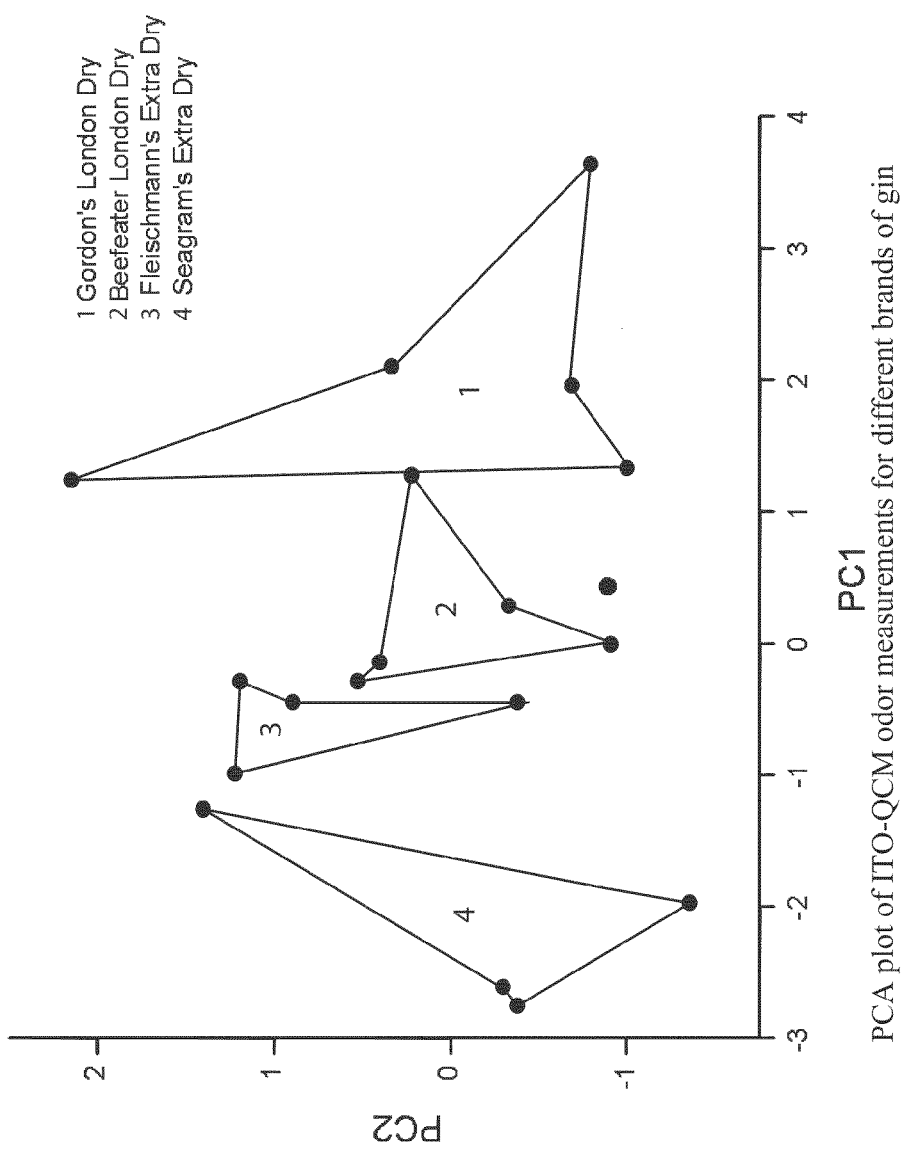
FIG. 43 is PCA plots of ITO-QCM odor measurements for different brands of gin.

In particular, the PCA plots of ITO-QCM measurements for the beverage data show isolation of clusters of all the tested alcoholic beverages. Hence, it shows good selectivity for each sample. Illustratively, FIG. 24 provides PCA plots of ITO-QCM odor measurements for beers, wines, and liquors. FIG. 25 provides PCA plots of ITO-QCM odor measurements for beers and wines. FIG. 27 provides PCA plots of ITO-QCM odor measurements for different brands of vodka. FIG. 28 provides PCA plots of ITO-QCM odor measurements for Northern Arctic Charcoal Filtered and Denaka vodkas. FIG. 29 provides PCA plots of ITO-QCM odor measurements of Absolut Country of Sweden and Denaka vodkas. FIG. 30 provides PCA plots of ITO-QCM odor measurements of Denaka (40%) and Denaka Raspberry Platinum vodkas (35%). FIG. 31 provides PCA plots of ITO-QCM odor measurements of Northern Arctic Charcoal Filtered (40%) and Denaka Raspberry Platinum vodkas (35%). FIG. 33 provides PCA plots of ITO-QCM measurements of Absolut brand vodkas having different flavors. FIG. 35 provides PCA plots of ITO-QCM odor measurements of 5 brands of whiskey. FIG. 37 is 3-D PCA plots of ITO-QCM odor measurements for three different brands of brandy. FIG. 39 provides PCA plots of ITO-QCM odor measurements for different brands of rum. FIG. 41 provides PCA plots of ITO-QCM odor measurements for different brands of tequila. FIG. 43 are PCA plots of ITO-QCM odor measurements for different brands of gin.

A nanocrystalline-thin film ITO-QCM sensor according to principles of the invention detected odors of various beers, wines, and liquors, producing data which allowed principal component analysis (PCA) to group and identify these beverages. The nanocrystalline ITO (as a thin film sensor), and the QCM (as a transducer) combined to show the change in frequency responses and surface resistances as a function of time for each odor tested. ITO-QCM sensors thus enable detection, classification and production of a unique signature for each category of alcohol beverages such as beer, wine, vodka, whiskeys, brandy, rums, tequila and gins via different measured parameters such as change in frequency, integrated frequency response, initial response slope, average return to baseline slope and transient response time. ITO-QCM odor sensors also measure and give a unique parameter of integrated surface resistance response. The change in surface resistance for all the alcoholic beverages samples, except rums was positive. Rums show initially little positive peak and then large negative peak value.

The data presented in PCA plots show clear formation of separate clusters in the PCA variable space. Any unknown sample within the previously measured set of samples can be identified/detected by measuring it using ITO-QCM odor sensors and looking up its position on a PCA plot. Of course, the lookup operation may be performed manually by reference to PCA plots of tested samples or automated using software and collected test sample data. PCA analysis showed selectivity for each group of alcoholic beverage odors and also for different brands for liquor samples, except vodka. In sum, ITO-QCM odor sensors and PCA distinguished between beer and wine. ITO-QCM odor sensors and PCA also distinguished limited brands and flavors of vodka, but may not identify all flavors of same brand having the same amount of alcohol due to the inherent nature and extensive filtration of vodkas. ITO-QCM odor sensors and PCA also identified different brands of whiskeys, gins, brandy, rums and tequila.

Based upon the foregoing, a method of detecting a gas using a ITO-QCM system, as described above, entails first exposing the ITO-QCM to a gas. Next, one or more parameters such as change in frequency, integrated frequency response, initial response slope, average return to baseline slope, transient response time and integrated surface resistance response are measured using the ITO-QCM. Third, the measured parameters are compared to previously determined parameters for tested gaseous compounds until a substantial match is found. Alternatively, a PCA plot may be constructed from the measured parameters, in which case the constructed plot may be compared with previously determined PCA data for tested gaseous compounds until a substantial match is found.

Referring now to FIGS. 44 to 56 graphs, plots and data pertaining to measured parameters for explosives are provided. Each explosive sample was contained in a cone frustum-shaped plastic (e.g., polyethylene) container with a sealed lid. The base radius of the container was 2.5 cm. The top radius of the container was 3.0 cm. The height of the container was 7.5 cm. The total volume of the container was 178.7 cm$^3$. The explosive samples were tested using an ITO-QCM sensor at a room temperature of about 20±2° C. Explosive sample vapors were measured by dynamic headspace analysis, whereby vapors from a sample are released into the headspace of a tightly sealed container until reaching a saturation equilibrium concentration. To increase the surface of the sample exposed to the air inside the sample container and accelerate the release of vapors into the headspace and the sample was gently shaken before each sample measurement and with the container lid closed. The headspace was then sampled with an open container. The ITO-QCM sensor was positioned upside-down (i.e., with the exposed ITO-QCM crystal facing downward) in open air above the exposed headspace for a determined time period (e.g., 10 seconds) and then removed. As the crystal was held upside-down, an increase in mass loading on the surface due to vapor adsorption would be indicated by an increase in the resonance frequency instead of the usual decrease in resonance frequency with an increase in mass loading when the quartz crystal unit is positioned facing up. The volumes for each explosive sample were not equal, but were adequate enough to significantly populate the headspace of the sample container with vapor in a short period of time of two minutes or so.

Various explosive material samples were tested using an ITO-QCM sensor in accordance with principles of the invention. One such material is Compound A5, a fine grain white powder. A mass of 12.2 g was tested. Composition A (also known as Compound A) consists of 91% RDX melted with 9% wax. Five varieties of Composition A have been developed and designated as Composition A-1, A-2, A-3, A-4 and A-5. Compositions A-4 and A-5 have a desensitizer added.

Another tested explosive material is Compound B, which is brittle and brown. Rectangular pieces, approximately 1 cm length and width, approximately 2 mm in thickness, with a mass of 9.3 g were tested. Composition B is an explosive consisting of castable mixtures of RDX and TNT. It is used as a burster in artillery projectiles, rockets, land mines, and hand grenades. The standard ratio of ingredients (by weight) is 59.5% RDX and 39.5% TNT, together with an additional 1% wax.

Another tested explosive material is Hexolite. This sample was a brown cylinder, 3 cm long, 2 cm diameter, with some residue sticking along edges of sample container, and a mass of 15.6 g. Hexolite is an explosive composed of TNT, RDX, aluminum powder, and calcium chloride. It is used in the heads of missiles.

Another tested explosive material is PETN (Pentaerythritol Tetranitrate): The tested sample was a slightly off-white, slightly beige, and fine grain powder with a mass of 7.3 g. The chemical formula of this compound is $C_5H_8N_4O_{12}$. Its molecular weight is 316.134 g/mole and vapor pressure at 25° C. is $1.035\times10^{-10}$ mm Hg. PETN is used as a base charge in blasting caps and detonators as the core explosives in detonating cord, in booster charges, in plastic explosives, and as an ingredient in other explosives. The chemical stability of PETN is very high and is considered to be more stable than all other nitrate esters.

Another tested explosive material is RDX (Hexahydro-1, 3,5-trinitro-1,3,5-triazine). This tested sample was a white powder that looks like confectionary sugar, with a mass of 9.2 g. Its chemical formula is $C_3H_6N_6O_6$. Its molecular weight is 222.116 g/mole and vapor pressure is $4.1\times10^{-9}$ mm Hg at 20° C. RDX stands for Royal Demolition Explosive. RDX is also known as cyclonite and hexogen. It is one of the most widely used military explosives used today. It has high chemical stability, lower than that of TNT, but an explosive power much greater than TNT. RDX is considerably more susceptible than TNT to shock detonation. RDX is used as a component in mixtures with other explosives such as TNT and as a plastic explosive. A well-known plastic explosive, Semtex is based on RDX and PETN. Mixtures of RDX and wax are used for booster charges in many military types of ammunition, especially in artillery shells.

Another tested explosive material is TNT (2,4,6-Trinitrotoluene). The tested sample was a light yellow powder with some pebble-like pieces, with a mass of 10.3 g. Its chemical formula is $C_7H_5N_3O_6$. Its molecular weight is 227.132 g/mole and vapor pressure is $8.02\times10^{-6}$ mm Hg at 25° C. TNT is the most widely used military explosive. Its main features include low melting point, stability, low sensitivity to impact; friction and high temperature and its relative safe methods of manufacture.

Another tested explosive material is 75% (pbw) Tetryl (2,4,6-trinitrophenylmethylnitramine) and 25% TNT: The tested sample was a yellow colored cylinder, 3 cm long, 2 cm diameter with some residue sticking along edges of sample container, and a mass of 16.3 g. Its chemical formula is $C_7H_5N_5O_8$. The molecular weight of Tetryl is 287.143 g/mole. The vapor Pressure of Tetryl is $5.66\times10^{-8}$ mm Hg at 25° C. Tetryl is a sensitive explosive compound used to make detonators and explosive booster charges. While Tetryl is no longer manufactured or used in the United States, it can still be found in legacy munitions.

Figure 44:
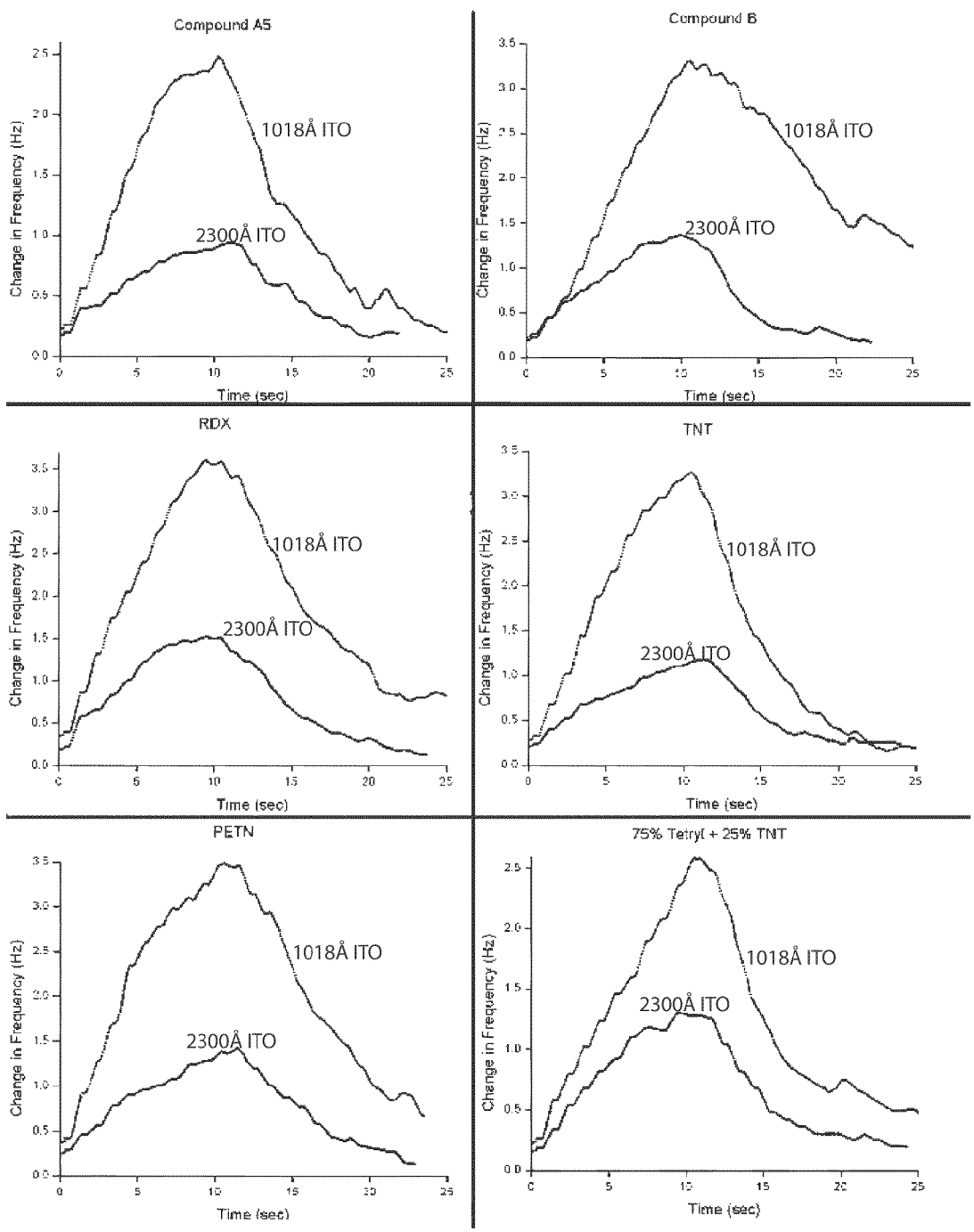
FIG. 44 are graphs comparing ITO-QCM explosive sample measurements with 1018 Å ITO and 2300 Å ITO thickness quartz crystals.
Figure 45:
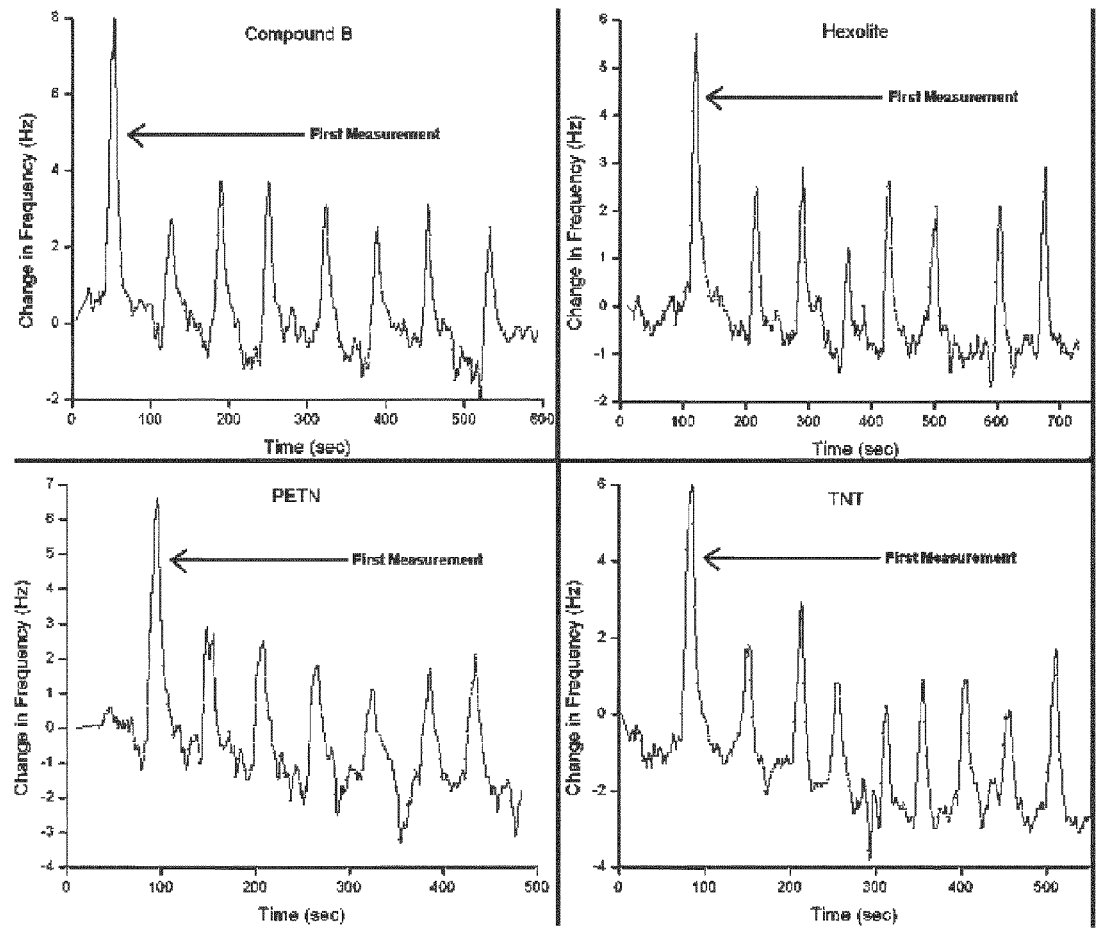
FIG. 45 are graphs of ITO-QCM measurements of explosive samples, with the first measurements highlighted.

ITO-QCM measurements of the explosive vapor samples were performed with two different ITO-coated AT-cut 5 MHz quartz crystals. One quartz crystal had an ITO thickness of 2300 Å, while the other quartz crystal had an ITO thickness of 1018 Å. FIG. 44 shows a comparison of the average of five 10-second measurements of each explosive sample with both the 2300 Å thick ITO quartz crystal and the 1018 Å thick ITO quartz crystal. ITO over the quartz crystal showed a higher change in frequency response rate for all explosive samples compared to the thicker 2300 Å ITO film. The first measurement in a series of measurements for the explosive samples showed the greatest change in frequency response, as shown in FIG. 45. The greater change in frequency for first measurements was attributed to a longer vapor build-up time in the sample container for the first measurement (1 hour+) compared to subsequent measurement intervals of about 2 to 3 minutes.

The powder explosive samples (Compound A5, PETN, RDX, TNT) provide roughly the same magnitude change in frequency response as the non-powder explosive samples (Compound B, Hexolite, 75% Tetryl+25% TNT). Based on the Sauerbrey equation, for a QCM with a 5 MHz AT cut quartz crystal having an active ITO thin film with a surface area of 1 cm$^2$, a change of 1 Hz in frequency corresponds to an increase in mass of 17.7 ng/cm$^2$. Thus, for the aforementioned crystal, a 1 Hz shift corresponds to 17.7 ng added mass.

Figure 46:
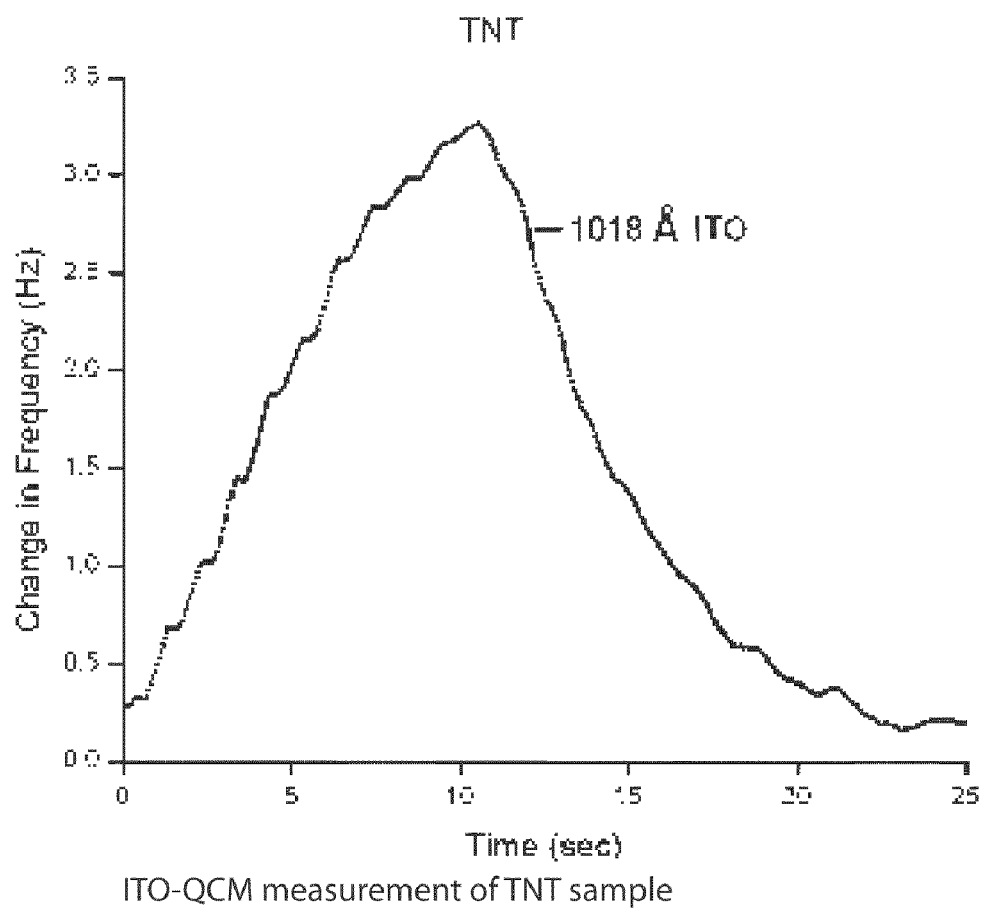
FIG. 46 is a graph of ITO-QCM measurement of a TNT sample.

Referring now to FIG. 46, the average of five measurements of change in frequency of an ITO-QCM sensor when exposed to a TNT sample container headspace for 10 seconds is provided. The average peak change in frequency for the 10-second measurement was approximately 3 Hz, which corresponds to an increase in mass of 53 ng. The average peak change in frequency responses for each of the explosive samples ranged from approximately 2.5 Hz to 3.5 Hz.

TNT has an equilibrium saturated vapor pressure concentration of 70 ng/L at 20° C. Thus, a sample container volume of 0.178 L corresponds to a maximum TNT vapor mass of 12.5 ng, which is insufficient to account for the observed ITO-QCM change in frequency, and the corresponding change in mass observed for the TNT sample, even if 100% of the explosive vapor was adsorbed on to the ITO of the quartz crystal. Impurities in the test sample help account for the change in frequency. Among impurities typically found in explosive-grade TNT are 1,3-Dinitrobenzene; 2,4-Dintrotoluene; and 2,4,6-Trinitrotoluene, each of which has a higher vapor pressure (i.e., than that of TNT, as shown in the table of FIG. 47. Thus the impurities yield higher vapor concentrations than that produced by the 2,4,6-TNT alone.

Figure 48:
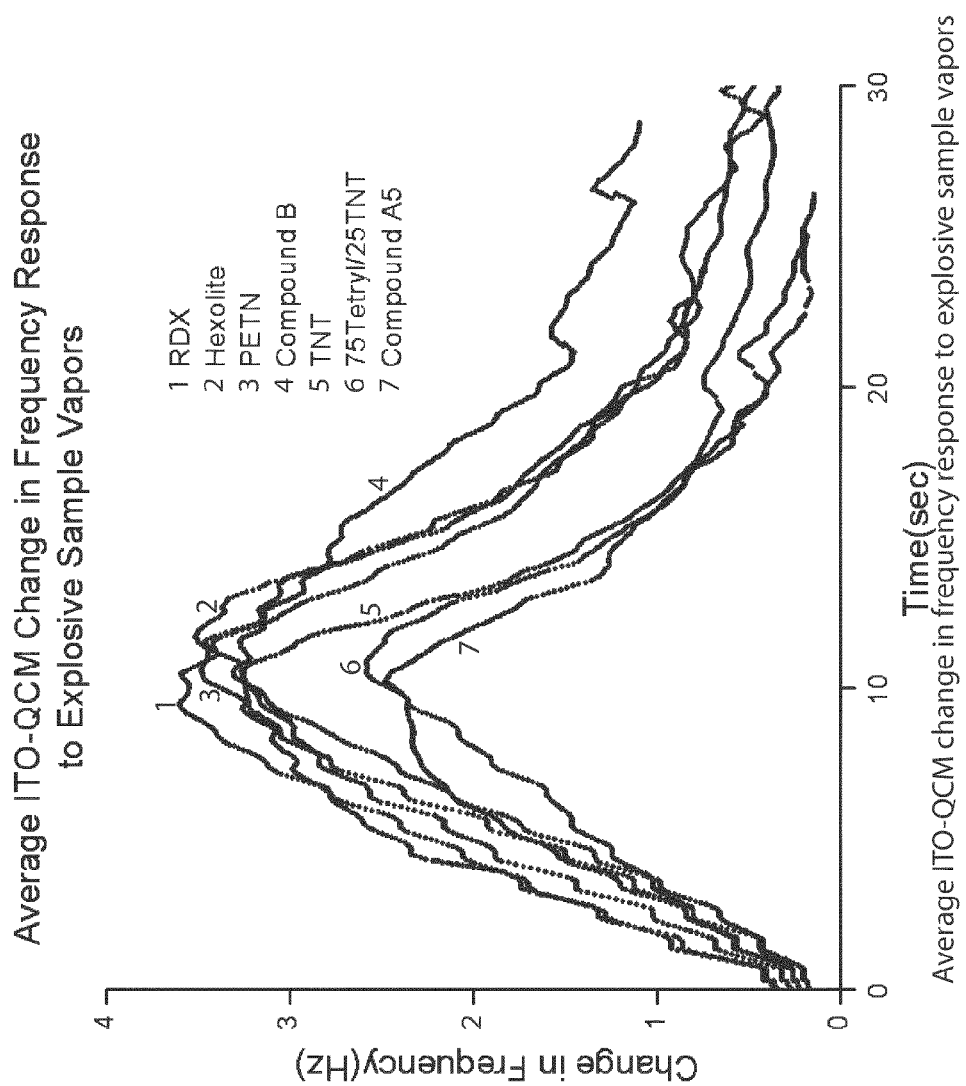
FIG. 48 is a graph of average ITO-QCM changes in frequency response for explosive sample vapors.

The observed ITO-QCM changes in frequency (as shown in FIG. 48) and the corresponding observed changes in mass for the RDX and PETN explosive vapor samples are also far more than what can be accounted for by the known equilibrium vapor pressure concentrations for each. RDX and PETN have even lower equilibrium saturated vapor pressure concentrations than TNT, at 0.04 ng/L and 0.09 ng/L, respectively. Such concentrations would correspond to saturated vapor pressure masses of 0.00712 ng for RDX and 0.01602 ng for PETN in a 0.178 liter container. Both of these values are far lower than the observed ITO-QCM change in frequency, and the corresponding observed change in mass for the RDX and PETN samples. Here, taggants can account for the difference. Vapor detection of plastic explosives is difficult because of the low vapor pressures of explosive components (i.e., RDX and PETN) present in the complex elastomeric matrix. To facilitate vapor detection of plastic explosives, detection agents (taggants) with higher vapor pressures can be added to bulk explosives during manufacture. Such taggants are typically high vapor pressure compounds, which evaporate much more easily than the explosive itself Examples of such taggants are Ethylene Glycol Dinitrate (EGDN), ortho-mononitrotoluene (o-MNT), para-mononitrotoluene (p-MNT), and dimethyldinitrobutane (DMNB). Each of these substances has a vapor pressure that facilitates vapor detection of explosives, particularly plastic explosives.

Likewise, plastic explosives such as Semtex and C4, which contain high-molecular-weight chemicals—pentaerythritol tetranitrate (PETN) and cyclotrimethylene Trinitramine (RDX)—are rarely detectable by vapor-phase measurements. Because of this insensitivity, and by international accord, all manufacturers of plastic explosives now include a volatile taggant compound, such as 2,3-dimethyl-2,3-dinitrobutane (DMNB) or mononitrotoluene (MNT), which facilitates identification by vapor detection systems and canines. Impurities and vapor taggants from RDX and PETN samples may be detected by the ITO-QCM measurements.

FIG. 48 shows average change in frequency measurements for each explosive sample. Five 10-second sample exposures of an ITO-QCM were averaged for each sample. Measurements were made with a 1018 Å thick ITO quartz crystal. The average maximum change in frequency for all explosive samples ranged from about 2.5 Hz to 3.5 Hz.

Figure 49:
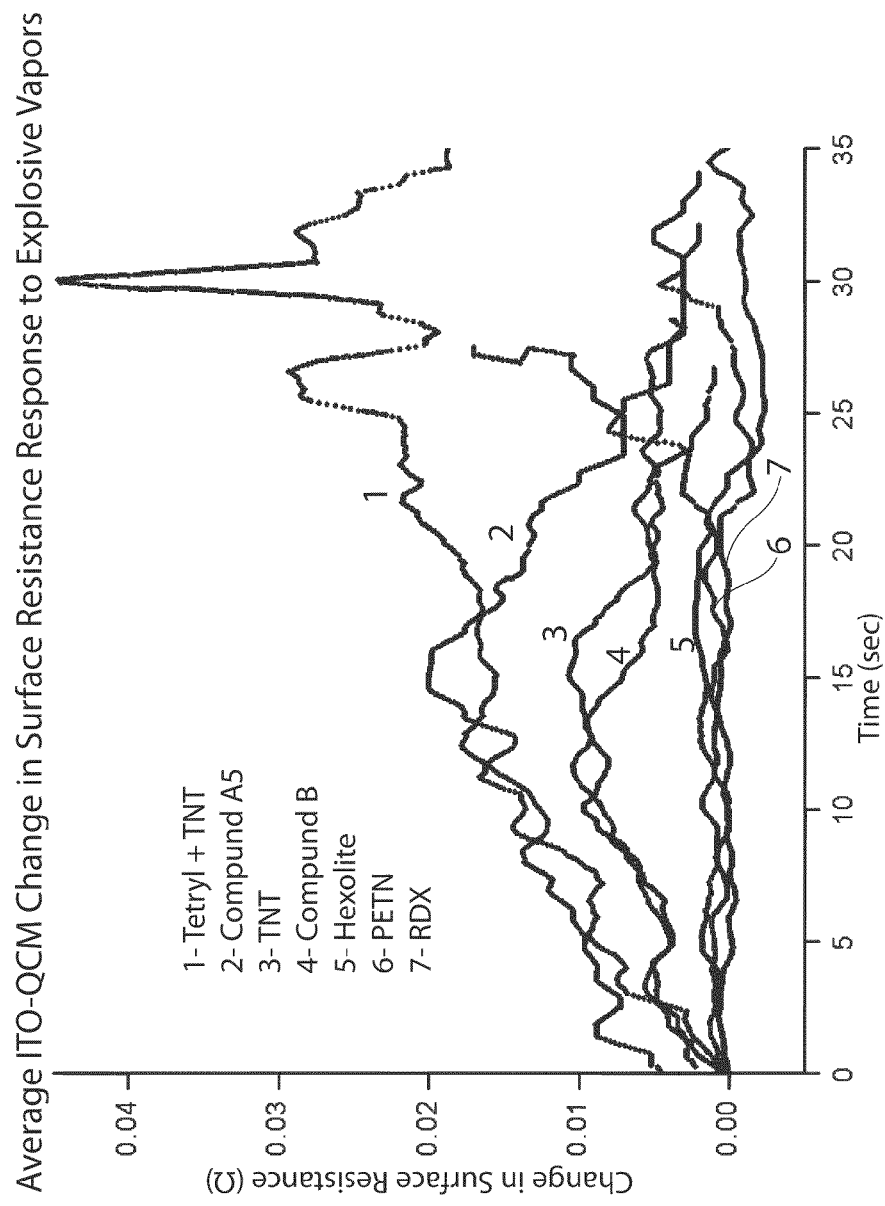
FIG. 49 is a graph of average ITO-QCM changes in surface resistance response to explosive sample vapors.

FIG. 49 shows average change in surface resistance (also referred to in the art as resonance resistance or motional resistance) measurements for each explosive sample. A change in this measured value would correspond to a change in the viscosity of the medium in contact with the quartz crystal surface. The change in surface resistance corresponds to any changes in the viscosity of the air/gas/vapor in contact with the ITO-quartz crystal surface. Illustratively, the surface resistance for air is about 10Ω, for water about 400Ω, and for glycerol about 3500 to 5000Ω. Five 10-second sample exposures of an ITO-QCM were averaged for each explosive sample. Measurements were made with a 1018 Å thick ITO quartz crystal. The average maximum change in surface resistance for all explosive samples ranged from about 0Ω to 0.04Ω. The data indicate how the change in surface resistance is relatable to the mass and frequency changes. Several analytes (e.g., Compound A5, TNT, Composition B, Hexolite, PETN and RDX) produce a similar mass change, similar frequency change and similar change in surface resistance. More specifically, the 75% Tetryl+25% TNT sample showed the greatest increase in surface resistance. Hexolite, PETN, and RDX explosive samples each showed very little change in surface resistance compared to the background air. Irregular fluctuations during sample measurement are attributed at least in part to vapor turbulence surrounding the ITO-quartz crystal.

For principal component analysis (PCA) for the explosive samples, at least five measurements were taken for each sample. If more than five measurements were taken for a sample, the largest response and the smallest measurement responses were omitted. The tables comprising FIGS. 50 and 51 show the ITO-QCM calculated parameters used for PCA for each of the explosive sample measurements.

Figure 52:
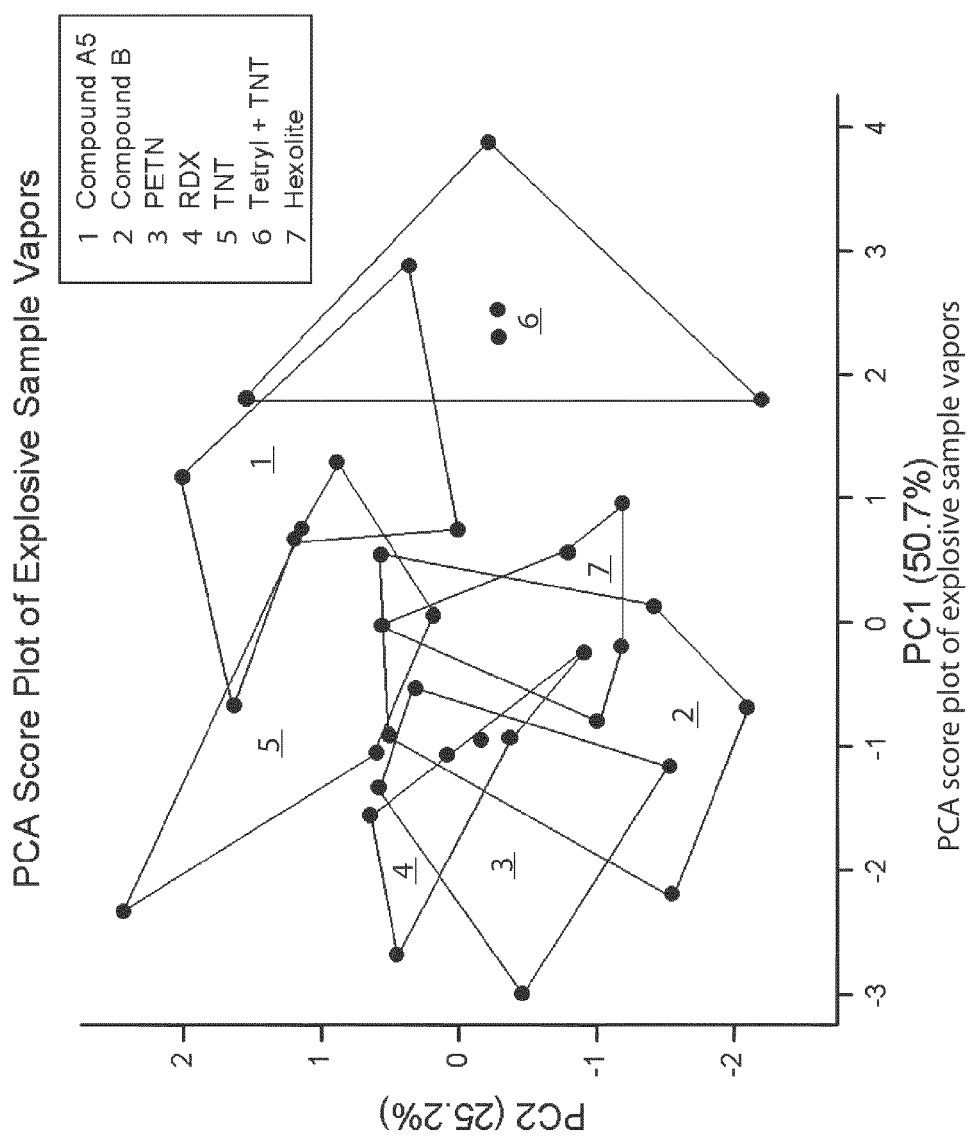
FIG. 52 is PCA score plots of ITO-QCM measurements for explosive vapors.

FIG. 52 shows ITO-QCM PCA results for each measurement taken for an explosive sample. Each data point represents a measurement for the particular sample indicated in the legend. The results are shown in 2-dimensions for illustrative purposes. More accurate results and better sample cluster separation can be obtained for the data in FIGS. 50 and 51 using three PCA dimensions.

Figure 53:
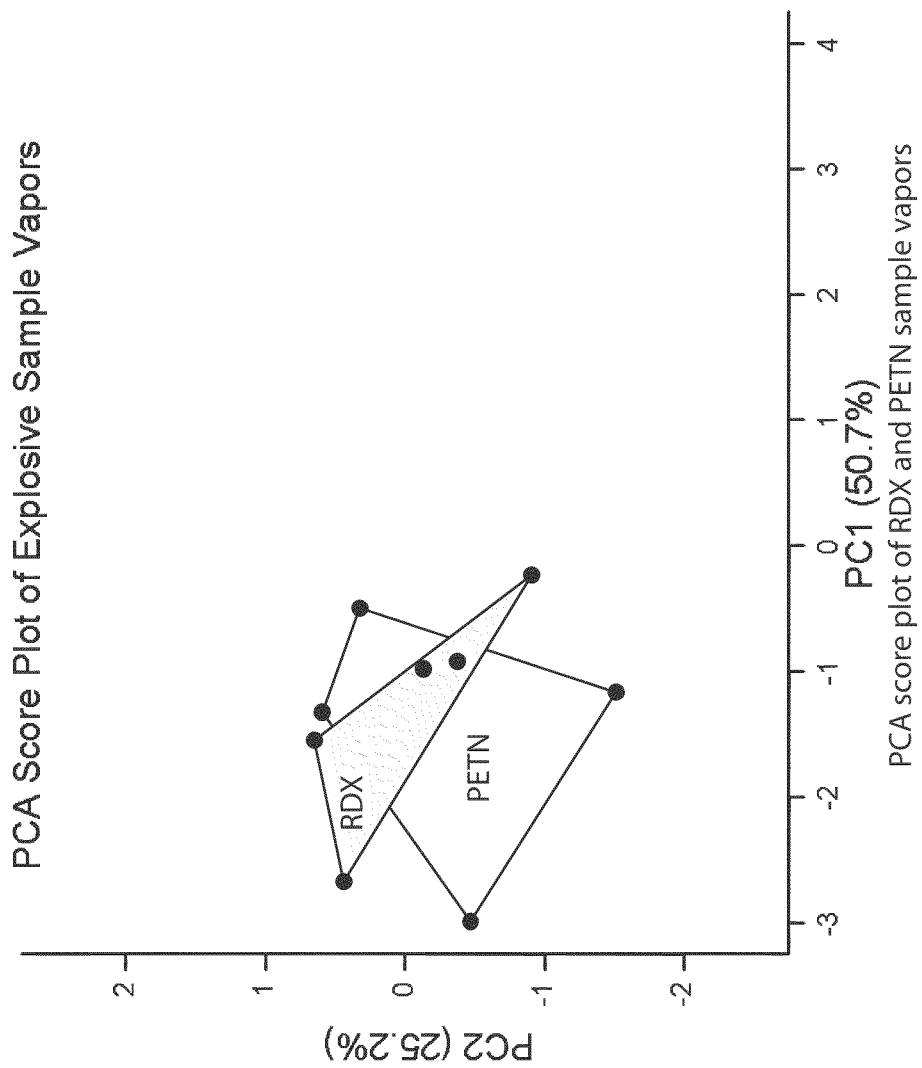
FIG. 53 is PCA score plots of ITO-QCM measurements for RDX and PETN vapors.

There is considerable overlap and also non-overlap in PCA space among some of the samples. Among the non-compound explosive samples, FIG. 53 shows a comparison of the PCA results for RDX and PETN. The PCA plots of the ITO-QCM measurements for RDX and PETN significantly overlap, which indicates that they cannot be distinguished by ITO-QCM measurements and PCA. The overlap is attributed in part to vapor taggants in common to RDX and PETN.

Figure 54:
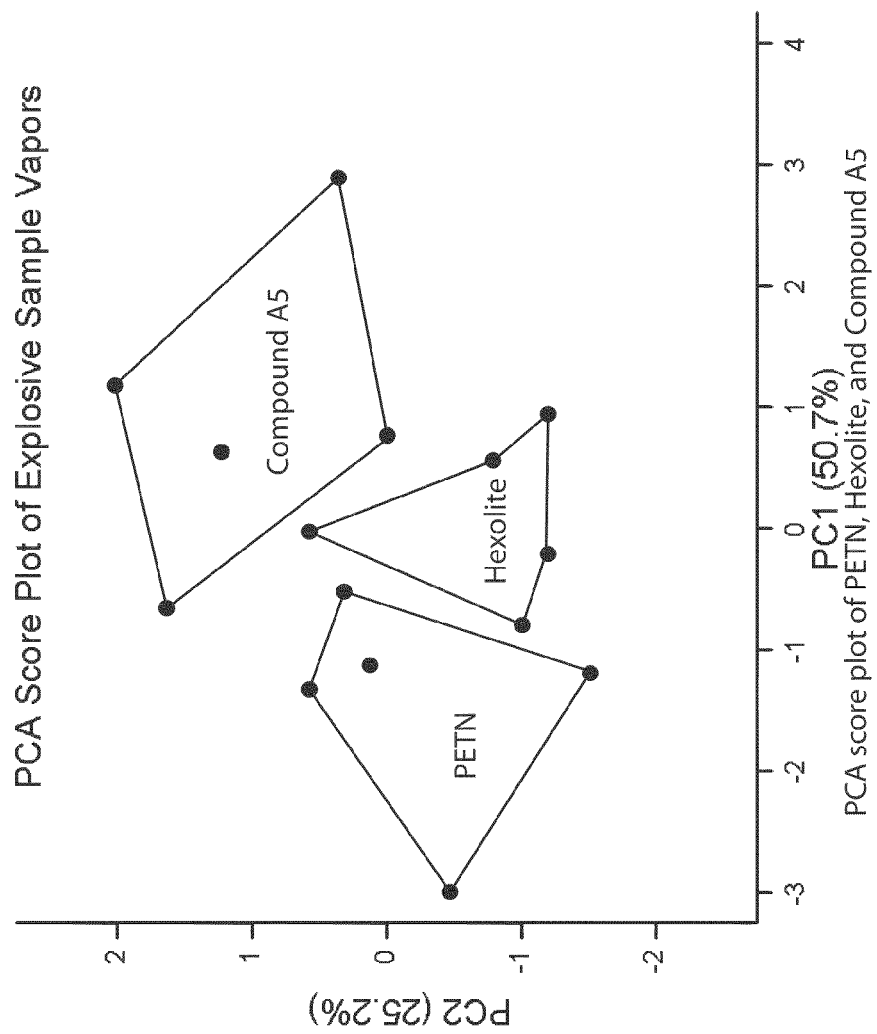
FIG. 54 is PCA score plots of ITO-QCM measurements for PETN, Hexolite and Compound A5 vapors.
Figure 55:
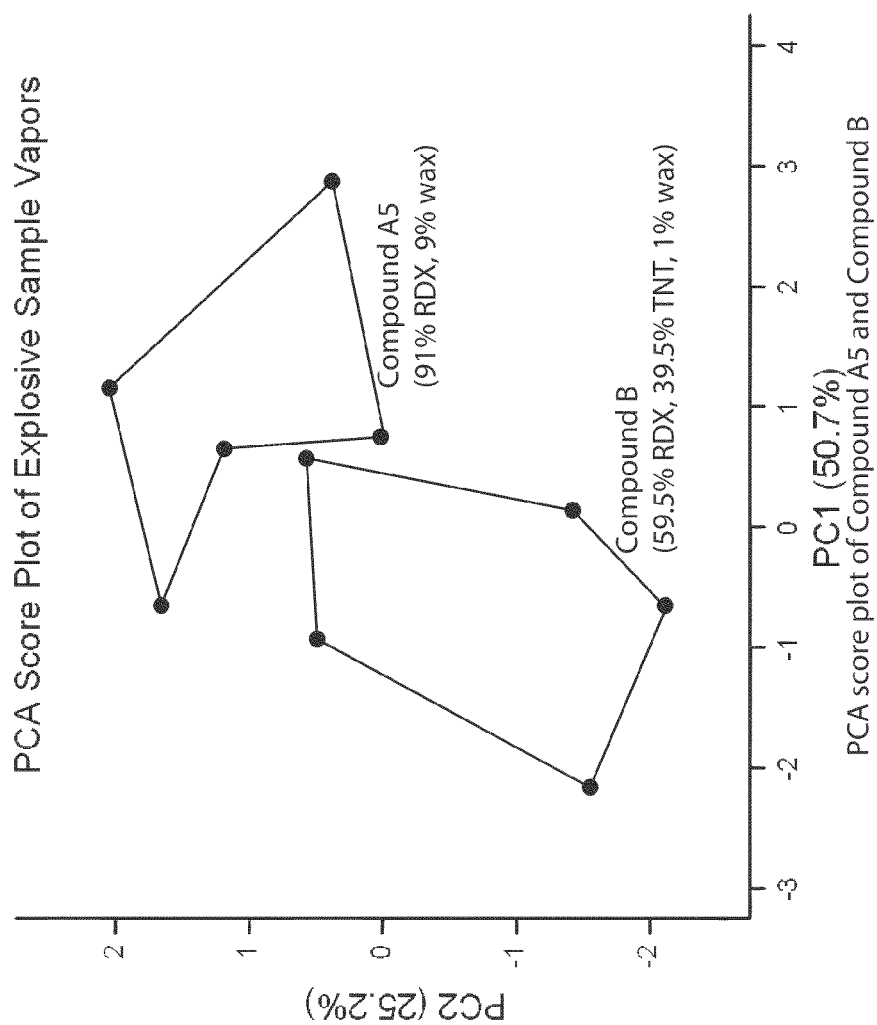
FIG. 55 is PCA score plots of ITO-QCM measurements for Compound A5 and Compound B vapors.
Figure 56:
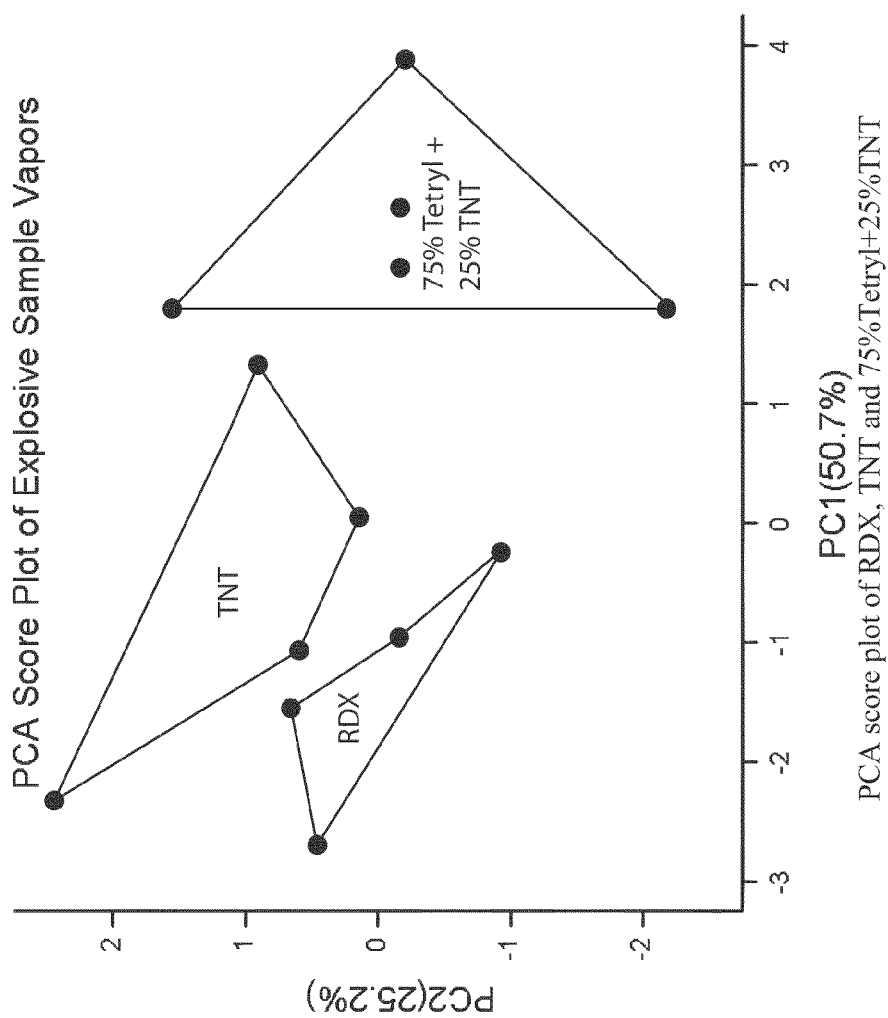
FIG. 56 is PCA score plots of ITO-QCM measurements for RDX, TNT, and 75% Tetryl+25% TNT (pbw) vapors.

Some groups of explosive materials can be clearly distinguished, as shown in FIGS. 54 to 56. FIG. 54 compares PCA plots for PETN, Hexolite, and Compound A5. As these samples do not overlap in PCA space, they can each be distinguished by ITO-QCM measurements. Similarly, FIG. 55 compares PCA plots for Compound A5 and Compound B. As these samples also do not overlap in PCA space, they can each be distinguished by ITO-QCM measurements. FIG. 56 compares PCA plots for RDX, TNT, and 75% Tetryl+25%

TNT. These samples also do not overlap in PCA space and can each be distinguished by ITO-QCM measurements.

Advantageously, a nanocrystalline ITO-QCM system and method according to principles of the invention can detect various explosive materials at ambient temperature. The ITO-QCM sensors detect, classify and produce a unique signature for each explosive material by measuring parameters such as change in frequency, integrated frequency response, initial response slope, average return to baseline slope and transient response time. The system and method does not require a heater or temperature controlling circuits, which not only saves power consumption and space, but also reduces any possibility of fire or an explosion during testing of the explosive materials vapors. The system and method also do not require any reagents, pre-sample conditioning or sample preparation for testing, which allows use of the system and method at any time. Additionally, the measurements may be made in real time and the measured data analyzed using a programmed computing system, or a functionally comparable apparatus, to provide determinations without appreciable delay. In addition, the ITO-QCM odor sensors also measure and give a unique parameter of integrated surface resistance response. PCA plots of ITO-QCM measurements distinguish between Compound A5 and Compound B; between PETN, Hexolite, and Compound A5; and between RDX, TNT and 75% Tetryl+25% TNT.

Referring now to FIGS. 57 to 68 graphs, plots and data pertaining to measured parameters for volatile organic compounds (VOCs) are provided. VOC solvent vapors were selected from several toxic industrial chemicals, highly flammable chemicals and chemicals that pose explosion hazards, namely, acetone, chloroform, ethanol, isopropyl alcohol, methanol, methylene chloride, tetrahydrofuran, toluene, benzyl alcohol, m-xylene, acetonitrile, benzene, and dimethylformadie. The chemical structure of each of the aforementioned VOCs is well known.

An Indium Tin Oxide (ITO) thin film deposited over a 5 MHz AT cut gold quartz crystal microbalance by vacuum deposition was used as vapor sensor for the detection of the tested VOCs. The ITO film had a nanocrystalline structure with an average grain size of 44±12 nm. A 15 µL drop of each VOC sample was applied to one end of a paper strip, then immediately held 2 cm over the ITO-quartz crystal surface for 10 seconds in an open glass jar (500 ml), and then removed. The paper strip was 20 cm in length, 2 cm wide and 0.3 mm thickness. A digital timer was used to measure the 10 second time period. A new paper strip was used for each run of each test sample. Parameters used in the determination of principal components analysis (PCA) of VOCs are integrated frequency response (Hz-sec), integrated surface resistance response (Ω-sec), initial response slope (Hz/sec), average return to baseline slope (Hz/sec) and average of all change in frequency data points, as described above. Five test vapor measurements were made for each VOC sample using ITO-QCM sensor.

The tables comprising FIGS. 57 through 63 shows the ITO-QCM vapor sensor results of all parameters calculations for each test run of VOC samples. These parameters were used to determine PCA score plots for all the VOC vapors. Software automated calculations of PCA parameters.

Figure 64:
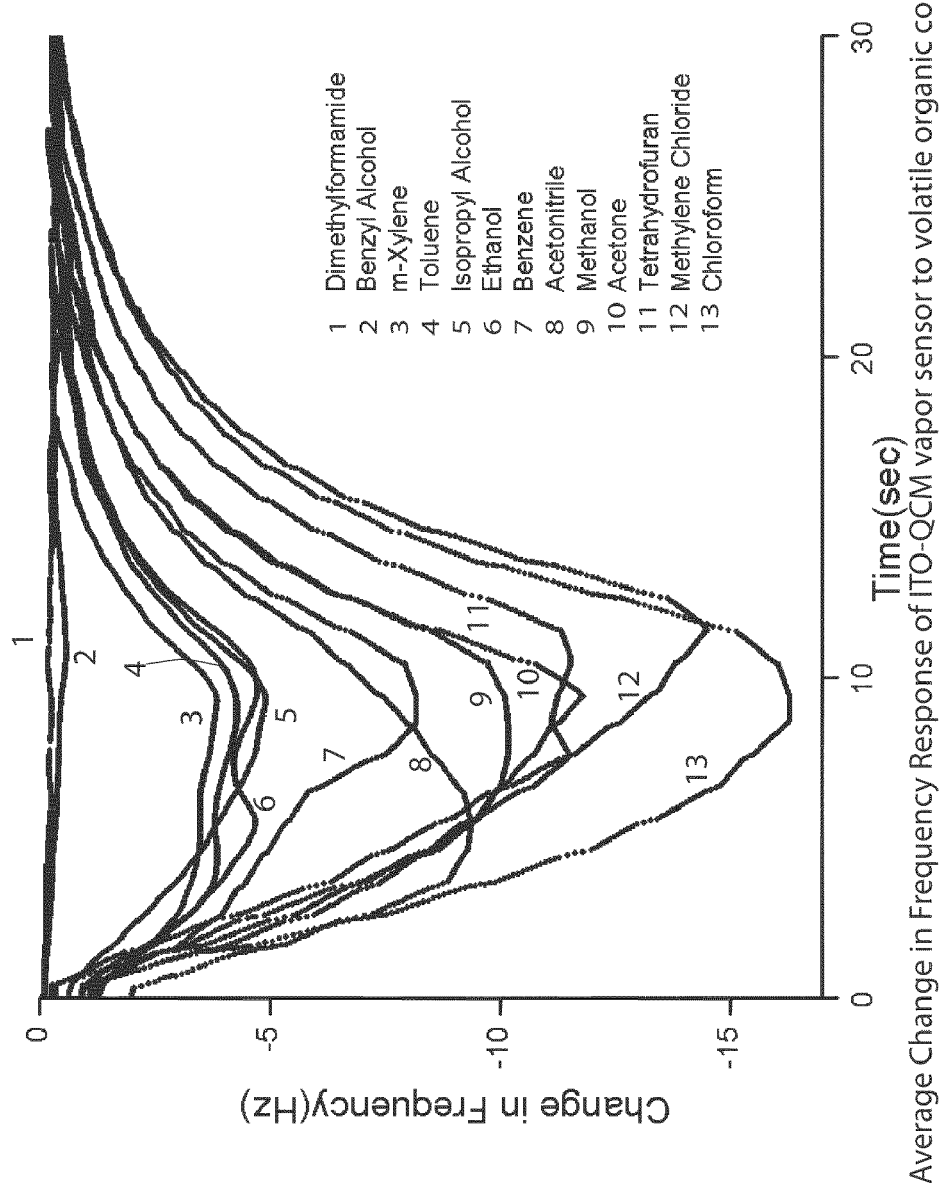
FIG. 64 is a graph of average change in frequency of ITO-QCM vapor sensor for volatile organic compounds.

The average change in frequency of the ITO-QCM vapor sensors with the tested VOCs is shown in FIG. 64. Chloroform showed the maximum negative change in the frequency, while dimethylformamide showed minimum change in frequency. Each VOC has a different peak value of frequency, as well as different response and recovery time characteristics, which provides preliminary identification of distinguishing signatures for each VOC.

Figure 65:
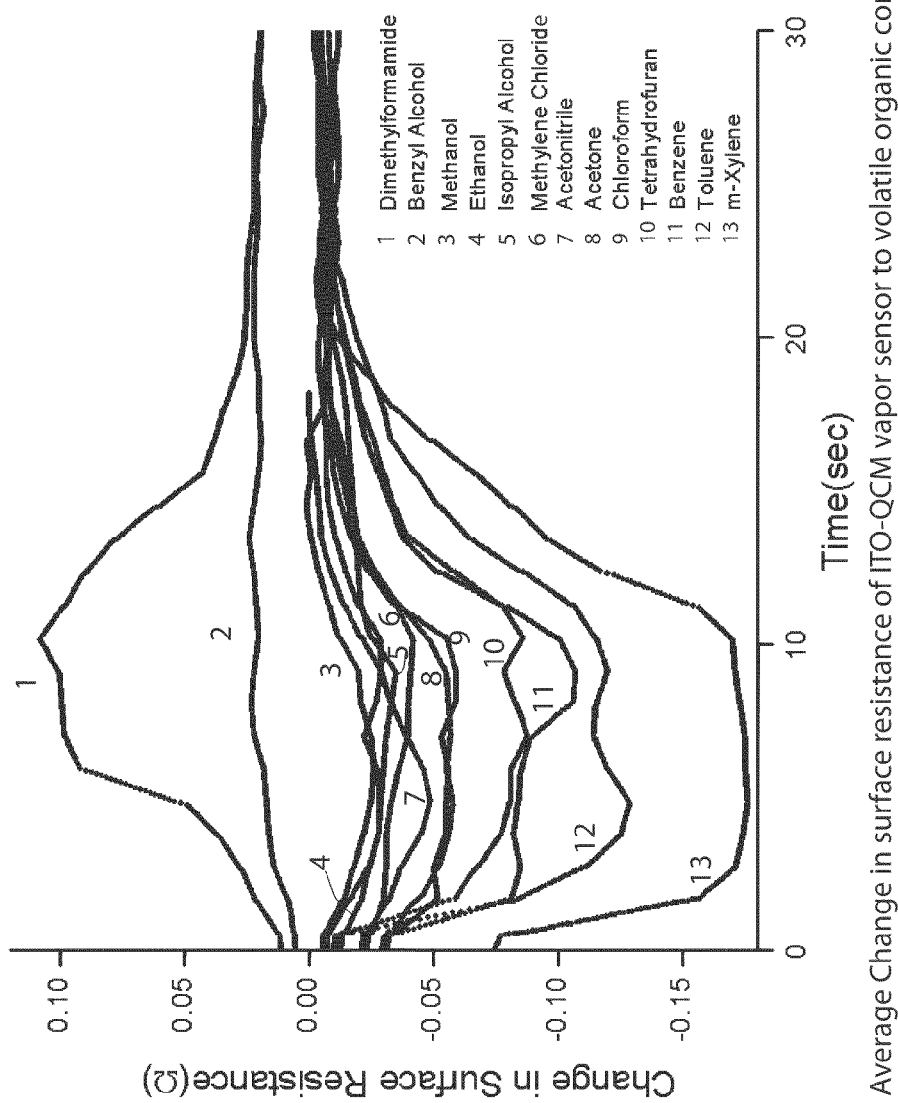
FIG. 65 is a graph of average change in surface resistance of ITO-QCM vapor sensor for volatile organic compounds.

Average change in surface resistance of the ITO-QCM vapor sensors with VOCs is shown in the FIG. 65. M-xylene shows maximum negative change in surface resistance, while methanol shows the minimum negative change in the surface resistance among the samples measured. Dimethylformamide showed the maximum increase in surface resistance, while benzyl alcohol showed a minimum increase in the surface resistance.

Figure 66:
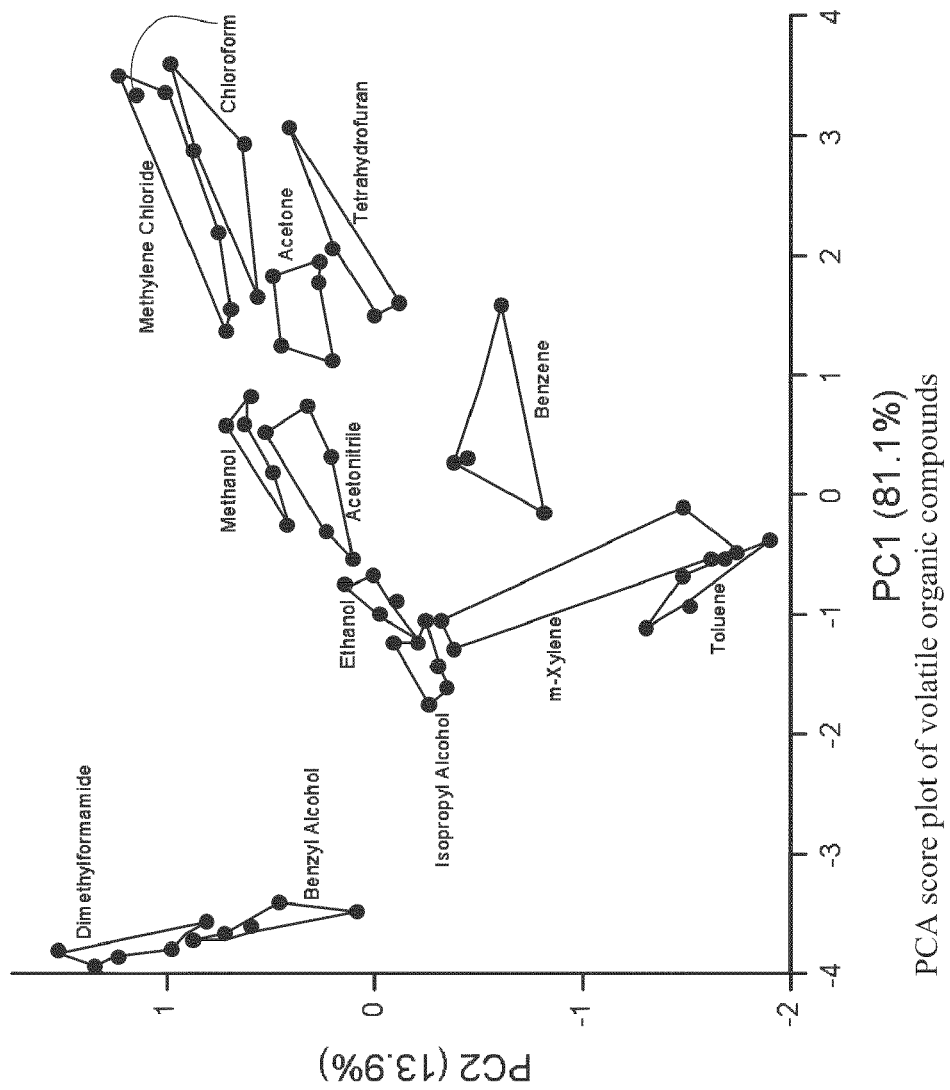
FIG. 66 is PCA score plots of ITO-QCM measurements for VOCs.

A PCA score plot for each different types of VOC tested is provide in FIG. 66. The plots shows clear separation into clusters, proving that ITO-QCM vapor sensor measurements can distinguish between each of the VOC vapors. Vapor pressure of the solvents generally increases from left to right on the graph. On the PCA score plot, there is a general decrease in surface resistance from top to bottom on the graph.

Figure 67:
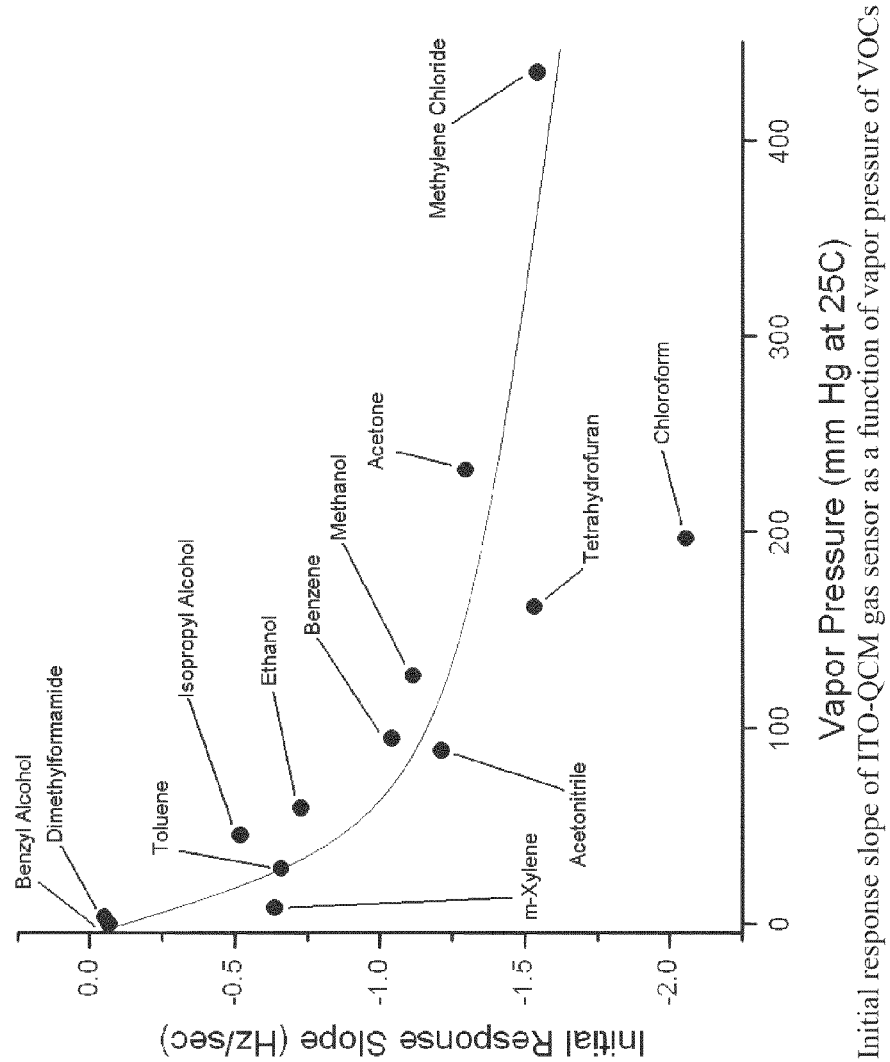
FIG. 67 is a graph of initial response slope of ITO-QCM measurements as a function of vapor pressure of VOCs.

FIG. 67 shows the trend of average initial response slope of ITO-QCM gas sensor with vapor pressure of VOCs. The vapor pressure data for each VOC was obtained from the chemistry literature. The initial response slope indicates the rate at which the analyte VOC vapor absorbs into ITO film on the quartz crystal when the source of the solvent vapor is inserted into the glass jar sample chamber. The variation shows that the initial response slope decreases with increasing vapor pressure of the VOCs.

Figure 68:
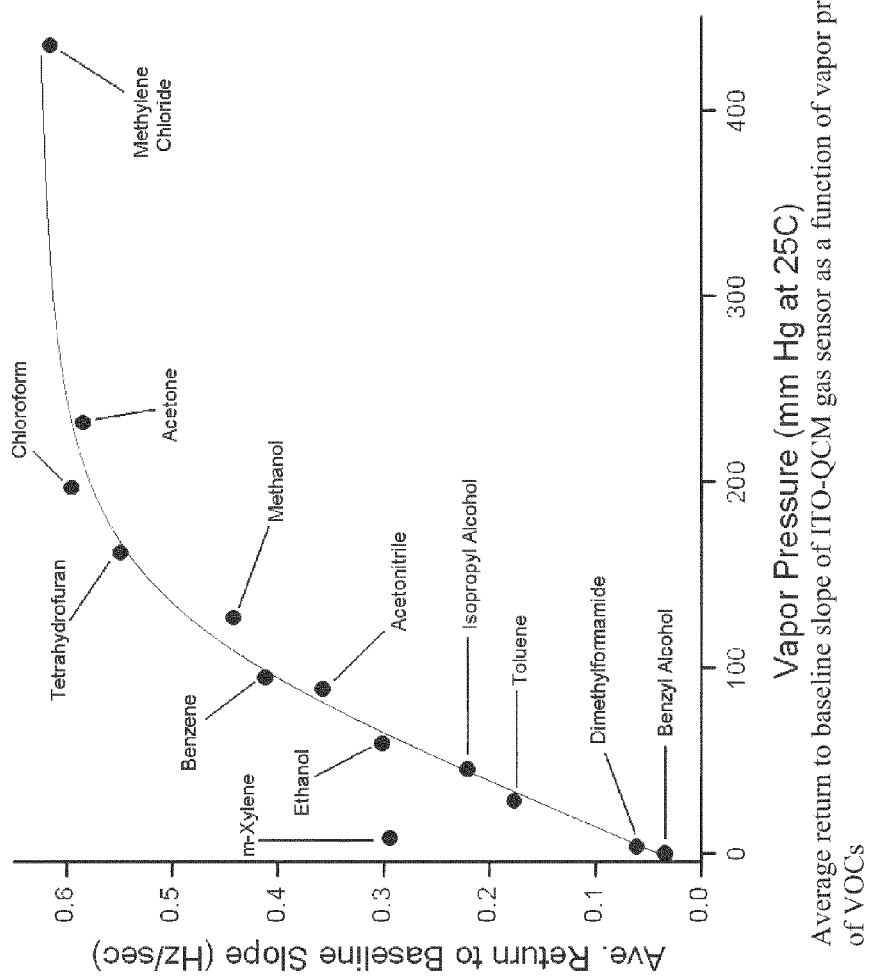
FIG. 68 is a graph of average return to baseline slope of ITO-QCM measurements as a function of vapor pressure of VOCs.
Figure 69:
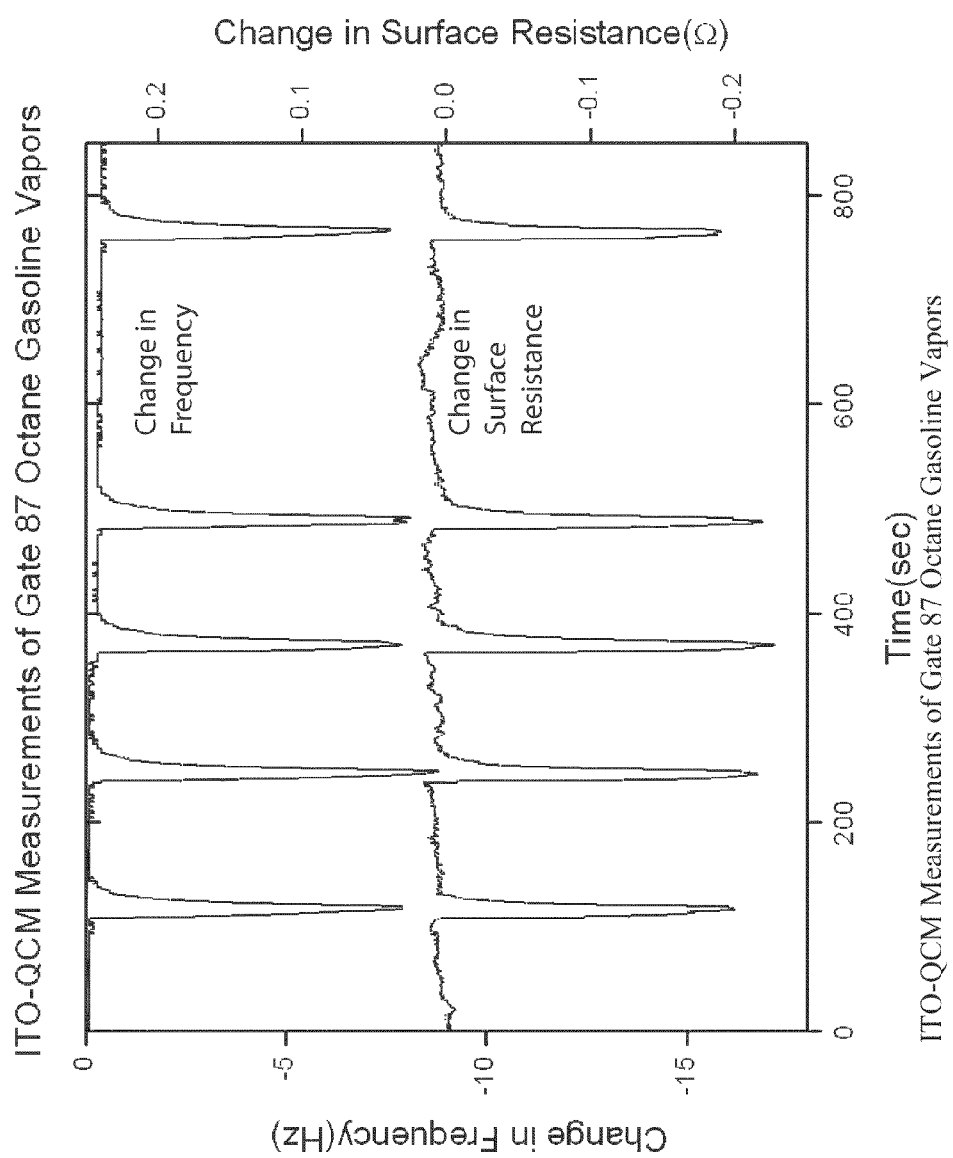
FIG. 69 is a graph of ITO-QCM Measurements of Gate 87 Octane Gasoline Vapors.
Figure 70:
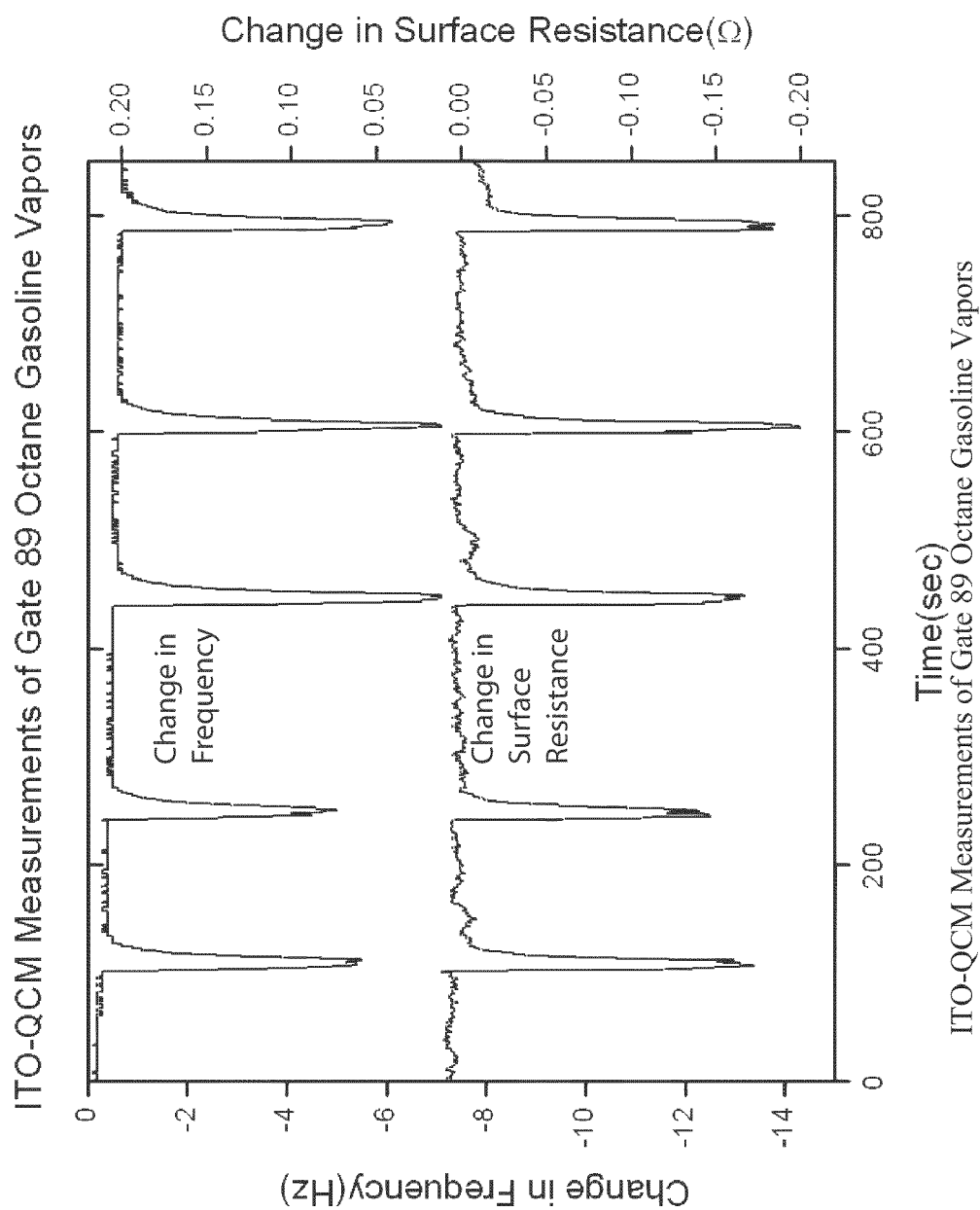
FIG. 70 is a graph of ITO-QCM Measurements of Gate 89 Octane Gasoline Vapors.
Figure 71:
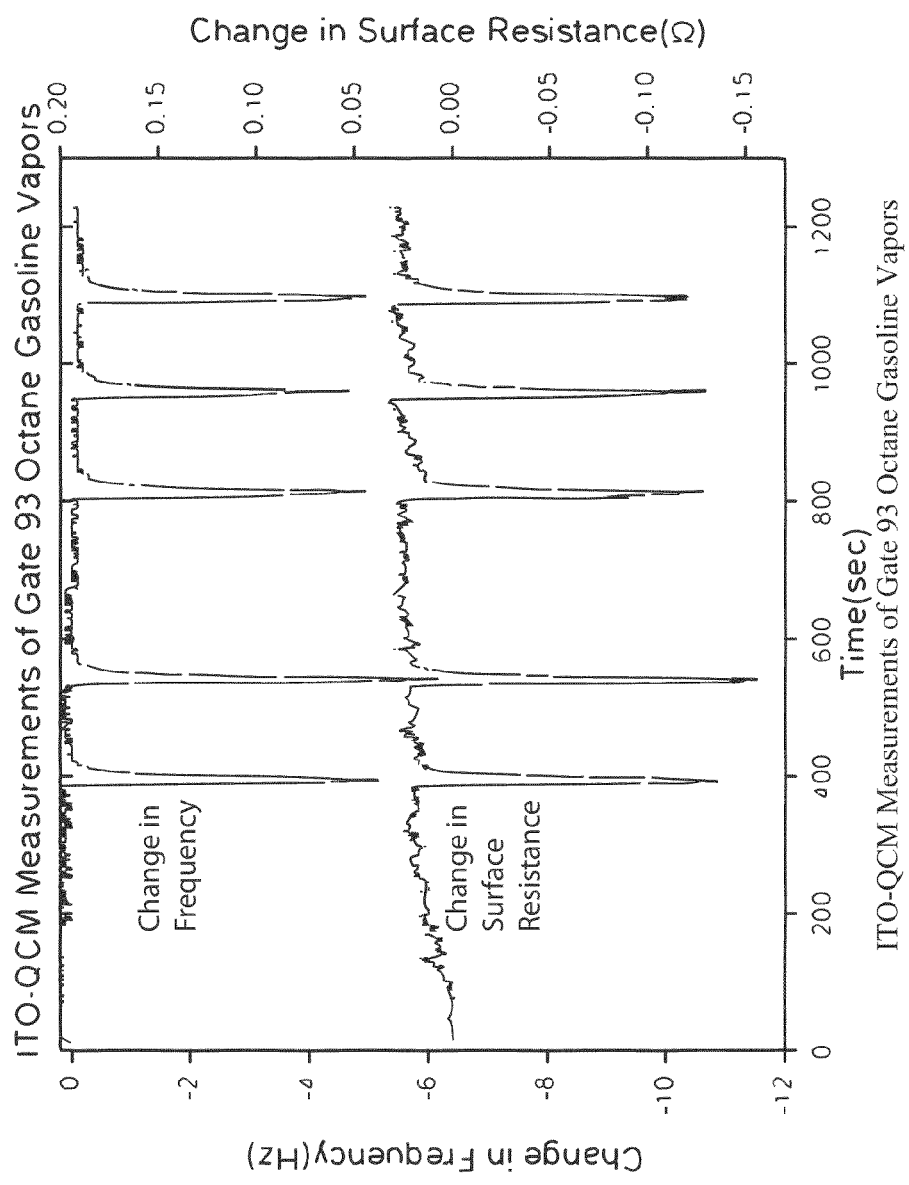
FIG. 71 is a graph of ITO-QCM Measurements of Gate 93 Octane Gasoline Vapors.
Figure 72:
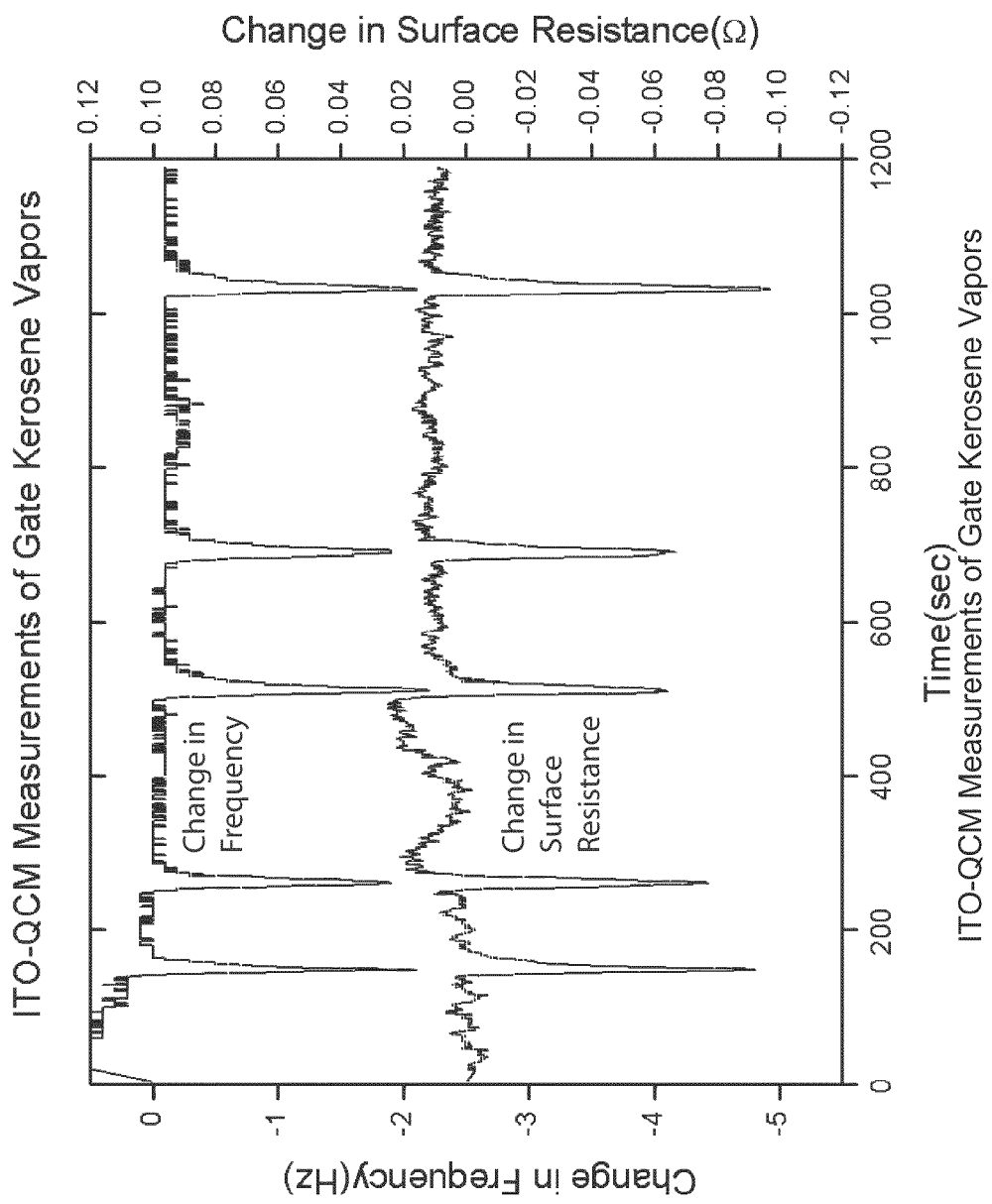
FIG. 72 is a graph of ITO-QCM Measurements of Gate Kerosene Vapors.
Figure 73:
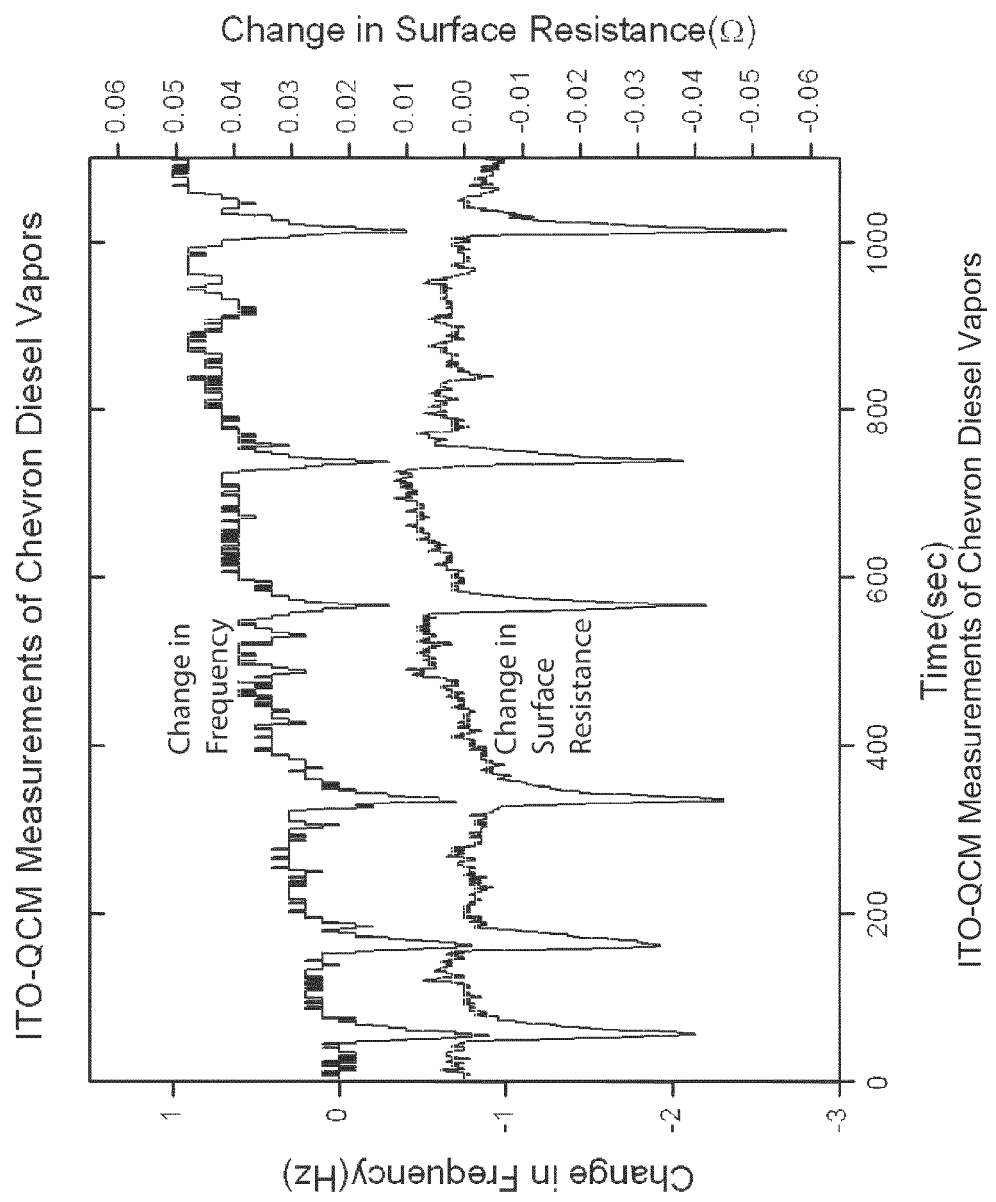
FIG. 73 is a graph of ITO-QCM Measurements of Chevron Diesel Vapors.
Figure 74:
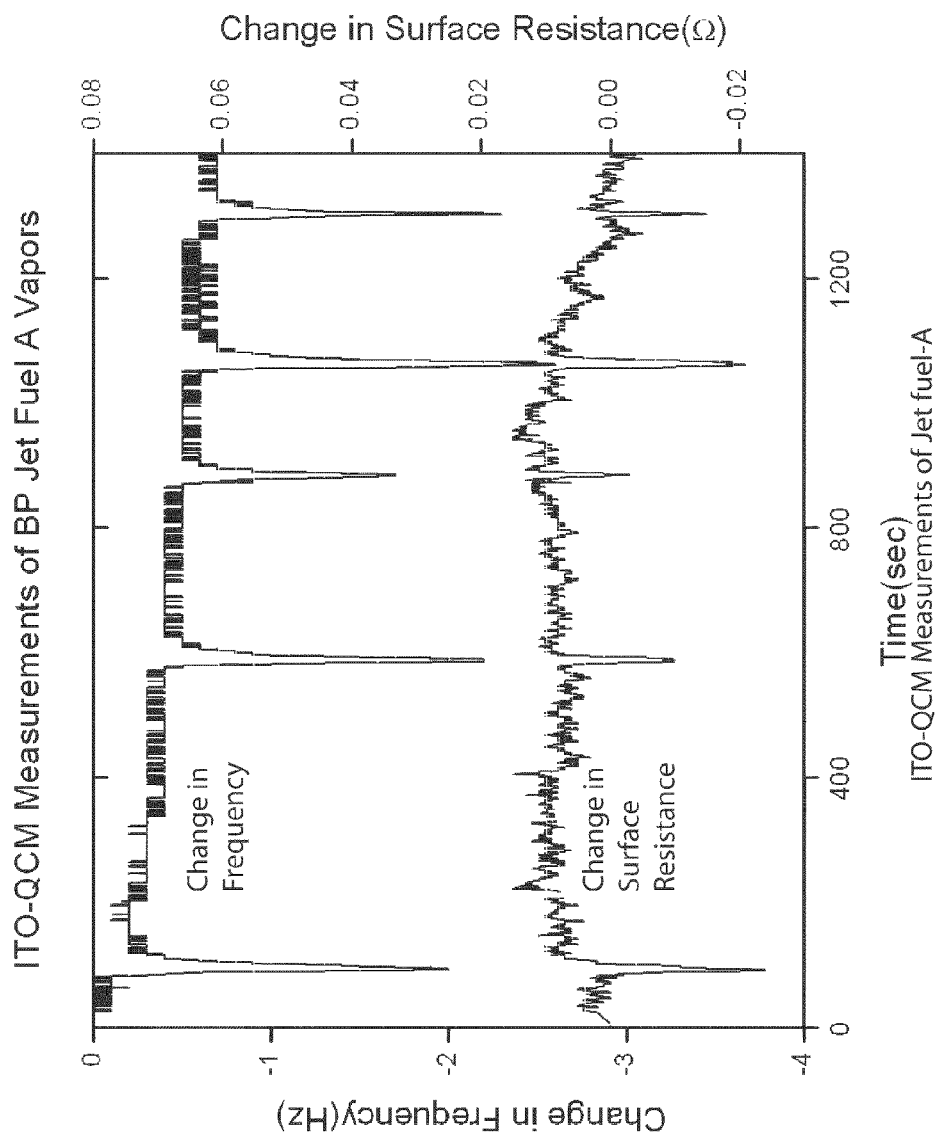
FIG. 74 is a graph of ITO-QCM Measurements of BP Jet fuel-A.
Figure 75:
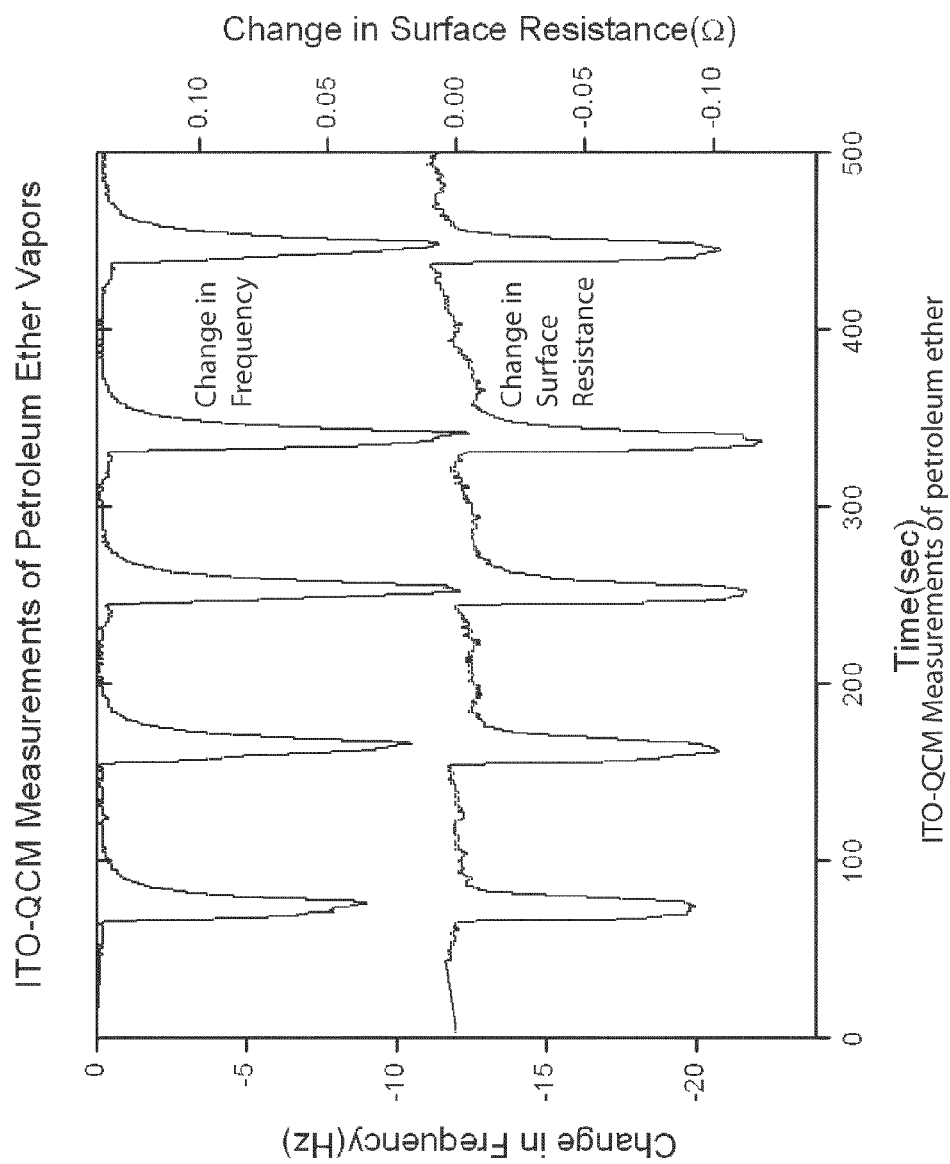
FIG. 75 is a graph of ITO-QCM Measurements of petroleum ether.

FIG. 68 shows average return to baseline slope of ITO-QCM gas sensor as a function of vapor pressure of VOCs. The average return to baseline slope of the ITO-QCM vapor sensor as a function of vapor pressure of VOCs indicates the rate at which the analyte VOC vapor desorbs from the ITO film on the quartz crystal after the source of the VOC vapor is removed from the glass jar sample chamber. The average return to baseline slope increases with increasing vapor pressure for the VOCs. The variation of initial response slope and average return to baseline slope with vapor pressure of the VOCs significantly contributes to the isolation of clusters of each VOC on the PCA score plot.

Advantageously, the nanocrystalline-thin film ITO-QCM sensors detects various volatile organic compounds at room temperature under dynamic mode. The ITO (as a thin film sensor), and the QCM (as a transducer) combine to show the change in frequency responses and surface resistance responses as a function of time for each VOC vapor tested. PCA analysis showed selectivity for each VOC analyte. The average initial response time of the ITO-QCM vapor sensor decreased with increasing vapor pressure of the VOC, while the average return to baseline slope increased with increasing vapor pressure of VOC.

Referring now to FIGS. 69 to 97 graphs, plots and data pertaining to measured parameters for petroleum products and alkanes are provided. An Indium Tin Oxide (ITO) thin film deposited over a 5 MHz AT cut gold quartz crystal microbalance by vacuum deposition was used as vapor sensor for the detection of the tested compounds. The ITO film had a nanocrystalline structure with an average grain size of 44±12 nm. A 15 µL drop of each petroleum products or alkane sample was applied to one end of a paper strip, then immediately held 2 cm over the ITO-quartz crystal surface for 10 seconds in an open glass jar (500 ml), and then removed. The paper strip was 20 cm in length, 2 cm wide and 0.3 mm thickness. A digital timer was used to measure the 10 second time period. A new paper strip was used for each run of each test sample. Parameters used in the determination of principal components analysis (PCA) of the petroleum products and alkanes are integrated frequency response (Hz-sec), integrated surface resistance response (Ω-sec), initial response slope (Hz/sec), average return to baseline slope (Hz/sec) and average of all change in frequency data points (Hz), as described above.

Figure 76:
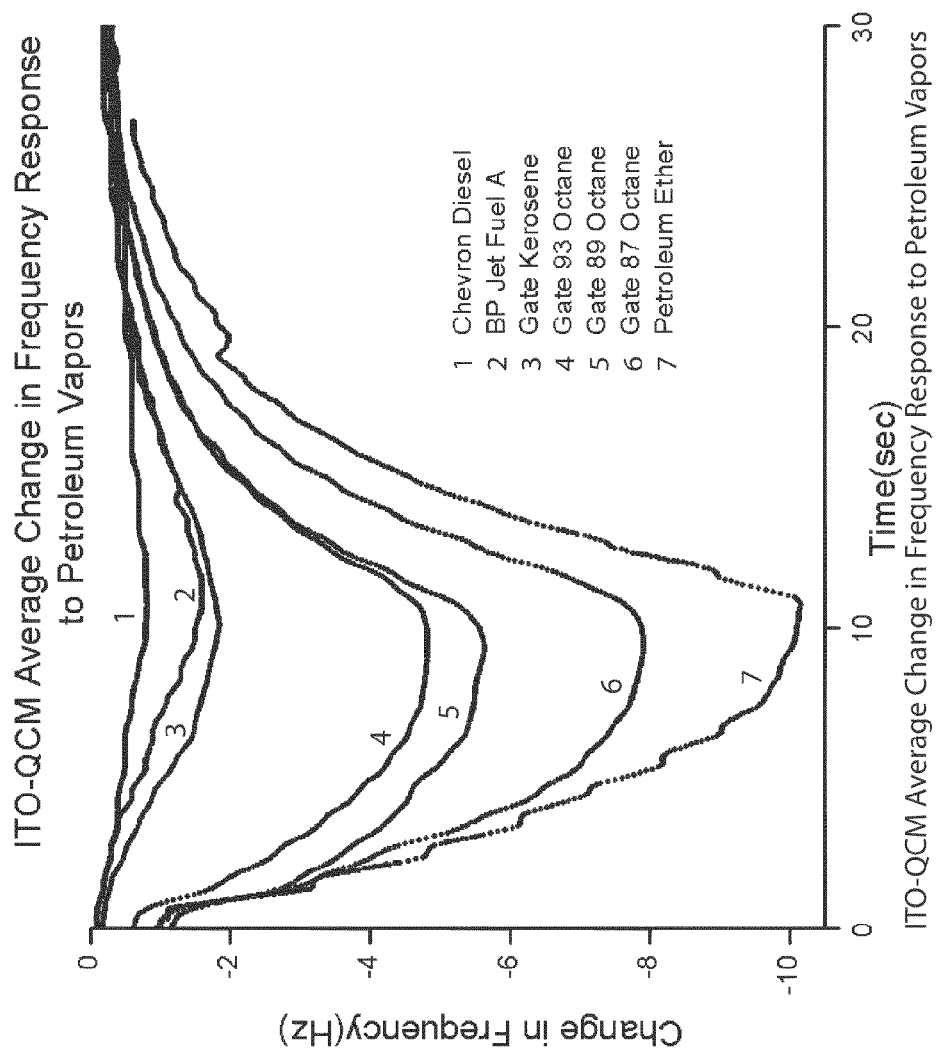
FIG. 76 is a graph of ITO-QCM Average Change in Frequency Response to Petroleum Vapors.
Figure 77:
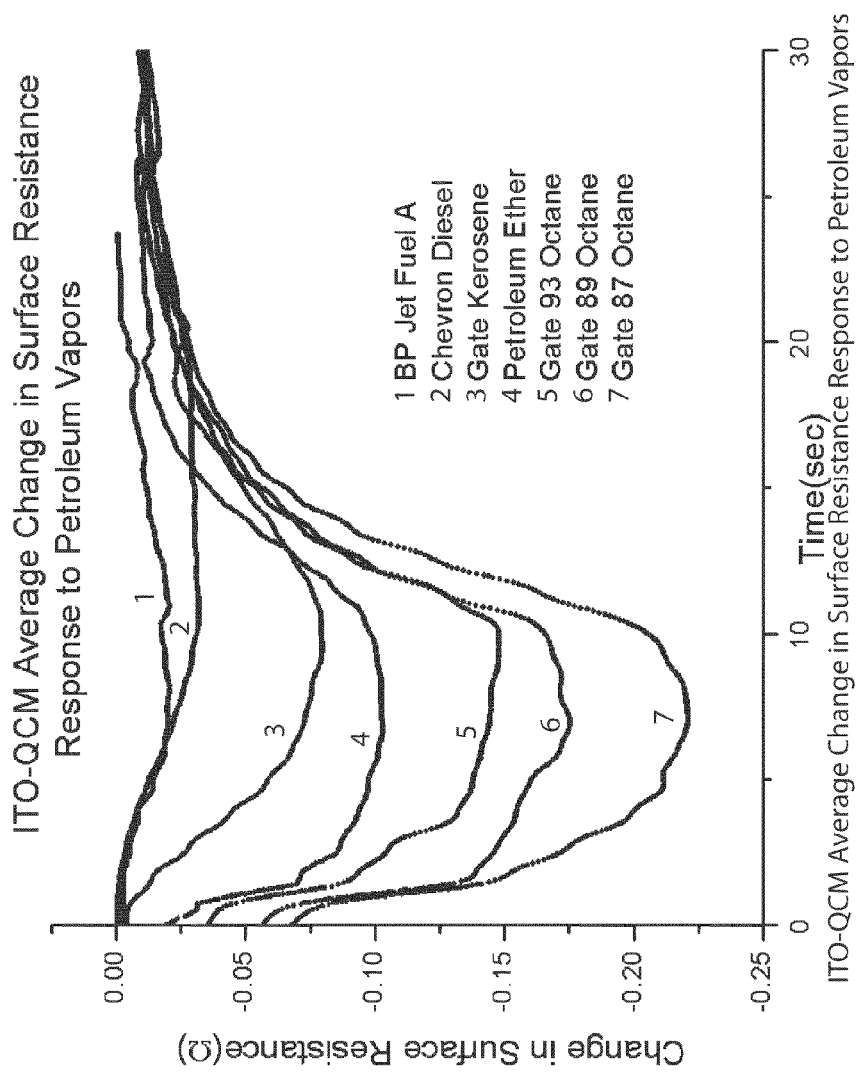
FIG. 77 is a graph of ITO-QCM Average Change in Surface Resistance Response to Petroleum Vapors.

Petroleum products tested include 87 octane gasoline, 89 octane gasoline, 93 octane gasoline, kerosene, diesel, petroleum ether and Jet-A fuel. Where indicated in the graphs, Gate®, Chevron® and BP® brand products were tested. FIGS. 69 to 75 show the actual ITO-QCM measurements of the change in frequency and surface resistance when a 15 µL drop of each petroleum product sample was applied to one end of paper strip, then immediately held 2 cm over the ITO-quartz crystal surface for 10 seconds in an open glass jar (500 ml), and then removed. A digital timer was used to measure the 10 second time period. A new paper strip having 20 cm length, 2 cm width and 0.3 mm thickness was used for each run of each test sample. The change in frequency response of the ITO-QCM sensor was highest for the most volatile petroleum ether, and lowest for the least volatile diesel fuel, as shown in FIG. 76. The surface resistance response of sensor was greatest for the 87 octane gasoline, and lowest and nearly the same for diesel fuel and Jet fuel A for first 6 seconds, then slightly lower for Jet fuel A as shown in FIG. 77. The surface resistance decreased in the presence of different types of petroleum vapors, perhaps due the fact that all petroleum products have a higher vapor density than that of air.

Related research on the detection of odor of samples for alcoholic beverages and fruits, which have high water content, showed an increase in the surface resistance because water vapor is less dense than air. Thus, surface resistance (i.e., surface resistance) provides a unique signature to identify the vapor of petroleum products from complex mixtures.

Figure 78:
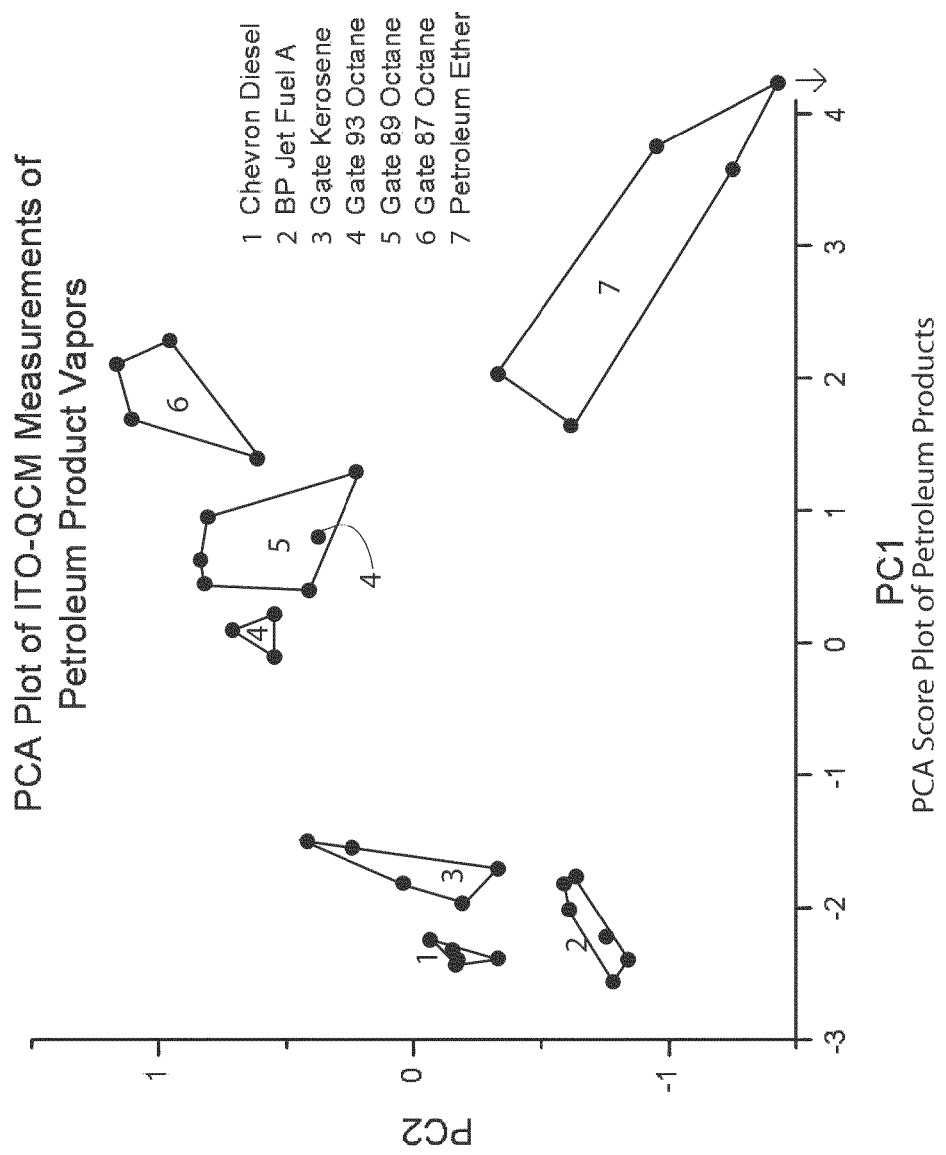
FIG. 78 is a PCA Score Plot of Petroleum Products.

A PCA score plot of the 87 octane gasoline, 89 octane gasoline, 93 octane gasoline, kerosene, diesel fuel, Jet fuel A and petroleum ether vapor measurements showed clear separation into clusters, as shown in FIG. 78. Thus, ITO-QCM measurements can distinguish between each of the petroleum vapors. In general, there is increasing volatility from left to right on the PCA score plot as shown in FIG. 78.

Figure 79:
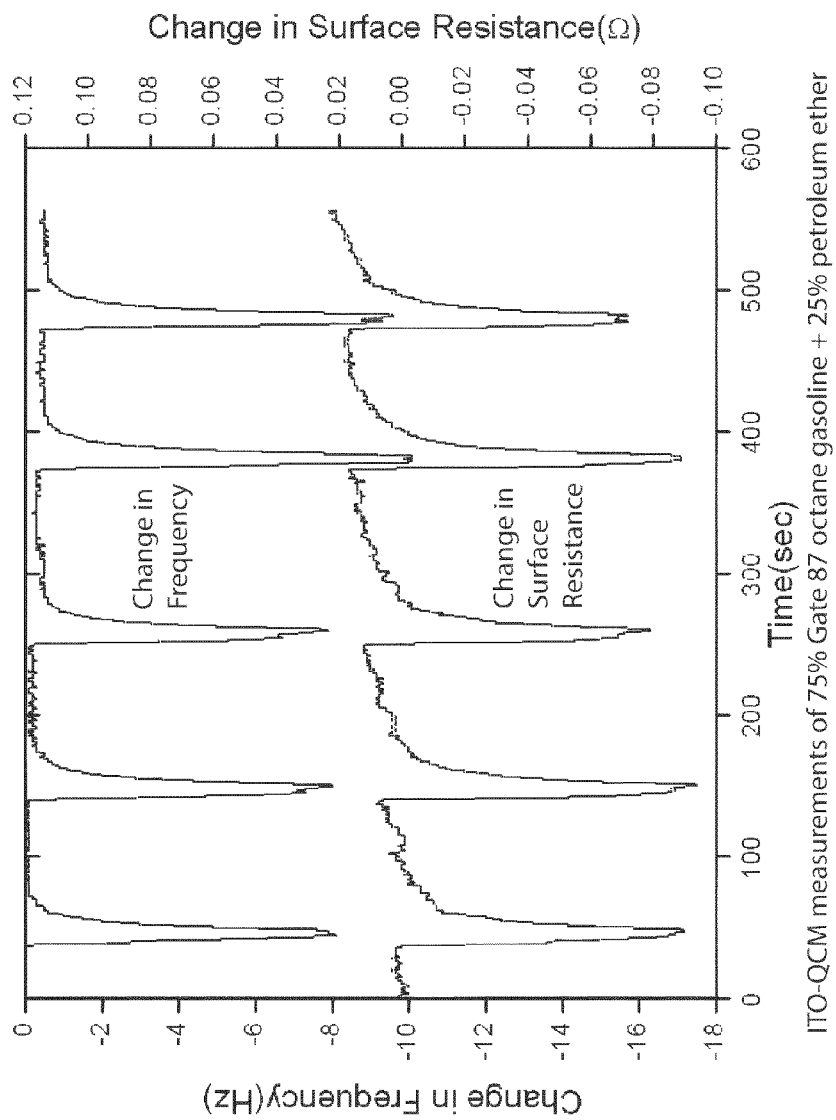
FIG. 79 is a graph of ITO-QCM measurements of 75% Gate 87 octane gasoline+25% petroleum ether.
Figure 80:
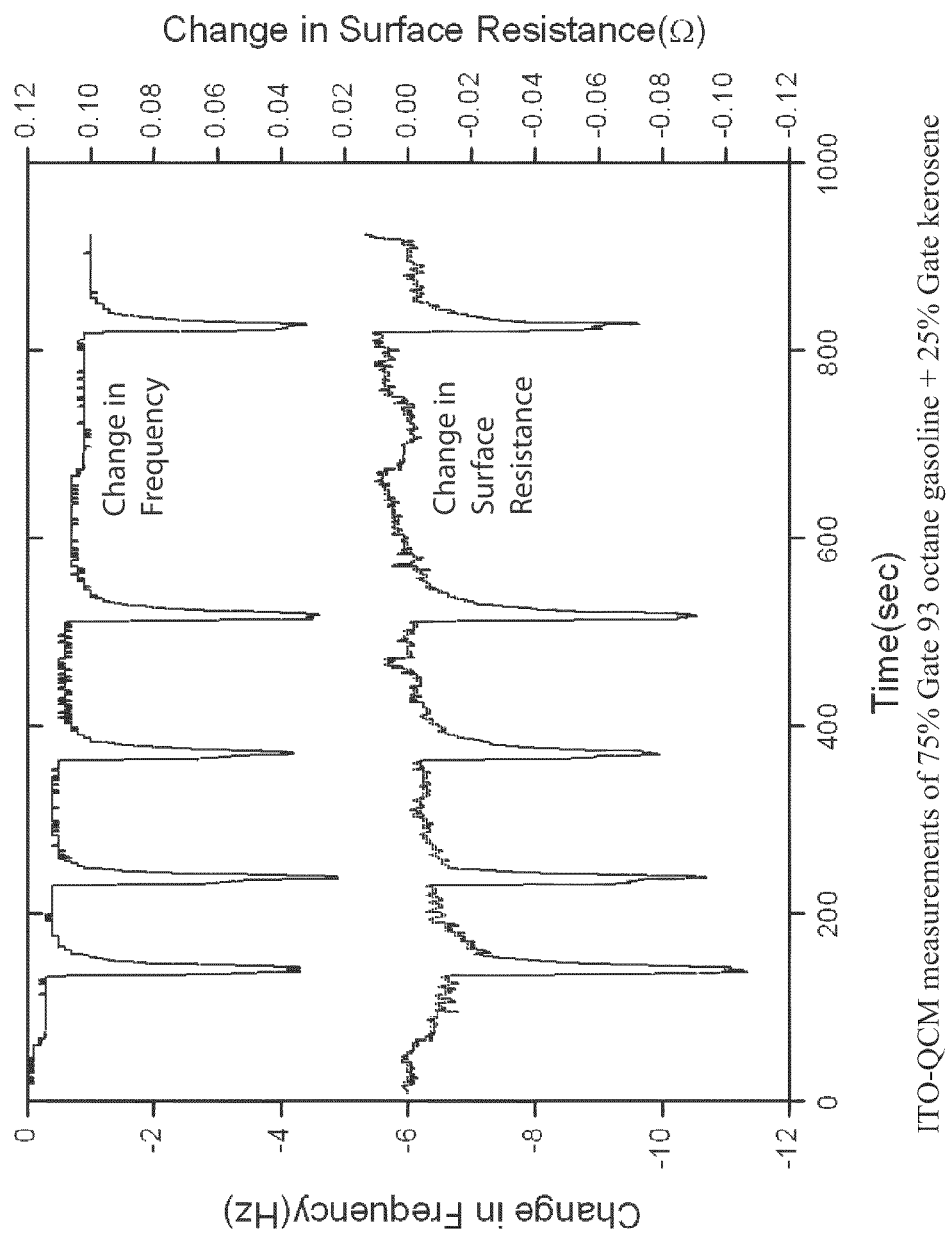
FIG. 80 is a graph of ITO-QCM measurements of 75% Gate 93 octane gasoline+25% Gate kerosene.

Additional experiments involved testing adulterated versions. For example, 87 octane gasoline was mixed with 25% (pbv) of petroleum ether, and 93 octane gasoline with 25% kerosene, in order to simulate adulterated gasoline. FIG. 79 shows ITO-QCM measurements of the change in frequency and surface resistance for a mixture of 87 octane gasoline and 25% petroleum ether, while FIG. 80 shows the ITO-QCM measurements of the change in frequency and surface resistance for a mixture of 93 octane gasoline and 25% kerosene.

Figure 81:
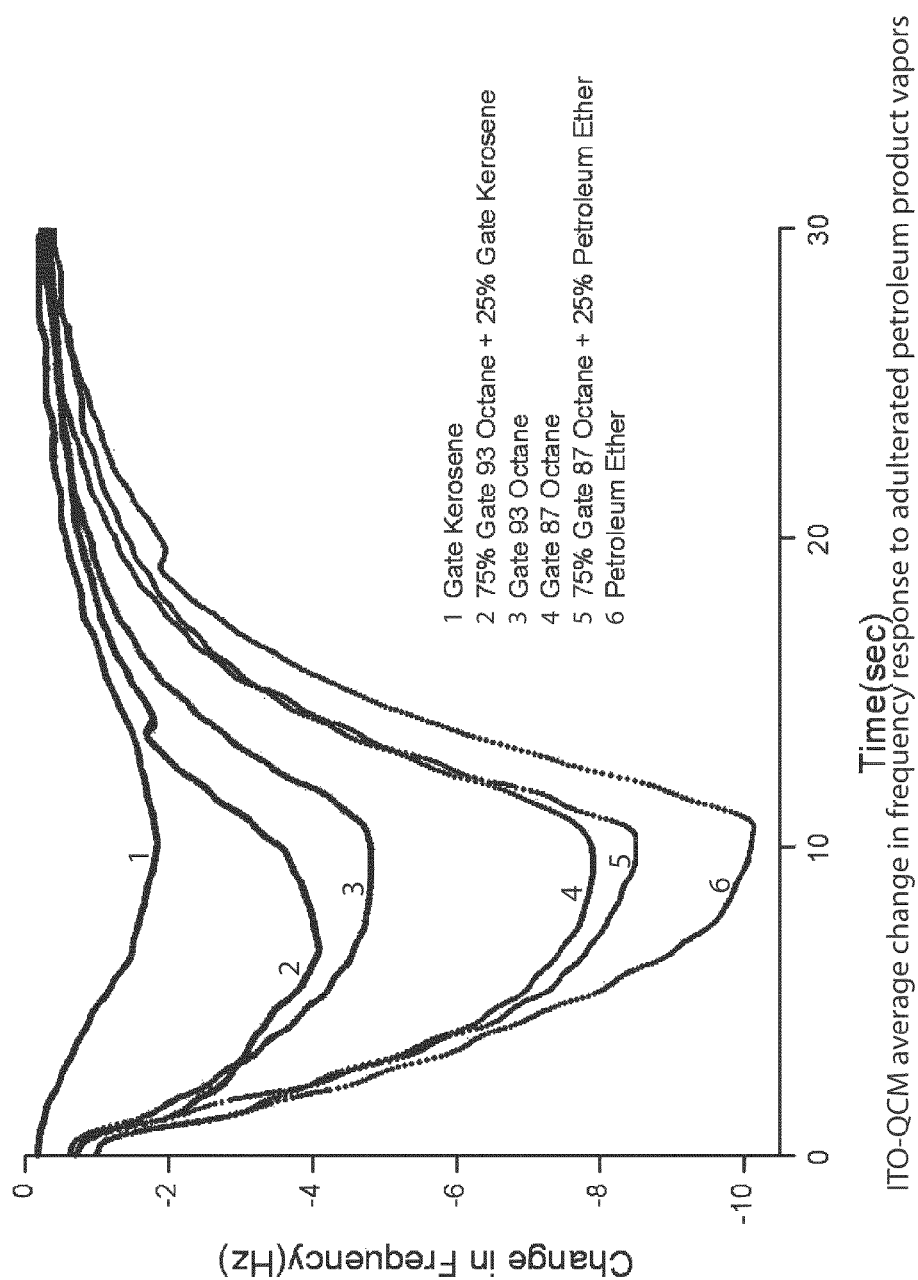
FIG. 81 is a graph of ITO-QCM average change in frequency response to adulterated petroleum product vapors.

ITO-QCM average change in frequency responses to adulterated petroleum product vapors is shown in FIG. 81. The expected responses for both 75% 87 octane gasoline mixed with 25% petroleum ether is between the 87 octane response and the petroleum ether response. The response for 75% 93 octane gasoline and 25% kerosene vapors is between the 93 octane response and the kerosene response.

Figure 82:
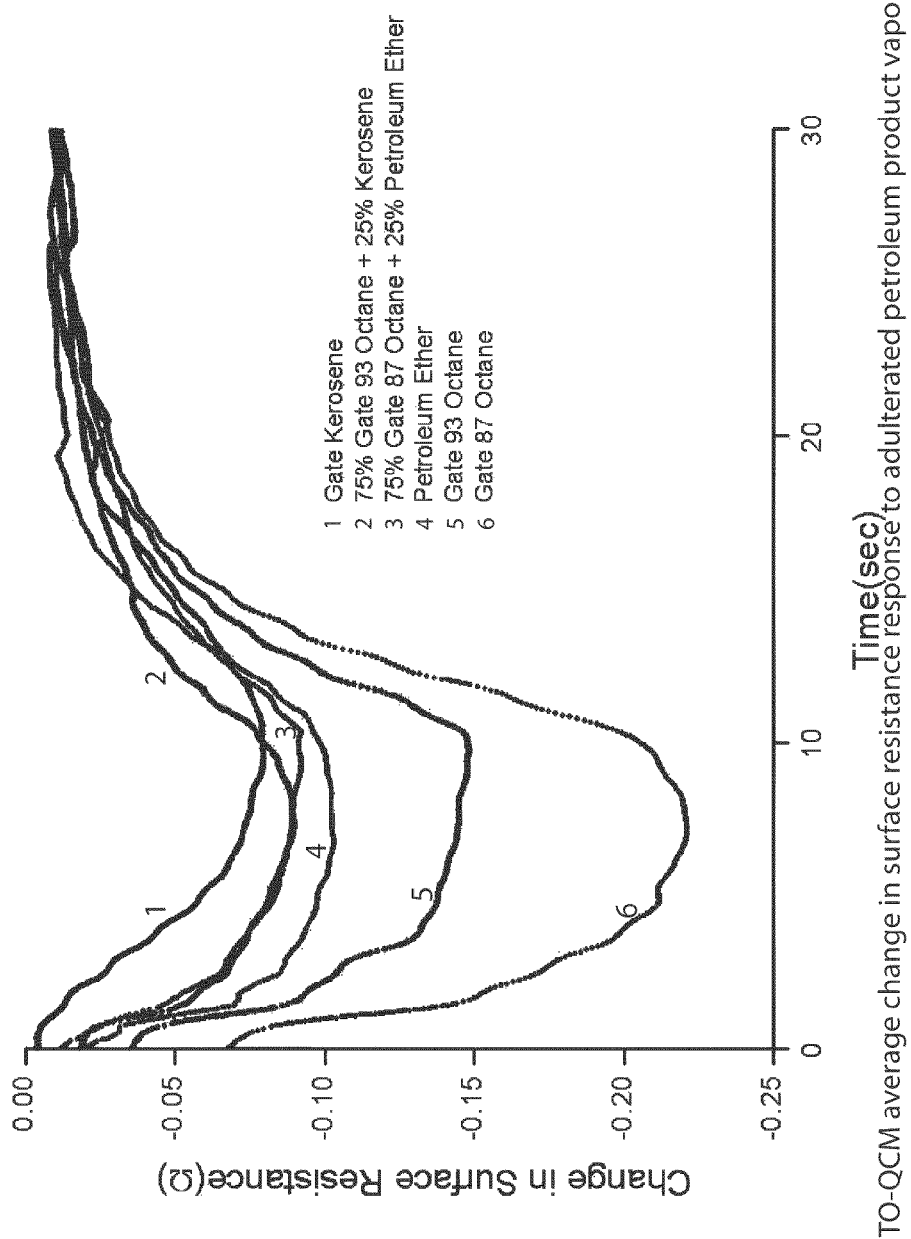
FIG. 82 is a graph of ITO-QCM average change in surface resistance response to adulterated petroleum product vapors.

The ITO-QCM average change in surface resistance response to adulterated petroleum product vapors is shown in FIG. 82. This graph shows the expected response for the 75% 93 octane gasoline mixed with 25% Gate kerosene vapor, which is between the 93 octane response and the kerosene response. The response for 75% Gate 87 octane gasoline mixed with 25% petroleum ether was less than both the average petroleum ether response and the average Gate 87 octane gasoline response, which may be due to the formation of a complex reaction in the mixture that reduces the formation of vapor molecules.

Figure 83:
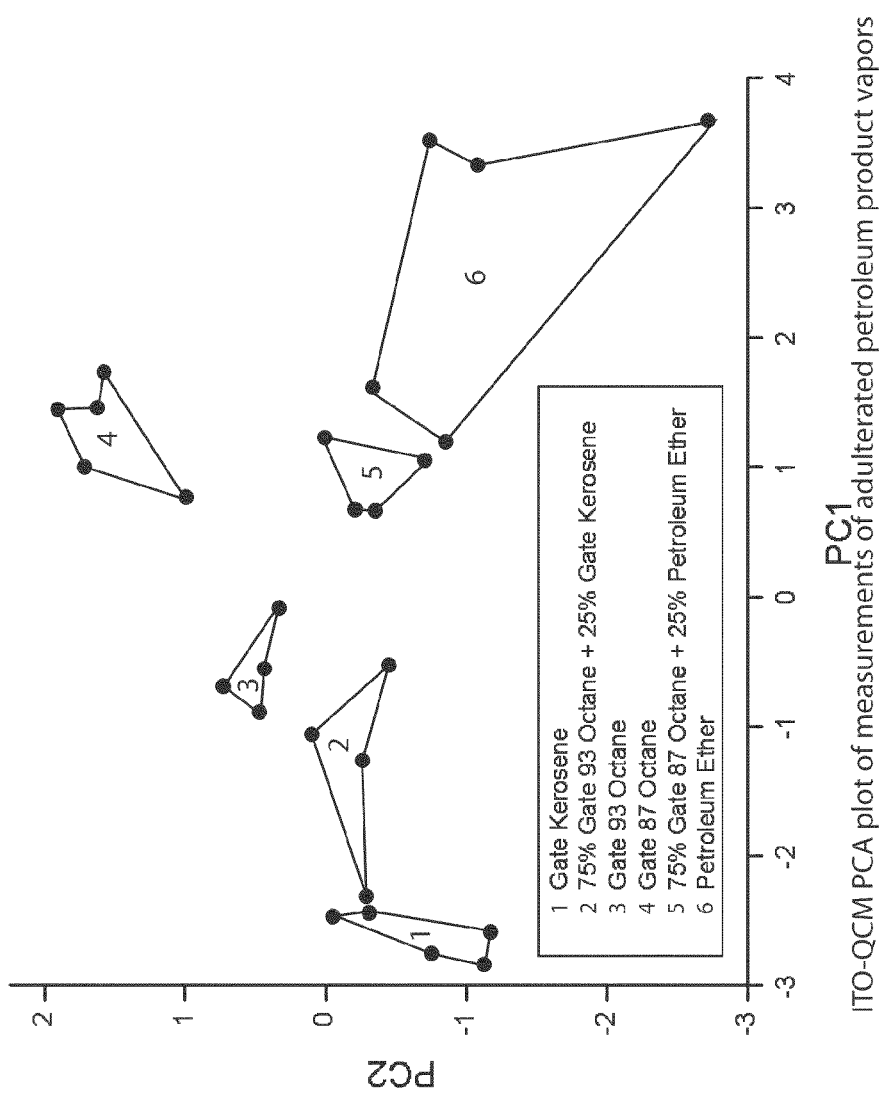
FIG. 83 is a graph of ITO-QCM PCA plots of measurements of adulterated petroleum product vapors.
Figure 85:
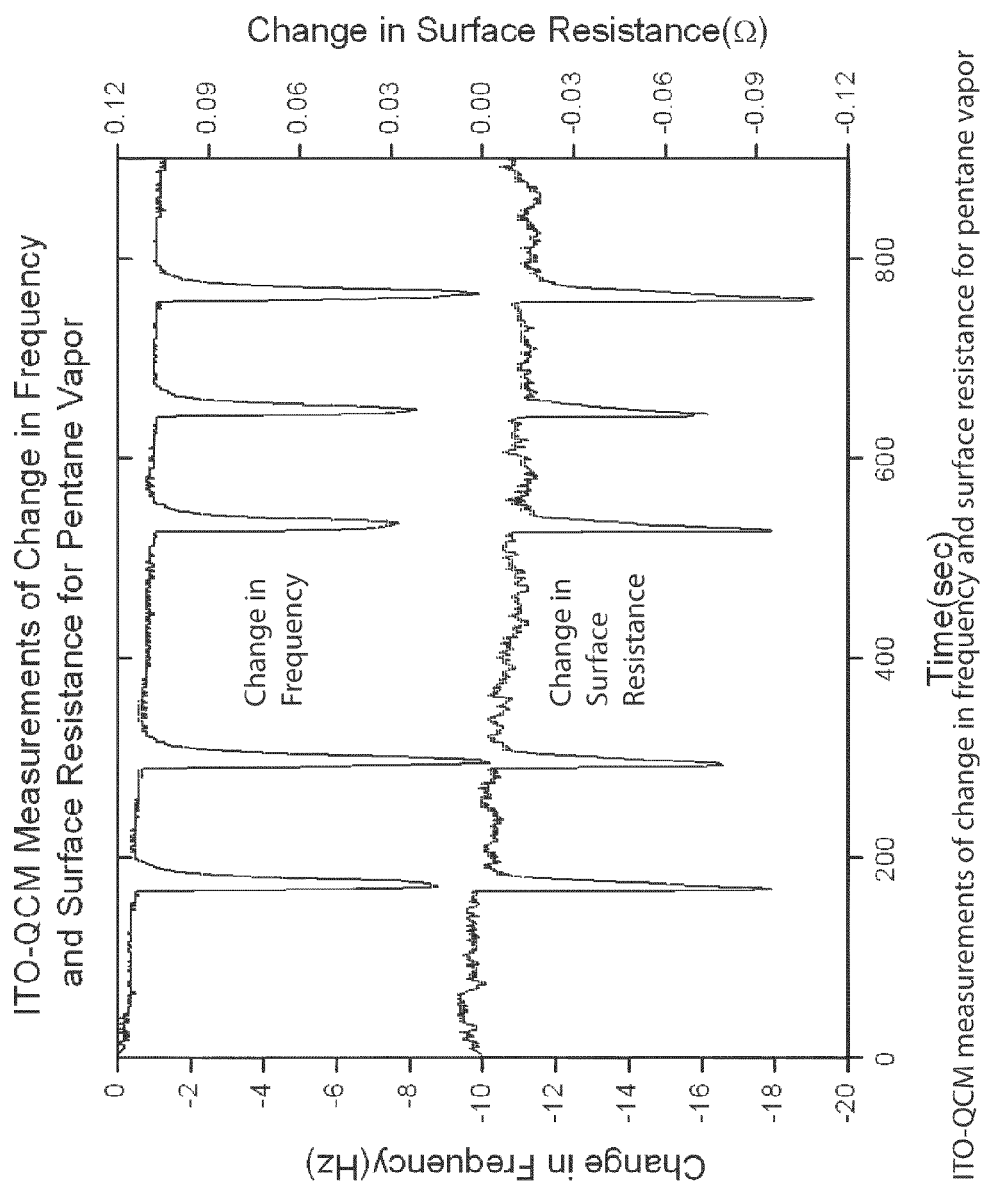
FIG. 85 is a graph of ITO-QCM measurements of change in frequency and surface resistance for pentane vapor.
Figure 86:
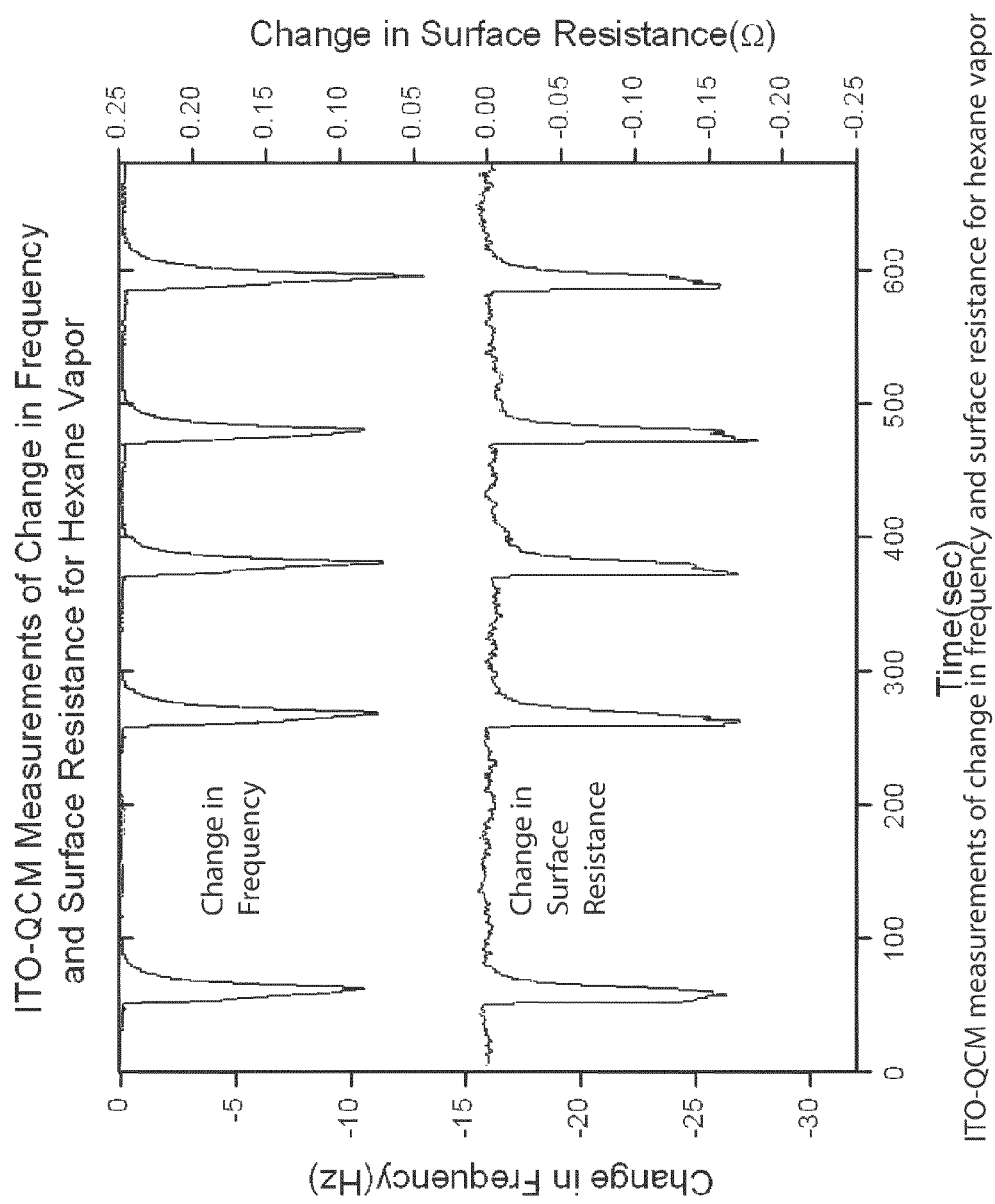
FIG. 86 is a graph of ITO-QCM measurements of change in frequency and surface resistance for hexane vapor.
Figure 87:
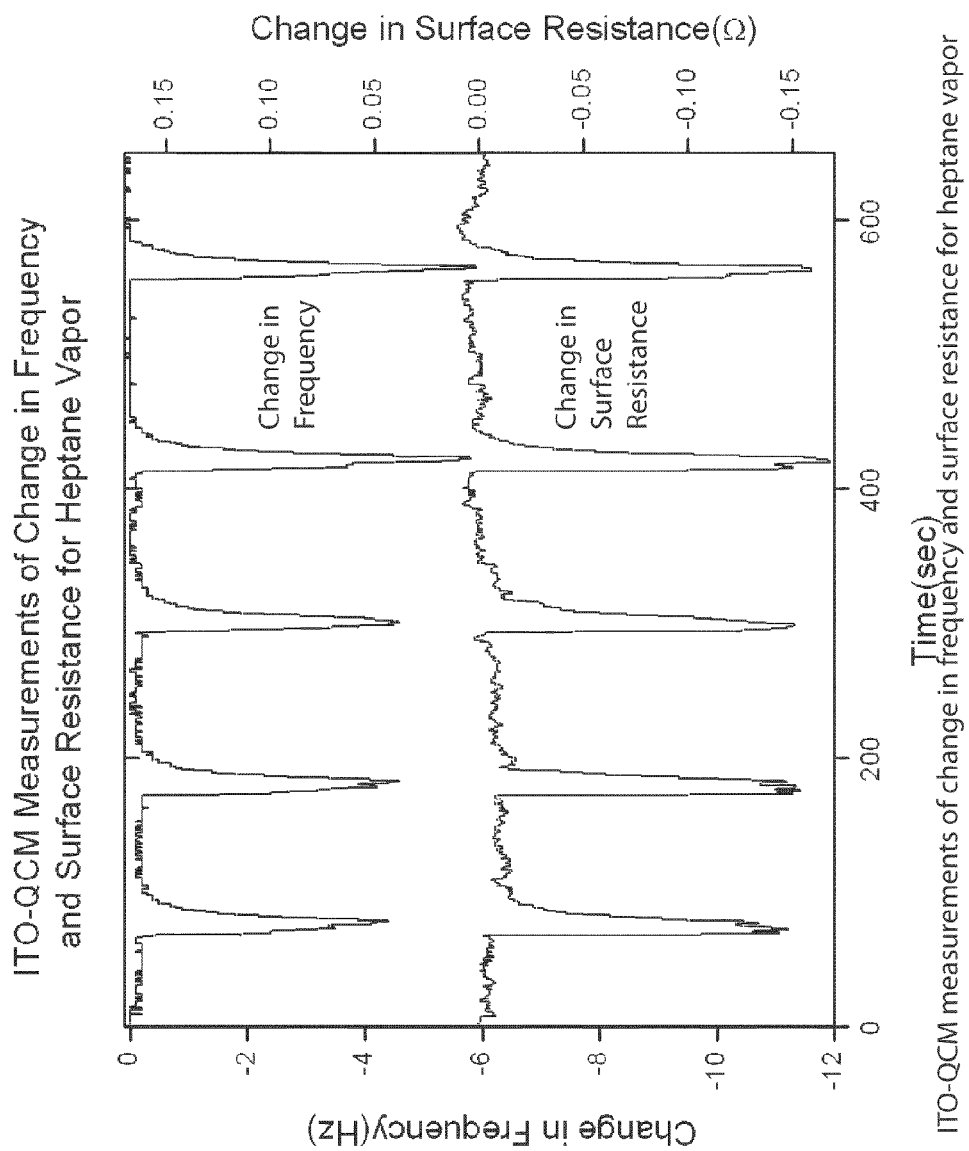
FIG. 87 is a graph of ITO-QCM measurements of change in frequency and surface resistance for heptane vapor.
Figure 88:
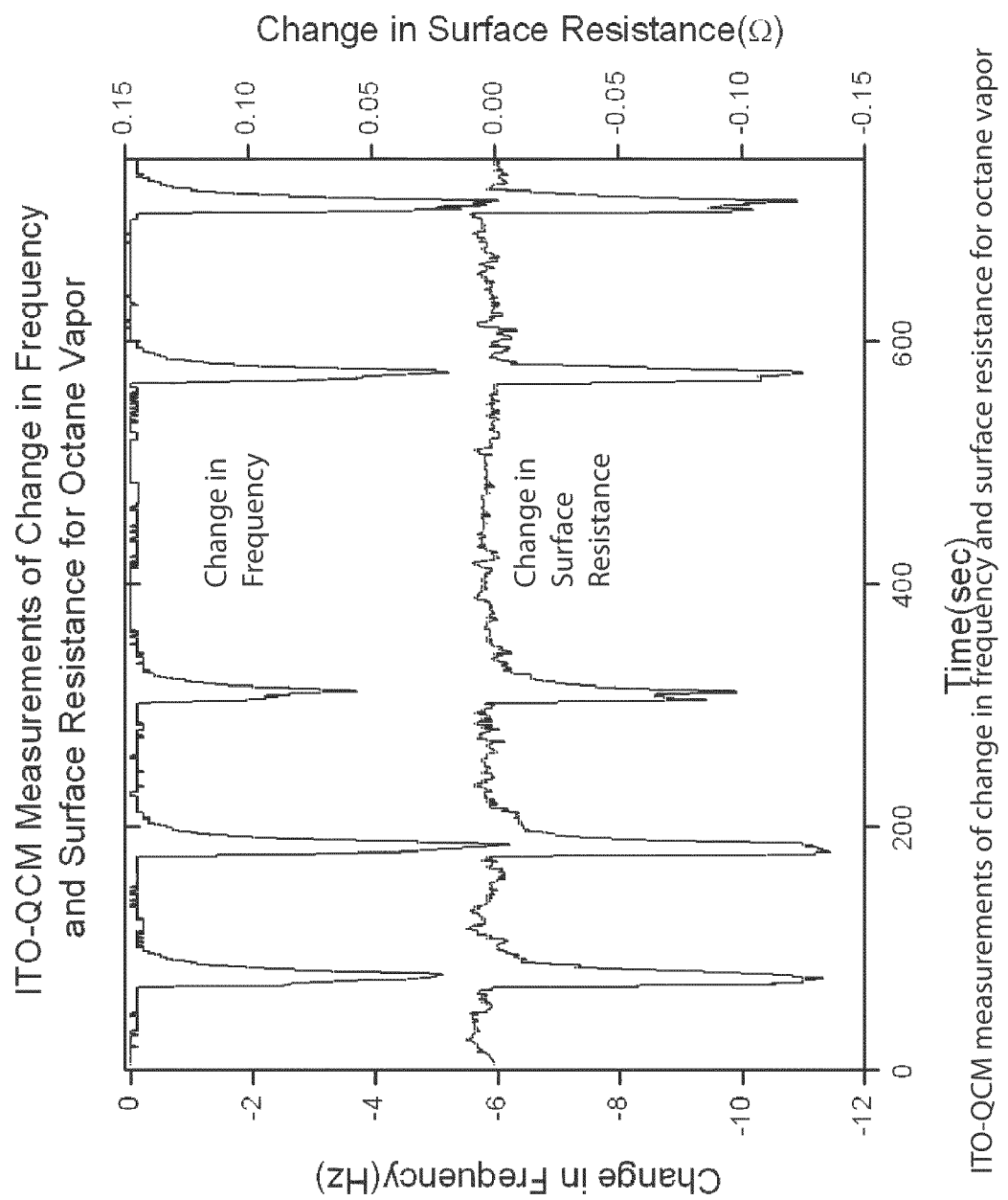
FIG. 88 is a graph of ITO-QCM measurements of change in frequency and surface resistance for octane vapor.
Figure 89:
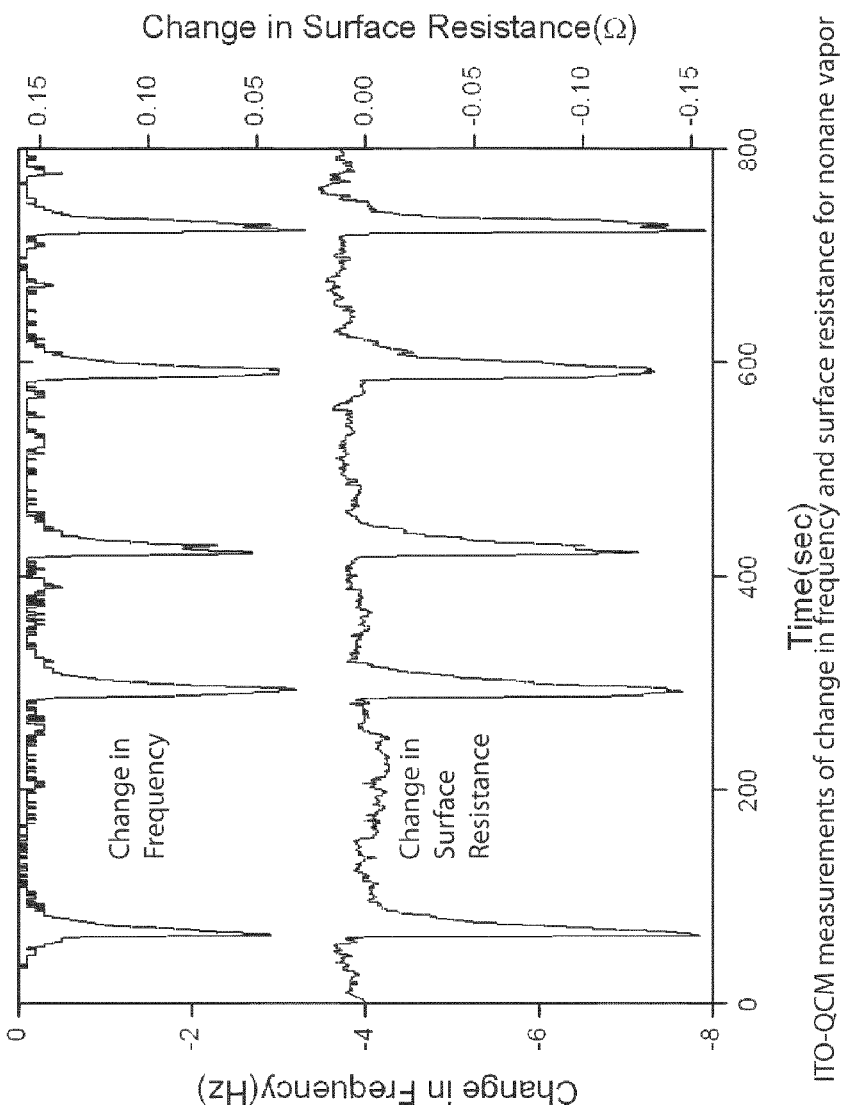
FIG. 89 is a graph of ITO-QCM measurements of change in frequency and surface resistance for nonane vapor.
Figure 90:
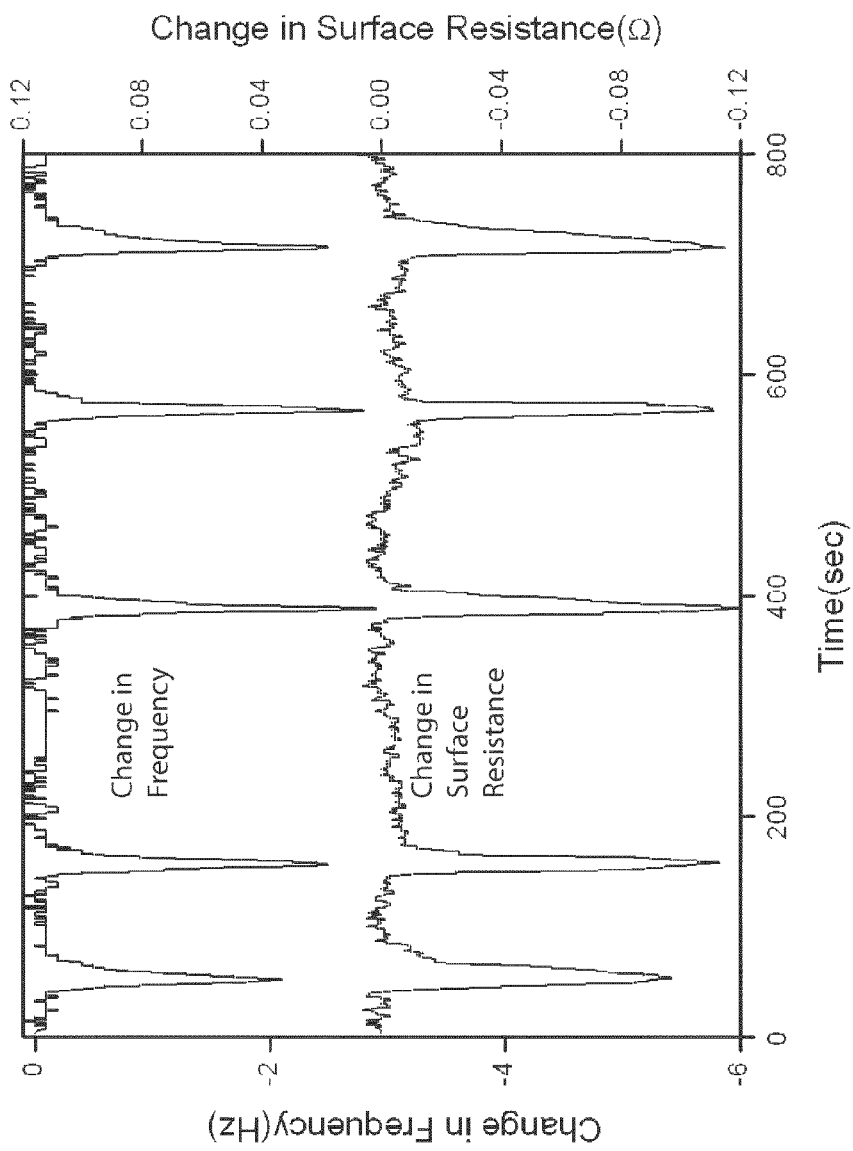
FIG. 90 is a graph of ITO-QCM measurements of change in frequency and surface resistance for decane vapor.
Figure 91:
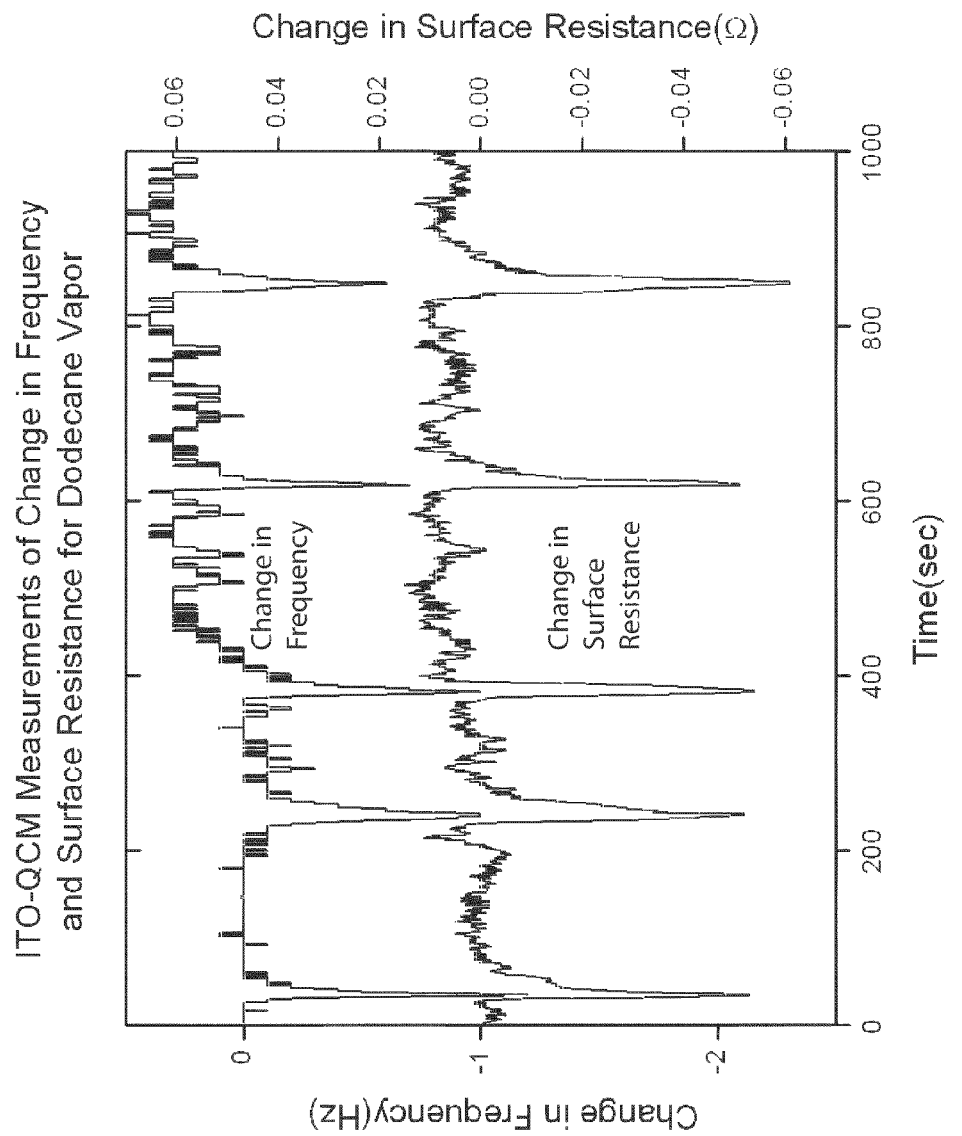
FIG. 91 is a graph of ITO-QCM measurements of change in frequency and surface resistance for dodecane vapor.
Figure 92:
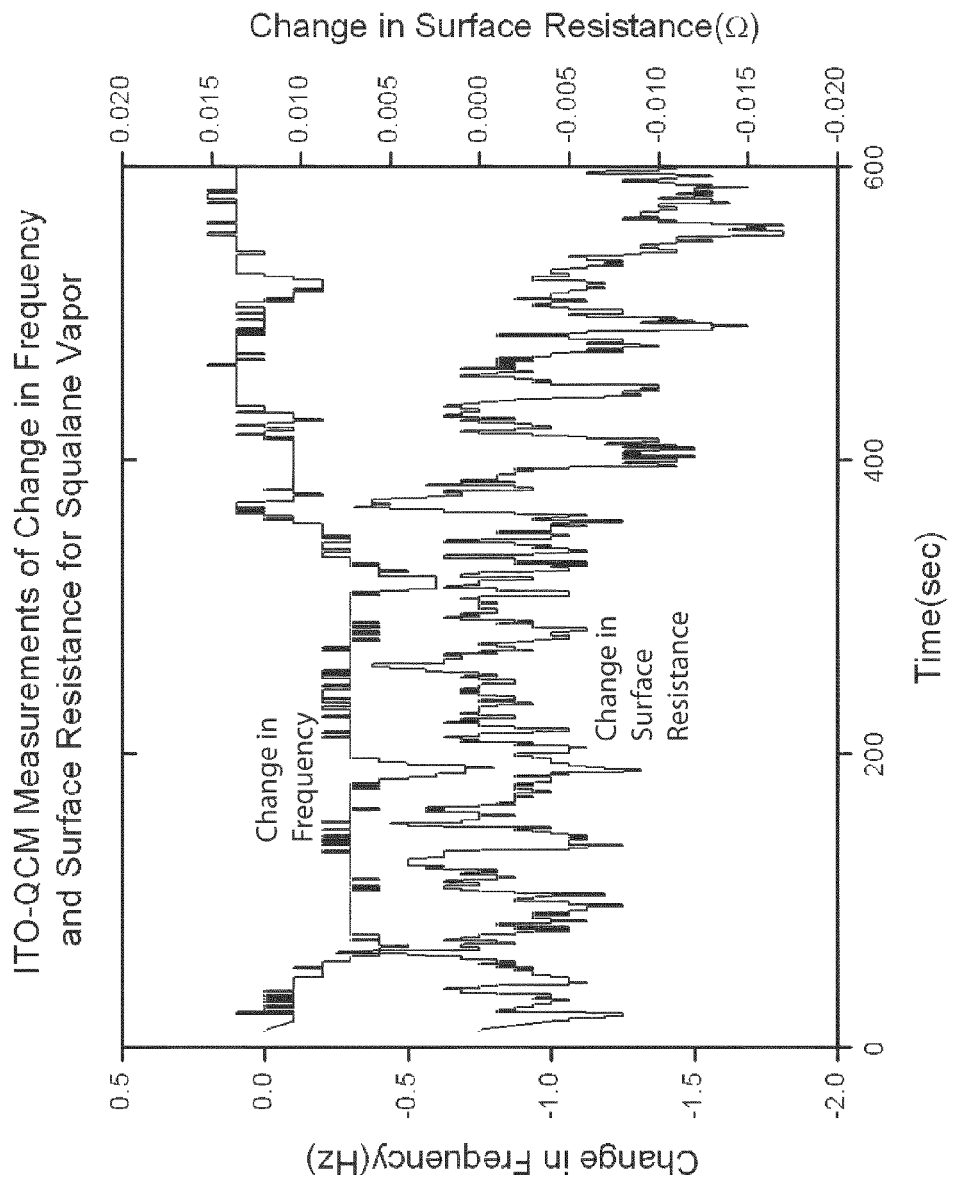
FIG. 92 is a graph of ITO-QCM measurements of change in frequency and surface resistance for squalane vapor.

PCA score plots of 87 octane gasoline, 93 octane gasoline, kerosene, petroleum ether, 87 octane gasoline mixed with 25% petroleum ether and 93 octane gasoline mixed with 25% kerosene vapor measurements, showed clear separation into clusters in FIG. 83. Thus an ITO-QCM sensor system according to principles of the invention can distinguish between each of the petroleum vapors and the adulterated petroleum vapors. In general, there is increasing volatility from left to right on the PCA score plot as shown in FIG. 83.

The Indium Tin Oxide (ITO) thin film over a 5 MHz AT cut gold quartz crystal microbalance was also used to measure the following alkane hydrocarbon vapors shown in the table comprising FIG. 84. The alkane hydrocarbon series represent the primary chemicals in a range of petroleum products. Pentane, hexane, and heptane are the primary chemicals in petroleum ethers. Octane is the primary chemical in gasoline. Nonane, decane, and dodecane are primary chemicals in kerosene, jet fuel, and diesel fuel. Squalane is an oily alkane hydrocarbon. ITO-QCM measurements with alkane hydrocarbons of known composition serve as reference samples for analyzing ITO-QCM changes in response to vapors, unlike commercial petroleum products which consist of non-standardized mixes of chemicals.

FIGS. 85 to 92 show actual ITO-QCM measurements of the change in frequency and surface resistance when a 15 µL drop of each alkane hydrocarbon sample was applied to one end of paper strip, then immediately held 2 cm over the ITO-quartz crystal surface for 10 seconds in an open glass jar (500 ml), and then removed. A digital timer was used to measure the 10 second time period. A new paper strip having a 20 cm length, 2 cm width and 0.3 mm thickness was used for each test.

Figure 93:
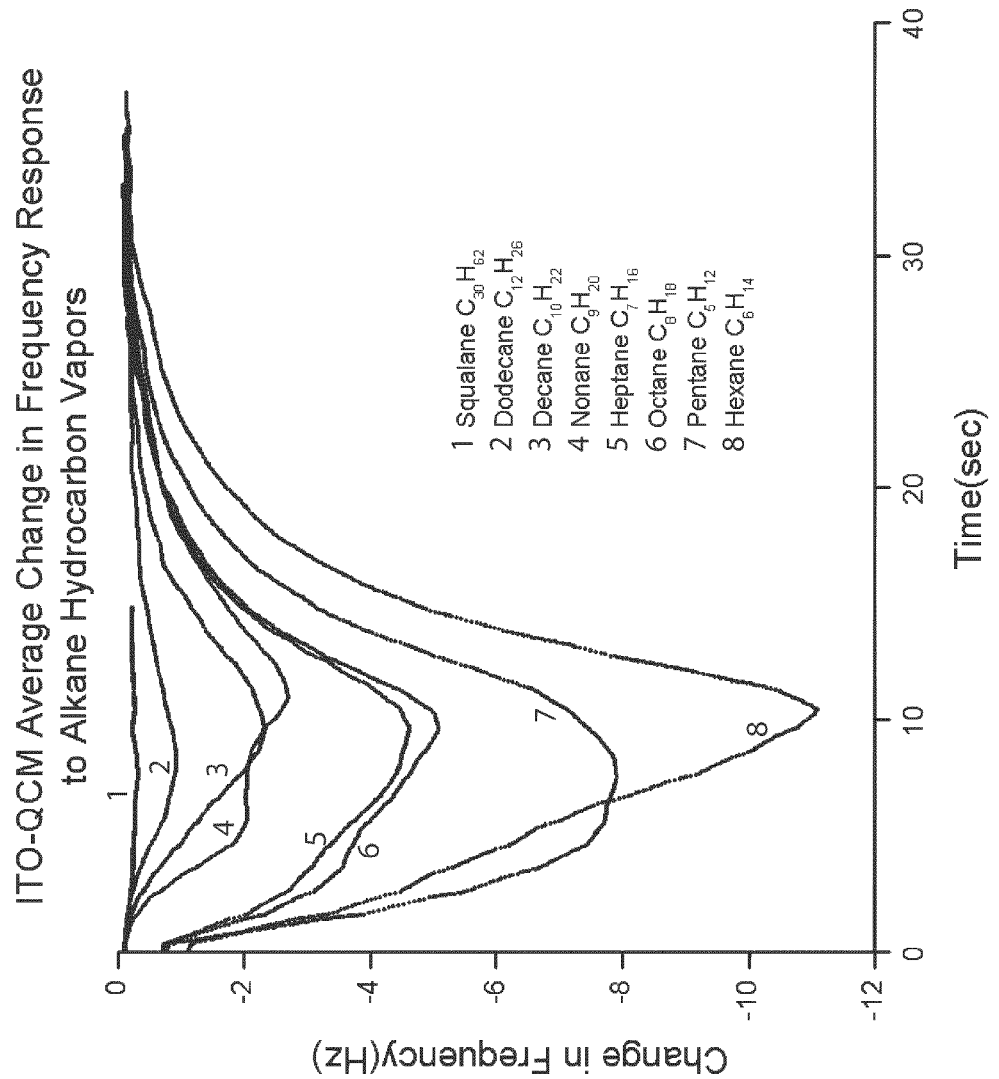
FIG. 93 is a graph of ITO-QCM average change in frequency response to alkane hydrocarbon vapors.
Figure 94:
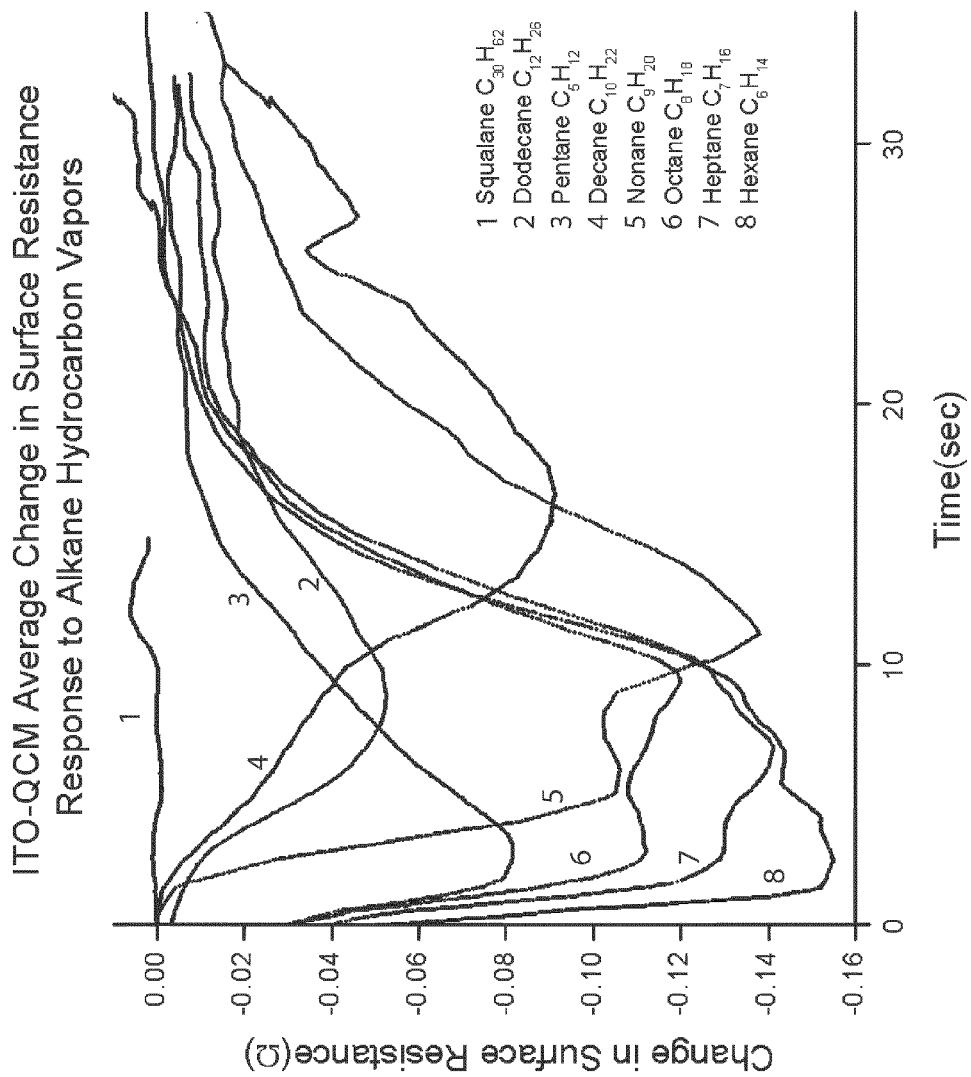
FIG. 94 is a graph of ITO-QCM average change in surface resistance response to alkane hydrocarbon vapors.
Figure 96:
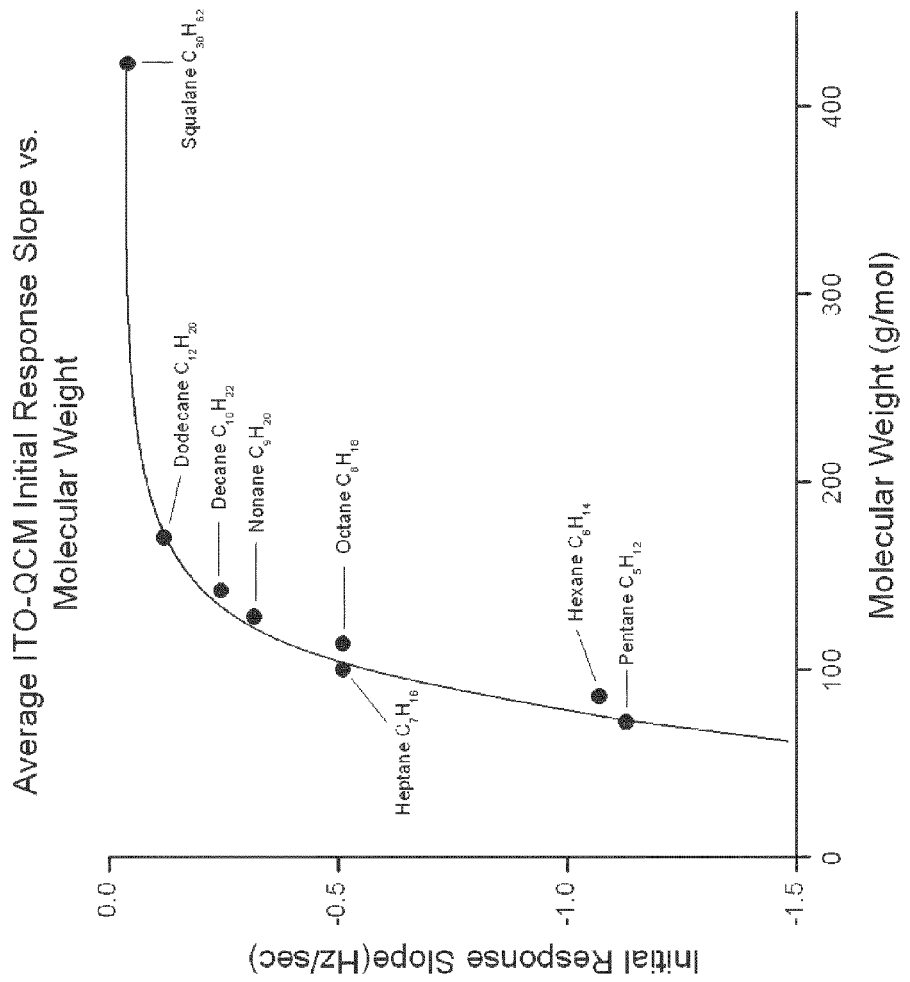
FIG. 96 is a graph of Average ITO-QCM initial response slope vs. molecular weight.
Figure 97:
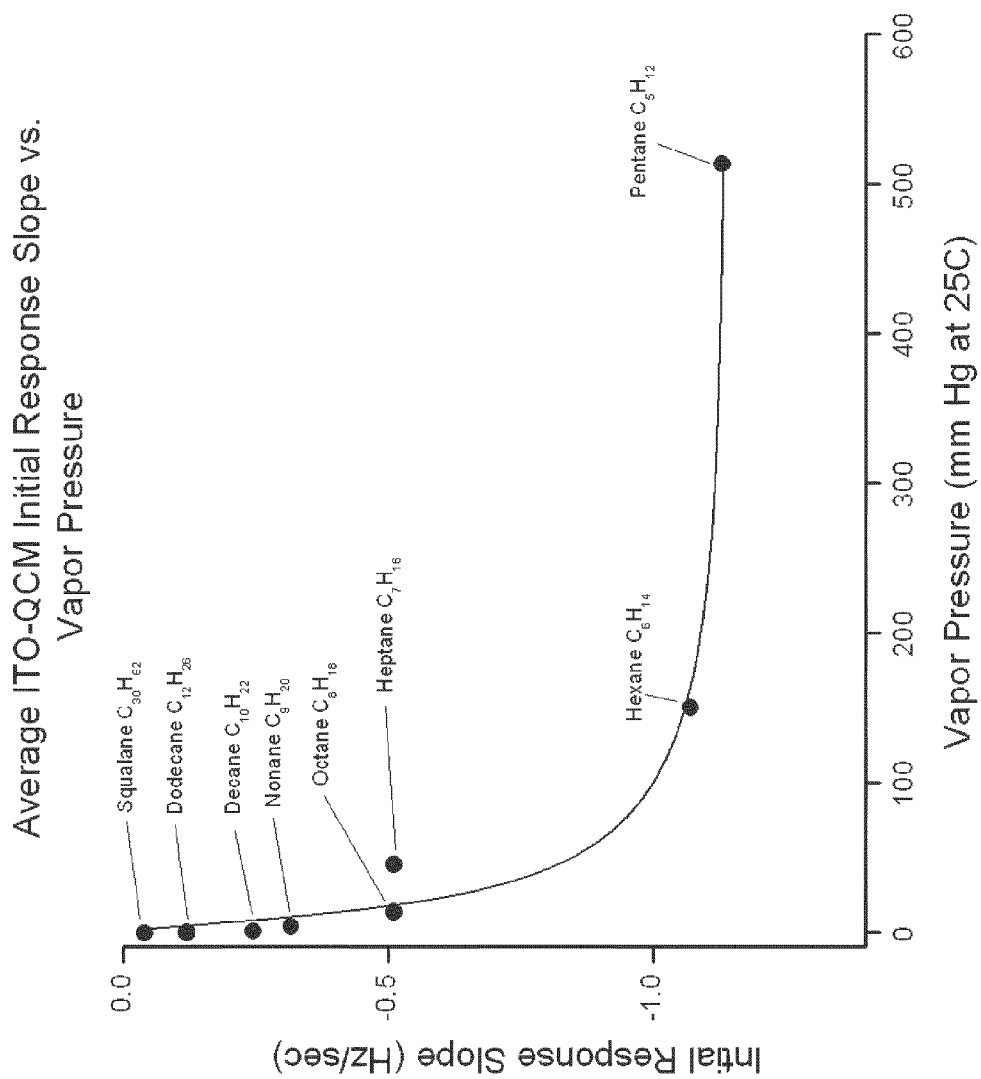
FIG. 97 is a graph of Average ITO-QCM initial response slope vs. vapor pressure.

ITO-QCM change in frequency and change in surface resistance responses to the alkane hydrocarbon test vapors were generally highest for the lower molecular weight, higher vapor pressure samples, and lowest for the higher molecular weight, lower vapor pressure samples, as shown in FIGS. 93 and 94. An exception was pentane, which showed a lower than expected response, which due to its very high volatility evaporated and dissipated before the end of the 10 second sample measurement period. In addition, it started to volatilize from the tip of a micro liter pipette applying the substance to the paper test media. Pentane vapor exhibited the greatest ITO-QCM change in initial response slope (change in frequency per time) as shown in FIGS. 96 and 97. Octane and heptane showed substantially similar responses for change in frequency as shown in FIG. 93.

Referring again to FIG. 94, the average change in the surface resistance of ITO-QCM odor sensor for each alkane hydrocarbon sample is shown. Surface resistance decreased for all alkane hydrocarbon samples, expect squalane. Some alkanes have a fluctuating response with time, which may due to small air turbulence in the testing vessel (i.e., the open glass jar). The decrease in the surface resistance may be due to the fact that the vapor density of the alkanes is higher than that of air. The surface resistance of the ITO-QCM sensor increases a very small amount in the presence of squalane. This may be due to the fact that squalane is a very viscous liquid and does not readily vaporize.

Figure 95:
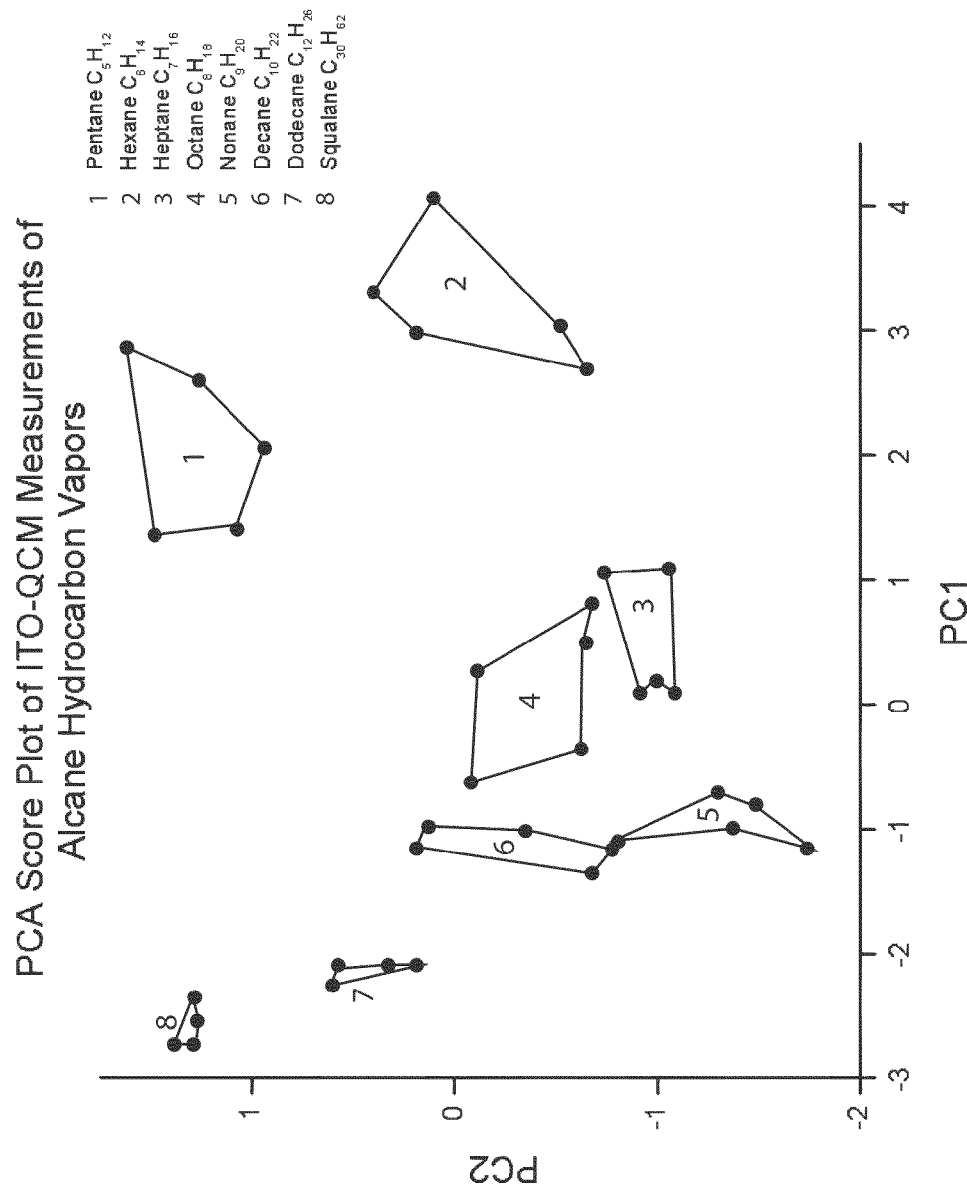
FIG. 95 is a PCA score plot of ITO-QCM measurements of alkane hydrocarbon vapors.

PCA score plots of different types of alkane vapor measurements showed clear separation into clusters, as in FIG. 95. Thus ITO-QCM odor sensor measurements can distinguish between each of the alkane vapors.

Initial response slopes of the ITO-QCM sensor was determined for all alkane vapors by measuring change in frequency over time. The initial response slope provides information about the molecular weight and vapor pressure of the analyte that can be obtained very quickly.

The average initial response slope of the ITO-QCM sensor as a function of the molecular weight of each alkane is shown in FIG. 96. The initial response slope increases with molecular weight up to about 200 g/mol and then nearly saturates up to 425 g/mol. The initial response slope of heptane and octane are nearly the same as their molecular weight are also very close in values.

Average initial response slope of the ITO-QCM sensor as a function of vapor pressure of each alkane is shown in FIG. 97. The initial response slope decreases with vapor pressure up to about 250 mm of Hg and then nearly saturates up to 525 mm of Hg.

Referring now to FIGS. 98 to 108, graphs, plots and data pertaining to measured parameters for aldehydes are provided. An aldehyde is an organic compound containing a terminal carbonyl group, which consists of a carbon atom bonded to a hydrogen atom and double-bonded to an oxygen atom, as known in the art. Aldehydes selected for detection using ITO-QCM sensors are considered to be among the simplest aldehydes and are prevalent in chemical industries. All of the aldehydes sampled are highly flammable, and their vapors can be explosive. They are all liquids at room temperature. Two of the simplest aldehydes, namely, formaldehyde and acetaldehyde, were not tested because both are gases at room temperature. Acrolein, another simple aldehyde, was not included in the study because it is not stable at room temperature and normal atmospheric pressure. In addition, its vapors are extremely hazardous.

An Indium Tin Oxide (ITO) thin film (e.g., about 200 nm thick) deposited over a 5 MHz AT cut gold quartz crystal microbalance by vacuum deposition was used as vapor sensor for the detection of the tested aldehyde compounds. The ITO film had a nanocrystalline structure with an average grain size of 44±12 nm. A 15 µL drop of each sample was applied to one end of a paper strip, then immediately held 1 cm over the ITO-quartz crystal surface for 20 seconds in an open glass jar (500 ml), and then removed. The paper strip was 20 cm in length, 2 cm wide and 0.3 mm thickness. A digital timer was used to measure the 20 second time period. A new paper strip was used for each run of each test sample. Parameters used in the determination of principal components analysis (PCA) of the petroleum products and alkanes are integrated frequency response (Hz-sec), integrated surface resistance response ($\Omega$-sec), initial response slope (Hz/sec), average return to baseline slope (Hz/sec) and average of all change in frequency data points (Hz), as described above.

Figure 104:
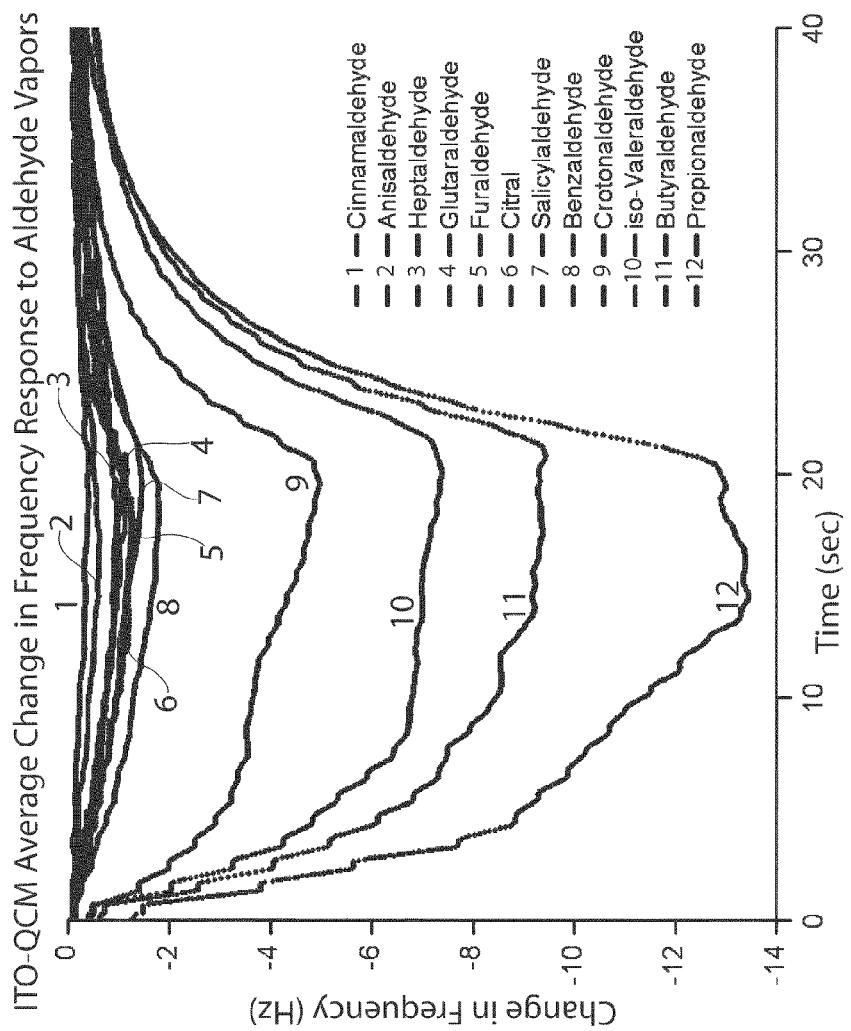
FIG. 104 is a graph of ITO-QCM average change in frequency response to aldehyde vapors.
Figure 105:
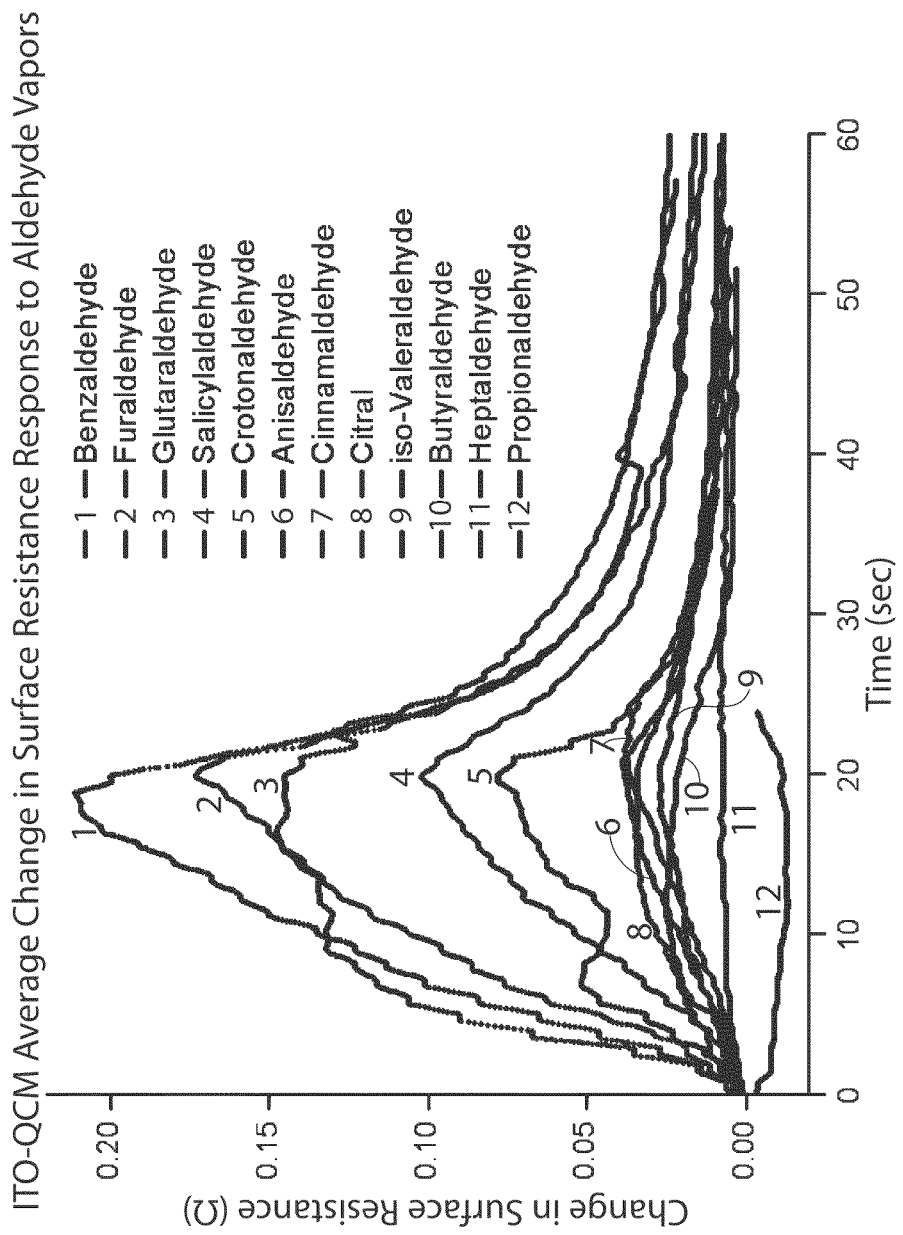
FIG. 105 is a graph of ITO-QCM average change in surface resistance response to aldehyde vapors.
Figure 107:
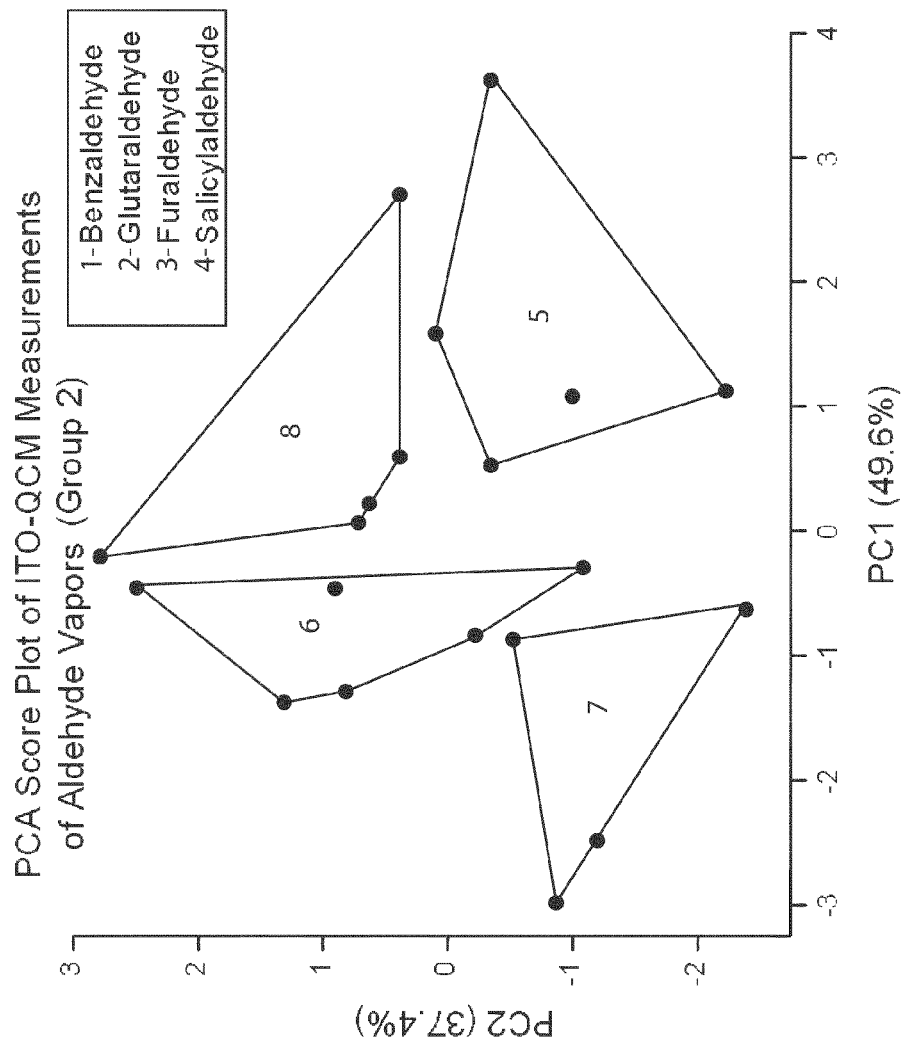
FIG. 107 is a PCA score plot of ITO-QCM measurements of Benzaldehyde, Glutaraldehyde, Furaldehyde, and Salicylaldehyde vapors.
Figure 108:
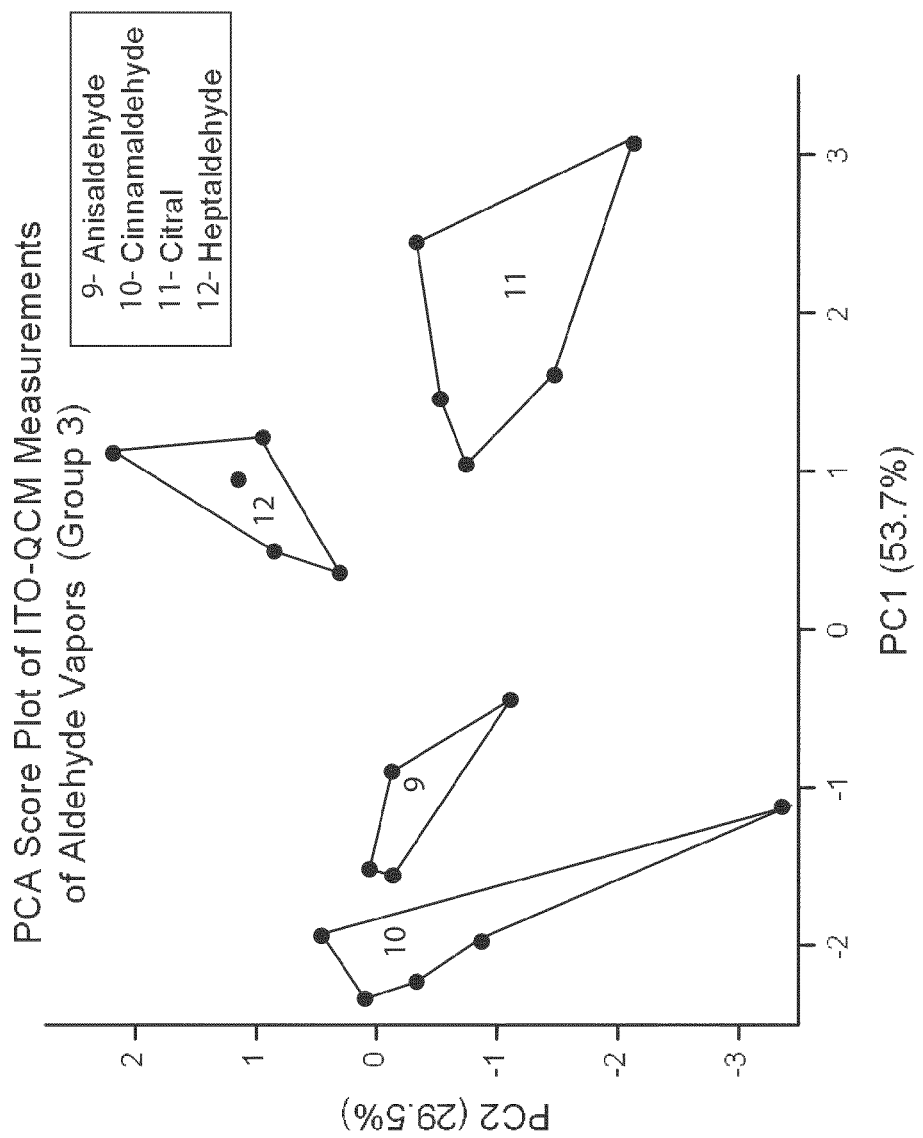
FIG. 108 is a PCA score plot of ITO-QCM measurements of Anisaldehyde, Cinnamaldehyde, Citral, and Heptaldehyde vapors.

Tables comprising FIGS. 98 to 103 show ITO-QCM vapor sensor results of all parameters determined for each test run of aldehyde samples. Changes in frequency and surface resistance as a function of time were recorded as vapor molecules from tested aldehydes were adsorbed on the ITO film, and then desorbed after the samples were removed from the jar. The average of the change in frequency of five measurements for each aldehyde sample with the ITO-QCM sensors is shown in FIG. 104. The average of the change in surface resistance of five measurements for each aldehyde sample with the ITO-QCM sensors is shown in FIG. 105. The measured parameters were used to determine PCA score plots for the aldehyde vapors, as illustrated in FIGS. 106-108.

With reference to FIG. 104, Propionaldeyde showed the maximum negative change in the frequency, while Cinnamaldehyde shows the minimum negative change in frequency. The Crotonaldeyde, iso-Valeraldehyde, Butyraldehyde, and Propionaldehyde ITO-QCM average change in frequency responses stand out from the other eight samples. These four samples have significantly higher vapor pressures than the other eight samples. Each aldehyde sample has a different peak value of frequency, as well as different response and recovery time characteristics, which provides preliminary identification of distinguishing signatures for each aldehyde.

With reference to FIG. 105, Benzaldehyde shows the maximum positive change in surface resistance, while Heptaldehyde shows the minimum positive change in surface resistance among the samples measured. Propionaldeyde was the only aldehyde to show a negative ITO-QCM measured change in surface resistance compared to the other tested aldehyde vapors. The QCM surface resistance parameter, which is also referred to as the "motional resistance" is a measure of the viscoelasticity of the ITO/quartz crystal sensor surface. An increase in the surface resistance indicates that the ITO/quartz crystal sensor surface is becoming more plastic or softer while the vapor sample is present in the test chamber. A decrease in the surface resistance indicates that the ITO/quartz crystal surface is becoming less plastic or more rigid, or stiffer while the sample vapor is present in the test chamber.

Figure 106:
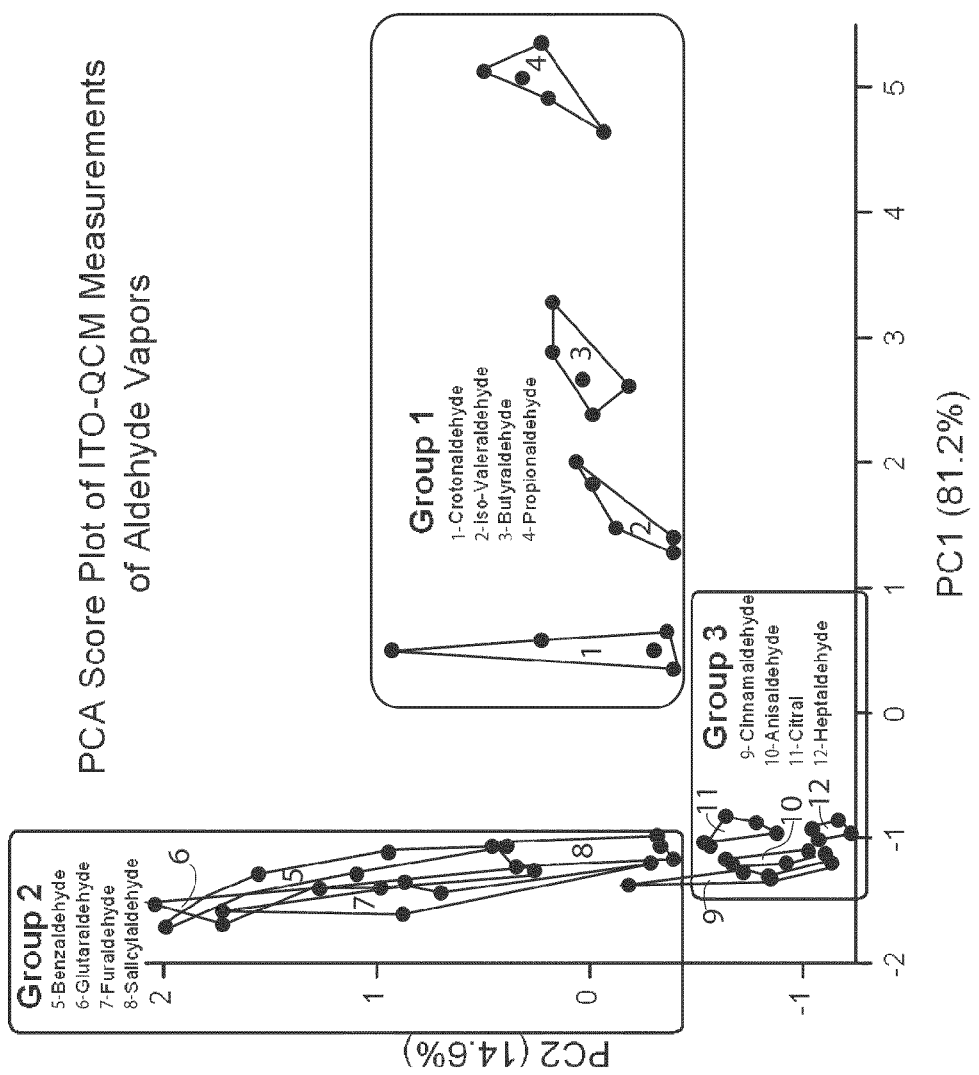
FIG. 106 is a PCA score plot of ITO-QCM measurements of aldehyde vapors.

With reference to the PCA score plot results for each of the aldehyde sample measurements as provided in FIG. 106, there is a roughly increasing average ITO-QCM change in frequency response among the aldehyde vapor samples from left to right on the PCA score plot graph, and a roughly increasing average ITO-QCM change in surface resistance response among the aldehyde vapor samples from bottom to top on the PCA score plot graph. The PCA score plot of the different types of aldehydes shows clear separation for the group-1 Crotonaldeyde, iso-Valeraldehyde, Butyraldehyde, and Propionaldehyde ITO-QCM sample measurements. The PCA score plot also shows four (group-2) samples in the PC2 range from about −0.5 to 2 on the left side of the graph that appear to overlap each other somewhat. The PCA score plot also shows another four (group-3) samples that are in separate clusters, but closely spaced in the bottom left portion of the PCA score plot graph. In order to better resolve the differences between the closely spaced group-2 and group-3 samples on the PCA score plot graph in FIG. 106, PCA was performed on just the group-2 only and group-3 only samples in the cluster with the same data used for the FIG. 106 score plot. Thus, an iterative process of performing PCA to better resolve the differences between closely spaced group samples is provided.

FIG. 107 shows a score plot of just the group-2 Benzaldehyde, Glutaraldehyde, Furaldehyde, and Salicylaldehyde ITO-QCM sample measurements. As explained above, an iterative process of performing PCA to better resolve the differences between closely spaced group-2 samples was performed. Well-defined separation among each of the group-2 samples can be seen in this PCA score plot graph, with the exception of one stray Furaldehyde measurement within the Glutaraldehyde cluster, which may be due to experimental error.

FIG. 108 shows a score plot of just the group-3 Anisaldehyde, Cinnamaldehyde, Citral, and Heptaldehyde ITO-QCM sample measurements. As explained above, an iterative process of performing PCA to better resolve the differences between closely spaced group-3 samples was performed. Well-defined separation among each of the group-3 samples can be seen in this PCA score plot graph as well.

In sum, nanocrystalline-thin film ITO-QCM sensors detected various aldehydes at room temperature. The ITO (as a thin film sensor), and the QCM (as a transducer) combined to show the change in frequency responses and surface resistance responses as a function of time for each aldehyde vapor tested. PCA analysis showed selectivity for several aldehyde vapors.

Referring now to FIGS. 109 to 116, graphs, plots and data pertaining to measured parameters for ketones are provided. A ketone is a type of compound which contains a carbonyl group (C=O) bonded to two other carbon atoms in the form $R_1$—(C=O)—$R_2$, and neither of the substituents $R_1$, $R_2$ is hydrogen. The ketones that were selected for detection using ITO-QCM sensors were chosen because they are not only considered among the simplest ketones, but because they also have various types of applications in chemical industries. They are all liquids at room temperature. All of the simpler ketones sampled are highly flammable, and their vapors can be explosive. Among the tested ketones, butanedione and heptanone are relatively safely present in foods, while acetone, acetyl acetone, butyric acid, chloroacetone, methyl isobutyl ketone, and pentanone have unpleasant odors and/or are moderately toxic, so being able to distinguish among them with an odor or vapor sensor is important.

The detection of ketones is very important for diabetic patients. In human bodies, acetone, acetoacetate and beta-hydroxybutyrate (Butyric acid with —OH hydroxyl group added) are generated from carbohydrates, fatty acids and amino acids. Ketones levels are elevated in the blood and urine after fasting, a night of sleep, and during starvation. Elevated ketone levels in blood and urine are also caused by hypoglycemia, metabolism deficiencies, and diabetic ketoacidosis. Colorimetric ketone strips are commercially available for the detection of acetoacetate in diabetics. These strips are only selective for acetoacetate, and suffer from cross interference by drugs and vitamins such as Pyridium, Azo Gantrisin, and Azo Gantanol, nitrofurantoin, vitamin C and riboflavin.

An Indium Tin Oxide (ITO) thin film (e.g., about 200 nm thick) deposited over a 5 MHz AT cut gold quartz crystal microbalance by vacuum deposition was used as vapor sensor for the detection of the tested ketone compounds. The ITO film had a nanocrystalline structure with an average grain size of 44±12 nm. A 15 μL drop of each sample was applied to one end of a paper strip, then immediately held 1 cm over the ITO-quartz crystal surface for 20 seconds in an open glass jar (500 ml), and then removed. The paper strip was 20 cm in length, 2 cm wide and 0.3 mm thickness. A digital timer was used to measure the 20 second time period. A new paper strip was used for each run of each test sample. Parameters used in the determination of principal components analysis (PCA) of the petroleum products and alkanes are integrated frequency response (Hz-sec), integrated surface resistance response (Ω-sec), initial response slope (Hz/sec), average return to baseline slope (Hz/sec) and average of all change in frequency data points (Hz), as described above.

Figure 114:
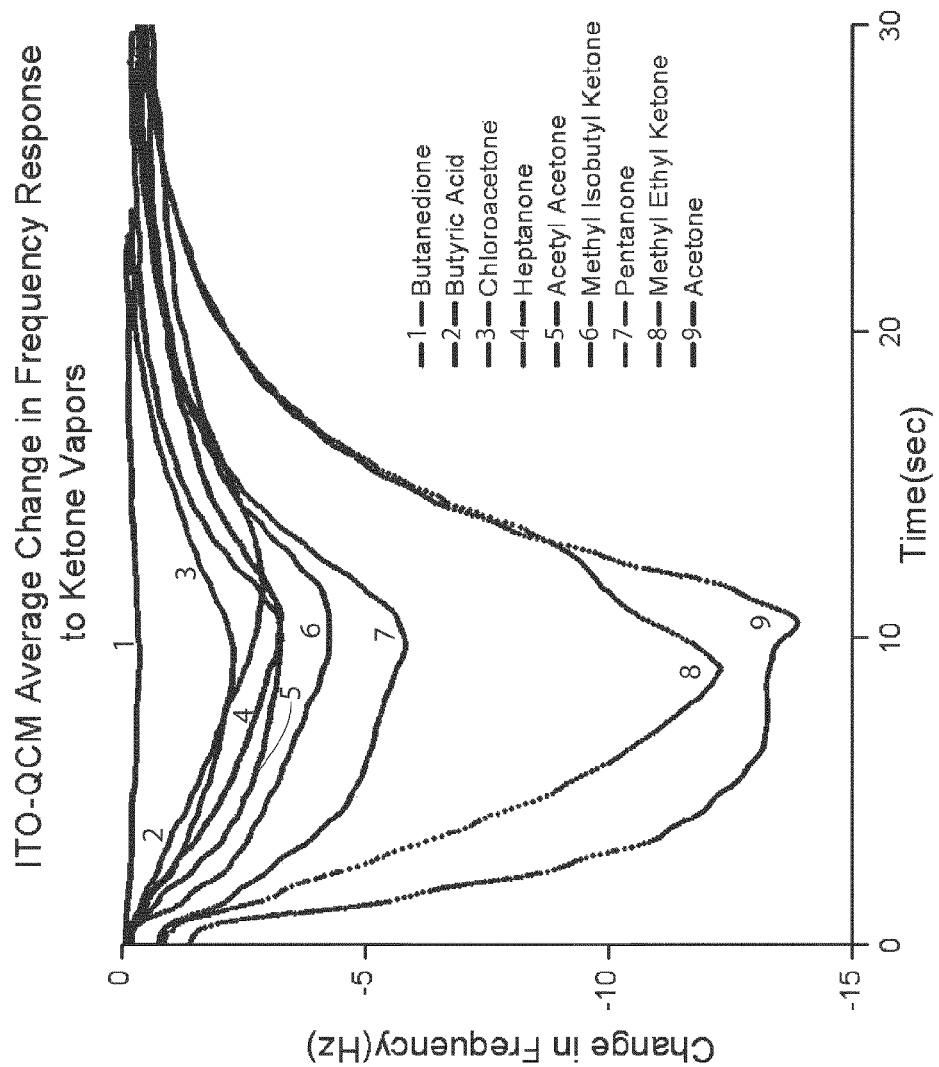
FIG. 114 is a graph of ITO-QCM average change in frequency response to ketone vapors.
Figure 115:
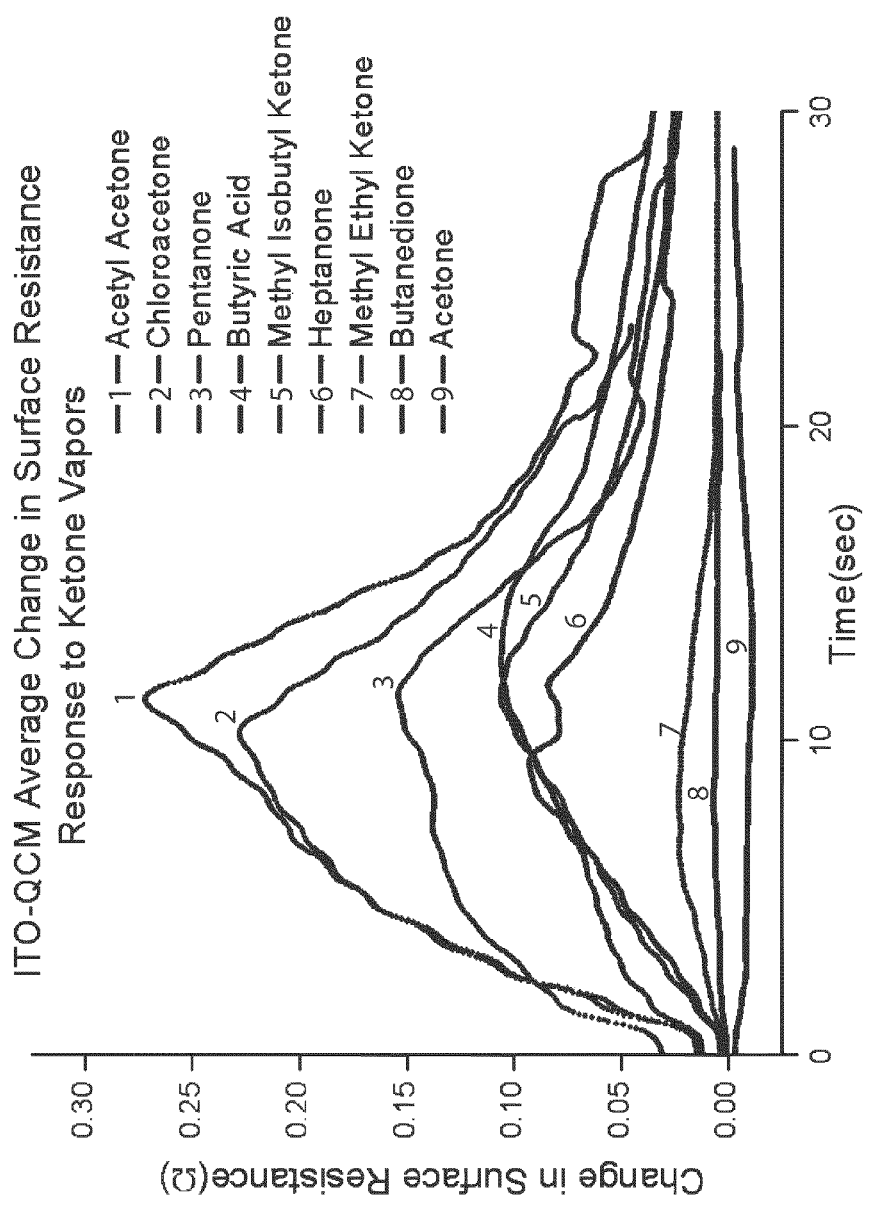
FIG. 115 is a graph of ITO-QCM average change in surface resistance response to ketone vapors.

Tables comprising FIGS. 109 to 113 show ITO-QCM vapor sensor results of all parameters determined for each test run of ketone samples. Changes in frequency and surface resistance as a function of time were recorded as vapor molecules from tested ketones were adsorbed on the ITO film, and then desorbed after the samples were removed from the jar. The average of the change in frequency of five measurements for each ketone sample with the ITO-QCM sensors is shown in FIG. 114. The average of the change in surface resistance of five measurements for each ketone sample with the ITO-QCM sensors is shown in FIG. 115. The measured parameters were used to determine PCA score plots for the ketone vapors, as illustrated in FIG. 116.

With reference to FIG. 114, the average of five change in frequency measurements for each ketone sample with ITO-QCM sensors is shown. Acetone shows the maximum negative change in the frequency, while butanedione shows the minimum change in frequency. Each ketone sample has a different peak value of frequency, as well as different response and recovery time characteristics, which provides preliminary identification of distinguishing signatures for each ketone.

The average of five change in surface resistance measurements for each ketone sample with the ITO-QCM sensors is shown in FIG. 115. Acetyl acetone shows the maximum positive change in surface resistance, while butanedione shows the minimum positive change in surface resistance among the samples measured. Acetone was the only ketone to show a negative ITO-QCM measured change in surface resistance compared to the other tested ketone vapors.

Figure 116:
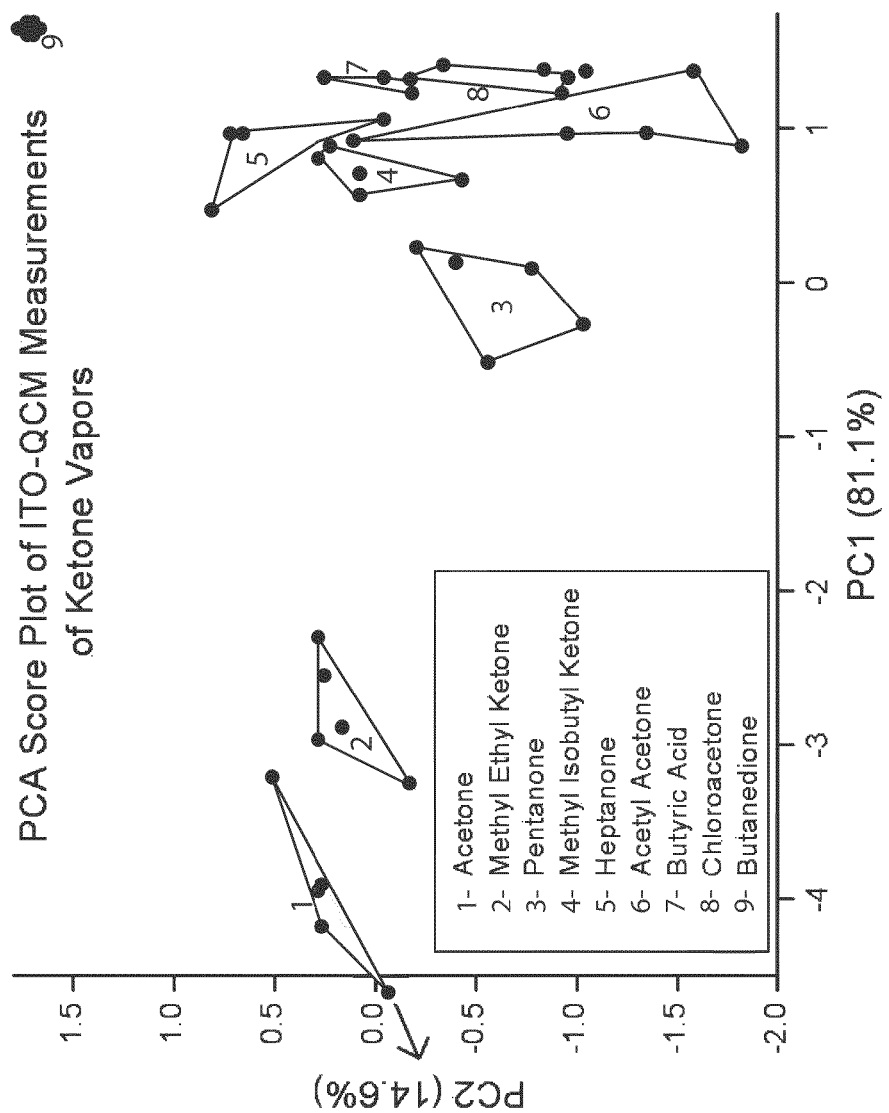
FIG. 116 is a PCA score plot of ITO-QCM measurements of ketone vapors.
Figure 120:
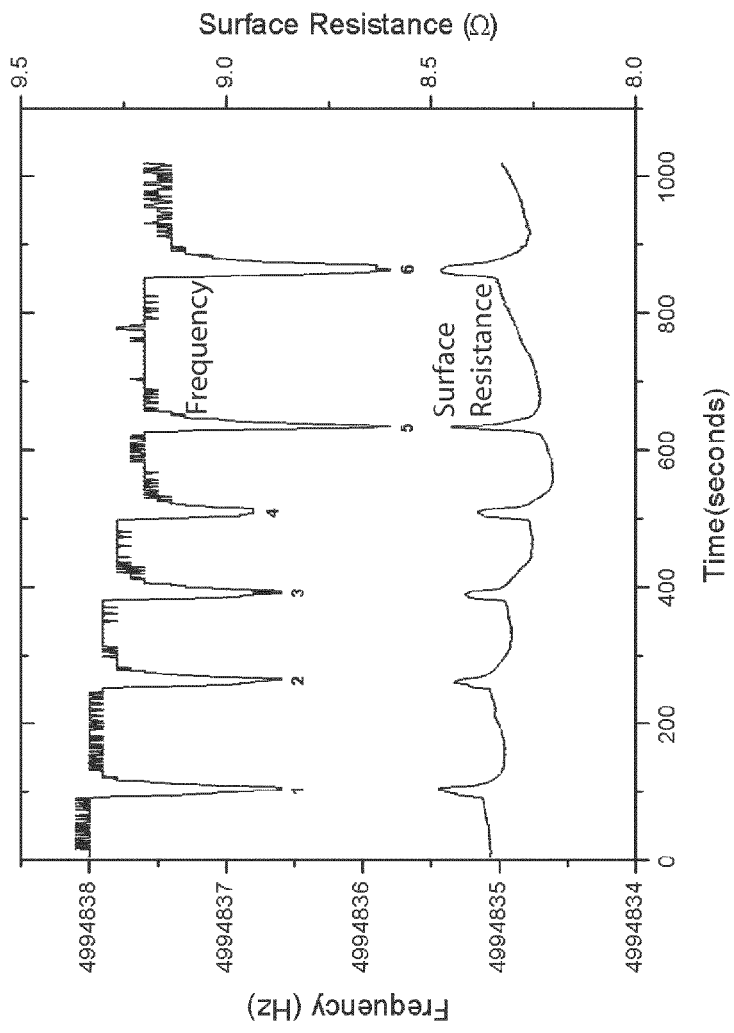
FIG. 120 is a graph of ITO-QCM average change in frequency response to apple odors.
Figure 121:
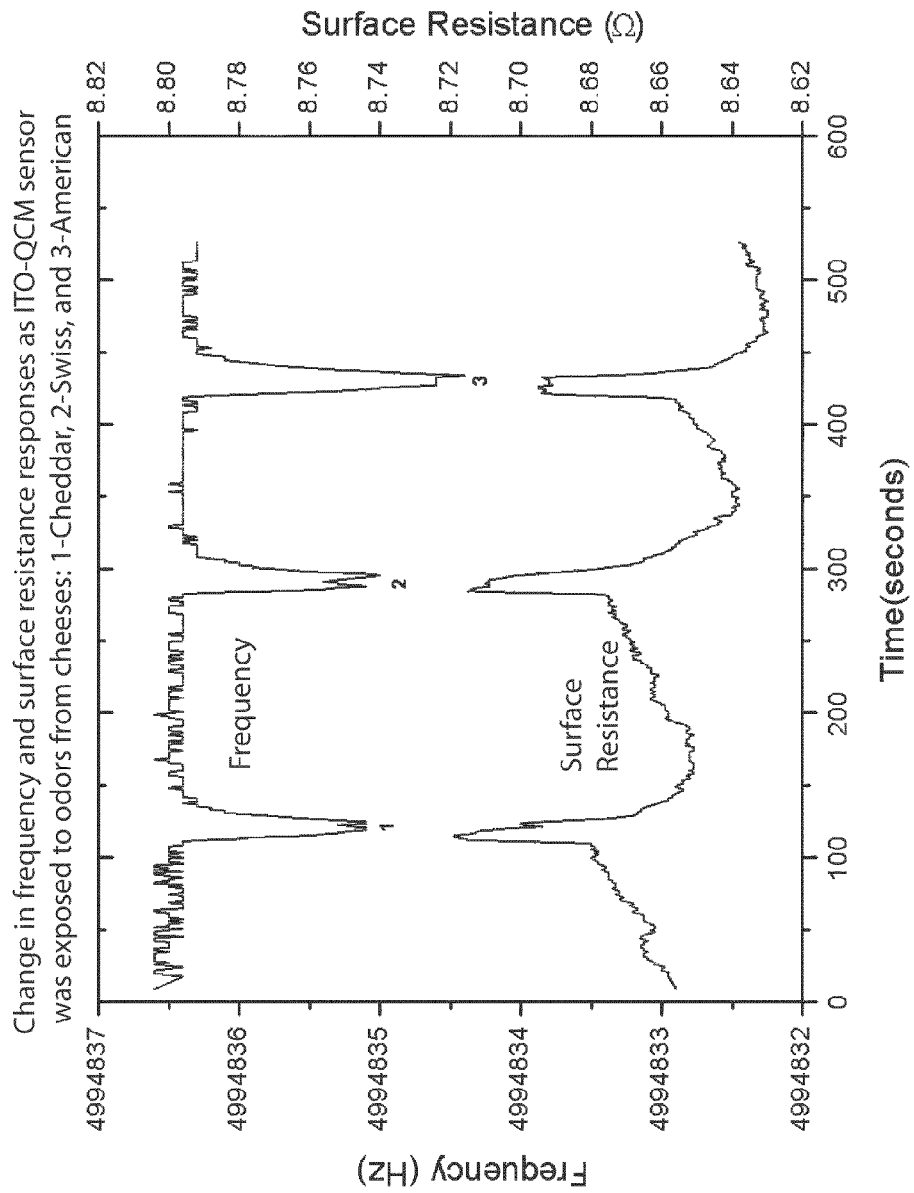
FIG. 121 is a graph of ITO-QCM average change in frequency response to cheese odors.
Figure 122:
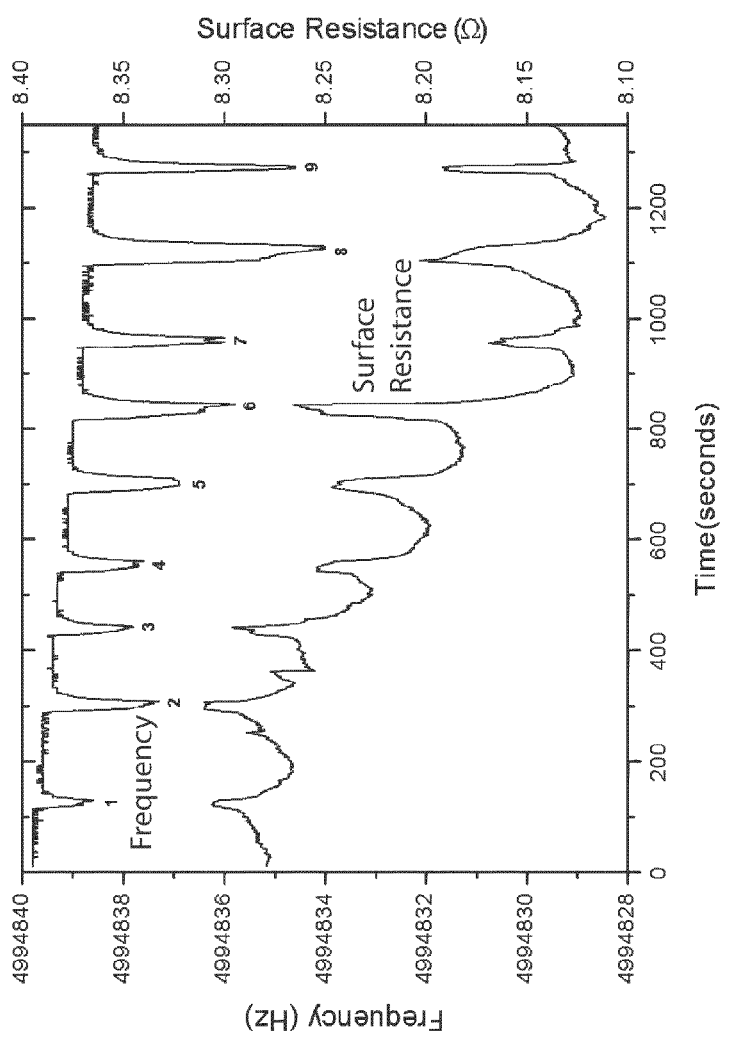
FIG. 122 is a graph of ITO-QCM average change in frequency response to assorted fruit odors.
Figure 123:
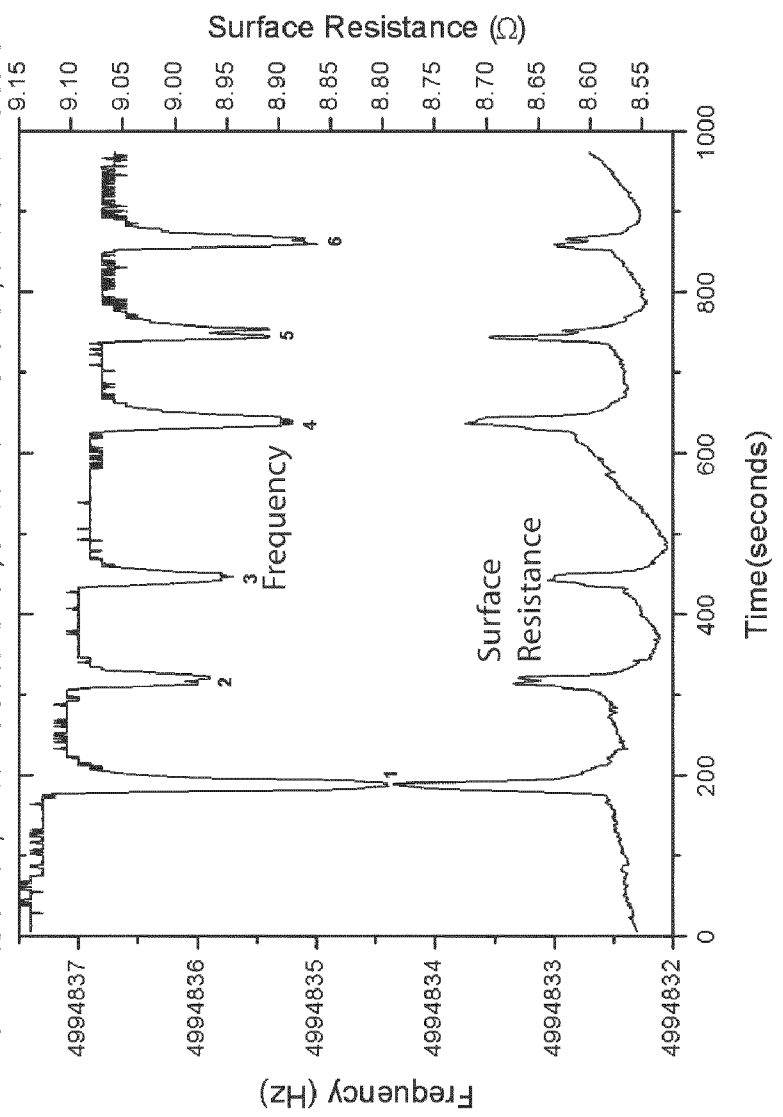
FIG. 123 is a graph of ITO-QCM average change in frequency response to onion and garlic odors.
Figure 124:
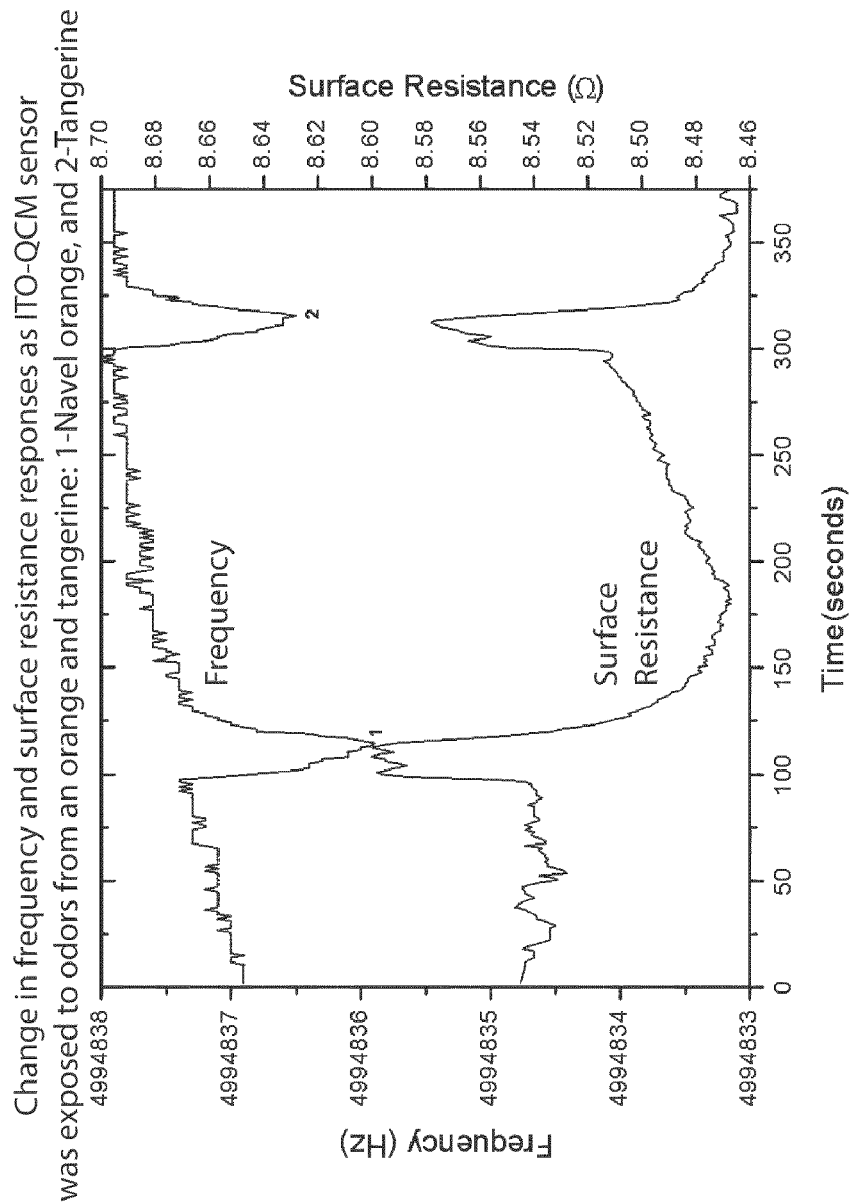
FIG. 124 is a graph of ITO-QCM average change in frequency response to orange and tangerine odors.
Figure 125:
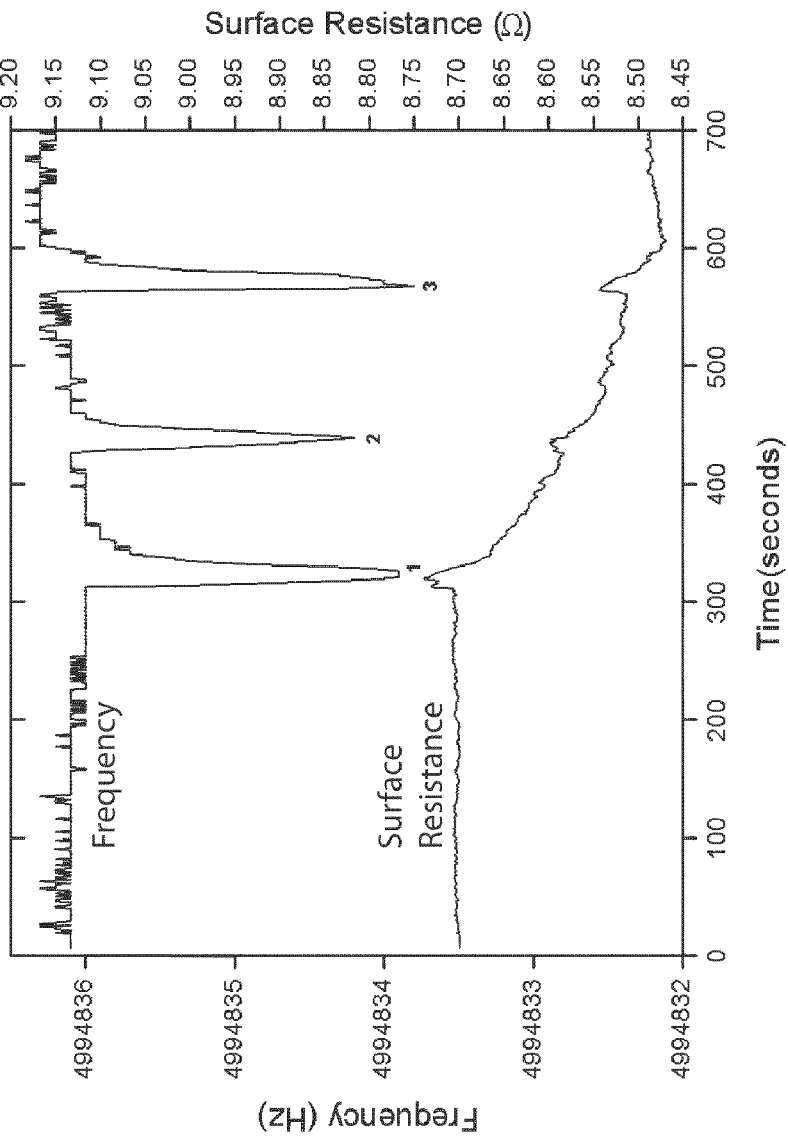
FIG. 125 is a graph of ITO-QCM average change in frequency response to wine odors.

A PCA score plot of different types of ketones, as provided in FIG. 116, shows clear separation into clusters, with the exception of one stray measurement for Butyric acid. There is a roughly increasing average ITO-QCM change in frequency response among the ketone vapor samples from right to left on the graph. There is a roughly increasing average ITO-QCM change in surface resistance response among the ketone vapor samples from top to bottom on the graph. This PCA score plot illustrates that the ITO-QCM vapor sensor measurements can distinguish between each of the ketones vapors.

In sum, nanocrystalline-thin film ITO-QCM sensors detected various ketones at room temperature under dynamic mode. The ITO (as a thin film sensor), and the QCM (as a transducer) combined to show the change in frequency responses and surface resistance responses as a function of time for each ketone vapor tested. PCA analysis showed selectivity for each ketone vapor.

Referring now to FIGS. 117 to 126, graphs, plots and data pertaining to measured parameters for consumable foods and beverages are provided. Among the tested food and beverage products are various types of fruits, onions, garlic, wines and cheeses.

An Indium Tin Oxide (ITO) thin film (e.g., about 200 nm thick) deposited over a 5 MHz AT cut gold quartz crystal microbalance by vacuum deposition was used as vapor sensor for the detection of the tested ketone compounds. The ITO film had a nanocrystalline structure with an average grain size of 44±12 nm. For beverages, a 15 μl drop was applied to one end of thick paper strips. An equal mass of crushed solid food sample was applied over one end of thick paper strips. Each paper strip was inserted in an open glass test jar (500 ml) and kept 2 cm above the surface of the ITO film for 10 seconds, and then removed from the jar. The paper strip was 20 cm in length, 2 cm wide and 0.3 mm thickness. A digital timer was used to measure the 10 second time period. A new paper strip was used for each run of each test sample. Parameters used in the determination of principal components analysis (PCA) of the petroleum products and alkanes are integrated frequency response (Hz-sec), integrated surface resistance response (Ω-sec), initial response slope (Hz/sec), average return to baseline slope (Hz/sec) and average of all change in frequency data points (Hz), as described above.

Tables comprising FIGS. 117 to 119 show ITO-QCM odor sensor results of all parameters determined for each test run of food and beverage samples. Changes in frequency and surface resistance as a function of time were recorded as odor molecules from tested foods and beverages were adsorbed on the ITO film, and then desorbed after the samples were removed from the jar. The average of the changes in frequency and surface resistance of five measurements for each food and beverage sample with ITO-QCM sensors is shown in FIGS. 120 to 125. Measured parameters were used to determine PCA score plots for the food and beverage odors, as illustrated in FIG. 126.

Figure 126:
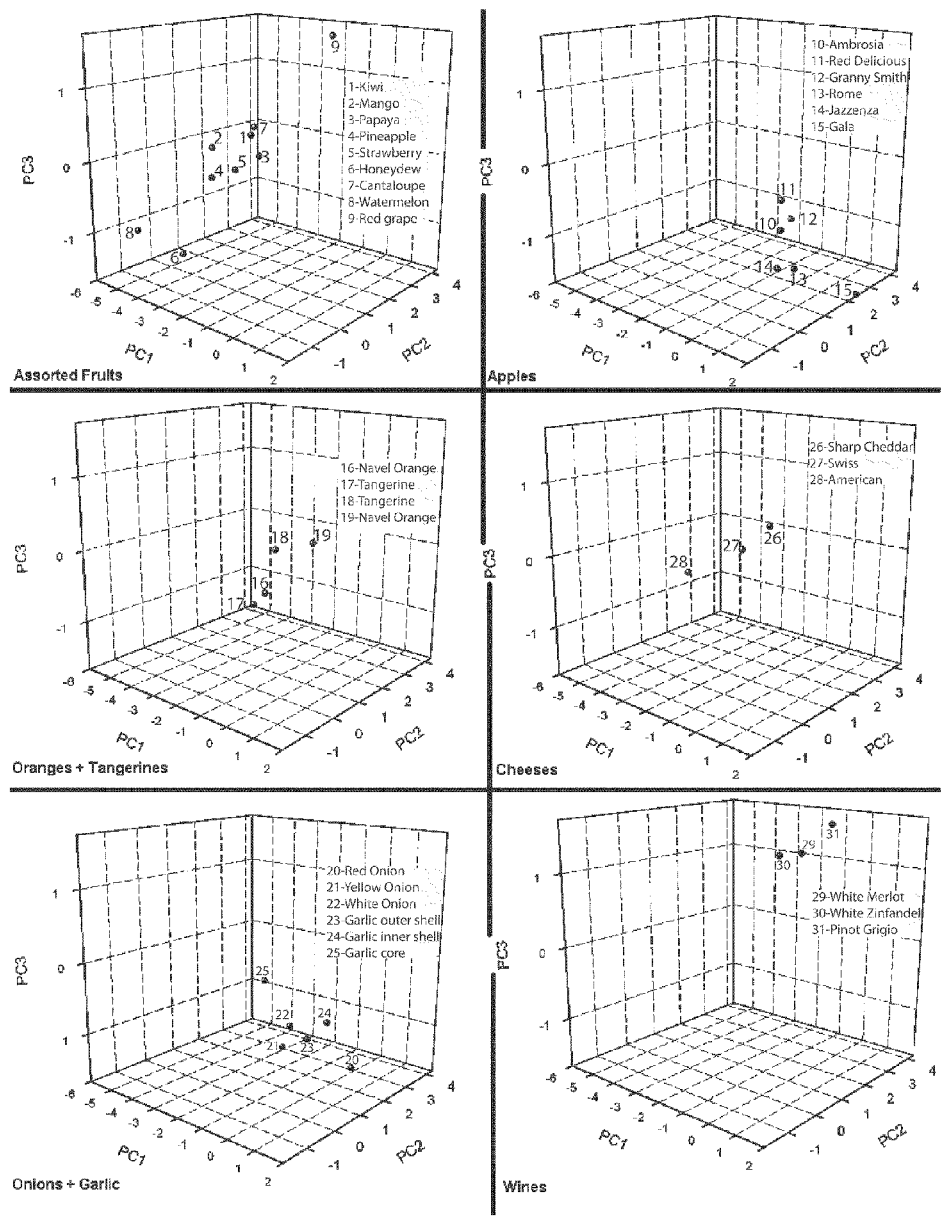
FIG. 126 comprises PCA score plots of ITO-QCM measurements of food and beverage odors.

A PCA score plot of different types of food and beverages, as provided in FIG. 126, shows clear groupings in the PCA variable space that seem intuitive when the food and beverage names are revealed. Oranges and tangerines were adjacent to, but do not overlap, other assorted fruits and apples. Onions were adjacent to and slightly overlapped the apples. One outlying apple data point was from a Gala apple that was stale, unlike the other five fresh apples that were measured. Out of all the assorted fruits, an outlying red grape was closest to the wine cluster, which makes sense since as these wines were made from grapes.

In sum, nanocrystalline-thin film ITO-QCM sensors detected various food and beverages at room temperature under dynamic mode. The ITO (as a thin film sensor), and the QCM (as a transducer) combined to show the change in frequency responses and surface resistance responses as a function of time for each food and beverage odor tested. PCA analysis showed selectivity for each food and beverage odor.

Figure 127:
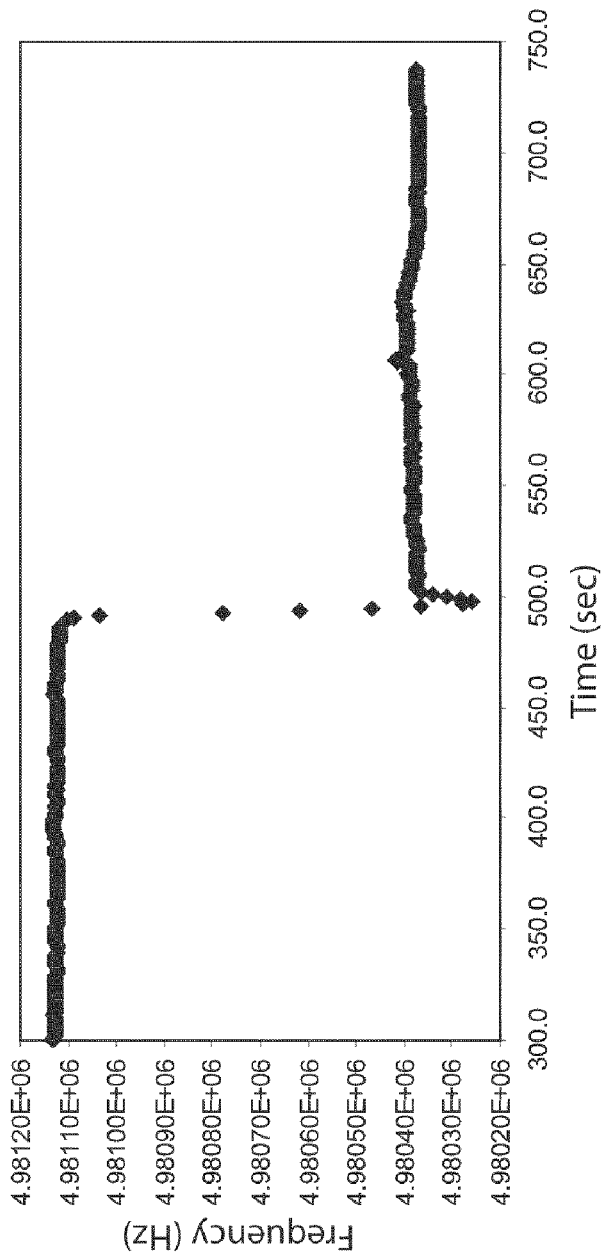
FIG. 127 is a graph of ITO-QCM frequency response to ethanol vapors.
Figure 128:
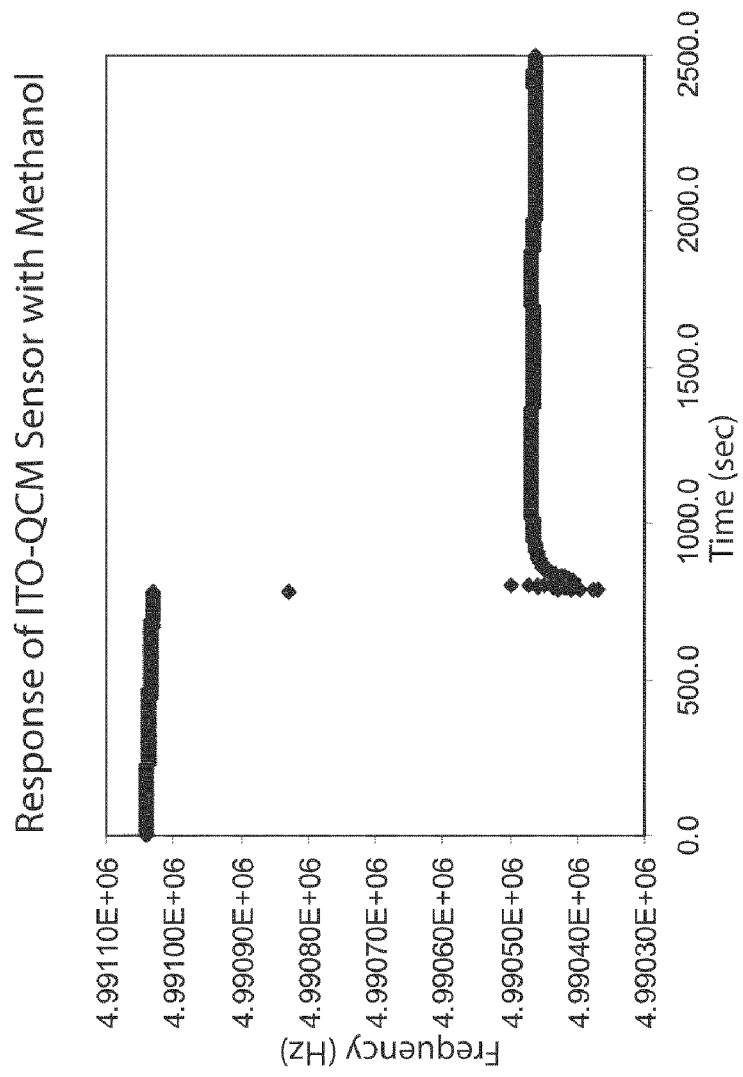
FIG. 128 is a graph of ITO-QCM frequency response to methanol vapors.
Figure 129:
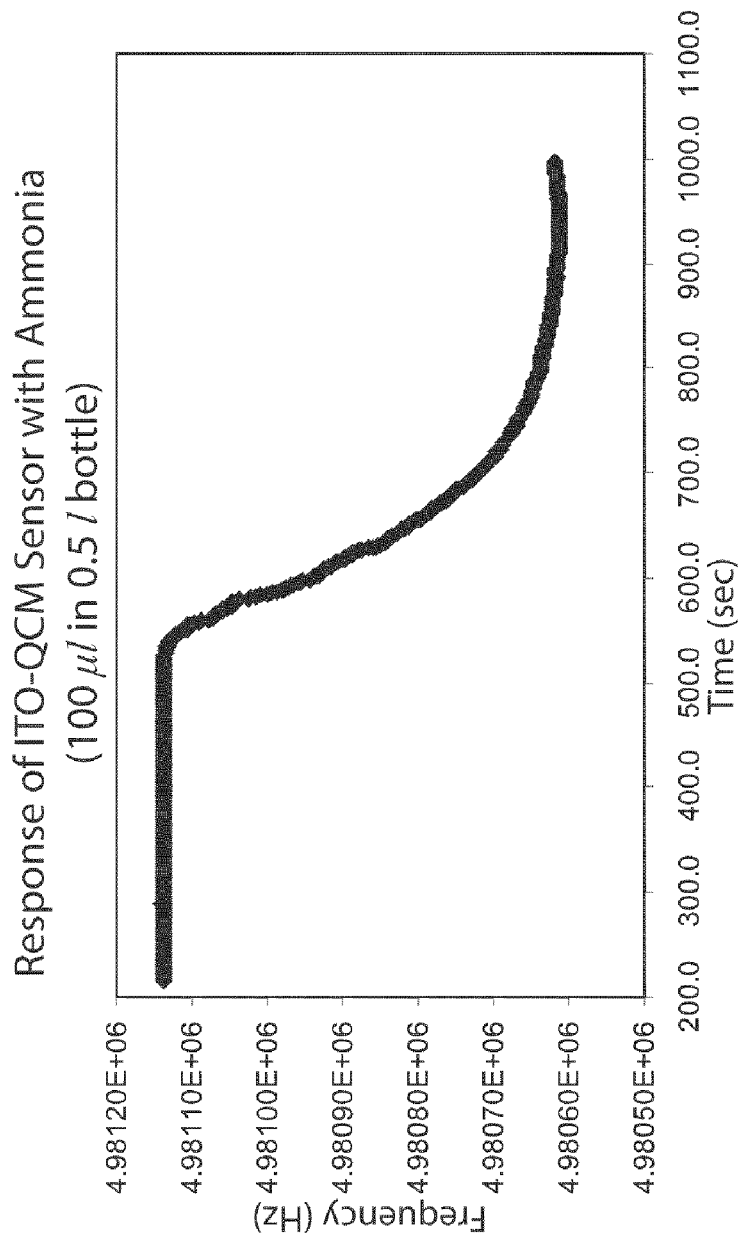
FIG. 129 is a graph of ITO-QCM frequency response to ammonia vapors.
Figure 130:
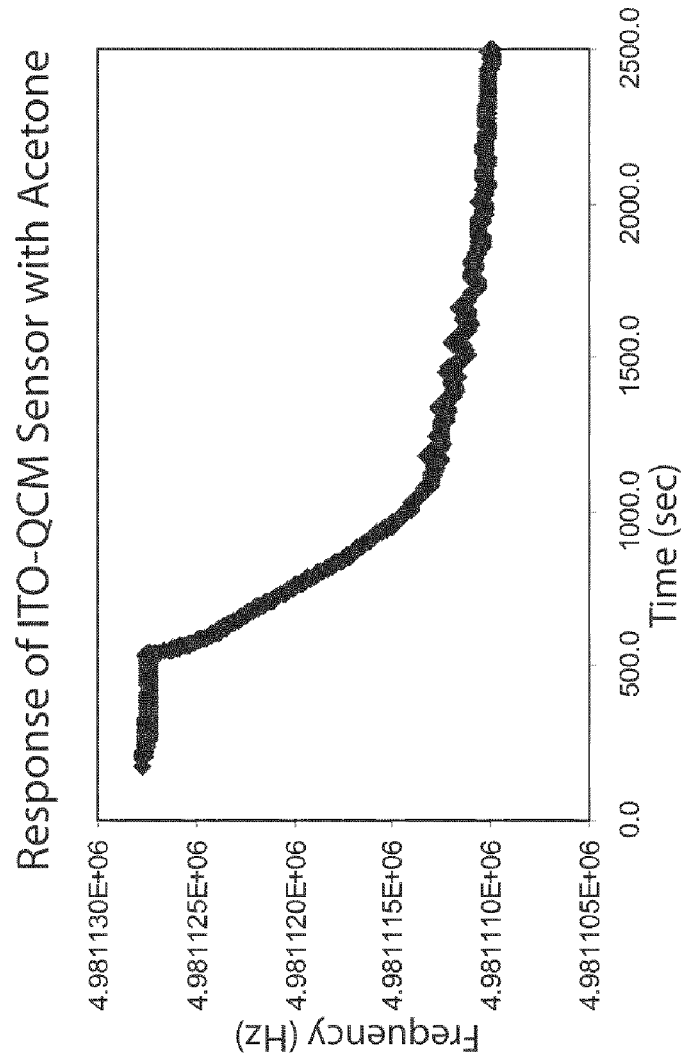
FIG. 130 is a graph of ITO-QCM frequency response to acetone vapors.

Additional tests were performed with a vessel (e.g., 500 ml glass test jar) closed during measurements. An ITO-QCM gas sensor holder was maintained inside an air-tight 500 ml closed glass jar. A known volume of ethanol, methanol, acetone, and ammonia gas were injected in bottom of glass bottle using a syringe. ITO-QCM gas sensors detected ethanol, methanol, acetone, and ammonia gas at room temperature. FIGS. 127 to 130 show responses of ITO-QCM thin film sensors with ethanol, methanol, ammonia and acetone at room temperature, respectively. Specifically, FIG. 127 shows the response of an ITO-QCM thin film gas sensor with ethanol (1000 ppmv). FIG. 128 shows the response of an ITO-QCM thin film gas sensor with methanol (2000 ppmv). The change in frequency with 1000 ppmv ethanol was about 79 Hz, while the change in frequency was about 60 Hz with 2000 ppmv methanol. This shows good selectivity between ethanol and methanol. FIG. 129 shows the response of an ITO-QCM thin film gas sensor with ammonia (1000 ppmv). FIG. 130 shows the response of an ITO-QCM thin film gas sensor with acetone (4000 ppmv).

Figure 131:
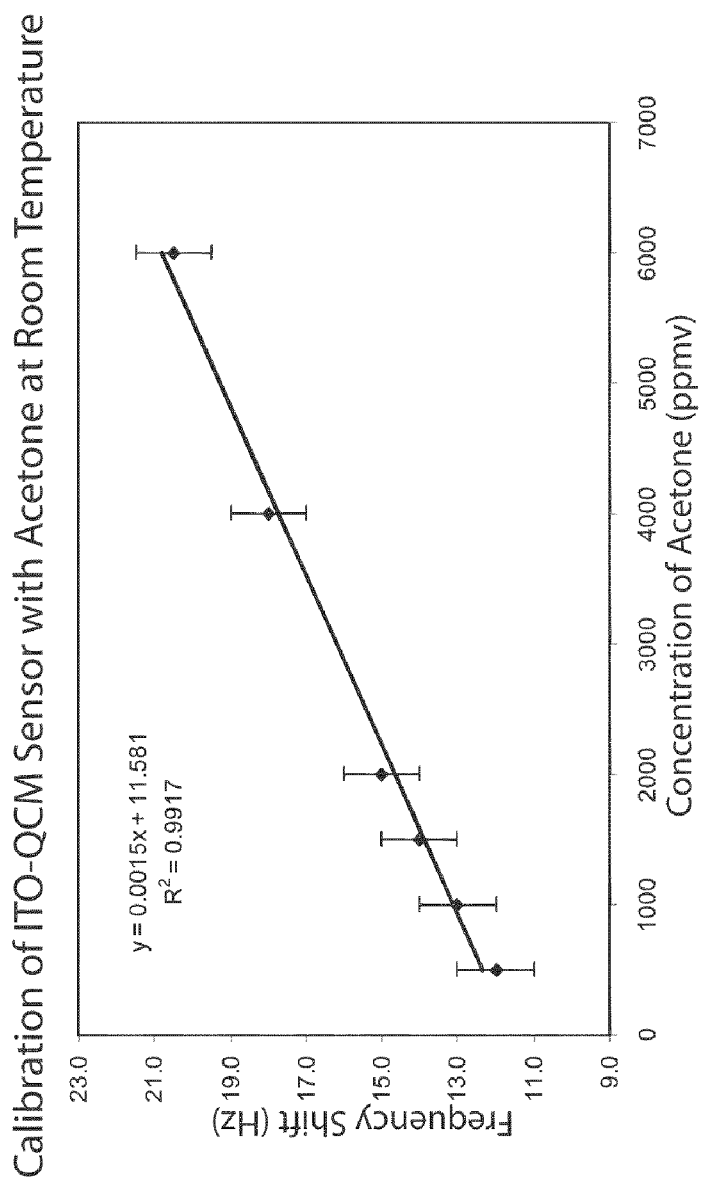
FIG. 131 is a graph of ITO-QCM frequency response to various concentrations of acetone vapors.

A calibration plot of an ITO-QCM gas sensor with acetone at room temperature is shown in FIG. 131. The calibration plot shows a linear response with correlation coefficient of 0.9917. The response of an ITO-QCM gas sensor is fast at room temperature, reproducible and nearly reversible.

An exemplary process for identifying unknown samples, entails ITO-QCM identification for reference samples followed by ITO-QCM characterization of the unknown sample. For each reference sample, ITO-QCM measurements are performed. Parameters for all reference samples are calculated for PCA. The calculations may be performed manually or automatically (e.g., using a programmed computer). The calculated parameters are used for PCA, with the principal components being stored for subsequent reference. The PCA results may also be presented in a 2-D or 3-D score plot graph. Next, ITO-QCM measurements are performed for a sample. Parameters for the unknown sample are calculated for PCA. The calculations may be performed manually or automatically (e.g., using a programmed computer). The calculated parameters are used for PCA, with the principal components being determined for subsequent comparison. The PCA results may also be presented in a 2-D or 3-D score plot graph. Based on the sample score plot coordinates, a determination is made if the sample lies within a cluster of the reference samples to possibly identify the sample.

In another implementation of the exemplary process, an iterative PCA step may be included. If PCA for reference samples shows some separate but closely spaced clusters in a PCA score plot graph, another round of PCA may be performed. In order to better resolve the differences between the closely spaced samples, the additional PCA may be performed on just those samples using the same data used for the original PCA score plot. Thus, an iterative process of performing PCA to better resolve the differences between closely spaced group samples is provided.

Determination ITO-QCM odor/vapor measurement parameters for PCA (Principal Component Analysis) may be performed using a programmed computer. A computer program may calculate the PCA coordinates of ITO-QCM vapor/odor measurements. The program may measure and calculate PCA coordinates for samples with appreciable changes in frequency and surface resistance responses. The program may calculate Integrated Frequency Response (Hz-sec), Integrated Surface Resistance Response ($\Omega$-Sec), Initial Response Slope (Hz/Sec), Average Return to Baseline Slope (Hz/sec), Average of all change in frequency data points (Hz).

Figure 132:
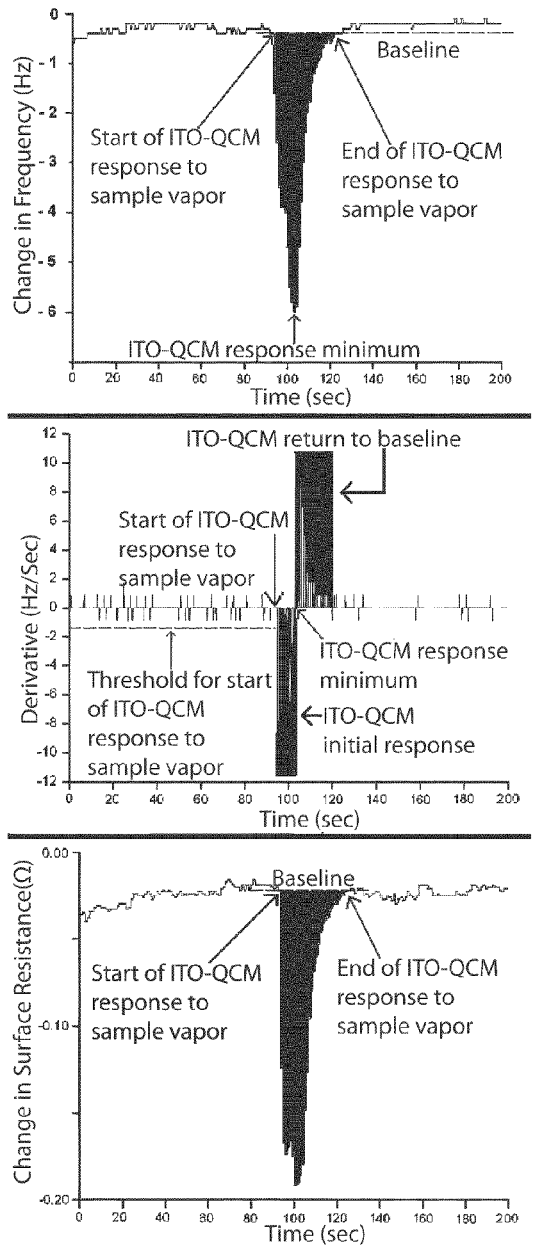
FIG. 132 provides graphs conceptually illustrating exemplary 10-second ITO-QCM measurement for a volatile organic compound vapor.

Illustratively, FIG. 132 provides graphs for a typical 10 second ITO-QCM measurement for a volatile organic compound vapor. The top graph shows the Change in Frequency vs. Time. The middle graph shows the Derivative of the Change in Frequency vs. Time. The bottom graph shows the Change in Surface Resistance vs. Time. The computer program reads and analyzes data from the ITO-QCM data acquisition log, such as a LabView® log file. Such data preferably includes frequency, surface resistance, and time values for each time increment (e.g., approximately every 0.1 seconds) throughout the time period (e.g., 10 seconds). FIG. 133 conceptually illustrates an excerpt of ITO-QCM data in a data acquisition log. The raw time, frequency, and surface resistance data for an ITO-QCM measurement is read into the program (e.g., assigned as array variables). The exemplary program identifies the start of the change in frequency measurement response by the moving average derivative (change in frequency/change in time) exceeding a threshold value greater than the typical baseline fluctuations. The program also identifies the end of the change in frequency measurement response (after reaching its minimum value corresponding to maximum adsorption of the sample odor/vapor molecules) by returning to within 0.1 Hz of the start of the change in frequency measurement. The integrated frequency response and the integrated surface resistance responses may be calculated using any numerical integration technique, such as the trapezoid method for numerical integration. As the Resonance/Surface Resistance ITO-QCM measurements show more relative baseline fluctuations than the ITO-QCM Frequency measurements, and often a less well defined end of response to the sample vapor, the start and end of the Resonance/Surface Resistance ITO-QCM measurement may be based on the start and end of the ITO-QCM Frequency measurements.

An exemplary program may output PCA coordinates of a sample based on a previous set of reference sample measurements. Optionally, PCA coordinate values that are outputted may be used to generate a graphical PCA plot. As another option, the program may be configured to identify a sample based on the ITO-QCM measurement. By way of example and not limitation, the PCA score plot coordinates for an unknown sample may be shown on a graph of known reference samples to identify the unknown sample. Graphing the PCA coordinates of an unknown sample on a PCA score plot of known reference samples will enable determining if the unknown sample is one of the reference samples, and, if so, which reference sample. In addition to automating identification of an ITO-QCM measurement of an unknown vapor sample after PCA has already been completed on a set of known reference ITO-QCM vapor samples, as described above, an exemplary program may also automate all of the PCA parameter and calculation steps needed to determine score plot coordinates after each reference sample is measured, not just after each unknown sample is measured.

As one example of computer software in accordance with principles of the invention, a Basic language computer program that calculates PCA coordinates of ITO-QCM vapor/odor measurements after completing measurements is provided for illustrative purposes in FIGS. 134 through 139. The FreeBasic™ <freebasic.net> compiler, an open-source, 32-bit BASIC compiler, was used to compile the source code. Those skilled in the art will appreciate that the program may be written in other computing languages, and may differ substantially from the structure and code illustrated in FIGS. 134 through 139, without departing from the spirit and scope of the invention. Additionally, the program may be implemented as software, firmware or any other means for controlling execution of a computing device, without departing from the spirit and scope of the invention. Furthermore, a program according to principles of the invention may be configured to run on a general purpose computer system, such as a PC, or on an embedded system, which may be incorporated into a multifunction electronic apparatus or comprise a special-purpose computing device designed to perform the programmed functions.

In sum, the nanocrystalline-thin film ITO-QCM sensors detected vapors and odors of various analytes, and enabled production of data which allowed PCA analysis to identify and group these analytes. The ITO (as a thin film sensor), and the QCM (as a transducer) combined to show the change in frequency responses and surface resistances as a function of time for each odor or vapor tested. In general, PCA analysis showed good selectivity. An iterative PCA process substantially improved resolution for cluttered groups. The nanocrystalline ITO-QCM odor sensor enables detection of various test odors at ambient temperature without using a heater or associated temperature controlling circuits. The absence of a heater not only saves power consumption and space, but also reduces any possibility of fire or an explosion during testing of flammable and/or explosive vapors. Again, there is no need for any reagent or pre-sample conditioning or sample preparation for testing, which facilitates use at any time. Advantageously, the response time of the ITO-QCM odor sensors with petroleum vapors is very fast and nearly in real time. The ITO-QCM sensors detect, classify and produce a unique signature for each analyte by sensing parameters such as change in frequency, integrated frequency response, initial response slope, average return to baseline slope and transient response time, as well as integrated surface resistance response. PCA plots of ITO-QCM measurements showed isolation of clusters of tested analyte samples and, therefore, exhibited good selectivity.

While an exemplary embodiment of the invention has been described, it should be apparent that modifications and variations thereto are possible, all of which fall within the true spirit and scope of the invention. With respect to the above description then, it is to be realized that the optimum relationships for the components and steps of the invention, including variations in order, form, content, function and manner of operation, are deemed readily apparent and obvious to one skilled in the art, and all equivalent relationships to those illustrated in the drawings and described in the specification are intended to be encompassed by the present invention. The above description and drawings are illustrative of modifications that can be made without departing from the present invention, the scope of which is to be limited only by the following claims. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents are intended to fall within the scope of the invention as claimed.

What is claimed is:

1. An indium tin oxide (ITO) quartz crystal microbalance (QCM) sensor system comprising:
   a quartz crystal with a pair of electrodes, said quartz crystal having a sensing surface and being configured for installation in and oscillation in a crystal holder, and said electrodes being configured for electrically coupling the quartz crystal to a crystal oscillator;
   a nanocrystalline ITO thin film formed as a sensing surface on said quartz crystal, said nanocrystalline ITO thin film comprising an adsorbent that attracts at least one gaseous compound emitted from an analyte;
   said system further comprising a means for oscillating the quartz crystal with the nanocrystalline ITO thin film formed thereon;
   a means for determining the frequency of oscillation of the quartz crystal with the nanocrystalline ITO thin film formed thereon;
   a means for determining surface resistance of the quartz crystal with the nanocrystalline ITO thin film formed thereon;
   a computing device configured for determining a parameter from the group consisting of integrated frequency response, integrated surface resistance response, initial response slope, average return to baseline slope, return to baseline time/initial response time ratio, and average change in frequency for the quartz crystal with the nanocrystalline ITO thin film formed thereon; and
   a principal component analysis means for determining principal components for the at least one gaseous compound.

2. An indium tin oxide (ITO) quartz crystal microbalance (QCM) sensor system according to claim 1, said nanocrystalline ITO thin film having a thickness of about 50 to 300 nm.

3. An indium tin oxide (ITO) quartz crystal microbalance (QCM) sensor system according to claim 1, said nanocrystalline ITO thin film having an average grain size of about 10 to 100 nm.

4. An indium tin oxide (ITO) quartz crystal microbalance (QCM) sensor system according to claim 1, said quartz crystal being a crystal from the group consisting of 5 MHz quartz crystal AT cut and 5 MHz quartz crystal IT cut.

5. An indium tin oxide (ITO) quartz crystal microbalance (QCM) sensor system according to claim 4, said electrodes comprising a conductor from the group consisting of gold and platinum.

6. An indium tin oxide (ITO) quartz crystal microbalance (QCM) sensor system according to claim 1, said nanocrystalline ITO thin film being deposited on the sensing surface of the quartz crystal by thermal evaporation.

7. An indium tin oxide (ITO) quartz crystal microbalance (QCM) sensor system according to claim 1, said system further comprising a means for comparing determined principal components with known principal components corresponding to known analytes.

8. An indium tin oxide (ITO) quartz crystal microbalance (QCM) sensor system according to claim 7, said analyte comprising a substance from the group consisting of an alcoholic beverage, an explosive compound, a VOC, a petroleum-based fuel, an alkane, an aldehyde, a ketone, a fruit, a cheese, and a vegetable.

9. An indium tin oxide (ITO) quartz crystal microbalance (QCM) sensor system according to claim 1, further comprising a sampling vessel with an opening, said vessel having a first volume configured to contain the analyte and a second volume configured to at least temporarily contain the at least one gaseous compound and the quartz crystal with the nanocrystalline ITO thin film formed thereon.

10. An indium tin oxide (ITO) quartz crystal microbalance (QCM) sensor system according to claim 1, further comprising a sampling vessel with an opening, said vessel having a first volume configured to contain the analyte and a second volume defining a dynamic headspace configured to at least temporarily contain the at least one gaseous compound, and the quartz crystal with the nanocrystalline ITO thin film formed thereon being positionable at the opening of the sampling vessel.

11. A method of detecting an analyte, said method comprising steps of:
   providing a piezoelectric crystal microbalance sensor system comprising:
      a piezoelectric crystal with a pair of electrodes and a sensing surface formed thereon, said electrodes being configured for electrically coupling the piezoelectric crystal to a crystal oscillator;
      a nanocrystalline oxide semiconductor thin film formed as the sensing surface on said piezoelectric crystal, said nanocrystalline oxide semiconductor thin film comprising an adsorbent that attracts at least one gaseous compound emitted from an analyte, and said piezoelectric crystal with the nanocrystalline oxide semiconductor thin film formed as the sensing surface being configured to oscillate at a determined frequency before a compound is adsorbed thereon;
   exposing said piezoelectric crystal with the nanocrystalline oxide semiconductor thin film formed as the sensing surface for a determined time period to at least one gaseous compound emitted from an analyte;
   oscillating said piezoelectric crystal with the nanocrystalline oxide semiconductor thin film formed as the sensing surface in the presence of the at least one gaseous compound emitted from the analyte; and
   determining at least one detection parameter of said piezoelectric crystal with the nanocrystalline oxide semiconductor thin film formed as the sensing surface oscillating in the presence of the at least one gaseous compound emitted from the analyte; and
   determining the analyte based upon the detection parameter.

12. A method of detecting an analyte according to claim 11, said detection parameter comprising a measurable parameter from group consisting of
   frequency of oscillation of the piezoelectric crystal with the nanocrystalline oxide semiconductor thin film formed thereon, and
   surface resistance of the piezoelectric crystal with the nanocrystalline oxide semiconductor thin film formed thereon, and
   integrated frequency response, and
   integrated surface resistance response, and
   initial response slope, and
   average return to baseline slope, and
   return to baseline time/initial response time ratio for the piezoelectric crystal with the nanocrystalline oxide semiconductor thin film formed thereon.

13. A method of detecting an analyte according to claim 11, further comprising a step applying principal component analysis to determine principal components for the at least one gaseous compound.

14. A method of detecting an analyte according to claim 13, said method further comprising comparing the determined principal components with known principal components corresponding to known analytes.

* * * * *